United States Patent
Lee et al.

(10) Patent No.: US 9,890,138 B2
(45) Date of Patent: *Feb. 13, 2018

(54) DIAMINOPYRIMIDINE DERIVATIVES AND PROCESSES FOR THE PREPARATION THEREOF

(75) Inventors: Hyun-Joo Lee, Seoul (KR);
Dong-Hoon Kim, Gyeonggi-do (KR);
Tae-Kyun Kim, Gyeonggi-do (KR);
Young-Ae Yoon, Seoul (KR);
Jae-Young Sim, Gyeonggi-do (KR);
Myung-Hun Cha, Gyeonggi-do (KR);
Eun-Jung Jung, Seoul (KR);
Kyoung-Kyu Ahn, Gyeonggi-do (KR);
Tai-Au Lee, Seoul (KR)

(73) Assignee: YUHAN CORPORATION, Seoul (KR)

( * ) Notice: Subject to any disclaimer, the term of this patent is extended or adjusted under 35 U.S.C. 154(b) by 664 days.

This patent is subject to a terminal disclaimer.

(21) Appl. No.: 14/001,489

(22) PCT Filed: Feb. 24, 2012

(86) PCT No.: PCT/KR2012/001427
§ 371 (c)(1),
(2), (4) Date: Aug. 23, 2013

(87) PCT Pub. No.: WO2012/115480
PCT Pub. Date: Aug. 30, 2012

(65) Prior Publication Data
US 2013/0338179 A1  Dec. 19, 2013
US 2015/0274700 A2  Oct. 1, 2015

(30) Foreign Application Priority Data

Feb. 25, 2011 (KR) ........................ 10-2011-0016981

(51) Int. Cl.
*C07D 403/04* (2006.01)
*C07D 401/04* (2006.01)
*C07D 413/04* (2006.01)
*C07D 413/14* (2006.01)
*C07D 417/04* (2006.01)

(52) U.S. Cl.
CPC ......... *C07D 403/04* (2013.01); *C07D 401/04* (2013.01); *C07D 413/04* (2013.01); *C07D 413/14* (2013.01); *C07D 417/04* (2013.01)

(58) Field of Classification Search
None
See application file for complete search history.

(56) References Cited

U.S. PATENT DOCUMENTS

| | | |
|---|---|---|
| 4,962,115 A | 10/1990 | Van Daele |
| 5,185,335 A | 2/1993 | Van Daele et al. |
| 5,262,418 A | 11/1993 | Van Daele et al. |
| 5,510,353 A | 4/1996 | Giger et al. |
| 5,744,489 A | 4/1998 | Greenwood |
| 5,750,531 A | 5/1998 | Lee et al. |
| 6,342,503 B1 | 1/2002 | Aldrich et al. |
| 6,352,993 B1 | 3/2002 | Lee et al. |
| 2006/0057972 A1 | 3/2006 | Wikel et al. |
| 2006/0128726 A1 | 6/2006 | Wang et al. |
| 2006/0188453 A1 | 8/2006 | Marquais-Bienewald et al. |
| 2008/0207690 A1 | 8/2008 | Noguchi et al. |
| 2008/0293942 A1 | 11/2008 | Cousins |

FOREIGN PATENT DOCUMENTS

| | | | |
|---|---|---|---|
| EP | 0 243 959 A1 | 4/1987 | |
| EP | 0 445 862 B1 | 4/2000 | |
| WO | WO 2005/011758 A2 * | 2/2005 | ............... A61L 2/18 |
| WO | WO 2005011758 A2 * | 2/2005 | ............. A01N 43/54 |
| WO | 2006-057972 A1 | 6/2006 | |
| WO | WO 2010129053 A2 * | 11/2010 | ........... C07D 403/14 |

OTHER PUBLICATIONS

NIH/PubMed Health, Gastrointestinal Tract (GI Tract), https://www.ncbi.nlm.nih.gov/pubmedhealth/PMHT002285.*
Ivashchenko et al., "Synthesis and Study of 2,4-Diamino- and 2-Amino-4-(1H-Pyrazol-1-yl)pyrimidine Derivatives", Chemistry of Heterocyclic Compounds, vol. 16, No. 3, pp. 309-312, (1980).
Yamanaka et al., "Studies on Pyrimidine Derivatives. XIII. Reaction of 4-Alkoxy-pyrimidine 1-Oxides with Phenyl Isocyanate and Phenyl Isothiocyanate", Chem. Pharm. Bull., vol. 27, No. 11, pp. 2642-2646, (1979).
Arvanitis et al., "Non-Peptide Corticotropin-Releasing Hormone Antagonists: Syntheses and Structure-Activity Relationships of 2-Anilinopyrimidines and -triazines", Journal of Medicinal Chemistry, 1999, vol. 42, No. 5, p. 805-818.
Om et al., "A Convenient Method for the Synthesis of 2-[(2-Benzimidazolyl)Amino]-6-Methyl-4-Pyrimidinols", Current Science, 1978, vol. 47, No. 1, p. 15-17.
Chemical Abstract, RN 946245-74-5, 1 page, (2007).
Chemical Abstract, RN 946245-42-7, 1 page, (2007).
Chemical Abstract, RN 946221-62-1, 1 page, (2007).

(Continued)

*Primary Examiner* — Kortney L Klinkel
*Assistant Examiner* — Tori M Strong
(74) *Attorney, Agent, or Firm* — Vorys, Sater, Seymour and Pease LLP; Mih Suhn Koh

(57) ABSTRACT

The present invention provides a diaminopyrimidine derivative or its pharmaceutically acceptable salt, a process for the preparation thereof, a pharmaceutical composition comprising the same, and a use thereof. The diaminopyrimidine derivative or its pharmaceutically acceptable salt functions as a 5-$HT_4$ receptor agonist, and therefore can be usefully applied for preventing or treating dysfunction in gastrointestinal motility, one of the gastrointestinal diseases, such as gastroesophageal reflux disease (GERD), constipation, irritable bowel syndrome (IBS), dyspepsia, post-operative ileus, delayed gastric emptying, gastroparesis, intestinal pseudo-obstruction, drug-induced delayed transit, or diabetic gastric atony.

1 Claim, No Drawings

(56) References Cited

OTHER PUBLICATIONS

Chemical Abstract, RN 1115306-26-7, 1 page, (2009).
Chemical Abstract, RN 923139-86-0, 1 page, (2007).
Chemical Abstract, RN 946268-08-2, 1 page, (2007).
Chemical Abstract, RN 946268-05-9, 1 page, (2007).
Chemical Abstract, RN 946245-09-6, 1 page, (2007).
Chemical Abstract, RN 946245-06-3, 1 page, (2007).
Michel Langlois and Rodolphe Fischmeister, "5-HT4 Receptor Ligands: Applications and New Prospects," Journal of Medicinal Chemistry, American Chemical Society, vol. 46, No. 3, Jan. 30, 2003, pp. 319-344.
The Supplementary European Search Report for European Application No. EP 12 75 0114; two pages; search completed on Jun. 12, 2014.

* cited by examiner

DIAMINOPYRIMIDINE DERIVATIVES AND PROCESSES FOR THE PREPARATION THEREOF

This is a National Phase Application filed under 35 U.S.C. § 371 as a national stage of PCT/KR2012/001427, filed on Feb. 24, 2012, an application claiming the benefit under 35 U.S.C. §119 of the Korean Application No. 10-2011-0016981, filed on Feb. 25, 2011 the content of each of which is hereby incorporated by reference in their entirety.

TECHNICAL FIELD

The present invention relates to a novel 5-HT$_4$ receptor agonist, more specifically a novel diaminopyrimidine derivative or its pharmaceutically acceptable salt having an activity as a 5-HT$_4$ receptor agonist, a process for the preparation thereof, a pharmaceutical composition comprising the same, and a use thereof.

BACKGROUND ART

Serotonin (5-hydroxytryptamine, 5-HT), one of the neurotransmitters, is broadly distributed throughout human body including both the central nervous system and the peripheral nervous system. Approximately 95% of the human body's total serotonin is found in the gastrointestinal tract, while about 5% thereof is found in the brain. Serotonin receptors are located in intestinal nerves, enterochromaffin cells, intestinal smooth muscle, immune tissues, etc. Serotonin receptor subtypes include 5-HT$_1$, 5-HT$_2$, 5-HT$_3$, 5-HT$_4$, 5-HT$_5$, 5-HT$_6$, and 5-HT$_7$. Interactions between these various receptors and serotonin are linked to various physiological functions. Therefore, various researches have been performed for developing therapeutic agents that are capable of interacting with a specific serotonin subtype as a target. The researches include identification of 5-HT$_4$ receptors and active agents interacting therewith (Langlois and Fischmeister, J. Med. Chem. 2003, 46, 319-344).

It has been found by the previous literatures that 5-HT$_4$ receptor agonists are useful for treating an abnormal gastrointestinal motility, i.e., dysfunction in gastrointestinal motility. The abnormal gastrointestinal motility may result in various disorders, for example irritable bowel syndrome (IBS), constipation, dyspepsia, delayed gastric emptying, gastroesophageal reflux disease (GERD), gastroparesis, post-operative ileus, intestinal pseudo-obstruction, drug-induced delayed transit, etc.

Representative 5-HT$_4$ receptor agonists disclosed in prior arts include tegaserod (an aminoguanidine derivative, U.S. Pat. No. 5,510,353), prucalopride (a benzofuran carboxamide derivative, EPO445862), cisapride (a benzamide derivative, U.S. Pat. No. 4,962,115), mosapride (EP0243959), etc. These compounds are known as an agent stimulating gastrointestinal motility.

DETAILED DESCRIPTION OF THE INVENTION

Technical Problem

The present inventors found that a certain diaminopyrimidine derivative functions as a 5-HT$_4$ receptor agonist, and therefore can be usefully applied for preventing or treating dysfunction in gastrointestinal motility.

Therefore, the present invention provides the above diaminopyrimidine derivative or its pharmaceutically acceptable salt, a process for the preparation thereof, a pharmaceutical composition comprising the same, and a use thereof.

Technical Solution

According to an aspect of the present invention, there is provided a use of a diaminopyrimidine derivative or its pharmaceutically acceptable salt for the manufacture of a medicament for preventing or treating a dysfunction in gastrointestinal motility According to another aspect of the present invention, there is provided a pharmaceutical composition for preventing or treating a dysfunction in gastrointestinal motility comprising a diaminopyrimidine derivative or its pharmaceutically acceptable salt as an active ingredient.

According to still another aspect of the present invention, there is provided a diaminopyrimidine derivative or its pharmaceutically acceptable salt.

According to still another aspect of the present invention, there is provided a process for preparing the diaminopyrimidine derivative or its pharmaceutically acceptable salt.

Advantageous Effects

The compound of the present invention, i.e., the diaminopyrimidine derivative or its pharmaceutically acceptable salt, functions as a 5-HT$_4$ receptor agonist, and therefore can be usefully applied for preventing or treating dysfunction in gastrointestinal motility, one of the gastrointestinal diseases, such as gastroesophageal reflux disease (GERD), constipation, irritable bowel syndrome (IBS), dyspepsia, post-operative ileus, delayed gastric emptying, gastroparesis, intestinal pseudo-obstruction, drug-induced delayed transit, or diabetic gastric atony.

BEST MODE FOR CARRYING OUT THE INVENTION

As used herein, the term "alkyl" refers to a straight or branched aliphatic hydrocarbon radical. For example, $C_1$-$C_6$ alkyl means a straight or branched aliphatic hydrocarbon having 1 to 6 carbon atoms, such as methyl, ethyl, propyl, n-butyl, n-pentyl, n-hexyl, isopropyl, isobutyl, sec-butyl, tert-butyl, neopentyl, and isopentyl.

The term "alkoxy or alkyloxy" refers to a radical formed by substituting the hydrogen atom of a hydroxyl group with an alkyl. For example, $C_1$-$C_6$ alkoxy includes methoxy, ethoxy, propoxy, n-butoxy, n-pentyloxy, isopropoxy, sec-butoxy, tert-butoxy, neopentyloxy, and isopentyloxy.

The term "alkenyl" refers to a straight or branched aliphatic hydrocarbon radical having one or more double bond(s). For example, $C_2$-$C_6$ alkenyl includes ethenyl, propenyl, butenyl, pentenyl, and hexenyl.

The term "alkynyl" refers to a straight or branched aliphatic hydrocarbon radical having one or more triple bond(s). For example, $C_2$-$C_6$ alkynyl includes ethynyl, propynyl, butynyl, pentynyl, and hexynyl.

The present invention provides a use of a compound of Formula 1 or its pharmaceutically acceptable salt for the manufacture of a medicament for preventing or treating a dysfunction in gastrointestinal motility:

<Formula 1>

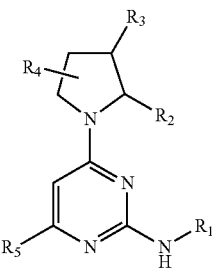

wherein,

R₁ is a phenyl group substituted with one or more substituents selected from the group consisting of hydroxy, amino, halogen, cyano, nitro, hydroxycarbonyl, $C_{1-5}$ alkyl (where the $C_{1-5}$ alkyl is optionally substituted with halogen or amino), $C_{2-6}$ alkenyl, $C_{2-6}$ alkynyl, $C_{1-5}$ alkoxy (where the $C_{1-5}$ alkoxy is optionally substituted with halogen), $C_{1-5}$ alkylthio, mono- or di-$C_{1-5}$ alkylamino, $C_{1-5}$ alkylsulfonylamino, $C_{1-5}$ alkylcarbonylamino, $C_{1-5}$ alkoxycarbonyl, aminosulfonyl, aminocarbonyl, $C_{1-5}$ alkylaminocarbonyl, and benzyloxycarbonylamino; or a heteroaryl group selected from the group consisting of pyridinyl, pyrimidinyl, pyrazinyl, imidazolyl, pyrazolyl, triazolyl, oxazolyl, thiazolyl, furanyl, pyrrolyl, thiophenyl, naphthyl, indanyl, quinolinyl, quinolinonyl, chromenonyl, dihydroindolonyl, isoindoline-1,3-dionyl, dihydrobenzoimidazolonyl, benzoxazolonyl, benzofuranyl, benzothiophenyl, benzo[d][1,3]dioxolyl, dihydrobenzo[1,4]dioxinyl, indolyl, indolinyl, benzimidazolyl, benzoxazolyl, benzothiazolyl, and indazolyl, wherein the heteroaryl group may be optionally substituted with one or more substituents selected from the group consisting of amino, di-$C_{1-5}$ alkylamino, cyano, nitro, halogen, $C_{1-5}$ alkyl (where the $C_{1-5}$ alkyl is optionally substituted with halogen), $C_{1-5}$ alkoxy (where the $C_{1-5}$ alkoxy is optionally substituted with halogen), acetyl, and $C_{1-5}$ alkylsulfonyl, R₂ is hydrogen; a $C_{1-5}$ alkyl group optionally substituted with a substituent selected from the group consisting of hydroxy, $C_{1-5}$ alkoxy, benzylamino (where the benzylamino is optionally substituted with halogen), phenylamino, $C_{1-5}$ alkylamino, $C_{3-6}$ cycloalkylamino, pyrrolidinyl, and hydroxy-$C_{1-5}$ alkylamino; a $C_{1-5}$ alkoxycarbonyl group; a hydroxycarbonyl group; an aminocarbonyl group; a formyl group; or an oxo(=O) group, R₃ is hydrogen; a hydroxyl group; a $C_{1-5}$ alkoxy group; a phenoxy group; a benzyloxy group; a $C_{1-5}$ alkyl group optionally substituted with a substituent selected from the group consisting of amino, $C_{1-5}$ alkoxycarbonylamino, and mono- or di-$C_{1-5}$ alkylamino; or a group selected from the group consisting of the following Formulas A to E (where * in Formulas A to E represents the position attached to the compounds of Formula 1),

A

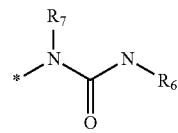

B

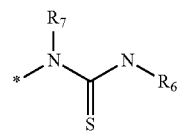

C

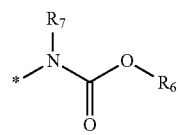

D

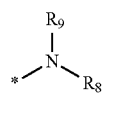

E

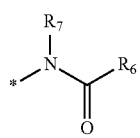

R₄ is hydrogen; a hydroxyl group; or a $C_{1-5}$ alkyl group optionally substituted with hydroxy, R₅ is a $C_{1-5}$ alkyl group optionally substituted with phenyl; or a $C_{2-6}$ alkenyl group optionally substituted with phenyl or $C_{3-6}$ cycloalkyl, R₆ is a $C_{1-10}$ alkyl group optionally substituted with a substituent selected from the group consisting of hydroxy, halogen, $C_{1-5}$ alkoxy, amino, $C_{1-5}$ alkoxycarbonylamino, benzyloxycarbonylamino, mono- or di-$C_{1-5}$ alkylamino, $C_{1-5}$ alkoxy-$C_{1-5}$ alkyloxy, phenoxy, benzyloxy, phenyl (where the phenyl is optionally substituted with one or more substituents selected from the group consisting of halogen, amino, $C_{1-5}$ alkoxy, and hydroxy), thiophenyl, pyridinyl, indolyl, pyrimidinyl, pyrazinyl, imidazolyl, pyrazolyl, triazolyl, oxazolyl, thiazolyl, furanyl, pyrrolyl, piperidinyl, piperazinyl (where the piperazinyl is optionally substituted with benzyl), $C_{3-6}$ cycloalkyl, acetyl, and benzoyl; a $C_{3-6}$ cycloalkyl group; a piperidinyl group optionally substituted with $C_{1-5}$ alkoxycarbonyl; a $C_{1-10}$ alkenyl group optionally substituted with phenyl; a trifluoromethyl group; a trifluoroethyl group; or a phenyl group optionally substituted with halogen, R₇ is hydrogen; or a $C_{1-5}$ alkyl group, R₈ and R₉ are, independently each other, hydrogen; a $C_{1-10}$ alkyl group optionally substituted with a substituent selected from the group consisting of amino, $C_{1-5}$ alkoxycarbonylamino, hydroxy, $C_{1-5}$ alkylthio, $C_{3-19}$ cycloalkyl, phenyl (where the phenyl is optionally substituted with one or more substituents selected from the group consisting of hydroxy, $C_{1-5}$ alkyl, mono- or di-$C_{1-5}$ alkylamino, trifluoromethyl, halogen, $C_{1-5}$ alkoxy, and $C_{1-5}$ alkylcarbonyloxy), thiophenyl, pyrrolyl, furanyl (where the furanyl is optionally substituted with mono- or di-$C_{1-5}$ alkyl), pyridinyl, pyrimidinyl, pyrazinyl, imidazolyl, pyrazolyl, triazolyl, tetrazolyl, oxazolyl, thiazolyl, and benzyloxy; a piperidinyl group optionally substituted with benzyl, benzoyl, $C_{1-5}$ alkyl, or $C_{1-5}$ alkylcarbonyl; an azetidinyl group optionally substituted with $C_{1-5}$ alkoxycarbonyl; a $C_{1-5}$ alkylsulfonyl group; a phenylsulfonyl group (where the phenyl moiety is optionally substituted with halogen); or a $C_{3-19}$ cycloalkyl group.

In the use for the manufacture of a medicament for preventing or treating a dysfunction in gastrointestinal motility according to the present invention, the dysfunction in gastrointestinal motility includes gastrointestinal diseases, such as gastroesophageal reflux disease (GERD), constipation, irritable bowel syndrome (IBS), dyspepsia, post-operative ileus, delayed gastric emptying, gastroparesis, intestinal pseudo-obstruction, drug-induced delayed transit, or diabetic gastric atony. The constipation includes chronic constipation, chronic idiopathic constipation (CIC), opioid-induced constipation (OIC), etc. And also, the dyspepsia includes functional dyspepsia.

In the use for the manufacture of a medicament for preventing or treating a dysfunction in gastrointestinal motility according to the present invention, the compound or its salt may be the compound of Formula 1 or its pharmaceutically acceptable salt wherein, $R_1$ is a phenyl group substituted with one or more substituents selected from the group consisting of hydroxy, amino, halogen, cyano, nitro, hydroxycarbonyl, $C_{1-5}$ alkyl (where the $C_{1-5}$ alkyl is optionally substituted with halogen or amino), $C_{1-5}$ alkoxy (where the $C_{1-5}$ alkoxy is optionally substituted with halogen), $C_{1-5}$ alkylthio, aminosulfonyl, aminocarbonyl, $C_{1-5}$ alkylaminocarbonyl, and benzyloxycarbonylamino; or a heteroaryl group selected from the group consisting of quinolinyl, chromenonyl, indolyl, indolinyl, and benzimidazolyl, wherein the heteroaryl group may be optionally substituted with one or more substituents selected from the group consisting of $C_{1-5}$ alkyl (where the $C_{1-5}$ alkyl is optionally substituted with halogen) and acetyl, $R_2$ is hydrogen; a $C_{1-5}$ alkyl group optionally substituted with a substituent selected from the group consisting of hydroxy, $C_{1-5}$ alkoxy, benzylamino (where the benzylamino is optionally substituted with halogen), phenylamino, $C_{1-5}$ alkylamino, $C_{3-6}$ cycloalkylamino, and hydroxy-$C_{1-5}$ alkylamino; a $C_{1-5}$ alkoxycarbonyl group; or a formyl group, $R_3$ is hydrogen; a hydroxyl group; a $C_{1-5}$ alkyl group optionally substituted with a substituent selected from the group consisting of amino, $C_{1-5}$ alkoxycarbonylamino, and mono- or di-$C_{1-5}$ alkylamino; or a group selected from the group consisting of the Formulas A, B, D and E, $R_4$ is hydrogen, $R_5$ is a $C_{1-5}$ alkyl group, $R_6$ is a $C_{1-10}$ alkyl group optionally substituted with a substituent selected from the group consisting of hydroxy, halogen, $C_{1-5}$ alkoxy, amino, $C_{1-5}$ alkoxycarbonylamino, benzyloxycarbonylamino, mono- or di-$C_{1-5}$ alkylamino, $C_{1-5}$ alkoxy-$C_{1-5}$ alkyloxy, phenoxy, benzyloxy, phenyl (where the phenyl is optionally substituted with one or more substituents selected from the group consisting of halogen, amino, $C_{1-5}$ alkoxy, and hydroxy), thiophenyl, pyridinyl, indolyl, piperidinyl, piperazinyl (where the piperazinyl is optionally substituted with benzyl), $C_{3-6}$ cycloalkyl, acetyl, and benzoyl; a $C_{3-6}$ cycloalkyl group; a piperidinyl group optionally substituted with $C_{1-5}$ alkoxycarbonyl; a $C_{1-10}$ alkenyl group optionally substituted with phenyl; a trifluoromethyl group; a trifluoroethyl group; or a phenyl group optionally substituted with halogen, $R_7$ is hydrogen, $R_8$ and $R_9$ are, independently each other, hydrogen; a $C_{1-10}$ alkyl group optionally substituted with a substituent selected from the group consisting of amino, $C_{1-5}$ alkoxycarbonylamino, hydroxy, $C_{1-5}$ alkylthio, $C_{3-19}$ cycloalkyl, phenyl (where the phenyl is optionally substituted with one or more substituents selected from the group consisting of hydroxy, $C_{1-5}$ alkyl, mono- or di-$C_{1-5}$ alkylamino, trifluoromethyl, halogen, $C_{1-5}$ alkoxy, and $C_{1-5}$ alkylcarbonyloxy), thiophenyl, pyrrolyl, furanyl (where the furanyl is optionally substituted with mono- or di-$C_{1-5}$ alkyl), pyridinyl, and benzyloxy; a piperidinyl group optionally substituted with benzyl, benzoyl, $C_{1-5}$ alkyl, or $C_{1-5}$ alkylcarbonyl; an azetidinyl group optionally substituted with $C_{1-5}$ alkoxycarbonyl; a $C_{1-5}$ alkylsulfonyl group; a phenylsulfonyl group (where the phenyl moiety is optionally substituted with halogen); or a $C_{3-10}$ cycloalkyl group.

The present invention also provides a pharmaceutical composition for preventing or treating a dysfunction in gastrointestinal motility comprising a therapeutically effective amount of a compound of Formula 1 or its pharmaceutically acceptable salt; and a pharmaceutically acceptable carrier:

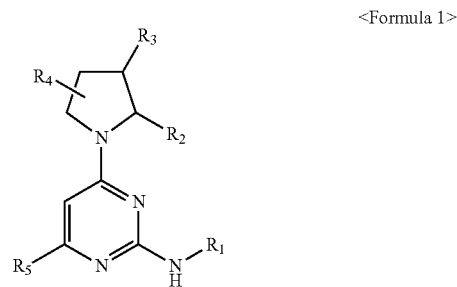

<Formula 1> wherein, $R_1$ is a phenyl group substituted with one or more substituents selected from the group consisting of hydroxy, amino, halogen, cyano, nitro, hydroxycarbonyl, $C_{1-5}$ alkyl (where the $C_{1-5}$ alkyl is optionally substituted with halogen or amino), $C_{2-6}$ alkenyl, $C_{2-6}$ alkynyl, $C_{1-5}$ alkoxy (where the $C_{1-5}$ alkoxy is optionally substituted with halogen), $C_{1-5}$ alkylthio, mono- or di-$C_{1-5}$ alkylamino, $C_{1-5}$ alkylsulfonylamino, $C_{1-5}$ alkylcarbonylamino, $C_{1-5}$ alkoxycarbonyl, aminosulfonyl, aminocarbonyl, $C_{1-5}$ alkylaminocarbonyl, and benzyloxycarbonylamino; or a heteroaryl group selected from the group consisting of pyridinyl, pyrimidinyl, pyrazinyl, imidazolyl, pyrazolyl, triazolyl, oxazolyl, thiazolyl, furanyl, pyrrolyl, thiophenyl, naphthyl, indanyl, quinolinyl, quinolinonyl, chromenonyl, dihydroindolonyl, isoindoline-1,3-dionyl, dihydrobenzimidazolonyl, benzoxazolonyl, benzofuranyl, benzothiophenyl, benzo[d][1,3]dioxolyl, dihydrobenzo[1,4]dioxinyl, indolyl, indolinyl, benzimidazolyl, benzoxazolyl, benzothiazolyl, and indazolyl, wherein the heteroaryl group may be optionally substituted with one or more substituents selected from the group consisting of amino, di-$C_{1-5}$ alkylamino, cyano, nitro, halogen, $C_{1-5}$ alkyl (where the $C_{1-5}$ alkyl is optionally substituted with halogen), $C_{1-5}$ alkoxy (where the $C_{1-5}$ alkoxy is optionally substituted with halogen), acetyl, and $C_{1-5}$ alkylsulfonyl, $R_2$ is hydrogen; a $C_{1-5}$ alkyl group optionally substituted with a substituent selected from the group consisting of hydroxy, $C_{1-5}$ alkoxy, benzylamino (where the benzylamino is optionally substituted with halogen), phenylamino, $C_{1-5}$ alkylamino, $C_{3-6}$ cycloalkylamino, pyrrolidinyl, and hydroxy-$C_{1-5}$ alkylamino; a $C_{1-5}$ alkoxycarbonyl group; a hydroxycarbonyl group; an aminocarbonyl group; a formyl group; or an oxo(=O) group, $R_3$ is hydrogen; a hydroxyl group; a $C_{1-5}$ alkoxy group; a phenoxy group; a benzyloxy group; a $C_{1-5}$ alkyl group optionally substituted with a substituent selected from the group consisting of amino, $C_{1-5}$ alkoxycarbonylamino, and mono- or di-$C_{1-5}$ alkylamino; or a group selected from the group consisting of the following Formulas A to E (where * in Formulas A to E represents the position attached to the compounds of Formula 1),

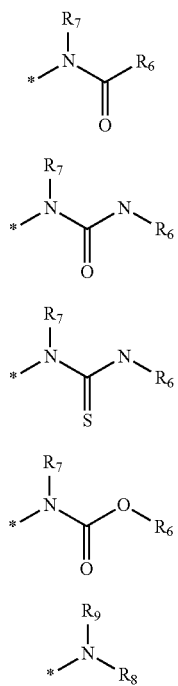

$R_4$ is hydrogen; a hydroxyl group; or a $C_{1-5}$ alkyl group optionally substituted with hydroxy, $R_5$ is a $C_{1-5}$ alkyl group optionally substituted with phenyl; or a $C_{2-6}$ alkenyl group optionally substituted with phenyl or $C_{3-6}$ cycloalkyl, $R_6$ is a $C_{1-10}$ alkyl group optionally substituted with a substituent selected from the group consisting of hydroxy, halogen, $C_{1-5}$ alkoxy, amino, $C_{1-5}$ alkoxycarbonylamino, benzyloxycarbonylamino, mono- or di-$C_{1-5}$ alkylamino, $C_{1-5}$-alkoxy-$C_{1-5}$ alkyloxy, phenoxy, benzyloxy, phenyl (where the phenyl is optionally substituted with one or more substituents selected from the group consisting of halogen, amino, $C_{1-5}$ alkoxy, and hydroxy), thiophenyl, pyridinyl, indolyl, pyrimidinyl, pyrazinyl, imidazolyl, pyrazolyl, triazolyl, oxazolyl, thiazolyl, furanyl, pyrrolyl, piperidinyl, piperazinyl (where the piperazinyl is optionally substituted with benzyl), $C_{3-6}$ cycloalkyl, acetyl, and benzoyl; a $C_{3-6}$ cycloalkyl group; a piperidinyl group optionally substituted with $C_{1-5}$ alkoxycarbonyl; a $C_{1-10}$ alkenyl group optionally substituted with phenyl; a trifluoromethyl group; a trifluoroethyl group; or a phenyl group optionally substituted with halogen, $R_7$ is hydrogen; or a $C_{1-5}$ alkyl group, $R_8$ and $R_9$ are, independently each other, hydrogen; a $C_{1-10}$ alkyl group optionally substituted with a substituent selected from the group consisting of amino, $C_{1-5}$ alkoxycarbonylamino, hydroxy, $C_{1-5}$ alkylthio, $C_{3-19}$ cycloalkyl, phenyl (where the phenyl is optionally substituted with one or more substituents selected from the group consisting of hydroxy, $C_{1-5}$ alkyl, mono- or di-$C_{1-5}$ alkylamino, trifluoromethyl, halogen, $C_{1-5}$ alkoxy, and $C_{1-5}$ alkylcarbonyloxy), thiophenyl, pyrrolyl, furanyl (where the furanyl is optionally substituted with mono- or di-$C_{1-5}$ alkyl), pyridinyl, pyrimidinyl, pyrazinyl, imidazolyl, pyrazolyl, triazolyl, tetrazolyl, oxazolyl, thiazolyl, and benzyloxy; a piperidinyl group optionally substituted with benzyl, benzoyl, $C_{1-5}$ alkyl, or $C_{1-5}$ alkylcarbonyl; an azetidinyl group optionally substituted with $C_{1-5}$ alkoxycarbonyl; a $C_{1-5}$ alkylsulfonyl group; a phenylsulfonyl group (where the phenyl moiety is optionally substituted with halogen); or a $C_{3-19}$ cycloalkyl group.

In the pharmaceutical composition according to the present invention, the dysfunction in gastrointestinal motility includes gastrointestinal diseases, such as gastroesophageal reflux disease (GERD), constipation, irritable bowel syndrome (IBS), dyspepsia, post-operative ileus, delayed gastric emptying, gastroparesis, intestinal pseudo-obstruction, drug-induced delayed transit, or diabetic gastric atony. The constipation includes chronic constipation, chronic idiopathic constipation (CIC), opioid-induced constipation (OIC), etc. And also, the dyspepsia includes functional dyspepsia.

In the pharmaceutical composition according to the present invention, the compound or its salt may be the compound of Formula 1 or its pharmaceutically acceptable salt wherein, $R_1$ is a phenyl group substituted with one or more substituents selected from the group consisting of hydroxy, amino, halogen, cyano, nitro, hydroxycarbonyl, $C_{1-5}$ alkyl (where the $C_{1-5}$ alkyl is optionally substituted with halogen or amino), $C_{1-5}$ alkoxy (where the $C_{1-5}$ alkoxy is optionally substituted with halogen), $C_{1-5}$ alkylthio, aminosulfonyl, aminocarbonyl, $C_{1-5}$ alkylaminocarbonyl, and benzyloxycarbonylamino; or a heteroaryl group selected from the group consisting of quinolinyl, chromenonyl, indolyl, indolinyl, and benzimidazolyl, wherein the heteroaryl group may be optionally substituted with one or more substituents selected from the group consisting of $C_{1-5}$ alkyl (where the $C_{1-5}$ alkyl is optionally substituted with halogen) and acetyl, $R_2$ is hydrogen; a $C_{1-5}$ alkyl group optionally substituted with a substituent selected from the group consisting of hydroxyl and $C_{1-5}$ alkoxy, benzylamino (where the benzylamino is optionally substituted with halogen), phenylamino, $C_{1-5}$ alkylamino, $C_{3-6}$ cycloalkylamino, and hydroxy-$C_{1-5}$ alkylamino; a $C_{1-5}$ alkoxycarbonyl group; or a formyl group, $R_3$ is hydrogen; a hydroxyl group; a $C_{1-5}$ alkyl group optionally substituted with a substituent selected from the group consisting of amino, $C_{1-5}$ alkoxycarbonylamino, and mono- or di-$C_{1-5}$ alkylamino; or a group selected from the group consisting of the Formulas A, B, D and E, $R_4$ is hydrogen, $R_5$ is a $C_{1-5}$ alkyl group, $R_6$ is a $C_{1-10}$ alkyl group optionally substituted with a substituent selected from the group consisting of hydroxy, halogen, $C_{1-5}$ alkoxy, amino, $C_{1-5}$ alkoxycarbonylamino, benzyloxycarbonylamino, mono- or di-$C_{1-5}$ alkylamino, $C_{1-5}$ alkoxy-$C_{1-5}$ alkyloxy, phenoxy, benzyloxy, phenyl (where the phenyl is optionally substituted with one or more substituents selected from the group consisting of halogen, amino, $C_{1-5}$ alkoxy, and hydroxy), thiophenyl, pyridinyl, indolyl, piperidinyl, piperazinyl (where the piperazinyl is optionally substituted with benzyl), $C_{3-6}$ cycloalkyl, acetyl, and benzoyl; a $C_{3-6}$ cycloalkyl group; a piperidinyl group optionally substituted with $C_{1-5}$ alkoxycarbonyl; a $C_{1-10}$ alkenyl group optionally substituted with phenyl; a trifluoromethyl group; a trifluoroethyl group; or a phenyl group optionally substituted with halogen, $R_7$ is hydrogen, $R_8$ and $R_9$ are, independently each other, hydrogen; a $C_{1-10}$ alkyl group optionally substituted with a substituent selected from the group consisting of amino, $C_{1-5}$ alkoxycarbonylamino, hydroxy, $C_{1-5}$ alkylthio, $C_{3-19}$ cycloalkyl, phenyl (where the phenyl is optionally substituted with one or more substituents selected from the group consisting of hydroxy, $C_{1-5}$ alkyl, mono- or di-$C_{1-5}$ alkylamino, trifluoromethyl, halogen, C$_{1-5}$ alkoxy, and C$_{1-5}$ alkylcarbonyloxy), thiophenyl, pyrrolyl, furanyl (where the furanyl is optionally substituted with mono- or di-C$_{1-5}$ alkyl), pyridinyl, and benzyloxy; a piperidinyl group optionally substituted with benzyl, benzoyl, C$_{1-5}$ alkyl, or C$_{1-5}$ alkylcarbonyl; an azetidinyl group optionally substituted with C$_{1-5}$ alkoxycarbonyl; a C$_{1-5}$ alkylsulfonyl group; a phenylsulfonyl group (where the phenyl moiety is optionally substituted with halogen); or a C$_{3-19}$ cycloalkyl group.

The pharmaceutical composition of the present invention may comprise a pharmaceutically acceptable carrier, such as diluents, disintegrants, sweeteners, lubricants, or flavoring agents. The pharmaceutical composition may be formulated to an oral dosage form such as tablets, capsules, powders, granules, suspensions, emulsions, or syrups; or a parenteral dosage form such as injection. The dosage form may be various forms, e.g., dosage forms for single administration or for multiple administrations.

The pharmaceutical composition of the present invention may comprise, for example, a diluent (e.g., lactose, corn starch, etc), a lubricant (e.g., magnesium stearate), an emulsifying agent, a suspending agent, a stabilizer, and/or an isotonic agent. If necessary, the composition further comprises sweeteners and/or flavoring agents.

The composition of the present invention may be administered orally or parenterally, including intravenous, intraperitoneal, subcutaneous, rectal and topical routes of administration. Therefore, the composition of the present invention may be formulated into various forms such as tablets, capsules, aqueous solutions or suspensions. In the case of tablets for oral administration, carriers such as lactose, corn starch, and lubricating agents, e.g. magnesium stearate, are conventionally used. In the case of capsules for oral administration, lactose and/or dried corn starch can be used as a diluent. When an aqueous suspension is required for oral administration, the active ingredient may be combined with emulsifying and/or suspending agents. If desired, certain sweetening and/or flavoring agents may be used. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition of the present invention may be in the form of an aqueous solution containing pharmaceutically acceptable carriers, e.g., saline having a pH level of 7.4. The solutions may be introduced into a patient's intramuscular blood-stream by local bolus injection.

The compound of Formula 1 or its pharmaceutically acceptable salt may be administered in a therapeutically effective amount ranging from about 0.001 mg/kg to about 10 mg/kg per day to a subject patient. Of course, the dosage may be changed according to the patient's age, weight, susceptibility, symptom, or activity of the compound.

The present invention also provides a method for treating a dysfunction in gastrointestinal motility, such as gastroesophageal reflux disease (GERD), constipation, irritable bowel syndrome (IBS), dyspepsia, post-operative ileus, delayed gastric emptying, gastroparesis, intestinal pseudo-obstruction, drug-induced delayed transit, or diabetic gastric atony, in a patient, which comprises administering a therapeutically effective amount of the compound of Formula 1 or its pharmaceutically acceptable salt to the patient in need thereof. The constipation includes chronic constipation, chronic idiopathic constipation (CIC), opioid-induced constipation (OIC), etc. And also, the dyspepsia includes functional dyspepsia.

The present invention also provides a compound of Formula 1 or its pharmaceutically acceptable salt:

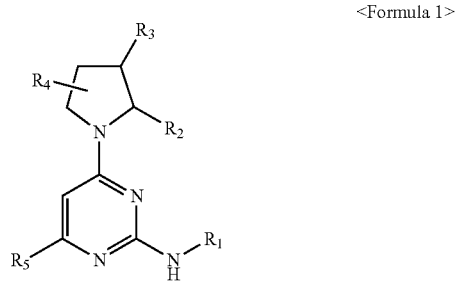

<Formula 1> wherein,

R$_1$ is a phenyl group substituted with one or more substituents selected from the group consisting of hydroxy, amino, halogen, cyano, nitro, hydroxycarbonyl, C$_{1-5}$ alkyl (where the C$_{1-5}$ alkyl is optionally substituted with halogen or amino), C$_{2-6}$ alkenyl, C$_{2-6}$ alkynyl, C$_{1-5}$ alkoxy (where the C$_{1-5}$ alkoxy is optionally substituted with halogen), C$_{1-5}$ alkylthio, mono- or di-C$_{1-5}$ alkylamino, C$_{1-5}$ alkylsulfonylamino, C$_{1-5}$ alkylcarbonylamino, C$_{1-5}$ alkoxycarbonyl, aminosulfonyl, aminocarbonyl, C$_{1-5}$ alkylaminocarbonyl, and benzyloxycarbonylamino; or a heteroaryl group selected from the group consisting of pyridinyl, pyrimidinyl, pyrazinyl, imidazolyl, pyrazolyl, triazolyl, oxazolyl, thiazolyl, furanyl, pyrrolyl, thiophenyl, naphthyl, indanyl, quinolinyl, quinolinonyl, chromenonyl, dihydroindolonyl, isoindoline-1,3-dionyl, dihydrobenzimidazolonyl, benzoxazolonyl, benzofuranyl, benzothiophenyl, benzo[d][1,3]dioxolyl, dihydrobenzo[1,4]dioxinyl, indolyl, indolinyl, benzimidazolyl, benzoxazolyl, benzothiazolyl, and indazolyl, wherein the heteroaryl group may be optionally substituted with one or more substituents selected from the group consisting of amino, di-C$_{1-5}$ alkylamino, cyano, nitro, halogen, C$_{1-5}$ alkyl (where the C$_{1-5}$ alkyl is optionally substituted with halogen), C$_{1-5}$ alkoxy (where the C$_{1-5}$ alkoxy is optionally substituted with halogen), acetyl, and C$_{1-5}$ alkylsulfonyl, R$_2$ is hydrogen; a C$_{1-5}$ alkyl group optionally substituted with a substituent selected from the group consisting of hydroxy, C$_{1-5}$ alkoxy, benzylamino (where the benzylamino is optionally substituted with halogen), phenylamino, C$_{1-5}$ alkylamino, C$_{3-6}$ cycloalkylamino, pyrrolidinyl, and hydroxy-C$_{1-5}$ alkylamino; a C$_{1-5}$ alkoxycarbonyl group; a hydroxycarbonyl group; an aminocarbonyl group; a formyl group; or an oxo(=O) group, R$_3$ is hydrogen; a hydroxyl group; a C$_{1-5}$ alkoxy group; a phenoxy group; a benzyloxy group; a C$_{1-5}$ alkyl group optionally substituted with a substituent selected from the group consisting of amino, C$_{1-5}$ alkoxycarbonylamino, and mono- or di-C$_{1-5}$ alkylamino; or a group selected from the group consisting of the following Formulas A to E (where * in Formulas A to E represents the position attached to the compounds of Formula 1),

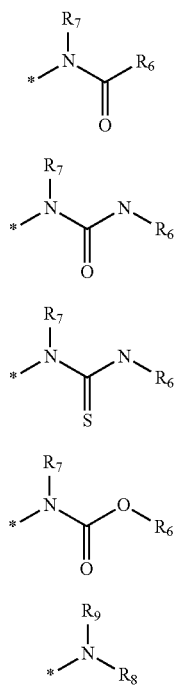

R<sub>4</sub> is hydrogen; a hydroxyl group; or a $C_{1-5}$ alkyl group optionally substituted with hydroxy, R<sub>5</sub> is a $C_{1-5}$ alkyl group optionally substituted with phenyl; or a $C_{2-6}$ alkenyl group optionally substituted with phenyl or $C_{3-6}$ cycloalkyl, R<sub>6</sub> is a $C_{1-10}$ alkyl group optionally substituted with a substituent selected from the group consisting of hydroxy, halogen, $C_{1-5}$ alkoxy, amino, $C_{1-5}$ alkoxycarbonylamino, benzyloxycarbonylamino, mono- or di-$C_{1-5}$ alkylamino, $C_{1-5}$ alkoxy-$C_{1-5}$ alkyloxy, phenoxy, benzyloxy, phenyl (where the phenyl is optionally substituted with one or more substituents selected from the group consisting of halogen, amino, $C_{1-5}$ alkoxy, and hydroxy), thiophenyl, pyridinyl, indolyl, pyrimidinyl, pyrazinyl, imidazolyl, pyrazolyl, triazolyl, oxazolyl, thiazolyl, furanyl, pyrrolyl, piperidinyl, piperazinyl (where the piperazinyl is optionally substituted with benzyl), $C_{3-6}$ cycloalkyl, acetyl, and benzoyl; a $C_{3-6}$ cycloalkyl group; a piperidinyl group optionally substituted with $C_{1-5}$ alkoxycarbonyl; a $C_{1-10}$ alkenyl group optionally substituted with phenyl; a trifluoromethyl group; a trifluoroethyl group; or a phenyl group optionally substituted with halogen, R<sub>7</sub> is hydrogen; or a $C_{1-5}$ alkyl group, R<sub>8</sub> and R<sub>9</sub> are, independently each other, hydrogen; a $C_{1-10}$ alkyl group optionally substituted with a substituent selected from the group consisting of amino, $C_{1-5}$ alkoxycarbonylamino, hydroxy, $C_{1-5}$ alkylthio, $C_{3-19}$ cycloalkyl, phenyl (where the phenyl is optionally substituted with one or more substituents selected from the group consisting of hydroxy, $C_{1-5}$ alkyl, mono- or di-$C_{1-5}$ alkylamino, trifluoromethyl, halogen, $C_{1-5}$ alkoxy, and $C_{1-5}$ alkylcarbonyloxy), thiophenyl, pyrrolyl, furanyl (where the furanyl is optionally substituted with mono- or di-$C_{1-5}$ alkyl), pyridinyl, pyrimidinyl, pyrazinyl, imidazolyl, pyrazolyl, triazolyl, tetrazolyl, oxazolyl, thiazolyl, and benzyloxy; a piperidinyl group optionally substituted with benzyl, benzoyl, $C_{1-5}$ alkyl, or $C_{1-5}$ alkylcarbonyl; an azetidinyl group optionally substituted with $C_{1-5}$ alkoxycarbonyl; a $C_{1-5}$ alkylsulfonyl group; a phenylsulfonyl group (where the phenyl moiety is optionally substituted with halogen); or a $C_{3-19}$ cycloalkyl group.

Preferably, the compound or its salt may be the compound of Formula 1 or its pharmaceutically acceptable salt wherein, R<sub>1</sub> is a phenyl group substituted with one or more substituents selected from the group consisting of hydroxy, amino, halogen, cyano, nitro, hydroxycarbonyl, $C_{1-5}$ alkyl (where the $C_{1-5}$ alkyl is optionally substituted with halogen or amino), $C_{1-5}$ alkoxy (where the $C_{1-5}$ alkoxy is optionally substituted with halogen), $C_{1-5}$ alkylthio, aminosulfonyl, aminocarbonyl, $C_{1-5}$ alkylaminocarbonyl, and benzyloxycarbonylamino; or a heteroaryl group selected from the group consisting of quinolinyl, chromenonyl, indolyl, indolinyl, and benzimidazolyl, wherein the heteroaryl group may be optionally substituted with one or more substituents selected from the group consisting of $C_{1-5}$ alkyl (where the $C_{1-5}$ alkyl is optionally substituted with halogen) and acetyl, R<sub>2</sub> is hydrogen; a $C_{1-5}$ alkyl group optionally substituted with a substituent selected from the group consisting of hydroxyl and $C_{1-5}$ alkoxy, benzylamino (where the benzylamino is optionally substituted with halogen), phenylamino, $C_{1-5}$ alkylamino, $C_{3-6}$ cycloalkylamino, and hydroxy-$C_{1-5}$ alkylamino; a $C_{1-5}$ alkoxycarbonyl group; or a formyl group, R<sub>3</sub> is hydrogen; a hydroxyl group; a $C_{1-5}$ alkyl group optionally substituted with a substituent selected from the group consisting of amino, $C_{1-5}$ alkoxycarbonylamino, and mono- or di-$C_{1-5}$ alkylamino; or a group selected from the group consisting of the Formulas A, B, D and E, R<sub>4</sub> is hydrogen, R<sub>5</sub> is a $C_{1-5}$ alkyl group, R<sub>6</sub> is a $C_{1-10}$ alkyl group optionally substituted with a substituent selected from the group consisting of hydroxy, halogen, $C_{1-5}$ alkoxy, amino, $C_{1-5}$ alkoxycarbonylamino, benzyloxycarbonylamino, mono- or di-$C_{1-5}$ alkylamino, $C_{1-5}$ alkoxy-$C_{1-5}$ alkyloxy, phenoxy, benzyloxy, phenyl (where the phenyl is optionally substituted with one or more substituents selected from the group consisting of halogen, amino, $C_{1-5}$ alkoxy, and hydroxy), thiophenyl, pyridinyl, indolyl, piperidinyl, piperazinyl (where the piperazinyl is optionally substituted with benzyl), $C_{3-6}$ cycloalkyl, acetyl, and benzoyl; a $C_m$ cycloalkyl group; a piperidinyl group optionally substituted with $C_{1-5}$ alkoxycarbonyl; a $C_{1-10}$ alkenyl group optionally substituted with phenyl; a trifluoromethyl group; a trifluoroethyl group; or a phenyl group optionally substituted with halogen, R<sub>7</sub> is hydrogen, R<sub>8</sub> and R<sub>9</sub> are, independently each other, hydrogen; a $C_{1-10}$ alkyl group optionally substituted with a substituent selected from the group consisting of amino, $C_{1-5}$ alkoxycarbonylamino, hydroxy, $C_{1-5}$ alkylthio, $C_{3-19}$ cycloalkyl, phenyl (where the phenyl is optionally substituted with one or more substituents selected from the group consisting of hydroxy, $C_{1-5}$ alkyl, mono- or di-$C_{1-5}$ alkylamino, trifluoromethyl, halogen, $C_{1-5}$ alkoxy, and $C_{1-5}$ alkylcarbonyloxy), thiophenyl, pyrrolyl, furanyl (where the furanyl is optionally substituted with mono- or di-$C_{1-5}$ alkyl), pyridinyl, and benzyloxy; a piperidinyl group optionally substituted with benzyl, benzoyl, $C_{1-5}$ alkyl, or $C_{1-5}$ alkylcarbonyl; an azetidinyl group optionally substituted with $C_{1-5}$ alkoxycarbonyl; a $C_{1-5}$ alkylsulfonyl group; a phenylsulfonyl group (where the phenyl moiety is optionally substituted with halogen); or a $C_{3-10}$ cycloalkyl group.

The compound of Formula 1 or its pharmaceutically acceptable salt may have substituents containing asymmetric carbon and therefore be in the form of racemic mixture (RS) or in forms of optical isomers, such as (R) or (S) isomer. The compound of Formula 1 or its pharmaceutically acceptable salt comprises both racemic mixture (RS) and optical isomers such as (R) or (S) isomer. And also, the compound of Formula 1 or its pharmaceutically acceptable salt may be in the form of cis- or trans-geometrical isomer, according to substituents having e.g., the double bond therein. The compound of Formula 1 or its pharmaceutically acceptable salt comprises both cis- and trans-geometrical isomers. And also, the compound of Formula 1 or its pharmaceutically acceptable salt may be in the form of one or more diastereomic isomer(s) or a mixture thereof. The compound of Formula 1 or its pharmaceutically acceptable salt comprises both diastereomic isomer(s) and a mixture thereof.

The compound of Formula 1 of the present invention may be in a pharmaceutically acceptable salt form. The salt may be an acid addition salt form, which includes e.g., salts derived from an inorganic acid such as hydrochloric acid, hydrobromic acid, sulfuric acid, sulfonic acid, sulfamic acid, phosphoric acid, or nitric acid; and salts derived from an organic acid such as acetic acid, propionic acid, succinic acid, glycolic acid, stearic acid, citric acid, maleic acid, malonic acid, methanesulfonic acid, ethanesulfonic acid, tartaric acid, hydroxymaleic acid, phenylacetic acid, glutamic acid, benzoic acid, salicylic acid, 2-acetoxybenzoic acid, fumaric acid, toluenesulfonic acid, benzenesulfonic acid, oxalic acid or trifluoroacetic acid. The salt may be prepared by reacting a compound of Formula 1 in the form of free base with a salt-forming inorganic or organic acid in stoichiometric amount or excessive amount, in a suitable solvent or a mixture of two or more solvents.

In the use, the pharmaceutical composition, the treatment method, and the compound according to the present invention, more preferable compounds include a compound (or its pharmaceutically acceptable salt) selected from the group consisting of:

N-(4-fluorophenyl)-4-propyl-6-(pyrrolidin-1-yl)pyrimidin-2-amine;
(S)-{1-[2-(4-fluorophenylamino)-6-propylpyrimidin-4-yl]pyrrolidin-2-yl}methanol;
1-[2-(4-fluorophenylamino)-6-propylpyrimidin-4-yl]pyrrolidin-3-ol;
(R)-{1-[2-(4-fluorophenylamino)-6-propylpyrimidin-4-yl]pyrrolidin-2-yl}methanol;
{1-[2-(4-fluorophenylamino)-6-propylpyrimidin-4-yl]pyrrolidin-2-yl}methanol;
N-(4-fluorophenyl)-4-(2-methylpyrrolidin-1-yl)-6-propylpyrimidin-2-amine;
(S)—N-(4-fluorophenyl)-4-[2-(methoxymethyl)pyrrolidin-1-yl]-6-propylpyrimidin-2-amine;
(R)—N-(4-fluorophenyl)-4-[2-(methoxymethyl)pyrrolidin-1-yl]-6-propylpyrimidin-2-amine;
(S)-1-[2-(4-fluorophenylamino)-6-propylpyrimidin-4-yl]pyrrolidin-2-carboxamide;
N-{1-[2-(4-fluorophenylamino)-6-propylpyrimidin-4-yl]pyrrolidin-3-yl}acetamide;
(R)—N-{1-[2-(4-fluorophenylamino)-6-propylpyrimidin-4-yl]pyrrolidin-3-yl}acetamide;
2,2,2-trifluoro-N-{1-[2-(4-fluorophenylamino)-6-propylpyrimidin-4-yl]pyrrolidin-3-yl}acetamide;
4-[3-(ethylamino)pyrrolidin-1-yl]-N-(4-fluorophenyl)-6-propylpyrimidin-2-amine;
4-[3-(dimethylamino)pyrrolidin-1-yl]-N-(4-fluorophenyl)-6-propylpyrimidin-2-amine;
(S)—N-(4-fluorophenyl)-4-propyl-6-[2-(pyrrolidin-1-ylmethyl)pyrrolidin-1-yl]pyrimidin-2-amine;
(S)—N-(4-fluorophenyl)-4-{2-[(phenylamino)methyl]pyrrolidin-1-yl}-6-propylpyrimidin-2-amine;
(S)—N-{1-[2-(4-fluorophenylamino)-6-propylpyrimidin-4-yl]pyrrolidin-3-yl}acetamide;
(S)-4-[3-(ethylamino)pyrrolidin-1-yl]-N-(4-fluorophenyl)-6-propylpyrimidin-2-amine;
(S)-tert-butyl 1-[2-(4-fluorophenylamino)-6-propylpyrimidin-4-yl]pyrrolidin-3-ylcarbamate;
4-(3-aminopyrrolidin-1-yl)-N-(4-fluorophenyl)-6-propylpyrimidin-2-amine;
4-[3-(diethylamino)pyrrolidin-1-yl]-N-(4-fluorophenyl)-6-propylpyrimidin-2-amine;
(S)—N-(4-fluorophenyl)-4-[3-(methylamino)pyrrolidin-1-yl]-6-propylpyrimidin-2-amine;
N-{1-[2-(4-fluorophenylamino)-6-propylpyrimidin-4-yl]pyrrolidin-3-yl}-N-methylacetamide;
(S)-1-[2-(4-fluorophenylamino)-6-propylpyrimidin-4-yl]pyrrolidin-3-ol;
(S)—N-{4-[2-(methoxymethyl)pyrrolidin-1-yl]-6-propylpyrimidin-2-yl}-1H-indol-6-amine;
(S)—N-{4-[2-(methoxymethyl)pyrrolidin-1-yl]-6-propylpyrimidin-2-yl}-1H-indol-5-amine;
(S)-4-[2-(methoxymethyl)pyrrolidin-1-yl]-N-(4-methoxyphenyl)-6-propylpyrimidin-2-amine;
(S)-4-[2-(methoxymethyl)pyrrolidin-1-yl]-N-(3-methoxyphenyl)-6-propylpyrimidin-2-amine;
(S)—N-(3-chlorophenyl)-4-[2-(methoxymethyl)pyrrolidin-1-yl]-6-propylpyrimidin-2-amine;
(S)—N-(4-fluoro-3-nitrophenyl)-4-[2-(methoxymethyl)pyrrolidin-1-yl]-6-propylpyrimidin-2-amine;
(S)-4-[2-(methoxymethyl)pyrrolidin-1-yl]-N-(3-nitrophenyl)-6-propyl pyrimidin-2-amine;
(S)—N-(4-chloro-3-nitrophenyl)-4-[2-(methoxymethyl)pyrrolidin-1-yl]-6-propylpyrimidin-2-amine;
(S)-3-{4-[2-(methoxymethyl)pyrrolidin-1-yl]-6-propyl pyrimidin-2-ylamino}benzonitrile;
(S)-4-[2-(methoxymethyl)pyrrolidin-1-yl]-N-[3-(methylthio)phenyl]-6-propylpyrimidin-2-amine;
(S)-4-[2-(methoxymethyl)pyrrolidin-1-yl]-6-propyl-N-[3-(trifluoromethyl)phenyl]pyrimidin-2-amine;
(S)-7-{4-[2-(methoxymethyl)pyrrolidin-1-yl]-6-propylpyrimidin-2-ylamino}-4-methyl-2H-chromen-2-one;
(S)—N-(5-chloro-2-methyl phenyl)-4-[2-(methoxymethyl)pyrrolidin-1-yl]-6-propylpyrimidin-2-amine;
(S)—N-(3-chloro-4-methyl phenyl)-4-[2-(methoxymethyl)pyrrolidin-1-yl]-6-propylpyrimidin-2-amine;
(S)-4-[2-(methoxymethyl)pyrrolidin-1-yl]-N-(4-methyl-3-nitrophenyl)-6-propylpyrimidin-2-amine;
(S)—N-[4-fluoro-3-(trifluoromethyl)phenyl]-4-[2-(methoxymethyl)pyrrolidin-1-yl]-6-propylpyrimidin-2-amine;
(S)—$N^1$-{4-[2-(methoxymethyl)pyrrolidin-1-yl]-6-propylpyrimidin-2-yl}-3-(trifluoromethyl)benzene-1,4-diamine;
(S)-2-fluoro-5-{4-[2-(methoxymethyl)pyrrolidin-1-yl]-6-propylpyrimidin-2-ylamino}benzonitrile;
(S)-5-{4-[2-(methoxymethyl)pyrrolidin-1-yl]-6-propylpyrimidin-2-ylamino}-2-methylbenzonitrile;
(S)-2-amino-5-{4-[2-(methoxymethyl)pyrrolidin-1-yl]-6-propylpyrimidin-2-ylamino}benzonitrile;
(S)—$N^1$-{4-[2-(methoxymethyl)pyrrolidin-1-yl]-6-propylpyrimidin-2-yl}-3-nitrobenzene-1,4-diamine;
(S)-4-(3-aminopyrrolidin-1-yl)-N-(4-fluorophenyl)-6-propylpyrimidin-2-amine;
(S)-tert-butyl 1-[2-(3-cyanophenylamino)-6-propylpyrimidin-4-yl]pyrrolidin-3-ylcarbamate;

3-{4-[3-(diethylamino)pyrrolidin-1-yl]-6-propylpyrimidin-2-ylamino}benzonitrile;
(S)-3-{4-[3-(methylamino)pyrrolidin-1-yl]-6-propylpyrimidin-2-ylamino}benzonitrile;
N-{1-[2-(3-cyanophenylamino)-6-propylpyrimidin-4-yl]pyrrolidin-3-yl}-N-methylacetamide;
(S)-3-[4-(3-hydroxypyrrolidin-1-yl)-6-propylpyrimidin-2-ylamino]benzonitrile;
(R)-3-[4-(2-methylpyrrolidin-1-yl)-6-propylpyrimidin-2-ylamino]benzonitrile;
(S)—N-{1-[2-(3-cyanophenylamino)-6-propylpyrimidin-4-yl]pyrrolidin-3-yl}acetamide;
(S)-3-{4-[3-(ethylamino)pyrrolidin-1-yl]-6-propylpyrimidin-2-ylamino}benzonitrile;
(R)-tert-butyl {1-[2-(3-cyanophenylamino)-6-propylpyrimidin-4-yl]pyrrolidin-3-yl}methylcarbamate;
(R)-3-[4-(3-hydroxypyrrolidin-1-yl)-6-propylpyrimidin-2-ylamino]benzonitrile;
(S)-3-[4-(3-methoxypyrrolidin-1-yl)-6-propylpyrimidin-2-ylamino]benzonitrile;
3-{4-[3-(methylamino)pyrrolidin-1-yl]-6-propylpyrimidin-2-ylamino}benzonitrile;
(S)-3-[4-(3-aminopyrrolidin-1-yl)-6-propylpyrimidin-2-ylamino]benzonitrile;
(S)—N-{1-[2-(3-cyanophenylamino)-6-propylpyrimidin-4-yl]pyrrolidin-3-yl}butyramide;
(S)—N-{1-[2-(3-cyanophenylamino)-6-propylpyrimidin-4-yl]pyrrolidin-3-yl}cyclopentanecarboxamide;
(S)—N-{1-[2-(3-cyanophenylamino)-6-propylpyrimidin-4-yl]pyrrolidin-3-yl}-3-(piperidin-1-yl)propanamide;
(S)—N-{1-[2-(3-cyanophenylamino)-6-propylpyrimidin-4-yl]pyrrolidin-3-yl}benzamide;
(S)—N-{1-[2-(3-cyanophenylamino)-6-propylpyrimidin-4-yl]pyrrolidin-3-yl}-4-fluorobenzamide;
(S)—N-{1-[2-(3-cyanophenylamino)-6-propylpyrimidin-4-yl]pyrrolidin-3-yl}-2-phenylacetamide;
(S)—N-{1-[2-(3-cyanophenylamino)-6-propylpyrimidin-4-yl]pyrrolidin-3-yl}-2-(4-fluorophenyl)acetamide;
(S)—N-{1-[2-(3-cyanophenylamino)-6-propylpyrimidin-4-yl]pyrrolidin-3-yl}-3-phenoxypropanamide;
(S)—N-{1-[2-(3-cyanophenylamino)-6-propylpyrimidin-4-yl]pyrrolidin-3-yl}-3-isobutoxypropanamide;
(S)-2-(4-benzylpiperazin-1-yl)-N-{1-[2-(3-cyanophenylamino)-6-propylpyrimidin-4-yl]pyrrolidin-3-yl}acetamide;
(S)—N-{1-[2-(3-cyanophenylamino)-6-propylpyrimidin-4-yl]pyrrolidin-3-yl}-2-(piperidin-1-yl)acetamide;
(S)—N-{1-[2-(3-cyanophenylamino)-6-propylpyrimidin-4-yl]pyrrolidin-3-yl}-4-oxo-4-phenylbutanamide;
(S)-2-(4-aminophenyl)-N-{1-[2-(3-cyanophenylamino)-6-propylpyrimidin-4-yl]pyrrolidin-3-yl}acetamide;
(S)—N-{1-[2-(3-cyanophenylamino)-6-propylpyrimidin-4-yl]pyrrolidin-3-yl}-2-cyclopentylacetamide;
(S)—N-{1-[2-(3-cyanophenylamino)-6-propylpyrimidin-4-yl]pyrrolidin-3-yl}-2-methoxyacetamide;
(S)—N-{1-[2-(3-cyanophenylamino)-6-propylpyrimidin-4-yl]pyrrolidin-3-yl}-2-(pyridin-2-yl)acetamide;
(S)—N-{1-[2-(3-cyanophenylamino)-6-propylpyrimidin-4-yl]pyrrolidin-3-yl}-2-(pyridin-3-yl)acetamide;
(S)—N-{1-[2-(3-cyanophenylamino)-6-propylpyrimidin-4-yl]pyrrolidin-3-yl}-2-(pyridin-4-yl)acetamide;
(S,E)-N-{1-[2-(3-cyanophenylamino)-6-propylpyrimidin-4-yl]pyrrolidin-3-yl}-4-phenylbut-3-enamide;
(S)—N-{1-[2-(3-cyanophenylamino)-6-propylpyrimidin-4-yl]pyrrolidin-3-yl}-2-(thiophen-2-yl)acetamide;
(S)—N-{1-[2-(3-cyanophenylamino)-6-propylpyrimidin-4-yl]pyrrolidin-3-yl}isobutyramide;
(S)—N-{1-[2-(3-cyanophenylamino)-6-propylpyrimidin-4-yl]pyrrolidin-3-yl}-3,3,3-trifluoropropanamide;
3-[4-(2-oxopyrrolidin-1-yl)-6-propylpyrimidin-2-ylamino]benzonitrile;
(S)-3-{4-[3-(hexylamino)pyrrolidin-1-yl]-6-propylpyrimidin-2-ylamino}benzonitrile;
(S)-3-{4-propyl-6-[3-(propylamino)pyrrolidin-1-yl]pyrimidin-2-ylamino}benzonitrile;
(S)-3-{4-[3-(cyclohexylmethylamino)pyrrolidin-1-yl]-6-propylpyrimidin-2-ylamino}benzonitrile;
(S)-3-{4-[3-(benzylamino)pyrrolidin-1-yl]-6-propylpyrimidin-2-ylamino}benzonitrile;
(S)-3-{4-[3-(phenethylamino)pyrrolidin-1-yl]-6-propylpyrimidin-2-ylamino}benzonitrile;
(S)-3-{4-[3-(3-phenylpropylamino)pyrrolidin-1-yl]-6-propylpyrimidin-2-ylamino}benzonitrile;
(S)-3-{4-[3-(3-fluorobenzylamino)pyrrolidin-1-yl]-6-propylpyrimidin-2-ylamino}benzonitrile;
(S)-3-{4-[3-(4-hydroxybenzylamino)pyrrolidin-1-yl]-6-propylpyrimidin-2-ylamino}benzonitrile;
(S)-3-{4-[3-(4-ethylbenzylamino)pyrrolidin-1-yl]-6-propylpyrimidin-2-ylamino}benzonitrile;
(S)-3-{4-[3-(isopentylamino)pyrrolidin-1-yl]-6-propylpyrimidin-2-ylamino}benzonitrile;
(S)-3-{4-[3-(pentylamino)pyrrolidin-1-yl]-6-propylpyrimidin-2-ylamino}benzonitrile;
3-{4-[(3S)-3-(2-methylbutylamino)pyrrolidin-1-yl]-6-propylpyrimidin-2-ylamino}benzonitrile;
(S)-3-{4-[3-(isobutylamino)pyrrolidin-1-yl]-6-propylpyrimidin-2-ylamino}benzonitrile;
(S)-3-{4-[3-(4-methoxybenzylamino)pyrrolidin-1-yl]-6-propylpyrimidin-2-ylamino}benzonitrile;
(S)-3-{4-[3-(4-fluorobenzylamino)pyrrolidin-1-yl]-6-propylpyrimidin-2-ylamino}benzonitrile;
(S)-3-{4-[3-(cyclopropylmethylamino)pyrrolidin-1-yl]-6-propylpyrimidin-2-ylamino}benzonitrile;
(S)-3-(4-{3-[bis(cyclopropylmethyl)amine]pyrrolidin-1-yl}-6-propylpyrimidin-2-ylamino)benzonitrile;
(S)-3-{4-propyl-6-[3-(pyridin-2-ylmethylamino)pyrrolidin-1-yl]pyrimidin-2-ylamino}benzonitrile;
(S)-3-{4-propyl-6-[3-(pyridin-3-ylmethylamino)pyrrolidin-1-yl]pyrimidin-2-ylamino}benzonitrile;
(S)-3-{4-propyl-6-[3-(pyridin-4-ylmethylamino)pyrrolidin-1-yl]pyrimidin-2-ylamino}benzonitrile;
(S)-3-{4-[3-(2-ethylbutylamino)pyrrolidin-1-yl]-6-propylpyrimidin-2-ylamino}benzonitrile;
(S)-3-{4-[3-(neopentylamino)pyrrolidin-1-yl]-6-propylpyrimidin-2-ylamino}benzonitrile;
(S)-3-{4-[3-(2-fluorobenzylamino)pyrrolidin-1-yl]-6-propylpyrimidin-2-ylamino}benzonitrile;
(S)-3-(4-propyl-6-{3-[3-(trifluoromethyl)benzylamino]pyrrolidin-1-yl}pyrimidin-2-ylamino)benzonitrile;
(S)-3-(4-propyl-6-{3-[4-(trifluoromethyl)benzylamino]pyrrolidin-1-yl}pyrimidin-2-ylamino)benzonitrile;
(S)-4-({1-[2-(3-cyanophenylamino)-6-propylpyrimidin-4-yl]pyrrolidin-3-ylamino}methyl)phenylacetate;
(S)-3-(4-{3-[4-(dimethylamino)benzylamino]pyrrolidin-1-yl}-6-propylpyrimidin-2-ylamino)benzonitrile;
(S)-3-(4-{3-[(1H-pyrrol-2-yl)methylamino]pyrrolidin-1-yl}-6-propylpyrimidin-2-ylamino)benzonitrile;
(S)-3-{4-propyl-6-[3-(thiophen-2-ylmethylamino)pyrrolidin-1-yl]pyrimidin-2-ylamino}benzonitrile;
(S)-3-{4-propyl-6-[3-(thiophen-3-ylmethylamino)pyrrolidin-1-yl]pyrimidin-2-ylamino}benzonitrile;
(S)-3-{4-[3-(di butylamino)pyrrolidin-1-yl]-6-propylpyrimidin-2-ylamino}benzonitrile;

(S)-3-(4-{3-bis[3-(methylthio)propyl]aminopyrrolidin-1-yl}-6-propylpyrimidin-2-ylamino)benzonitrile;
(S)-3-{4-[3-(butylamino)pyrrolidin-1-yl]-6-propylpyrimidin-2-ylamino}benzonitrile;
(S)-3-(4-{3-[3-(methylthio)propylamino]pyrrolidin-1-yl}-6-propyl pyrimidin-2-ylamino)benzonitrile;
(S)—N-{4-[3-(methylamino)pyrrolidin-1-yl]-6-propylpyrimidin-2-yl}-1H-indol-6-amine;
(S)—N¹-{4-[3-(methylamino)pyrrolidin-1-yl]-6-propylpyrimidin-2-yl}-3-(trifluoromethyl)benzene-1,4-diamine;
(S)—N-{1-[2-(3-cyanophenylamino)-6-propylpyrimidin-4-yl]pyrrolidin-3-yl}isopropane-2-sulfonamide;
(S)—N-{1-[2-(3-cyanophenylamino)-6-propylpyrimidin-4-yl]pyrrolidin-3-yl}methanesulfonamide;
(S)—N-{1-[2-(3-cyanophenylamino)-6-propylpyrimidin-4-yl]pyrrolidin-3-yl}-4-fluorobenzenesulfonamide;
3-{4-[(3S)-3-(sec-butylamino)pyrrolidin-1-yl]-6-propyl pyrimidin-2-ylamino}benzonitrile;
(S)-3-{4-[3-(pentan-3-ylamino)pyrrolidin-1-yl]-6-propylpyrimidin-2-ylamino}benzonitrile;
(S)-3-{4-[3-(2,6-dimethylheptan-4-ylamino)pyrrolidin-1-yl]-6-propylpyrimidin-2-ylamino}benzonitrile;
(S)-3-{4-[3-(4,4-dimethylpentan-2-ylamino)pyrrolidin-1-yl]-6-propylpyrimidin-2-ylamino}benzonitrile;
(S)-3-{4-[3-(3-hydroxy-3-methylbutan-2-ylamino)pyrrolidin-1-yl]-6-propylpyrimidin-2-ylamino}benzonitrile;
(S)-3-{4-[3-(heptan-4-ylamino)pyrrolidin-1-yl]-6-propylpyrimidin-2-ylamino}benzonitrile;
(S)-3-{4-[3-(n-hexan-2-ylamino)pyrrolidin-1-yl]-6-propylpyrimidin-2-ylamino}benzonitrile;
(S)-3-{4-[3-(5-methylhexan-2-ylamino)pyrrolidin-1-yl]-6-propylpyrimidin-2-ylamino}benzonitrile;
(S)-3-{4-[3-(cyclohexylamino)pyrrolidin-1-yl]-6-propylpyrimidin-2-ylamino}benzonitrile;
(S)-tert-butyl 2-{1-[2-(3-cyanophenylamino)-6-propylpyrimidin-4-yl]pyrrolidin-3-ylamino}ethylcarbamate;
(S)-3-{4-[3-(1-benzylpiperidin-4-ylamino)pyrrolidin-1-yl]-6-propylpyrimidin-2-ylamino}benzonitrile;
(S)-3-{4-[3-(isopropylamino)pyrrolidin-1-yl]-6-propylpyrimidin-2-ylamino}benzonitrile;
(S)-3-{4-[3-(1-benzoylpiperidin-4-ylamino)pyrrolidin-1-yl]-6-propylpyrimidin-2-ylamino}benzonitrile;
(S)-3-{4-[3-(1-acetylpiperidin-4-ylamino)pyrrolidin-1-yl]-6-propylpyrimidin-2-ylamino}benzonitrile;
(S)-3-{4-[3-(cyclooctylamino)pyrrolidin-1-yl]-6-propylpyrimidin-2-ylamino}benzonitrile;
(S)-3-{4-[3-(cyclobutylamino)pyrrolidin-1-yl]-6-propylpyrimidin-2-ylamino}benzonitrile;
(S)-3-{4-[3-(cyclopentylamino)pyrrolidin-1-yl]-6-propylpyrimidin-2-ylamino}benzonitrile;
(S)-tert-butyl 3-{1-[2-(3-cyanophenylamino)-6-propylpyrimidin-4-yl]pyrrolidin-3-ylamino}azetidine-1-carboxylate;
(S)-3-(4-{3-[2-(benzyloxy)ethylamino]pyrrolidin-1-yl}-6-propylpyrimidin-2-ylamino)benzonitrile;
(S)—N-{1-[2-(3-cyanophenylamino)-6-propylpyrimidin-4-yl]pyrrolidin-3-yl}propionamide;
(S)—N-{1-[2-(3-cyanophenylamino)-6-propylpyrimidin-4-yl]pyrrolidin-3-yl}pivalamide;
(S)—N-{1-[2-(3-cyanophenylamino)-6-propylpyrimidin-4-yl]pyrrolidin-3-yl}-2,2-dimethylbutanamide;
(S,E)-N-{1-[2-(3-cyanophenylamino)-6-propylpyrimidin-4-yl]pyrrolidin-3-yl}-2-methylbut-2-enamide;
(S)—N-{1-[2-(3-cyanophenylamino)-6-propylpyrimidin-4-yl]pyrrolidin-3-yl}hexanamide;
(S)—N-{1-[2-(3-cyanophenylamino)-6-propylpyrimidin-4-yl]pyrrolidin-3-yl}-3-phenylpropanamide;
(S)—N-{1-[2-(3-cyanophenylamino)-6-propylpyrimidin-4-yl]pyrrolidin-3-yl}-2-(1H-indol-3-yl)acetamide;
(S)—N-{1-[2-(3-cyanophenylamino)-6-propylpyrimidin-4-yl]pyrrolidin-3-yl}-2-hydroxy-2-methylpropanamide;
(S)—N-{1-[2-(3-cyanophenylamino)-6-propylpyrimidin-4-yl]pyrrolidin-3-yl}-3-(4-methoxyphenyl)propanamide;
(S)—N-{1-[2-(3-cyanophenylamino)-6-propylpyrimidin-4-yl]pyrrolidin-3-yl}-3-(4-hydroxyphenyl)propanamide;
(S)—N-{1-[2-(3-cyanophenylamino)-6-propylpyrimidin-4-yl]pyrrolidin-3-yl}-4-oxopentanamide;
(S)—N-{1-[2-(3-cyanophenylamino)-6-propylpyrimidin-4-yl]pyrrolidin-3-yl}-2-hydroxyacetamide;
(S)-2-benzyloxy-N-{1-[2-(3-cyanophenylamino)-6-propylpyrimidin-4-yl]pyrrolidin-3-yl}acetamide;
(S)—N-{1-[2-(3-cyanophenylamino)-6-propylpyrimidin-4-yl]pyrrolidin-3-yl}-2-phenoxyacetamide;
(S)—N-{1-[2-(3-cyanophenylamino)-6-propylpyrimidin-4-yl]pyrrolidin-3-yl}-2-(dimethylamino)acetamide;
(S)—N-{1-[2-(3-cyanophenylamino)-6-propylpyrimidin-4-yl]pyrrolidin-3-yl}-3-(dimethylamino)propanamide;
(S)—N-{1-[2-(3-cyanophenylamino)-6-propylpyrimidin-4-yl]pyrrolidin-3-yl}-4-dimethylaminobutanamide;
N—(S)-{1-[2-(3-cyanophenylamino)-6-propylpyrimidin-4-yl]pyrrolidin-3-yl}-2-ethoxyacetamide;
N—(S)-{1-[2-(3-cyanophenylamino)-6-propylpyrimidin-4-yl]pyrrolidin-3-yl}-2-(2-methoxyethoxy)acetamide;
(S)-benzyl-2-{1-[2-(3-cyanophenylamino)-6-propylpyrimidin-4-yl]pyrrolidin-3-ylamino}-2-oxoethylcarbamate;
(S)-tert-butyl 3-{1-[2-(3-cyanophenylamino)-6-propylpyrimidin-4-yl]pyrrolidin-3-ylamino}-3-oxobutylcarbamate;
(S)-tert-butyl 4-{1-[2-(3-cyanophenylamino)-6-propylpyrimidin-4-yl]pyrrolidin-3-ylcarbamoyl}piperidine-1-carboxylate;
(R)-2-methyl-5-[4-(2-methylpyrrolidin-1-yl)-6-propylpyrimidin-2-ylamino]benzonitrile;
(R)-2-amino-5-[4-(2-methylpyrrolidin-1-yl)-6-propylpyrimidin-2-ylamino]benzonitrile;
(S)-2-methyl-5-{4-[3-(methylamino)pyrrolidin-1-yl]-6-propylpyrimidin-2-ylamino}benzonitrile;
(S)-5-{4-[3-(ethylamino)pyrrolidin-1-yl]-6-propylpyrimidin-2-ylamino}-2-methylbenzonitrile;
5-{4-[3-(ethylamino)pyrrolidin-1-yl]-6-propylpyrimidin-2-ylamino}-2-methylbenzonitrile;
(S)—N¹-{4-[3-(methylamino)pyrrolidin-1-yl]-6-propylpyrimidin-2-yl}-3-nitrobenzene-1,4-diamine;
(S)—N¹-{4-[3-(ethylamino)pyrrolidin-1-yl]-6-propylpyrimidin-2-yl}-3-nitrobenzene-1,4-diamine;
(R)-3-{4-[3-(aminomethyl)pyrrolidin-1-yl]-6-propylpyrimidin-2-ylamino}benzonitrile;
(S)-2-fluoro-5-{4-[3-(methylamino)pyrrolidin-1-yl]-6-propylpyrimidin-2-ylamino}benzonitrile;
(S)-2-fluoro-5-{4-[3-(ethylamino)pyrrolidin-1-yl]-6-propylpyrimidin-2-ylamino}benzonitrile;
5-[4-(3-aminopyrrolidin-1-yl)-6-propylpyrimidin-2-ylamino]-2-fluorobenzonitrile;
N-(4-fluorophenyl)-4-methyl-6-(pyrrolidin-1-yl)pyrimidin-2-amine;
(3R,5S)-1-[2-(4-fluorophenyl)-6-propylpyrimidin-4-yl]-5-(hydroxymethyl)pyrrolidin-3-ol;
(S)-{1-[2-(1H-indol-6-ylamino)-6-propylpyrimidin-4-yl]pyrrolidin-2-yl}methanol;
(R)-{1-[2-(1H-indol-6-ylamino)-6-propylpyrimidin-4-yl]pyrrolidin-2-yl}methanol;
{1-[2-(1H-indol-6-ylamino)-6-propylpyrimidin-4-yl]pyrrolidin-2-yl}methanol;

(R)—N-{4-[2-(methoxymethyl)pyrrolidin-1-yl]-6-propyl pyrimidin-2-yl}-1H-indol-6-amine;
N-[4-(2-methylpyrrolidin-1-yl)-6-propylpyrimidin-2-yl]-1H-indol-6-amine;
(S)-methyl 1-[2-(1H-indol-6-ylamino)-6-propylpyrimidin-4-yl]pyrrolidine-2-carboxylate;
N-{1-[2-(1H-indol-6-ylamino)-6-propylpyrimidin-4-yl]pyrrolidin-3-yl}acetamide;
(S)-3-{4-[2-(hydroxymethyl)pyrrolidin-1-yl]-6-propylpyrimidin-2-ylamino}benzonitrile;
(S)-(1-{2-[3-(methylthio)phenylamino]-6-propylpyrimidin-4-yl}pyrrolidin-2-yl)methanol;
(S)-{1-[2-(4-chloro-3-nitrophenylamino)-6-propylpyrimidin-4-yl]pyrrolidin-2-yl}methanol;
(S)-{1-[2-(1H-indol-5-ylamino)-6-propylpyrimidin-4-yl]pyrrolidin-2-yl}methanol;
(S)-{1-[2-(1H-benzo[d]imidazol-5-ylamino)-6-propylpyrimidin-4-yl]pyrrolidin-2-yl}methanol;
(S)-(1-{6-propyl-2-[2-(trifluoromethyl)-1H-benzo[d]imidazol-5-ylamino]pyrimidin-4-yl}pyrrolidin-2-yl)methanol;
(S)-{1-[2-(4-methoxyphenylamino)-6-propylpyrimidin-4-yl]pyrrolidin-2-yl}methanol;
(S)-{1-[2-(3-chlorophenylamino)-6-propylpyrimidin-4-yl]pyrrolidin-2-yl}methanol;
(S)-{1-[2-(3-methoxyphenylamino)-6-propylpyrimidin-4-yl]pyrrolidin-2-yl}methanol;
(S)-(1-{6-propyl-2-[3-(trifluoromethyl)phenylamino]pyrimidin-4-yl}pyrrolidin-2-yl)methanol;
(S)-{1-[2-(5-chloro-2-methyl phenylamino)-6-propyl pyrimidin-4-yl]pyrrolidin-2-yl}methanol;
(S)-{1-[2-(5-methoxy-2-methylphenylamino)-6-propylpyrimidin-4-yl]pyrrolidin-2-yl}methanol;
(S)-{1-[2-(3-chloro-4-methylphenylamino)-6-propylpyrimidin-4-yl]pyrrolidin-2-yl}methanol;
(S)-{1-[2-(3-nitrophenylamino)-6-propylpyrimidin-4-yl]pyrrolidin-2-yl}methanol;
(S)-{1-[2-(4-fluoro-3-nitrophenylamino)-6-propylpyrimidin-4-yl]pyrrolidin-2-yl}methanol;
(S)-{1-[6-propyl-2-(quinolin-6-ylamino)pyrimidin-4-yl]pyrrolidin-2-yl}methanol;
(S)-{1-[2-(4-methyl-3-nitrophenylamino)-6-propylpyrimidin-4-yl]pyrrolidin-2-yl}methanol;
(S)-(1-{2-[4-amino-3-(trifluoromethyl)phenylamino]-6-propylpyrimidin-4-yl}pyrrolidin-2-yl)methanol;
(S)-{1-[2-(4-amino-3-nitrophenylamino)-6-propylpyrimidin-4-yl]pyrrolidin-2-yl}methanol;
(S)-5-{4-[2-(hydroxymethyl)pyrrolidin-1-yl]-6-propylpyrimidin-2-ylamino}-2-methylbenzonitrile;
(S)-2-fluoro-5-{4-[2-(hydroxymethyl)pyrrolidin-1-yl]-6-propylpyrimidin-2-ylamino}benzonitrile;
(S)-2-amino-5-{4-[2-(hydroxymethyl)pyrrolidin-1-yl]-6-propylpyrimidin-2-ylamino}benzonitrile;
(S)-{1-[6-propyl-2-(quinolin-3-ylamino)pyrimidin-4-yl]pyrrolidin-2-yl}methanol;
(S)-{1-[2-(indolin-6-ylamino)-6-propylpyrimidin-4-yl]pyrrolidin-2-yl}methanol;
(S)-3-{4-[3-(aminoethylamino)pyrrolidin-1-yl]-6-propylpyrimidin-2-ylamino}benzonitrile;
(S)-3-{4-[3-(piperidin-4-ylamino)pyrrolidin-1-yl]-6-propylpyrimidin-2-ylamino}benzonitrile;
(S)-3-{4-[3-(1-butylpiperidin-4-ylamino)pyrrolidin-1-yl]-6-propylpyrimidin-2-ylamino}benzonitrile;
(S)—N-{1-[6-butyl-2-(3-cyanophenylamino)pyrimidin-4-yl]pyrrolidin-3-yl}acetamide;
(S)-3-{4-butyl-6-[2-(hydroxymethyl)pyrrolidin-1-yl]pyrimidin-2-ylamino}benzonitrile;
(R)-3-[4-butyl-6-(2-methylpyrrolidin-1-yl)pyrimidin-2-ylamino]benzonitrile;
(S)-3-{4-butyl-6-[3-(methylamino)pyrrolidin-1-yl]pyrimidin-2-ylamino}benzonitrile;
(S)-tert-butyl 1-[6-butyl-2-(3-cyanophenylamino)pyrimidin-4-yl]pyrrolidin-3-ylcarbamate;
(S)—N-{1-[6-butyl-2-(3-cyano-4-methyl phenylamino)pyrimidin-4-yl]pyrrolidin-3-yl}acetamide;
(S)-5-{4-butyl-6-[2-(hydroxymethyl)pyrrolidin-1-yl]pyrimidin-2-ylamino}-2-methylbenzonitrile;
(R)-5-[4-butyl-6-(2-methylpyrrolidin-1-yl)pyrimidin-2-ylamino]-2-methylbenzonitrile;
(S)-5-{4-butyl-6-[3-(methylamino)pyrrolidin-1-yl]pyrimidin-2-ylamino}-2-methylbenzonitrile;
(S)-tert-butyl 1-[6-butyl-2-(3-cyano-4-methyl phenylamino)pyrimidin-4-yl]pyrrolidin-3-ylcarbamate;
(S)-3-[4-(3-aminopyrrolidin-1-yl)-6-butylpyrimidin-2-ylamino]benzonitrile;
(S)-5-[4-(3-aminopyrrolidin-1-yl)-6-butylpyrimidin-2-ylamino]-2-methylbenzonitrile;
(S)-3-{4-butyl-6-[3-(isopropylamino)pyrrolidin-1-yl]pyrimidin-2-ylamino}benzonitrile;
(S)-3-{4-butyl-6-[3-(diethylamino)pyrrolidin-1-yl]pyrimidin-2-ylamino}benzonitrile;
(S)-3-{4-butyl-6-[3-(cyclopropylmethylamino)pyrrolidin-1-yl]pyrimidin-2-ylamino}benzonitrile;
(S)-5-{4-butyl-6-[3-(isopropylamino)pyrrolidin-1-yl]pyrimidin-2-ylamino}-2-methylbenzonitrile;
(S)-5-{4-butyl-6-[3-(diethylamino)pyrrolidin-1-yl]pyrimidin-2-ylamino}-2-methylbenzonitrile;
(S)-5-{4-butyl-6-[3-(cyclopropylmethylamino)pyrrolidin-1-yl]pyrimidin-2-ylamino}-2-methylbenzonitrile;
(S)—N-{1-[2-(4-chloro-3-nitrophenylamino)-6-propylpyrimidin-4-yl]pyrrolidin-3-yl}acetamide;
(S)—N-(1-{2-[3-(methylthio)phenylamino]-6-propylpyrimidin-4-yl}pyrrolidin-3-yl)acetamide;
(S)—N-{1-[2-(1H-indol-6-ylamino)-6-propylpyrimidin-4-yl]pyrrolidin-3-yl}acetamide;
(S)—N-(1-{6-propyl-2-[3-(trifluoromethyl)phenylamino]pyrimidin-4-yl}pyrrolidin-3-yl)acetamide;
(S)—N-{1-[2-(4-methyl-2-oxo-2H-chromen-7-ylamino)-6-propylpyrimidin-4-yl]pyrrolidin-3-yl}acetamide;
(S)—N-{1-[2-(3-chloro-4-methylphenylamino)-6-propylpyrimidin-4-yl]pyrrolidin-3-yl}acetamide;
(S)—N-{1-[2-(3-nitrophenylamino)-6-propylpyrimidin-4-yl]pyrrolidin-3-yl}acetamide;
(S)—N-{1-[2-(4-fluoro-3-nitrophenylamino)-6-propylpyrimidin-4-yl]pyrrolidin-3-yl}acetamide;
(S)—N-{1-[2-(4-methyl-3-nitrophenylamino)-6-propylpyrimidin-4-yl]pyrrolidin-3-yl}acetamide;
(S)-benzyl 5-[4-(3-acetamidopyrrolidin-1-yl)-6-propylpyrimidin-2-ylamino]-2-methoxyphenylcarbamate;
(S)—N-{1-[2-(3-cyano-4-fluorophenylamino)-6-propylpyrimidin-4-yl]pyrrolidin-3-yl}acetamide;
(S)—N-{1-[2-(3-cyano-4-methylphenylamino)-6-propylpyrimidin-4-yl]pyrrolidin-3-yl}acetamide;
(S)—N-(1-{2-[4-fluoro-3-(trifluoromethyl)phenylamino]-6-propylpyrimidin-4-yl}pyrrolidin-3-yl)acetamide;
(S)—N-{1-[2-(4-amino-3-nitrophenylamino)-6-propylpyrimidin-4-yl]pyrrolidin-3-yl}acetamide;
(S)—N-{1-[2-(5-chloro-2-methylphenylamino)-6-propylpyrimidin-4-yl]pyrrolidin-3-yl}acetamide;
(S)-3-[4-(3-acetamidopyrrolidin-1-yl)-6-propylpyrimidin-2-ylamino]benzamide;
(S)-3-{[4-(3-acetamidopyrrolidin-1-yl)-6-propylpyrimidin-2-yl]amino}-N-methylbenzamide;

(S)—N-[1-(2-{[3-(aminomethyl)phenyl]amino}-6-propylpyrimidin-4-yl)pyrrolidin-3-yl]acetamide;
(S)-3-{[4-(3-acetamidopyrrolidin-1-yl)-6-propylpyrimidin-2-yl]amino}-4-chlorobenzamide;
(S)—N-{1-[2-(4-amino-3-cyanophenylamino)-6-propylpyrimidin-4-yl]pyrrolidin-3-yl}acetamide;
(S)—N-(1-{2-[4-amino-3-(trifluoromethyl)phenylamino]-6-propylpyrimidin-4-yl}pyrrolidin-3-yl)acetamide;
(S)—N-{1-[2-(3-amino-5-cyanophenylamino)-6-propylpyrimidin-4-yl]pyrrolidin-3-yl}acetamide;
(S)—N-{1-[2-(3-amino-4-fluorophenylamino)-6-propylpyrimidin-4-yl]pyrrolidin-3-yl}acetamide;
(S)—N-(1-{2-[3-amino-5-(trifluoromethyl)phenylamino]-6-propylpyrimidin-4-yl}pyrrolidin-3-yl)acetamide;
(S)—N-(1-{2-[(4-aminophenyl)amino]-6-propylpyrimidin-4-yl}pyrrolidin-3-yl)acetamide;
(S)—N-(1-{2-[(4-chloro-3-hydroxyphenyl)amino]-6-propylpyrimidin-4-yl}pyrrolidin-3-yl)acetamide;
(S)-4-{[4-(3-acetamidopyrrolidin-1-yl)-6-propylpyrimidin-2-yl]amino}-2-hydroxybenzoic acid;
(S)-5-{[4-(3-acetamidopyrrolidin-1-yl)-6-propylpyrimidin-2-yl]amino}-2-hydroxybenzoic acid;
(S)—N-(1-{2-[(3-hydroxy-4-methylphenyl)amino]-6-propylpyrimidin-4-yl}pyrrolidin-3-yl)acetamide;
(S)—N-(1-{2-[(3-chloro-4-hydroxyphenyl)amino]-6-propylpyrimidin-4-yl}pyrrolidin-3-yl)acetamide;
(S)—N-(1-{2-[(4-hydroxy-3-methylphenyl)amino]-6-propylpyrimidin-4-yl}pyrrolidin-3-yl)acetamide;
(S)—N-(1-{2-[(3-fluoro-4-hydroxyphenyl)amino]-6-propylpyrimidin-4-yl}pyrrolidin-3-yl)acetamide;
(S)—N-(1-{2-[(3-hydroxy-4-methoxyphenyl)amino]-6-propylpyrimidin-4-yl}pyrrolidin-3-yl)acetamide;
(S)—N-(1-{2-[(3-methoxy-4-methylphenyl)amino]-6-propylpyrimidin-4-yl}pyrrolidin-3-yl)acetamide;
(S)—N-(1-(2-{[4-methyl-3-(trifluoromethyl)phenyl]amino}-6-propylpyrimidin-4-yl)pyrrolidin-3-yl)acetamide;
(S)—N-(1-{2-[(3,4-dimethylphenyl)amino]-6-propylpyrimidin-4-yl}pyrrolidin-3-yl)acetamide;
(S)—N-(1-{2-[(3-fluoro-4-methylphenyl)amino]-6-propylpyrimidin-4-yl}pyrrolidin-3-yl)acetamide;
(S)—N-{1-[2-(3-amino-4-methoxyphenylamino)-6-propylpyrimidin-4-yl]pyrrolidin-3-yl}acetamide;
(S)—N-{1-[2-(3-amino-4-chlorophenylamino)-6-propylpyrimidin-4-yl]pyrrolidin-3-yl}acetamide;
(S)—N-{1-[2-(3-amino-4-methylphenylamino)-6-propylpyrimidin-4-yl]pyrrolidin-3-yl}acetamide;
N-{1-[2-(4-amino-3-nitrophenylamino)-6-propylpyrimidin-4-yl]pyrrolidin-3-yl}acetamide
N-{1-[2-(3-cyanophenylamino)-6-propylpyrimidin-4-yl]pyrrolidin-3-yl}acetamide;
N-{1-[2-(3-nitrophenylamino)-6-propylpyrimidin-4-yl]pyrrolidin-3-yl}acetamide;
N-{1-[2-(4-fluoro-3-nitrophenylamino)-6-propylpyrimidin-4-yl]pyrrolidin-3-yl}acetamide;
N-{1-[2-(4-chloro-3-nitrophenylamino)-6-propylpyrimidin-4-yl]pyrrolidin-3-yl}acetamide;
N-{1-[2-(3-methoxyphenylamino)-6-propylpyrimidin-4-yl]pyrrolidin-3-yl}acetamide;
N-{1-[2-(5-methoxy-2-methylphenylamino)-6-propylpyrimidin-4-yl]pyrrolidin-3-yl}acetamide;
N-{1-[2-(4-methoxyphenylamino)-6-propylpyrimidin-4-yl]pyrrolidin-3-yl}acetamide;
N-(1-{6-propyl-2-[3-(trifluoromethyl)phenylamino]pyrimidin-4-yl}pyrrolidin-3-yl)acetamide;
N-{1-[2-(3-chlorophenylamino)-6-propylpyrimidin-4-yl]pyrrolidin-3-yl}acetamide;
N-{1-[2-(5-chloro-2-methylphenylamino)-6-propylpyrimidin-4-yl]pyrrolidin-3-yl}acetamide;
N-{1-[2-(3-chloro-4-methylphenylamino)-6-propylpyrimidin-4-yl]pyrrolidin-3-yl}acetamide;
N-(1-{2-[3-(methylthio)phenylamino]-6-propylpyrimidin-4-yl}pyrrolidin-3-yl)acetamide;
N-{1-[2-(1H-indol-5-ylamino)-6-propylpyrimidin-4-yl]pyrrolidin-3-yl}acetamide;
N-(1-{6-propyl-2-[2-(trifluoromethyl)-1H-benzo[d]imidazol-5-ylamino]pyrimidin-4-yl}pyrrolidin-3-yl)acetamide;
N-{1-[6-propyl-2-(quinolin-6-ylamino)pyrimidin-4-yl]pyrrolidin-3-yl}acetamide;
N-{1-[2-(4-methyl-2-oxo-2H-chromen-7-ylamino)-6-propyl pyrimidin-4-yl]pyrrolidin-3-yl}acetamide;
N-{1-[6-propyl-2-(quinolin-3-ylamino)pyrimidin-4-yl]pyrrolidin-3-yl}acetamide;
N-{1-[2-(4-amino-3-cyanophenylamino)-6-propylpyrimidin-4-yl]pyrrolidin-3-yl}acetamide;
N-{1-[2-(3-amino-4-fluorophenylamino)-6-propylpyrimidin-4-yl]pyrrolidin-3-yl}acetamide;
(R)—N-(4-chloro-3-nitrophenyl)-4-(2-methylpyrrolidin-1-yl)-6-propyl pyrimidin-2-amine;
(R)-4-(2-methylpyrrolidin-1-yl)-N-[3-(methylthio)phenyl]-6-propylpyrimidin-2-ylamine;
(R)—N-[4-(2-methylpyrrolidin-1-yl)-6-propylpyrimidin-2-yl]-1H-indol-6-amine;
(R)-4-(2-methylpyrrolidin-1-yl)-6-propyl-N-[3-(trifluoromethyl)phenyl]pyrimidin-2-amine;
(R)-4-methyl-7-[4-(2-methylpyrrolidin-1-yl)-6-propyl pyrimidin-2-ylamino]-2H-chromen-2-one;
(R)—N-(3-chloro-4-methyl phenyl)-4-(2-methylpyrrolidin-1-yl)-6-propylpyrimidin-2-amine;
(R)-4-(2-methylpyrrolidin-1-yl)-N-(3-nitrophenyl)-6-propylpyrimidin-2-ylamine;
(R)—N-(4-fluoro-3-nitrophenyl)-4-(2-methylpyrrolidin-1-yl)-6-propylpyrimidin-2-amine;
(R)—N-(4-methyl-3-nitrophenyl)-4-(2-methylpyrrolidin-1-yl)-6-propyl pyrimidin-2-amine;
(R)—N-[4-fluoro-3-(trifluoromethyl)phenyl]-4-(2-methylpyrrolidin-1-yl)-6-propylpyrimidin-2-ylamine;
(R)—N$^1$-[4-(2-methylpyrrolidin-1-yl)-6-propyl pyrimidin-2-yl]-3-(trifluoromethyl)benzene-1,4-diamine;
(R)-benzyl 2-methoxy-5-[4-(2-methylpyrrolidin-1-yl)-6-propyl pyrimidin-2-ylamino]phenylcarbamate;
(R)-2-fluoro-5-[4-(2-methylpyrrolidin-1-yl)-6-propylpyrimidin-2-ylamino]benzonitrile;
(R)—N$^1$-[4-(2-methylpyrrolidin-1-yl)-6-propyl pyrimidin-2-yl]-3-nitrobenzene-1,4-diamine;
(R)-1-{6-[4-(2-methylpyrrolidin-1-yl)-6-propylpyrimidin-2-ylamino]indolin-1-yl}ethanone;
(R)—N-(5-chloro-2-methyl phenyl)-4-(2-methylpyrrolidin-1-yl)-6-propylpyrimidin-2-amine;
(R)-4-methoxy-N$^1$-[4-(2-methylpyrrolidin-1-yl)-6-propylpyrimidin-2-yl]benzene-1,3-diamine;
(R)-4-chloro-N$^1$-[4-(2-methylpyrrolidin-1-yl)-6-propylpyrimidin-2-yl]benzene-1,3-diamine;
(R)-4-fluoro-N$^1$-[4-(2-methylpyrrolidin-1-yl)-6-propyl pyrimidin-2-yl]benzene-1,3-diamine;
(R)-4-methyl-N$^1$-[4-(2-methylpyrrolidin-1-yl)-6-propyl pyrimidin-2-yl]benzene-1,3-diamine;
(S)-3-{4-[3-(2-hydroxyethylamino)pyrrolidin-1-yl]-6-propyl pyrimidin-2-ylamino}benzonitrile;
(S)—N-{1-[2-(4-amino-3-nitrophenylamino)-6-butylpyrimidin-4-yl]pyrrolidin-3-yl}acetamide;
(S)—N$^1$-{4-butyl-6-[3-(methylamino)pyrrolidin-1-yl]pyrimidin-2-yl}-3-nitrobenzene-1,4-diamine;

(S)—N¹-[4-(3-aminopyrrolidin-1-yl)-6-propylpyrimidin-2-yl]-5-(trifluoromethyl)benzene-1,3-diamine;
(S)—N¹-[4-(3-aminopyrrolidin-1-yl)-6-propylpyrimidin-2-yl]-3-methyl benzene-1,4-diamine;
(S)-4-(3-aminopyrrolidin-1-yl)-N-(4-chloro-3-nitrophenyl)-6-propylpyrimidin-2-amine;
(S)-4-(3-aminopyrrolidin-1-yl)-N-[3-(methylthio)phenyl]-6-propyl pyrimidin-2-amine;
(S)—N-[4-(3-aminopyrrolidin-1-yl)-6-propylpyrimidin-2-yl]-1H-indol-6-amine;
(S)-4-(3-aminopyrrolidin-1-yl)-6-propyl-N-[3-(trifluoromethyl)phenyl]pyrimidin-2-amine;
(S)-4-(3-aminopyrrolidin-1-yl)-N-(5-chloro-2-methylphenyl)-6-propylpyrimidin-2-amine;
(S)-4-(3-aminopyrrolidin-1-yl)-N-(3-chloro-4-methylphenyl)-6-propylpyrimidin-2-amine;
(S)-4-(3-aminopyrrolidin-1-yl)-N-(3-nitrophenyl)-6-propylpyrimidin-2-amine;
(S)-4-(3-aminopyrrolidin-1-yl)-N-(4-methyl-3-nitrophenyl)-6-propylpyrimidin-2-amine;
(S)—N¹-[4-(3-aminopyrrolidin-1-yl)-6-propylpyrimidin-2-yl]-3-(trifluoromethyl)benzene-1,4-diamine;
(S)-5-[4-(3-aminopyrrolidin-1-yl)-6-propylpyrimidin-2-ylamino]-2-fluorobenzonitrile;
(S)-5-[4-(3-aminopyrrolidin-1-yl)-6-propylpyrimidin-2-ylamino]-2-methylbenzonitrile;
(S)-2-amino-5-[4-(3-aminopyrrolidin-1-yl)-6-propylpyrimidin-2-ylamino]benzonitrile;
(S)-benzyl 5-[4-(3-aminopyrrolidin-1-yl)-6-propylpyrimidin-2-ylamino]-2-methoxyphenylcarbamate;
(S)-4-(3-aminopyrrolidin-1-yl)-N-[4-fluoro-3-(trifluoromethyl)phenyl]-6-propylpyrimidin-2-amine;
(S)-4-(3-aminopyrrolidin-1-yl)-N-(4-fluoro-3-nitrophenyl)-6-propylpyrimidin-2-amine;
(S)—N-[4-(3-aminopyrrolidin-1-yl)-6-propylpyrimidin-2-yl]-3-nitrobenzene-1,4-diamine;
(S)-4-(3-aminopyrrolidin-1-yl)-N-[3,5-bis(trifluoromethyl)phenyl]-6-propylpyrimidin-2-amine;
(S)-4-(3-aminopyrrolidin-1-yl)-N-(3,5-dimethoxyphenyl)-6-propylpyrimidin-2-amine;
(S)-3-amino-5-{[4-(3-aminopyrrolidin-1-yl)-6-propylpyrimidin-2-yl]amino}benzonitrile;
(S)-3-[4-(3-aminopyrrolidin-1-yl)-6-propylpyrimidin-2-ylamino]benzenesulfonamide;
(S)—N¹-{4-[2-(methoxymethyl)pyrrolidin-1-yl]-6-propylpyrimidin-2-yl}benzene-1,3-diamine;
(S)-4-fluoro-N¹-{4-[2-(methoxymethyl)pyrrolidin-1-yl]-6-propylpyrimidin-2-yl}benzene-1,3-diamine;
(S)—N¹-{4-[2-(methoxymethyl)pyrrolidin-1-yl]-6-propylpyrimidin-2-yl}-4-methylbenzene-1,3-diamine;
(S)-4-methoxy-N¹-{4-[2-(methoxymethyl)pyrrolidin-1-yl]-6-propylpyrimidin-2-yl}benzene-1,3-diamine;
(S)—N-{4-[2-(methoxymethyl)pyrrolidin-1-yl]-6-propyl pyrimidin-2-yl}indolin-6-amine;
(S)—N¹-[4-(3-aminopyrrolidin-1-yl)-6-propylpyrimidin-2-yl]-4-methyl benzene-1,3-diamine;
(S)—N¹-[4-(3-aminopyrrolidin-1-yl)-6-propylpyrimidin-2-yl]-4-fluorobenzene-1,3-diamine;
(S)—N-(4-chloro-3-nitrophenyl)-4-[3-(cyclopropylmethylamino)pyrrolidin-1-yl]-6-propylpyrimidin-2-amine;
(S)-4-[3-(cyclopropylmethylamino)pyrrolidin-1-yl]-N-(4-fluoro-3-nitrophenyl)-6-propylpyrimidin-2-amine;
(S)-4-[3-(cyclopropylmethylamino)pyrrolidin-1-yl]-N-(4-methyl-3-nitrophenyl)-6-propylpyrimidin-2-amine;
(S)-4-[3-(cyclopropylmethylamino)pyrrolidin-1-yl]-N-(3-nitrophenyl)-6-propylpyrimidin-2-amine;
(S)-5-{4-[3-(cyclopropylmethylamino)pyrrolidin-1-yl]-6-propylpyrimidin-2-ylamino}-2-fluorobenzonitrile;
(S)-5-{4-[3-(cyclopropylmethylamino)pyrrolidin-1-yl]-6-propylpyrimidin-2-ylamino}-2-methylbenzonitrile;
(S)-4-[3-(cyclopropylmethylamino)pyrrolidin-1-yl]-N-[3-(methylthio)phenyl]-6-propylpyrimidin-2-amine;
(S)-4-[3-(cyclopropylmethylamino)pyrrolidin-1-yl]-6-propyl-N-[3-(trifluoromethyl)phenyl]pyrimidin-2-amine;
(S)—N-(5-chloro-2-methylphenyl)-4-[3-(cyclopropylmethylamino)pyrrolidin-1-yl]-6-propylpyrimidin-2-amine;
(S)—N-(3-chloro-4-methylphenyl)-4-[3-(cyclopropylmethylamino)pyrrolidin-1-yl]-6-propylpyrimidin-2-amine;
(S)-4-[3-(cyclopropylmethylamino)pyrrolidin-1-yl]-N-[4-fluoro-3-(trifluoromethyl)phenyl]-6-propylpyrimidin-2-amine;
(S)—N¹-{4-[3-(cyclopropylmethylamino)pyrrolidin-1-yl]-6-propylpyrimidin-2-yl}-4-methylbenzene-1,3-diamine;
(S)—N¹-{4-[3-(cyclopropylmethylamino)pyrrolidin-1-yl]-6-propylpyrimidin-2-yl}benzene-1,3-diamine;
3-{4-[3-(cyclopropylmethylamino)pyrrolidin-1-yl]-6-propylpyrimidin-2-ylamino}benzonitrile;
(S)-{1-[6-ethyl-2-(4-fluorophenylamino)pyrimidin-4-yl]pyrrolidin-2-yl}methanol;
(S)—N-{1-[6-ethyl-2-(4-fluorophenylamino)pyrimidin-4-yl]pyrrolidin-3-yl}acetamide;
(S)-4-ethyl-N-(4-fluorophenyl)-6-(2-methoxymethylpyrrolidin-1-yl)pyrimidin-2-amine;
4-ethyl-N-(4-fluorophenyl)-6-(2-methylpyrrolidin-1-yl)pyrimidin-2-amine;
(S)-4-ethyl-6-[3-(ethylamino)pyrrolidin-1-yl]-N-(4-fluorophenyl)pyrimidin-2-amine;
(S)-3-[4-(3-phenoxypyrrolidin-1-yl)-6-propylpyrimidin-2-ylamino]benzonitrile;
(S)-2-amino-N-{1-[2-(3-cyanophenylamino)-6-propylpyrimidin-4-yl]pyrrolidin-3-yl}acetamide;
(S)-{1-[2-(3-amino-4-methylphenylamino)-6-propylpyrimidin-4-yl]pyrrolidin-2-yl}methanol;
(S)-{1-[2-(3-amino-4-fluorophenylamino)-6-propylpyrimidin-4-yl]pyrrolidin-2-yl}methanol;
(S)-{1-[2-(3-amino-4-chlorophenylamino)-6-propylpyrimidin-4-yl]pyrrolidin-2-yl}methanol;
(S)-3-[4-(2-formylpyrrolidin-1-yl)-6-propylpyrimidin-2-ylamino]benzonitrile;
(S)-3-(4-{2-[(methylamino)methyl]pyrrolidin-1-yl}-6-propylpyrimidin-2-ylamino)benzonitrile;
(S)-3-(4-{2-[(cyclobutylamino)methyl]pyrrolidin-1-yl}-6-propylpyrimidin-2-ylamino)benzonitrile;
(S)-3-(4-{2-[(4-fluorobenzylamino)methyl]pyrrolidin-1-yl}-6-propyl pyrimidin-2-ylamino)benzonitrile;
(S)-3-(4-propyl-6-{2-[(propylamino)methyl]pyrrolidin-1-yl}pyrimidin-2-ylamino)benzonitrile;
(S)-3-(4-{2-[(2-hydroxyethylamino)methyl]pyrrolidin-1-yl}-6-propylpyrimidin-2-ylamino)benzonitrile;
(S)-2-methyl-5-{4-propyl-6-[3-(propylamino)pyrrolidin-1-yl]pyrimidin-2-ylamino}benzonitrile;
(S)-2-methyl-5-(4-{3-[3-(methylthio)propylamino]pyrrolidin-1-yl}-6-propylpyrimidin-2-ylamino)benzonitrile;
(S)-5-(4-{3-[(1H-pyrrol-2-yl)methylamino]pyrrolidin-1-yl}-6-propylpyrimidin-2-ylamino)-2-methylbenzonitrile;
(S)-5-{4-[3-(4-hydroxybenzylamino)pyrrolidin-1-yl]-6-propyl pyrimidin-2-ylamino}-2-methylbenzonitrile;
(S)-5-{4-[3-(isopropylamino)pyrrolidin-1-yl]-6-propylpyrimidin-2-ylamino}-2-methylbenzonitrile;
(S)-5-{4-[3-(cyclobutylamino)pyrrolidin-1-yl]-6-propyl pyrimidin-2-ylamino}-2-methylbenzonitrile;
(S)-5-{4-[3-(cyclopentylamino)pyrrolidin-1-yl]-6-propylpyrimidin-2-ylamino}-2-methylbenzonitrile;

(S)-5-{4-[3-(cyclohexylamino)pyrrolidin-1-yl]-6-propylpyrimidin-2-ylamino}-2-methylbenzonitrile;
(S)-2-methyl-5-{4-[3-(pentylamino)pyrrolidin-1-yl]-6-propyl pyrimidin-2-ylamino}benzonitrile;
(S)-2-methyl-5-{4-[3-(neopentylamino)pyrrolidin-1-yl]-6-propylpyrimidin-2-ylamino}benzonitrile;
(S)-5-(4-{3-[(4,5-dimethylfuran-2-yl)methylamino]pyrrolidin-1-yl]-6-propylpyrimidin-2-ylamino)-2-methylbenzonitrile;
(S)—N-{1-[2-(3-cyano-4-methylphenylamino)-6-propylpyrimidin-4-yl]pyrrolidin-3-yl}propionamide;
(S)—N-{1-[2-(3-cyano-4-methylphenylamino)-6-propylpyrimidin-4-yl]pyrrolidin-3-yl}-2-phenylacetamide;
(S)—N-{1-[2-(3-cyano-4-methylphenylamino)-6-propylpyrimidin-4-yl]pyrrolidin-3-yl}-2-(piperidin-1-yl)acetamide;
(S)—N-{1-[2-(3-cyano-4-methylphenylamino)-6-propylpyrimidin-4-yl]pyrrolidin-3-yl}-2-(pyridin-3-yl)acetamide;
(S)—N-{1-[2-(3-cyano-4-methylphenylamino)-6-propylpyrimidin-4-yl]pyrrolidin-3-yl}-2-(pyridin-4-yl)acetamide;
(S)—N-{1-[2-(3-cyano-4-methylphenylamino)-6-propylpyrimidin-4-yl]pyrrolidin-3-yl}-2-(thiophen-2-yl)acetamide;
(S)—N-{1-[2-(3-cyano-4-methylphenylamino)-6-propylpyrimidin-4-yl]pyrrolidin-3-yl}methanesulfonamide;
(S)-1-(1-{2-[(3-cyano-4-methylphenyl)amino]-6-propylpyrimidin-4-yl}pyrrolidin-3-yl)-3-ethylurea;
(R)-3-(4-{3-[(diethylamino)methyl]pyrrolidin-1-yl}-6-propylpyrimidin-2-ylamino)benzonitrile;
(S)—N-{1-[6-butyl-2-(4-methyl-3-nitrophenylamino)pyrimidin-4-yl]pyrrolidin-3-yl}acetamide;
(S)—N-{1-[6-butyl-2-(4-fluoro-3-nitrophenylamino)pyrimidin-4-yl]pyrrolidin-3-yl}acetamide;
(S)—N-{1-[6-butyl-2-(4-chloro-3-nitrophenylamino)pyrimidin-4-yl]pyrrolidin-3-yl}acetamide;
(S)—N-{1-[2-(3-amino-5-cyanophenylamino)-6-butylpyrimidin-4-yl]pyrrolidin-3-yl}acetamide;
(S)—N-(1-{2-[3-amino-5-(trifluoromethyl)phenylamino]-6-butylpyrimidin-4-yl}pyrrolidin-3-yl)acetamide;
(S)—N-(1-{2-[4-amino-3-(trifluoromethyl)phenylamino]-6-butylpyrimidin-4-yl}pyrrolidin-3-yl)acetamide;
(S)—N-(1-{6-butyl-2-[4-fluoro-3-(trifluoromethyl)phenylamino]pyrimidin-4-yl}pyrrolidin-3-yl)acetamide;
(S)—N-{1-[6-butyl-2-(3-cyano-4-fluorophenylamino)pyrimidin-4-yl]pyrrolidin-3-yl}acetamide;
(S)—N-{1-[2-(3-amino-4-fluorophenylamino)-6-butylpyrimidin-4-yl]pyrrolidin-3-yl}acetamide;
(S)—N-{1-[2-(3-amino-4-chlorophenylamino)-6-butylpyrimidin-4-yl]pyrrolidin-3-yl}acetamide;
(S)—N-{1-[2-(4-amino-3-cyanophenylamino)-6-butylpyrimidin-4-yl]pyrrolidin-3-yl}acetamide;
(S)-2-amino-5-{4-butyl-6-[3-(methylamino)pyrrolidin-1-yl]pyrimidin-2-ylamino}benzonitrile;
(S)-4-butyl-N-(4-methyl-3-nitrophenyl)-6-[3-(methylamino)pyrrolidin-1-yl]pyrimidin-2-amine;
(S)-4-butyl-N-(4-fluoro-3-nitrophenyl)-6-[3-(methylamino)pyrrolidin-1-yl]pyrimidin-2-amine;
(S)-4-butyl-N-(4-chloro-3-nitrophenyl)-6-[3-(methylamino)pyrrolidin-1-yl]pyrimidin-2-amine;
(S)-3-amino-5-{4-butyl-6-[3-(methylamino)pyrrolidin-1-yl]pyrimidin-2-ylamino}benzonitrile;
(S)—N$^1$-{4-butyl-6-[3-(methylamino)pyrrolidin-1-yl]pyrimidin-2-yl}-5-(trifluoromethyl)benzene-1,3-diamine;
(S)—N$^1$-{4-butyl-6-[3-(methylamino)pyrrolidin-1-yl]pyrimidin-2-yl}-3-(trifluoromethyl)benzene-1,4-diamine;
(S)-4-butyl-N-[4-fluoro-3-(trifluoromethyl)phenyl]-6-[3-(methylamino)pyrrolidin-1-yl]pyrimidin-2-amine;
(S)-5-{4-butyl-6-[3-(methylamino)pyrrolidin-1-yl]pyrimidin-2-ylamino}-2-fluorobenzonitrile;
(S)—N$^1$-{4-butyl-6-[3-(methylamino)pyrrolidin-1-yl]pyrimidin-2-yl}-4-fluorobenzene-1,3-diamine;
(S)—N$^1$-{4-butyl-6-[3-(methylamino)pyrrolidin-1-yl]pyrimidin-2-yl}-4-chlorobenzene-1,3-diamine;
(S)-2-amino-5-{4-butyl-6-[3-(ethylamino)pyrrolidin-1-yl]pyrimidin-2-ylamino}benzonitrile;
(S)-3-{4-butyl-6-[3-(ethylamino)pyrrolidin-1-yl]pyrimidin-2-ylamino}benzonitrile;
(S)-5-{4-butyl-6-[3-(ethylamino)pyrrolidin-1-yl]pyrimidin-2-ylamino}-2-methylbenzonitrile;
(S)—N$^1$-{4-butyl-6-[3-(ethylamino)pyrrolidin-1-yl]pyrimidin-2-yl}-3-nitrobenzene-1,4-diamine;
(S)-4-butyl-6-[3-(ethylamino)pyrrolidin-1-yl]-N-(4-methyl-3-nitrophenyl)pyrimidin-2-amine;
(S)-4-butyl-6-[3-(ethylamino)pyrrolidin-1-yl]-N-(4-fluoro-3-nitrophenyl)pyrimidin-2-amine;
(S)-4-butyl-N-(4-chloro-3-nitrophenyl)-6-[3-(ethylamino)pyrrolidin-1-yl]pyrimidin-2-amine;
(S)-3-amino-5-{4-butyl-6-[3-(ethylamino)pyrrolidin-1-yl]pyrimidin-2-ylamino}benzonitrile;
(S)—N$^1$-{4-butyl-6-[3-(ethylamino)pyrrolidin-1-yl]pyrimidin-2-yl}-5-(trifluoromethyl)benzene-1,3-diamine;
(S)—N$^1$-{4-butyl-6-[3-(ethylamino)pyrrolidin-1-yl]pyrimidin-2-yl}-3-(trifluoromethyl)benzene-1,4-diamine;
(S)-4-butyl-6-[3-(ethylamino)pyrrolidin-1-yl]-N-[4-fluoro-3-(trifluoromethyl)phenyl]pyrimidin-2-amine;
(S)-5-{4-butyl-6-[3-(ethylamino)pyrrolidin-1-yl]pyrimidin-2-ylamino}-2-fluorobenzonitrile;
(S)—N$^1$-{4-butyl-6-[3-(ethylamino)pyrrolidin-1-yl]pyrimidin-2-yl}-4-fluorobenzene-1,3-diamine;
(S)—N$^1$-{4-butyl-6-[3-(ethylamino)pyrrolidin-1-yl]pyrimidin-2-yl}-4-chlorobenzene-1,3-diamine;
(S)—N-{1-[2-(3-cyano-4-methylphenylamino)-6-propylpyrimidin-4-yl]pyrrolidin-3-yl}-2-hydroxyacetamide;
(S)—N-{1-[2-(3-cyano-4-fluorophenylamino)-6-propylpyrimidin-4-yl]pyrrolidin-3-yl}-2-hydroxyacetamide;
(S)—N-{1-[2-(3-amino-5-cyanophenylamino)-6-propylpyrimidin-4-yl]pyrrolidin-3-yl}-2-hydroxyacetamide;
(S)—N-(1-{2-[3-amino-5-(trifluoromethyl)phenylamino]-6-propylpyrimidin-4-yl}pyrrolidin-3-yl)-2-hydroxyacetamide;
(S)—N-(1-{2-[4-amino-3-(trifluoromethyl)phenylamino]-6-propylpyrimidin-4-yl}pyrrolidin-3-yl)-2-hydroxyacetamide;
(S)—N-(1-{2-[4-fluoro-3-(trifluoromethyl)phenylamino]-6-propylpyrimidin-4-yl}pyrrolidin-3-yl)-2-hydroxyacetamide;
(S)—N-{1-[2-(3-amino-4-fluorophenylamino)-6-propylpyrimidin-4-yl]pyrrolidin-3-yl}-2-hydroxyacetamide;
(S)—N-{1-[2-(3-amino-4-chlorophenylamino)-6-propylpyrimidin-4-yl]pyrrolidin-3-yl}-2-hydroxyacetamide;
(S)—N-{1-[2-(3-chloro-4-methylphenylamino)-6-propylpyrimidin-4-yl]pyrrolidin-3-yl}-2-hydroxyacetamide;
(S)-2-hydroxy-N-(1-{2-[4-methyl-3-(trifluoromethyl)phenylamino]-6-propylpyrimidin-4-yl}pyrrolidin-3-yl)acetamide;
(S)-4-fluoro-N$^1$-{4-[3-(methylamino)pyrrolidin-1-yl]-6-propylpyrimidin-2-yl}benzene-1,3-diamine;
(S)-3-amino-5-({4-[3-(methylamino)pyrrolidin-1-yl]-6-propylpyrimidin-2-yl}amino)benzonitrile;
(S)-2-amino-5-({4-[3-(methylamino)pyrrolidin-1-yl]-6-propylpyrimidin-2-yl}amino)benzonitrile;
(S)—N$^1$-{4-[3-(methylamino)pyrrolidin-1-yl]-6-propylpyrimidin-2-yl}-5-(trifluoromethyl)benzene-1,3-diamine;

(S)—N¹-{4-[3-(ethylamino)pyrrolidin-1-yl]-6-propylpyrimidin-2-yl}-3-(trifluoromethyl)benzene-1,4-diamine;

(S)-2-amino-5-({4-[3-(ethylamino)pyrrolidin-1-yl]-6-propylpyrimidin-2-yl}amino)benzonitrile;

(S)—N-[4-fluoro-3-(trifluoromethyl)phenyl]-4-[3-(methylamino)pyrrolidin-1-yl]-6-propylpyrimidin-2-amine;

(S)-4-[3-(ethylamino)pyrrolidin-1-yl]-N-[4-fluoro-3-(trifluoromethyl)phenyl]-6-propylpyrimidin-2-amine; and (S)—N-(1-{2-[(3,4-diaminophenyl)amino]-6-propylpyrimidin-4-yl}pyrrolidin-3-yl)acetamide.

In the use, the pharmaceutical composition, the treatment method, and the compound according to the present invention, still more preferable compounds in terms of pharmacological activity include the compound (or its pharmaceutically acceptable salt) described in Table 2-1 to Table 2-3.

The present invention includes, within its scope, a process for preparing a compound of Formula 1 or its pharmaceutically acceptable salt, which comprises reacting a compound of Formula 2 with a compound of Formula 3 to obtain a compound of Formula 4; performing a methylation of the compound of Formula 4 to obtain a compound of Formula 5; reacting the compound of Formula 5 with $R_1$—$NH_2$ to obtain a compound of Formula 6; performing a halogenation of the compound of Formula 6 to obtain a compound of Formula 7; and reacting the compound of Formula 7 with a compound of Formula 8 to obtain a compound of Formula 1:

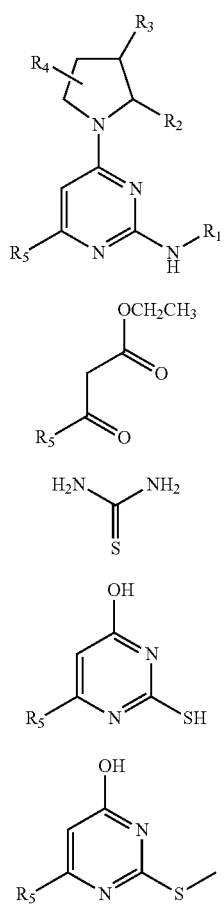

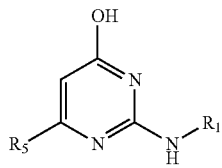

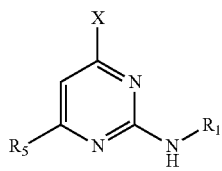

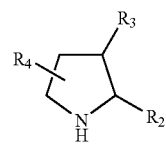

wherein, $R_1$, $R_2$, $R_3$, $R_4$, and $R_5$ are the same as defined in the above; and X is halogen.

The compounds of Formula 2 and 3 are commercially available. The reaction between the compound of Formula 2 and the compound of Formula 3 may be performed in the presence of a base and a solvent. The base may be potassium carbonate, sodium carbonate, etc and the solvent may be an aqueous solvent such as water. Typically, the reaction may be carried out under heating.

The methylation of the compound of Formula 4 may be carried out using a methylating agent such as iodomethane. The methylation may be performed in the presence of a base and a solvent. The base may be sodium hydroxide, potassium hydroxide, etc and the solvent may be an aqueous solvent such as water. Typically, the methylation may be carried out at room temperature or under heating.

The reaction between the compound of Formula 5 and $R_1$—$NH_2$ may be performed in the absence of a solvent or in the presence of a solvent such as diglyme. The reaction may be carried out at a temperature ranging from 140° C. to 180° C.

The halogenation of the compound of Formula 6 may be carried out using a halogenating agent such as phosphorus oxychloride. The halogenation may be performed preferably at a temperature of about 100° C. or higher. And also, for improving reaction rate and/or yield, the halogenation may be performed in the presence of N,N-dimethylaniline or N,N-dimethylformamide in a catalytic amount.

The reaction between the compound of Formula 7 and the compound of Formula 8 may be performed in the presence of an organic solvent, such as anhydrous tetrahydrofuran, alcohol, and 1,4-dioxane. Typically, the reaction may be carried out under heating. And also, for improving reaction rate and/or yield, the reaction may be performed in the presence of a metallic catalyst (e.g., palladium), a ligand, and a base such as cesium carbonate, triethylamine and diisopropylethylamine; or performed under microwave ranging from 300 W to 600 W.

The compound of Formula 5 may be also prepared by reacting a compound of Formula 2 with a compound of Formula 9:

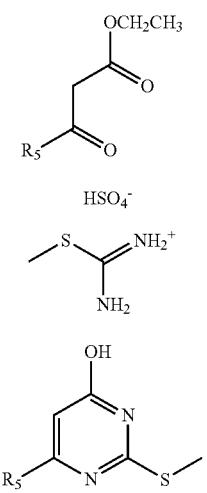

2

9

10

5 wherein, $R_5$ is the same as defined in the above.

The compound of Formula 9 is commercially available. The reaction between the compound of Formula 2 and the compound of Formula 9 may be performed in the presence of a base and a solvent. The base may be potassium carbonate, sodium carbonate, etc and the solvent may be an aqueous solvent such as water. Typically, the reaction may be carried out at room temperature or under heating.

The compound of Formula 6 may be also prepared by reacting a compound of Formula 2 with a compound of Formula 10:

2

10

6 wherein, $R_1$ and $R_5$ are the same as defined in the above.

The compound of Formula 10 may be easily prepared by using known methods, e.g., EP0560726. The reaction between the compound of Formula 2 and the compound of Formula 10 may be performed in the presence of a base and a solvent. The base may be sodium methoxide, sodium ethoxide, etc and the solvent may be an alcohol. Typically, the reaction may be carried out under heating.

The present invention also provides a process for preparing a compound of Formula 1 or its pharmaceutically acceptable salt, which comprises performing a halogenation of a compound of Formula 4 to obtain a compound of Formula 11; reacting the compound of Formula 11 with a compound of Formula 8 to obtain a compound of Formula 12; and reacting the compound of Formula 12 with $R_1$—$NH_2$ to obtain a compound of Formula 1:

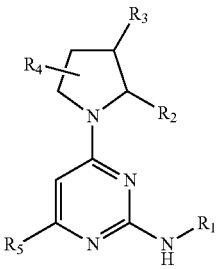

1

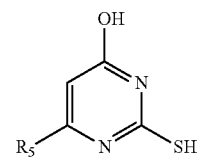

4

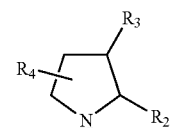

8

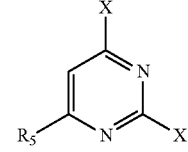

11

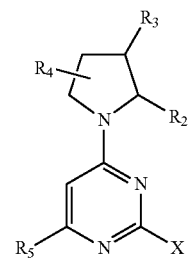

12 wherein, $R_1$, $R_2$, $R_3$, $R_4$, and $R_5$ are the same as defined in the above; and X is halogen.

The halogenation of the compound of Formula 4 may be carried out using a halogenating agent such as phosphorus oxychloride. The halogenation may be performed preferably at a temperature of about 100° C. or higher. And also, for improving reaction rate and/or yield, the halogenation may be performed in the presence of N,N-dimethylaniline or N,N-dimethylformamide in a catalytic amount.

The reaction between the compound of Formula 11 and the compound of Formula 8 may be performed in the presence of an organic solvent, such as anhydrous tetrahydrofuran, alcohol, chloroform, and N,N-dimethylformamide. Typically, the reaction may be carried out at room temperature or under heating. And also, for improving reaction rate and/or yield, the reaction may be performed in the presence of a base such as triethylamine and diisopropylethylamine.

The reaction between the compound of Formula 12 and R₁—NH₂ may be performed in the presence of a solvent such as alcohol, toluene, 1,4-dioxane, and N,N-dimethylformamide. The reaction may be carried out under heating. And also, for improving reaction rate and/or yield, the reaction may be performed in the presence of a metallic catalyst (e.g., palladium), a ligand, and a base (e.g., cesium carbonate); or performed under microwave ranging from 300 W to 600 W.

The compound of Formula 11 may be also prepared by reacting a compound of Formula 5 with an acid to obtain a compound of Formula 13; and then performing a halogenation of the compound of Formula 13:

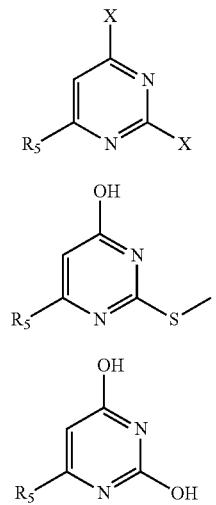

11

5

13 wherein, $R_5$ and X are the same as defined in the above.

The reaction between the compound of Formula 5 and the acid may be performed using an organic acid (e.g., acetic acid, etc) and an inorganic acid (e.g. hydrochloric acid, etc). The reaction may be performed in an aqueous solvent such as water. Typically, the reaction may be carried out under heating.

The halogenation of the compound of Formula 13 may be carried out using a halogenating agent such as phosphorus oxychloride. The halogenation may be performed preferably at a temperature of about 100° C. or higher. And also, for improving reaction rate and/or yield, the halogenation may be performed in the presence of N,N-dimethylaniline or N,N-dimethylformamide in a catalytic amount.

In accordance with an embodiment of the present invention, there is provided a process for preparing a compound of Formula 1b or its pharmaceutically acceptable salt, which comprises reacting a compound of Formula 1a with an organic acid or an acyl halide:

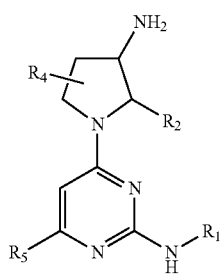

1a

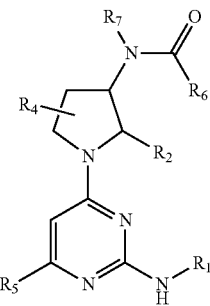

1b wherein, $R_1$, $R_2$, $R_4$, $R_5$, $R_6$, and $R_7$ are the same as defined in the above.

The reaction between the compound of Formula 1a and the organic acid may be performed through amide coupling reaction, using a coupling agent such as (benzotriazol-1-yloxy)-tris-(dimethylamino)phosphonium hexafluorophosphate, N-(3-dimethylaminopropyl)-N'-ethylcarbodiimide hydrochloride, and 1-hydroxybenzotriazole hydrate; and a base such as diisopropylethylamine and triethylamine. The coupling reaction may be performed in an organic solvent such as dichloromethane, and N,N-dimethylformamide. Typically, the coupling reaction is performed at room temperature.

And also, the reaction between the compound of Formula 1a and the acyl halide may be performed through amide coupling reaction, using an organic base (e.g., diisopropylethylamine, triethylamine, etc) or an inorganic base (e.g., sodium hydroxide, etc). The coupling reaction may be performed in an organic solvent such as dichloromethane or a mixed solvent of an organic solvent and water. Typically, the coupling reaction is performed at room temperature.

The compound of Formula 1b or its pharmaceutically acceptable salt may be also prepared by reacting a compound of Formula 12a with an organic acid or an acyl halide to obtain a compound of Formula 12b; and then reacting the compound of Formula 12b with $R_1$—NH₂ to obtain a compound of Formula 1b:

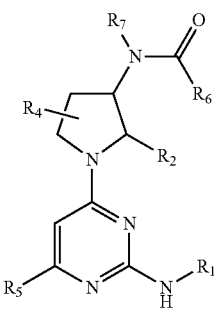

1b

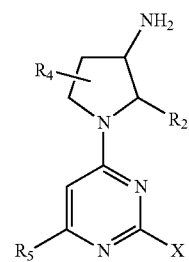

12a

-continued

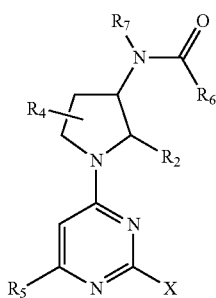

12b wherein, $R_1$, $R_2$, $R_4$, $R_5$, $R_6$, and $R_7$ are the same as defined in the above; and X is halogen.

The reaction between the compound of Formula 12a and the organic acid may be performed through amide coupling reaction, using a coupling agent such as (benzotriazol-1-yloxy)-tris-(dimethylamino)phosphonium hexafluorophosphate, N-(3-dimethylaminopropyl)-N'-ethylcarbodiimide hydrochloride, and 1-hydroxybenzotriazole hydrate; and a base such as diisopropylethylamine or triethylamine. The coupling reaction may be performed in an organic solvent such as dichloromethane, and N,N-dimethylformamide. Typically, the coupling reaction is performed at room temperature.

And also, the reaction between the compound of Formula 12a and the acyl halide may be performed through amide coupling reaction, using an organic base (e.g., diisopropylethylamine, triethylamine, etc) or an inorganic base (e.g., sodium hydroxide, etc). The coupling reaction may be performed in an organic solvent such as dichloromethane or a mixed solvent of an organic solvent and water. Typically, the coupling reaction is performed at room temperature.

The reaction between the compound of Formula 12b and $R_1$—$NH_2$ may be performed in an organic solvent such as alcohol, toluene, 1,4-dioxane, and N,N-dimethylformamide, etc. Typically, the reaction may be performed under heating. And also, for improving reaction rate and/or yield, the reaction may be performed in the presence of a metallic catalyst (e.g., palladium), a ligand, and a base (e.g., cesium carbonate); or performed under microwave ranging from 300 W to 600 W.

In accordance with another embodiment of the present invention, there is provided a process for preparing a compound of Formula 1c or its pharmaceutically acceptable salt, which comprises performing a reductive amination using an aldehyde or a ketone with respect to a compound of Formula 1a:

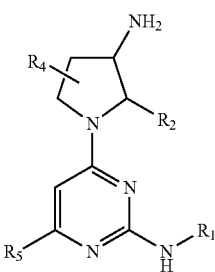

1a

-continued

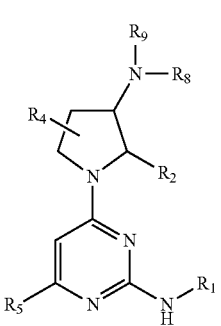

1c wherein, $R_1$, $R_2$, $R_4$, $R_5$, $R_8$, and $R_9$ are the same as defined in the above.

The reductive amination may be performed using a reducing agent such as sodium borohydride, sodium triacetoxyborohydride, and sodium cyanoborohydride. The reductive amination may be performed in an organic solvent (e.g., alcohol) at room temperature or at low temperature (e.g., at 0° C. or less). And also, for improving reaction rate and/or yield, the reaction may be performed in the presence of acetic acid, etc.

The compound of Formula 1c or its pharmaceutically acceptable salt may be prepared by introducing an amine-protecting group to a compound of Formula 12a to obtain a compound of Formula 12c; performing an alkylation of the compound of Formula 12c to obtain a compound of Formula 12d; and reacting a compound of Formula 12d with $R_1$—$NH_2$, followed by removing the amine-protecting group:

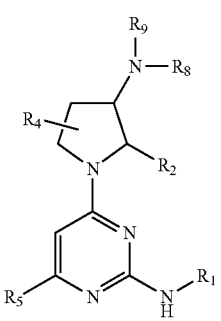

1c

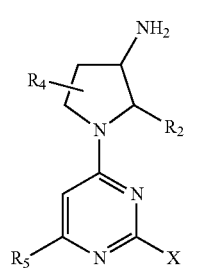

12a

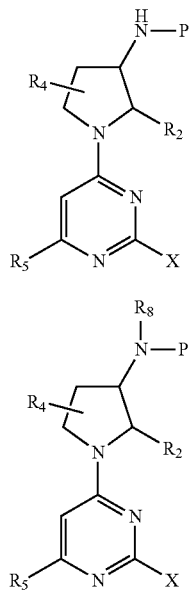

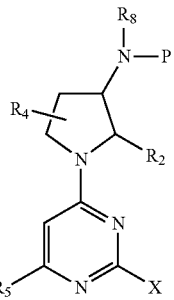

wherein, $R_1$, $R_2$, $R_4$, $R_5$, and $R_8$ are the same as defined in the above; X is halogen; and $R_9$ is hydrogen. P is an amine-protecting group such as tert-butoxycarbonyl.

The reaction for introducing an amine-protecting group to the compound of Formula 12a may be performed in an organic solvent such as dichloromethane, chloroform, and 1,4-dioxane at room temperature or at low temperature (e.g., at 0° C. or less). And also, the reaction may be performed in the presence of a base such as triethylamine, diisopropylethylamine, and 4-dimethylaminopyridine.

The alkylation of the compound of Formula 12c may be performed using an alkyl halide. The alkylation may be performed in the presence of a base (e.g., sodium hydride) in an organic solvent (e.g., N,N-dimethylformamide). The alkylation may be performed at room temperature or under heating.

The reaction between the compounds of Formula 12d and $R_1$—$NH_2$ may be performed in an organic solvent such as alcohol, toluene, 1,4-dioxane, and N,N-dimethylformamide. Typically, the reaction is performed under heating. And also, for improving reaction rate and/or yield, the reaction may be performed in the presence of a metallic catalyst (e.g., palladium), a ligand, and a base (e.g., cesium carbonate); or performed under microwave ranging from 300 W to 600 W. The reaction for removing the amine-protecting group may be performed using an acid (e.g., hydrochloric acid, trifluoroacetic acid, etc) in an organic solvent such as ethyl acetate and methanol. Typically, the reaction may be performed at room temperature or at low temperature (e.g., at 0° C. or less).

The compound of Formula 12d may be also prepared by performing a reductive amination with respect to a compound of Formula 12a to obtain a compound of Formula 12e; and then introducing an amine-protecting group to the compound of Formula 12e:

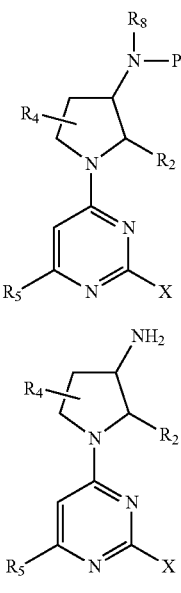

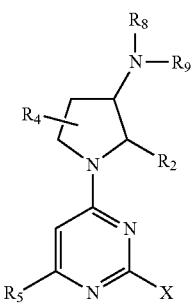

wherein, $R_2$, $R_4$, $R_5$, and $R_8$ are the same as defined in the above; X is halogen; and $R_9$ is hydrogen. P is an amine-protecting group such as tert-butoxycarbonyl.

The reductive amination of the compound of Formula 12a may be performed using a reducing agent such as sodium borohydride, sodium triacetoxyborohydride, and sodium cyanoborohydride. The reductive amination may be in an organic solvent (e.g., alcohol) at room temperature or at low temperature (e.g., at 0° C. or less). And also, for improving reaction rate and/or yield, the reaction may be performed in the presence of acetic acid, etc.

The reaction for introducing an amine-protecting group to the compound of Formula 12e may be performed in an organic solvent such as dichloromethane, chloroform and 1,4-dioxane at room temperature or at low temperature (e.g., at 0° C. or less). And also, the reaction may be performed in the presence of a base such as triethylamine, diisopropylethylamine, and 4-dimethylaminopyridine.

The following examples and experimental examples are provided for illustration purposes only, and are not intended to limit the scope of the invention.

Preparation 1. 4-chloro-N-(4-fluorophenyl)-6-propylpyrimidin-2-amine

<Step 1>
2-(methylthio)-6-propylpyrimidin-4(3H)-one

A mixture of 6-n-propyl-2-thiouracil (25.0 g, 0.15 mol), sodium hydroxide (5.9 g, 0.15 mol), iodomethane (10.2 ml, 0.17 mol), and water (300 ml) was stirred at room temperature overnight and then filtered. The resulting solid was dried in vacuo to give the titled compound (25.0 g) as a white solid. The product was used in the subsequent reaction without further purification.

<Step 2> 2-(4-fluorophenylamino)-6-propylpyrimidin-4(3H)-one

A mixture of 2-(methylthio)-6-propylpyrimidin-4(3H)-one (3.7 g, 0.02 mol) prepared in Step 1 and 4-fluoroaniline (6.7 g, 0.06 mol) was stirred at 160° C. overnight. The reaction mixture was cooled to room temperature, and then ethanol (50 ml) and charcoal (1 g) were added thereto. The reaction mixture was stirred for 1 hour and then filtered. The filtrate was concentrated under reduced pressure. Ethanol (20 ml) was added to the resulting residue, which was then stirred for 1 hour. The reaction mixture was filtered to give the titled compound as a gray solid.

$^1$H-NMR (400 MHz, CD$_3$OD) δ 7.70-7.50 (m, 2H), 7.07 (t, 2H), 5.75 (s, 1H), 2.43 (t, 2H), 1.70 (q, 2H), 0.98 (t, 3H)<

Step 3> 4-chloro-N-(4-fluorophenyl)-6-propylpyrimidin-2-amine 2-(4-Fluorophenylamino)-6-propylpyrimidin-4(3H)-one (2.2 g, 8.9 mmol) prepared in Step 2 was added to phosphorus oxychloride (1.5 ml, 16.2 mmol), which was then stirred at 110° C. for 5 hours. After cooling to room temperature, ice water was added to the reaction mixture, which was then basified to pH 9 with sodium hydroxide. The aqueous layer was extracted with ethyl acetate. The resulting organic layer was dried on anhydrous sodium sulfate and then concentrated under reduced pressure. The resulting residue was purified with silica gel column chromatography (ethyl acetate) to give 2.2 g of the titled compound as a yellow solid.

$^1$H-NMR (400 MHz, CDCl$_3$) δ 7.65-7.50 (m, 2H), 7.03 (t, 2H), 6.63 (s, 1H), 2.60 (t, 2H), 1.75 (q, 2H), 0.99 (t, 3H)

Preparation 2. (S)-2-chloro-4-[2-(methoxymethyl)pyrrolidin-1-yl]-6-propylpyrimidine <Step 1> 2,4-dichloro-6-propylpyrimidine Phosphorus oxychloride (100 ml) was slowly added at room temperature to 6-propyl-2-thiouracil (17.7 g, 0.1 mol), which was then stirred at 110° C. overnight. The reaction mixture was added to ice water and then neutralized with a saturated aqueous solution of sodium bicarbonate. The reaction mixture was extracted with dichloromethane. The organic layer was dried on anhydrous magnesium sulfate, filtered, and then concentrated under reduced pressure. The resulting residue was purified with silica gel column chromatography (n-hexane/ethyl acetate=50/1) to give 10.3 g of the titled compound as pale yellow oil.

$^1$H-NMR (400 MHz, CDCl$_3$) δ 7.16 (s, 1H), 2.73 (t, 2H), 1.78 (m, 2H), 0.99 (t, 3H)<

Step 2> (S)-2-chloro-4-[2-(methoxymethyl)pyrrolidin-1-yl]-6-propylpyrimidine 2,4-Dichloro-6-propylpyrimidine (1.4 g, 7.3 mmol) prepared in Step 1 was dissolved in tetrahydrofuran (15 ml), and then (S)-2-(methoxymethyl)pyrrolidine (1.2 g, 10.4 mmol) was added thereto at room temperature. The reaction mixture was stirred at 60° C. overnight and then cooled to room temperature. The reaction mixture was concentrated under reduced pressure. The resulting residue was purified with silica gel column chromatography (n-hexane/ethyl acetate=10/1) to give 1.5 g of the titled compound as pale yellow oil. The product was used in the subsequent reaction without further purification.

Preparation 3. 3-(4-chloro-6-propylpyrimidin-2-ylamino)benzonitrile

<Step 1> 3-(6-oxo-4-propyl-1,6-dihydropyrimidin-2-ylamino)benzonitrile

A mixture of 2-(methylthio)-6-propylpyrimidin-4(3H)-one (6.4 g, 34.7 mmol) prepared in Step 1 of Preparation 1 and 3-aminobenzonitrile (12.3 g, 104.1 mmol) was stirred at 160° C. overnight. The reaction mixture was cooled to room temperature and then ethanol (50 ml) was added thereto. The reaction mixture was stirred for 1 hour and then filtered to give 3.5 g of the titled compound as a pale brown solid.

$^1$H-NMR (400 MHz, CD$_3$OD) δ 8.22 (s, 1H), 7.90-7.80 (m, 1H), 7.55-7.45 (m, 1H), 7.45-7.35 (m, 1H), 5.84 (s, 1H), 2.49 (t, 2H), 1.80-1.65 (m, 2H), 1.00 (t, 3H)<

Step 2> 3-(4-chloro-6-propylpyrimidin-2-ylamino)benzonitrile 3-(6-oxo-4-propyl-1,6-dihydropyrimidin-2-ylamino)benzonitrile (3.3 g, 13.0 mmol) prepared in Step 1 was added to phosphorus oxychloride (10 ml). The reaction mixture was stirred at 110° C. for 2 hours and then cooled to room temperature. The reaction mixture was added to ice water and then basified to pH 9 with sodium hydroxide. The aqueous layer was extracted with ethyl acetate. The resulting organic layer was dried on anhydrous sodium sulfate and then concentrated under reduced pressure. The resulting residue was purified with silica gel column chromatography (n-hexane/ethyl acetate=10/1) to give 3.2 g of the titled compound as a yellow solid.

$^1$H-NMR (400 MHz, CDCl$_3$) δ 8.18 (s, 1H), 7.75-7.65 (m, 1H), 7.50-7.20 (m, 3H), 6.72 (s, 1H), 2.65 (t, 2H), 1.78 (q, 2H), 1.01 (t, 3H)

Preparation 4. N-(4-chloro-6-propylpyrimidin-2-yl)-1H-indol-6-amine

<Step 1> 2-(1H-indol-6-ylamino)-6-propylpyrimidin-4 (3H)-one

A mixture of 2-(methylthio)-6-propylpyrimidin-4 (3H)-one (1 g, 5.43 mmol) prepared in Step 1 of Preparation 1 and 6-aminoindole (789 mg, 5.97 mmol) was stirred at 150° C. overnight and then cooled to room temperature. The resulting residue was purified with silica gel column chromatography (dichloromethane/methanol=40/1) to give 1.4 g of the titled compound as a pale brown solid.

$^1$H-NMR (400 MHz, CD$_3$OD) δ 7.81 (s, 1H), 7.51 (d, 1H), 7.21 (d, 1H), 6.95 (dd, 1H), 6.42 (d, 1H), 5.70 (s, 1H), 2.44 (dd, 1H), 1.75-1.70 (m, 2H), 0.99 (t, 3H).

<Step 2> N-(4-chloro-6-propylpyrimidin-2-yl)-1H-indol-6-amine

A solution of 2-(1H-indol-6-ylamino)-6-propylpyrimidin-4 (3H)-one (1.2 g, 4.47 mmol) prepared in Step 1, phosphorus oxychloride (822 mg, 5.37 mmol), and diisopropylethylamine (1.9 ml, 10.7 mmol) in 1,4-dioxane (45 ml) was refluxed under stirring for 30 minutes. The reaction mixture was cooled to room temperature and then concentrated under reduced pressure. The resulting residue was purified with silica gel column chromatography (n-hexane/ethyl acetate=4/1) to give 1.1 g of the titled compound as a white solid.

$^1$H-NMR (400 MHz, CDCl$_3$) δ 8.17 (brs, 1H), 8.05 (s, 1H), 7.53 (d, 1H), 7.25 (d, 1H), 7.11 (dd, 1H), 6.98 (dd, 1H), 6.58 (s, 1H), 6.48 (s, 1H), 2.59 (dd, 2H), 1.81-1.71 (m, 2H), 0.99 (t, 3H).

Preparation 5. (S)-1-(2-chloro-6-propylpyrimidin-4-yl)-N-methylpyrrolidin-3-amine 2,4-Dichloro-6-propylpyrimidine (1 g, 5.2 mmol) prepared in Step 1 of Preparation 2 was dissolved in ethanol (10 ml) and then (3S)-(−)-3-(methylamino)pyrrolidine (1 g, 10 mmol) was slowly added thereto at 0° C. The reaction mixture was stirred at room temperature overnight and then concentrated under reduced pressure. The resulting residue was purified with silica gel column chromatography (dichloromethane/methanol=40/1) to give 1 g of the titled compound as pale yellow oil.

$^1$H-NMR (400 MHz, CDCl$_3$) δ 6.03 (s, 1H), 3.90-3.30 (m, 5H), 2.52 (t, 2H), 2.49 (s, 3H), 2.30-2.15 (m, 1H), 2.10-1.90 (m, 1H), 1.70 (q, 2H), 0.95 (t, 3H)

Preparation 6. 5-(4-chloro-6-propylpyrimidin-2-ylamino)-2-methylbenzonitrile

<Step 1> 2-methyl-5-(6-oxo-4-propyl-1,6-dihydropyrimidin-2-ylamino)benzonitrile

A mixture of 2-(methylthio)-6-propylpyrimidin-4 (3H)-one (5 g, 27.1 mmol) prepared in Step 1 of Preparation 1 and 5-amino-2-methylbenzonitrile (7 g, 53 mmol) was stirred at 160° C. overnight. The reaction mixture was cooled to room temperature and then ethanol (30 ml) was added thereto. The reaction mixture was stirred for 1 hour and then filtered to give 6.3 g of the titled compound as a pale yellow solid.

$^1$H-NMR (400 MHz, CD$_3$OD) δ 8.12 (d, 1H), 7.70-7.60 (m, 1H), 7.35 (d, 1H), 5.80 (s, 1H), 2.50-2.40 (m, 5H), 1.73 (q, 2H), 0.99 (t, 3H)<

Step 2> 5-(4-chloro-6-propylpyrimidin-2-ylamino)-2-methylbenzonitrile

2-Methyl-5-(6-oxo-4-propyl-1,6-dihydropyrimidin-2-ylamino)benzonitrile (6.3 g, 23.5 mmol) prepared in Step 1 was added to phosphorus oxychloride (10 ml). The reaction mixture was stirred at 110° C. for 2 hours and then cooled to room temperature. The reaction mixture was added to ice water and then basified to pH 9 with sodium hydroxide. The aqueous layer was extracted with ethyl acetate. The resulting organic layer was dried on anhydrous sodium sulfate and then concentrated under reduced pressure to give 6 g of the titled compound as a yellow solid. The product was used in the subsequent reaction without further purification.

Preparation 7. N$^1$-(4-chloro-6-propylpyrimidin-2-yl)-3-nitrobenzene-1,4-diamine <Step 1> 2-(4-amino-3-nitrophenylamino)-6-propylpyrimidin-4(3H)-one A mixture of 2-(methylthio)-6-propylpyrimidin-4(3H)-one (3 g, 16.3 mmol) prepared in Step 1 of Preparation 1 and 2-nitrobenzene-1,4-diamine (5 g, 32.6 mmol) was stirred at 160° C. overnight. The reaction mixture was cooled to 70° C. and then ethanol (30 ml) was added thereto. The reaction mixture was stirred for 1 hour and then filtered to give 4.5 g of the titled compound as a red solid.

$^1$H-NMR (400 MHz, CD$_3$OD) δ 8.42 (s, 1H), 7.55-7.45 (m, 1H), 6.96 (d, 1H), 5.73 (s, 1H), 2.43 (t, 2H), 1.73 (q, 2H), 0.98 (t, 3H)<

Step 2> N$^1$-(4-chloro-6-propylpyrimidin-2-yl)-3-nitrobenzene-1,4-diamine

The titled compound (0.4 g) in the form of pale yellow solid was prepared in accordance with the same procedures as in Step 3 of Preparation 1, using 2-(4-amino-3-nitrophenylamino)-6-propylpyrimidin-4(3H)-one (4.5 g, 15.5 mmol) prepared in Step 1.

$^1$H-NMR (400 MHz, CDCl$_3$) δ 8.65 (s, 1H), 7.78 (d, 1H), 7.40 (brs, 1H), 7.19 (d, 1H), 6.81 (s, 1H), 2.70 (t, 2H), 1.81 (q, 2H), 1.03 (t, 3H)

Preparation 8. 5-(4-chloro-6-propylpyrimidin-2-ylamino)-2-fluorobenzonitrile

<Step 1> 2-fluoro-5-(6-oxo-4-propyl-1,6-dihydropyrimidin-2-ylamino)benzonitrile

A mixture of 2-(methylthio)-6-propylpyrimidin-4(3H)-one (8.8 g, 47.8 mmol) prepared in Step 1 of Preparation 1 and 5-amino-2-fluorobenzonitrile (7.9 g, 57.2 mmol) was stirred at 160° C. overnight. The reaction mixture was cooled to 70° C. and then ethanol (50 ml) was added thereto. The reaction mixture was stirred for 1 hour and then filtered to give 10 g of the titled compound as a pale brown solid. The product was used in the subsequent reaction without further purification <Step 2> 5-(4-chloro-6-propylpyrimidin-2-ylamino)-2-fluorobenzonitrile The titled compound (10.8 g) in the form of pale brown solid was prepared in accordance with the same procedures as in Step 3 of Preparation 1, using 2-fluoro-5-(6-oxo-4-propyl-1,6-dihydropyrimidin-2-ylamino)benzonitrile (10 g, 36.7 mmol) prepared in Step 1.

$^1$H-NMR (400 MHz, CDCl$_3$) δ 8.20-8.10 (m, 1H), 7.75-7.65 (m, 1H), 7.30-7.10 (m, 2H), 6.72 (s, 1H), 2.64 (t, 2H), 1.77 (q, 2H), 1.00 (t, 3H)

Preparation 9. 4-chloro-6-ethyl-N-(4-fluorophenyl)pyrimidin-2-amine

<Step 1>
6-ethyl-2-(4-fluorophenylamino)pyrimidin-4-ol

A mixture of ethylpropionyl acetate (1.03 ml, 7.18 mmol), N-(4-fluorophenyl)guanidine (1 g, 6.53 mmol), sodium methoxide (0.39 g, 7.18 mmol), and ethanol (30 ml) was refluxed under stirring overnight. The reaction mixture was cooled to room temperature and then concentrated under reduced pressure. The resulting residue was dissolved in water, acidified to pH 4 with a 1N hydrochloric acid solution, and then filtered. The resulting white solid (0.82 g) was dried in vacuo and then used in the subsequent reaction without further purification.

<Step 2> 4-chloro-6-ethyl-N-(4-fluorophenyl)pyrimidin-2-amine

6-Ethyl-2-(4-fluorophenylamino)-pyrimidin-4-ol (0.82 g, 3.52 mmol) prepared in Step 1 was added to phosphorus oxychloride (1.5 ml, 16.2 mmol), which was then stirred at 110° C. for 1 hour. After cooling to room temperature, the reaction mixture was added to ice water and then basified to pH 9 with potassium hydroxide. The aqueous layer was extracted with dichloromethane. The resulting organic layer was dried on anhydrous sodium sulfate and then concentrated under reduced pressure. The resulting residue was purified with silica gel column chromatography (ethyl acetate/n-hexane=2/1) to give 432.2 mg of the titled compound as a white solid.

$^1$H-NMR (400 MHz, CDCl$_3$) δ 7.18 (m, 2H), 7.08 (m, 2H), 6.63 (s, 1H), 2.61 (m, 2H), 1.23 (t, 3H)

Preparation 10. 4-chloro-N-(4-fluorophenyl)-6-methylpyrimidin-2-amine

<Step 1>
2-(4-fluorophenylamino)-6-methylpyrimidin-4-ol

The titled compound (8.2 g) was prepared in accordance with the same procedures as in Step 1 of Preparation 9, using ethyl acetoacetate (10 g, 76.8 mmol), N-(4-fluorophenyl) guanidine (10.7 g, 69.8 mmol) and sodium methoxide (4.2 g, 71.8 mmol). The product was used in the subsequent reaction without further purification <Step 2> 4-chloro-N-(4-fluorophenyl)-6-methylpyrimidin-2-amine The titled compound (4.5 g) in the form of white solid was prepared in accordance with the same procedures as in Step 2 of Preparation 9, using 2-(4-fluorophenylamino)-6-methylpyrimidin-4-ol (8.2 g, 37.4 mmol) prepared in Step 1 and phosphorus oxychloride (15.9 ml, 172.0 mmol).

$^1$H-NMR (400 MHz, CDCl$_3$) δ 7.57-7.54 (m, 2H), 7.21 (brs, 1H), 7.05-7.01 (m, 2H), 6.64 (s, 1H), 2.39 (s, 3H)

Preparation 11. 3-(4-butyl-6-chloropyrimidin-2-ylamino)benzonitrile

<Step 1>
6-butyl-2-(methylthio)pyrimidin-4(3H)-one

A solution of ethyl 3-oxoheptanoate (10 g, 58.1 mmol), 2-methyl-2-thiopseudourea sulfate (11.7 g, 63.9 mmol), and sodium carbonate (9.8 g, 92.9 mmol) in water (116 ml) was stirred at room temperature for 2 days and then filtered. The resulting white solid was dried in vacuo to give the titled compound (11 g). The product was used in the subsequent step without further purification.

<Step 2> 3-(4-butyl-6-oxo-1,6-dihydropyrimidin-2-ylamino)benzonitrile

A solution of 6-butyl-2-(methylthio)pyrimidin-4(3H)-one (500 mg, 2.52 mmol) prepared in Step 1 and 3-aminobenzonitrile (298 mg, 2.52 mmol) in n-butanol (3 ml) was stirred at 170° C. overnight. The reaction mixture was cooled to room temperature and then purified with silica gel column chromatography (dichloromethane/methanol=50/1) to give 310 mg of the titled compound as a brown solid.

$^1$H-NMR (400 MHz, CDCl$_3$) δ 9.47 (brs 1H), 8.27 (s, 1H), 7.80 (d, 1H), 7.37 (d, 1H), 5.88 (s, 1H), 2.58 (dd, 2H), 1.74-1.70 (m, 2H), 1.46-1.40 (m, 2H), 0.98 (t, 3H)<

Step 3> 3-(4-butyl-6-chloropyrimidin-2-ylamino) benzonitrile

The titled compound in the form of pale yellow solid was prepared in accordance with the same procedures as in Step 2 of Preparation 9, using 3-(4-butyl-6-oxo-1,6-dihydropyrimidin-2-ylamino)benzonitrile prepared in Step 2 and phosphorus oxychloride.

$^1$H-NMR (400 MHz, CDCl$_3$) δ 8.19 (s, 1H), 7.69 (d, 1H), 7.42 (t, 1H), 7.33 (d, 1H), 7.26 (brs, 1H), 6.72 (s, 1H), 2.67 (t, 2H), 1.80-1.65 (m, 2H), 1.50-1.30 (m, 2H), 0.97 (t, 3H); (Yield: 80%)

Preparation 12. 5-(4-butyl-6-chloropyrimidin-2-ylamino)-2-methylbenzonitrile

<Step 1> 5-(4-butyl-6-oxo-1,6-dihydropyrimidin-2-ylamino)-2-methylbenzonitrile

A mixture of 6-butyl-2-(methylthio)pyrimidin-4(3H)-one (800 mg, 4.03 mmol) prepared in Step 1 of Preparation 11 and 5-amino-2-methylbenzonitrile (586 mg, 4.44 mmol) was stirred at 170° C. for 6 hours. The reaction mixture was cooled to room temperature and then purified with silica gel column chromatography (dichloromethane/methanol=100/1) to give 650 mg of the titled compound as a brown solid.

$^1$H-NMR (400 MHz, CDCl$_3$) δ 9.45 (brs 1H), 8.10 (s, 1H), 7.63 (d, 1H), 7.25 (d, 1H), 5.78 (s, 1H), 2.55-2.48 (m, 5H), 1.70-1.65 (m, 2H), 1.44-1.37 (m, 2H), 0.98 (t, 3H)<

Step 2> 5-(4-butyl-6-chloropyrimidin-2-ylamino)-2-methylbenzonitrile

The titled compound in the form of white solid was prepared in accordance with the same procedures as in Step 2 of Preparation 9, using 5-(4-butyl-6-oxo-1,6-dihydropyrimidin-2-ylamino)-2-methylbenzonitrile prepared in Step 1 and phosphorus oxychloride.

$^1$H-NMR (400 MHz, CDCl$_3$) δ 8.08 (d, 1H), 7.57 (dd, 1H), 7.25 (m, 2H), 6.69 (s, 1H), 2.65 (dd, 2H), 2.51 (s, 3H), 1.75-1.68 (m, 2H), 1.45-1.36 (m, 2H), 0.96 (t, 3H); (Yield: 85%)

Preparation 13. (S)—N-[1-(2-chloro-6-propylpyrimidin-4-yl)pyrrolidin-3-yl]acetamide A solution of 2,4-dichloro-6-propylpyrimidine (1 g, 5.23 mmol) prepared in Step 1 of Preparation 2, (3S)-(−)-3-acetamidopyrrolidine (1 g, 7.85 mmol), and diisopropylethylamine (1.8 ml, 10.46 mmol) in chloroform (52 ml) was stirred at 60° C. for 1 hour. The reaction mixture was cooled to room temperature, washed by water, and then extracted with dichloromethane. The organic layer was dried on anhydrous sodium sulfate and then filtered. The filtrate was concentrated under reduced pressure. The resulting residue was purified with silica gel column chromatography (n-hexane/ethyl acetate=1/1) to give 1.2 g of the titled compound as a white solid.

$^1$H NMR (400 MHz, CDCl$_3$) δ 6.52 (brs, 1H), 6.02 (s, 1H), 4.59 (brs, 1H), 3.65-3.25 (m, 4H), 2.53 (dd, 2H), 2.28-2.24 (m, 1H), 2.02 (s, 3H), 2.02-1.98 (m, 1H), 1.74-1.65 (m, 2H), 0.96 (t, 3H)

Preparation 14. N-[1-(2-chloro-6-propylpyrimidin-4-yl)pyrrolidin-3-yl]acetamide A solution of 2,4-dichloro-6-propylpyrimidine (200 mg, 1.05 mmol) prepared in Step 1 of Preparation 2, 3-acetamidopyrrolidine (201 mg, 1.57 mmol), diisopropylethylamine (0.36 ml, 2.09 mmol) in chloroform (10.5 ml) was stirred at 40° C. for 1 hour. The reaction mixture was cooled to room temperature, washed by water, and then extracted with dichloromethane. The organic layer was dried on anhydrous sodium sulfate and then filtered. The filtrate was concentrated under reduced pressure. The resulting residue was purified with silica gel column chromatography (n-hexane/ethyl acetate=1/1) to give 205 mg of the titled compound as a white solid.

$^1$H NMR (400 MHz, CDCl$_3$) δ 6.52 (brs, 1H), 6.02 (s, 1H), 4.59 (brs, 1H), 3.65-3.25 (m, 4H), 2.53 (dd, 2H), 2.28-2.24 (m, 1H), 2.02 (s, 3H), 2.02-1.98 (m, 1H), 1.74-1.65 (m, 2H), 0.96 (t, 3H)

Preparation 15. (R)-2-chloro-4-(2-methylpyrrolidin-1-yl)-6-propylpyrimidine

A solution of 2,4-dichloro-6-propylpyrimidine (1 g, 5.23 mmol) prepared in Step 1 of Preparation 2, (R)-2-methylpyrrolidine (668 mg, 7.85 mmol), diisopropylethylamine (1.8 ml, 10.46 mmol) in chloroform (52 ml) was stirred at 60° C. for 1 hour. The reaction mixture was cooled to room temperature, washed by water, and then extracted with dichloromethane. The organic layer was dried on anhydrous sodium sulfate and then filtered. The filtrate was concentrated under reduced pressure. The resulting residue was purified with silica gel column chromatography (n-hexane/ethyl acetate=20/1) to give 910 mg of the titled compound as colorless liquid.

$^1$H NMR (400 MHz, CDCl$_3$) δ 6.00 (brs, 1H), 4.44-3.25 (m, 3H), 2.52 (dd, 2H), 2.12-1.95 (m, 3H), 1.75-1.66 (m, 3H), 1.22 (d, 3H), 0.96 (t, 3H)

Preparation 16. N$^1$-(4-butyl-6-chloropyrimidin-2-yl)-3-nitrobenzene-1,4-diamine <Step 1> 2-(4-amino-3-nitrophenylamino)-6-butylpyrimidin-4(3H)-one The titled compound in the form of yellow solid was prepared in accordance with the same procedures as in Step 2 of Preparation 11, using 6-butyl-2-(methylthio)pyrimidin-4(3H)-one prepared in Step 1 of Preparation 11 and 2-nitrobenzene-1,4-diamine.

$^1$H-NMR (400 MHz, CD$_3$OD) δ 8.45 (s 1H), 7.47 (d, 1H), 6.96 (d, 1H), 5.73 (s, 1H), 4.61 (brs, 2H), 2.45 (d, 2H), 1.71-1.67 (m, 2H), 1.42-1.37 (m, 2H), 0.96 (t, 3H); (Yield: 85%)<

Step 2> N$^1$-(4-butyl-6-chloropyrimidin-2-yl)-3-nitrobenzene-1,4-diamine

The titled compound in the form of pale yellow solid was prepared in accordance with the same procedures as in Step 2 of Preparation 9, using 2-(4-amino-3-nitrophenylamino)-6-butylpyrimidin-4(3H)-one prepared in Step 1 and phosphorus oxychloride.

$^1$H NMR (400 MHz, CDCl$_3$) δ 8.65 (s, 1H), 7.77 (d, 1H), 7.48 (brs, 1H), 7.20 (d, 1H), 6.80 (s, 1H), 2.72 (dd, 2H), 1.77-1.71 (m, 2H), 1.46-1.40 (m, 2H), 0.98 (t, 3H); (Yield: 37%)

Preparation 17. (R)-3-hydroxypyrrolidine hydrochloride

Hydrogen chloride gas was added at 0° C. to a solution of (R)-1-(tert-butoxycarbonyl)-3-pyrrolidinol (3 g, 16.0 mmol) in ethyl acetate (100 ml). The reaction mixture was stirred at room temperature overnight and then filtered. The resulting white solid was dried in vacuo to give 1.3 g of the titled compound.

$^1$H-NMR (400 MHz, CD$_3$OD) δ 4.55 (m, 1H), 3.41-3.36 (m, 2H), 3.22 (m, 2H), 2.06-2.04 (m, 2H)

Preparation 18. (S)-3-methoxypyrrolidine

<Step 1> (S)-3-methoxypyrrolidin-1-carboxylic acid tert-butyl ester

Sodium hydride (32 mg, 0.81 mmol, 60 wt %) was added at 0° C. to a solution of (S)-1-(tert-butoxycarbonyl)-3-pyrrolidinol (100 mg, 0.53 mmol) in N,N-dimethylformamide (2 ml). The reaction mixture was stirred for 30 minutes and iodomethane (99.7 μl, 1.60 mmol) was added thereto. The reaction mixture was stirred at room temperature overnight and then water was added thereto. The reaction mixture was concentrated under reduced pressure. The resulting residue was dissolved in dichloromethane. The resulting solution was washed with water, dried on anhydrous sodium sulfate, and then concentrated under reduced pressure. The resulting residue was purified with silica gel column chromatography (n-hexane/ethyl acetate=5/2) to give 50 mg of the titled compound as colorless oil.

$^1$H-NMR (400 MHz, CDCl$_3$) δ 4.55 (m, 1H), 3.41-3.36 (m, 2H), 3.22 (m, 2H), 2.06-2.04 (m, 2H)<

Step 2> (S)-3-methoxypyrrolidine

Trifluoroacetic acid (0.5 ml) was added to a solution of (S)-3-methoxypyrrolidin-1-carboxylic acid tert-butyl ester (50 mg, 0.25 mmol) prepared in Step 1 in dichloromethane (5 ml). The reaction mixture was stirred at room temperature for 1 hour and then concentrated under reduced pressure. The resulting residue was dissolved in dichloromethane and then basified with an aqueous saturated solution of sodium bicarbonate. The resulting organic layer was dried on anhydrous sodium sulfate and then concentrated under reduced pressure to give 7.5 mg of the titled compound as pale yellow oil. The product was used in the subsequent step without further purification.

Preparation 19. 2,5-diaminobenzonitrile

A mixture of 5-nitroanthranilonitrile (200 mg, 1.23 mmol) and palladium/charcoal (10 mg, 10 wt %) in methanol (3 ml) was stirred at room temperature under hydrogen atmosphere overnight and then filtered through a celite pad. The resulting filtrate was concentrated under reduced pressure. The resulting residue was purified with silica gel column chromatography (n-hexane/ethyl acetate=1/2) to give 160.3 mg of the titled compound as a pale yellow solid.

$^1$H-NMR (400 MHz, CDCl$_3$) δ 6.79 (d, 1H), 6.72 (s, 1H), 6.61 (d, 1H), 4.01 (brs, NH), 3.45 (brs, NH)

Preparation 20. (S)-[1-(2-chloro-6-propylpyrimidin-4-yl)pyrrolidin-2-yl]methanol The titled compound in the form of colorless oil was prepared in accordance with the same procedures as Step 2 of Preparation 2, using 2,4-dichloro-6-propylpyrimidine prepared in Step 1 of Preparation 2 and (S)-(+)-2-pyrrolidinemethanol.

¹H-NMR (400 MHz, CDCl₃) δ 6.08 (s, 1H), 4.79 (br, 1H), 4.34 (br, 1H), 3.74 (m, 1H), 3.65 (m, 1H), 3.47-3.39 (m, 2H), 2.54 (t, 2H), 2.11-2.01 (m, 3H), 1.99 (br, 1H), 1.76 (m, 2H), 1.62 (s, 1H), 0.92 (t, 3H); (Yield: 47%)

Preparation 21. (S)-tert-butyl 1-(2-chloro-6-propylpyrimidin-4-yl)pyrrolidin-3-ylcarbamate 2,4-Dichloro-6-propylpyrimidine (1.5 g, 7.85 mmol) prepared in Step 1 of Preparation 2 was dissolved in ethanol (10 ml) and then (3S)-(-)-3-(tert-butoxycarbonylamino)pyrrolidine (2.9 g, 15.7 mmol) was added thereto at 0° C. The reaction mixture was stirred at room temperature overnight and then concentrated under reduced pressure. The resulting residue was purified with silica gel column chromatography (n-hexane/ethyl acetate=1/1) to give 1.2 g of the titled compound as a white solid.

¹H-NMR (400 MHz, CDCl₃) δ 6.02 (s, 1H), 4.67 (br, 1H), 4.33 (br, 1H), 3.84 (br, 2H), 3.24 (br, 2H), 2.54 (t, 2H), 2.26 (m, 1H), 1.93 (br, 1H), 1.71 (m, 2H), 1.45 (s, 9H), 0.95 (t, 3H)

Preparation 22. 1H-benzo[d]imidazol-5-amine 5-nitrobenzimidazole (200 mg, 1.2 mmol) was dissolved in a mixed solvent of methanol and tetrahydrofuran (1:1, 10 ml) and then palladium/charcoal (200 mg, 10 wt %) was added thereto. The reaction mixture was stirred at room temperature under hydrogen atmosphere (30 bar) for 3 hours and then filtered through a celite pad. The resulting filtrate was concentrated under reduced pressure to give 150 mg of the titled compound as a pale yellow solid. The product was used in the subsequent reaction without further purification.

Preparation 23. 2-methylbenzene-1,4-diamine

The titled compound (54 mg) in the form of pale yellow solid was prepared in accordance with the same procedures as in Preparation 22, using 2-methyl-4-nitroaniline. The product was used in the subsequent reaction without further purification.

Preparation 24. (S)—N-[1-(6-butyl-2-chloropyrimidin-4-yl)pyrrolidin-3-yl]acetamide <Step 1> 6-butylpyrimidin-2,4-diol A mixture of 6-butyl-2-(methylthio)pyrimidin-4(3H)-one (2.1 g, 10.6 mmol) prepared in Step 1 of Preparation 11, acetic acid (15 ml) and water (7 ml) was refluxed under stirring for 2 days. The reaction mixture was cooled to room temperature and then concentrated under reduced pressure. The resulting residue was dried in vacuo to give 1.7 g of the titled compound as a pale yellow solid.

¹H-NMR (400 MHz, DMSO-d₆) δ 10.87 (brs, OH), 10.78 (brs, OH), 5.31 (s, 1H), 2.27 (m, 2H), 1.50 (m, 2H), 1.27 (m, 2H), 0.88 (t, 3H)<

Step 2> 4-butyl-2,6-dichloropyrimidine

A mixture of 6-butylpyrimidin-2,4-diol (1.7 g, 10.2 mmol) prepared in Step 1 and phosphorus oxychloride (5 ml) was refluxed under stirring for 1 hour. The reaction mixture was cooled to room temperature, added to ice water, and then basified to pH 8 with sodium bicarbonate. The aqueous layer was extracted with ethyl acetate. The resulting organic layer was dried on anhydrous magnesium sulfate and then concentrated under reduced pressure. The resulting residue was purified with silica gel column chromatography (ethyl acetate/n-hexane=1/50) to give 1.435 g of the titled compound as brown oil.

¹H-NMR (400 MHz, CDCl₃) δ 7.16 (s, 1H), 2.75 (t, 2H), 1.71 (m, 2H), 1.40 (m, 2H), 0.95 (t, 3H)<

Step 3> (S)—N-[1-(6-butyl-2-chloropyrimidin-4-yl)pyrrolidin-3-yl]acetamide

The titled compound in the form of colorless oil was prepared in accordance with the same procedures as in Preparation 13, using 4-butyl-2,6-dichloropyrimidine prepared in Step 2 and (3S)-(-)-3-acetamidopyrrolidine.

¹H-NMR (400 MHz, CDCl₃) δ 7.25 (brs, NH), 6.02 (s, 1H), 4.54 (m, 1H), 3.64-3.41 (m, 4H), 2.54 (t, 2H), 2.24 (m, 1H), 2.04-2.01 (m, 1H+3H), 1.63 (m, 2H), 1.36 (m, 2H), 0.93 (t, 3H); (Yield: 56%)

Preparation 25. (S)-tert-butyl 1-(6-butyl-2-chloropyrimidin-4-yl)pyrrolidin-3-yl(methyl)carbamate Diisopropylethylamine (4.46 ml, 25.6 mmol) was added to a solution of 4-butyl-2,6-dichloropyrimidine (2.5 g, 12.1 mmol) prepared in Step 2 of Preparation 24 and (3S)-(-)-3-(methylamino)pyrrolidine (1.43 ml, 13.4 mmol) in chloroform (50 ml). The reaction mixture was stirred at 50° C. for 3 hours and then di-tert-butyldicarbonate (2.66 g, 12.2 mmol) was added thereto. The reaction mixture was stirred at room temperature overnight, washed with water, dried on anhydrous magnesium sulfate, and then concentrated under reduced pressure. The resulting residue was purified with silica gel column chromatography (ethyl acetate/n-hexane=1/5) to give 3.29 g of the titled compound as colorless oil.

¹H-NMR (400 MHz, CDCl₃) δ 6.02 (s, 1H), 4.81 (m, 1H), 3.50 (m, 4H), 2.80 (s, 3H), 2.56 (t, 2H), 2.17 (m, 1H), 1.67 (m, 2H), 1.48 (s, 9H+1H), 1.36 (m, 2H), 0.93 (t, 3H)

Preparation 26. (S)-tert-butyl 1-(6-butyl-2-chloropyrimidin-4-yl)pyrrolidin-3-yl(ethyl)carbamate The titled compound in the form of pale yellow oil was prepared in accordance with the same procedures as in Preparation 25, using 4-butyl-2,6-dichloropyrimidine prepared in Step 2 of Preparation 24 and (3S)-(-)-3-(ethylamino)pyrrolidine.

¹H-NMR (400 MHz, CDCl₃) δ 6.00 (s, 1H), 4.64 (m, 1H), 3.91-3.14 (m, 6H), 2.55 (t, 2H), 2.18 (m, 1H), 1.65 (m, 2H), 1.47 (s, 9H+1H), 1.37 (m, 2H), 1.15 (t, 3H), 0.92 (t, 3H); (Yield: 74%)

Preparation 27. (S)—N-[1-(2-chloro-6-propylpyrimidin-4-yl)pyrrolidin-3-yl]-2-hydroxyacetamide <Step 1> (S)-1-(2-chloro-6-propylpyrimidin-4-yl)pyrrolidin-3-amine Diisopropylethylamine (1.09 ml, 6.28 mmol) was added to a solution of 2,4-dichloro-6-propylpyrimidine (1 g, 5.23 mmol) prepared in Step 1 of Preparation 2 and (S)-(-)-3-aminopyrrolidine (0.55 ml, 6.28 mmol) in ethanol (30 ml), which was then stirred at room temperature overnight. Dichloromethane was added to the reaction mixture, which was then washed with water. The organic layer was dried on anhydrous magnesium sulfate, and then concentrated under reduced pressure. The resulting residue was used in the subsequent reaction without further purification.

<Step 2> (S)—N-[1-(2-chloro-6-propylpyrimidin-4-yl)pyrrolidin-3-yl]-2-hydroxyacetamide A mixture of (S)-1-(2-chloro-6-propylpyrimidin-4-yl)pyrrolidin-3-amine (1.25 g, 5.23 mmol) prepared in Step 1, glycolic acid (0.44 g, 5.79 mmol), N-(3-dimethylaminopropyl)-N'-ethylcarbodiimide hydrochloride (1.1 g, 5.79 mmol), 1-hydroxybenzotriazole hydrate (0.78 g, 5.79 mmol), diisopropylethylamine (1.8 ml, 10.3 mmol), and dichloromethane (30 ml) was stirred at room temperature for 3 days. The reaction mixture was diluted with dichloromethane, washed with water and an aqueous saturated solution of sodium bicarbonate, dried on anhydrous sodium sulfate, and then concentrated under reduced pressure. The resulting residue was purified with silica gel column chromatography (dichloromethane/methanol=20/1) to give 680 mg of the titled compound as a white solid.
$^1$H-NMR (400 MHz, CDCl$_3$) δ 6.65 (s, NH), 6.03 (s, 1H), 4.65 (m, 1H), 4.14 (s, 2H), 3.80-3.41 (m, 4H), 2.54 (t, 2H), 2.39 (m, 1H), 2.10 (m, 1H), 1.72 (m, 2H), 0.96 (t, 3H)

Preparation 28. (S)-tert-butyl 1-(2-chloro-6-propylpyrimidin-4-yl)pyrrolidin-3-yl(methyl)carbamate 2,4-Dichloro-6-propylpyrimidine (2 g, 10.5 mmol) prepared in Step 1 of Preparation 2 and diisopropylethylamine (4.6 ml, 26.3 mmol) were dissolved in chloroform (100 ml) and (3S)-(–)-3-(methylamino)pyrrolidine (1.1 g, 10.5 mmol) was added thereto at room temperature. The reaction mixture was then stirred at 50° C. for 1 hour and then cooled to room temperature. Di-tert-butyl dicarbonate (2.5 g, 11.6 mmol) was added to the reaction mixture, which was then was stirred at 50° C. for 1 hour. Water was added to the reaction mixture, which was then extracted with ethyl acetate. The organic layer was dried on anhydrous sodium sulfate, filtered, and then concentrated under reduced pressure. The resulting residue was purified with silica gel column chromatography (n-hexane/ethyl acetate=3/1) to give 2.1 g of the titled compound as pale yellow oil.
$^1$H-NMR (400 MHz, CDCl$_3$) δ 6.02 (s, 1H), 4.85 (brs, 1H), 4.00-3.10 (m, 4H), 2.80 (s, 3H), 2.54 (t, 2H), 2.30-2.00 (m, 2H), 1.80-1.60 (m, 2H), 1.48 (s, 9H), 0.96 (t, 3H)

Preparation 29. (S)-tert-butyl 1-(2-chloro-6-propylpyrimidin-4-yl)pyrrolidin-3-yl(ethyl)carbamate The titled compound in the form of white solid was prepared in accordance with the same procedures as in Preparation 28, using 2,4-dichloro-6-propylpyrimidine prepared in Step 1 of Preparation 2 and (3S)-(–)-3-(ethylamino)pyrrolidine.
$^1$H-NMR (400 MHz, CDCl$_3$) δ 6.01 (s, 1H), 4.63 (brs, 1H), 3.91 (brs, 1H), 3.70-3.10 (m, 5H), 2.53 (t, 2H), 2.30-2.05 (m, 2H), 1.72 (q, 2H), 1.48 (s, 9H), 1.15 (t, 3H), 0.95 (t, 3H); (Yield: 65%)

Preparation 30. 4-chloro-N-[4-fluoro-3-(trifluoromethyl)phenyl]-6-propylpyrimidin-2-amine <Step 1> 2-{[4-fluoro-3-(trifluoromethyl)phenyl]amino}-6-propylpyrimidin-4(3H)-one A mixture of 2-(methylthio)-6-propylpyrimidin-4(3H)-one (1.8 g, 9.8 mmol) prepared in Step 1 of Preparation 1 and 5-amino-2-fluorobenzotrifluoride (2 g, 11.2 mmol) was stirred at 160° C. overnight. The reaction mixture was cooled to 80° C. and then ethyl acetate (20 ml) was added thereto. The reaction mixture was refluxed under stirring for 1 hour and then filtered to give 2.2 g of the titled compound as a white solid.
$^1$H-NMR (400 MHz, CD$_3$OD) δ 8.20 (s, 1H), 7.80-7.70 (m, 1H), 7.29 (t, 1H), 5.81 (s, 1H), 2.46 (t, 2H), 1.73 (q, 2H), 0.98 (t, 3H)<

Step 2> 4-chloro-N-[4-fluoro-3-(trifluoromethyl)phenyl]-6-propylpyrimidin-2-amine A mixture of 2-{[4-fluoro-3-(trifluoromethyl)phenyl]amino}-6-propylpyrimidin-4(3H)-one (2.2 g, 7.0 mmol) prepared in Step 1 and phosphorus oxychloride (10 ml) was stirred at 110° C. overnight. The reaction mixture was cooled to room temperature, added to ice water, and then basified to pH 9 with sodium hydroxide. The aqueous layer was extracted with ethyl acetate. The resulting organic layer was dried on anhydrous sodium sulfate and then concentrated under reduced pressure. The resulting residue was purified with silica gel column chromatography (n-hexane/ethyl acetate=4/1) to give 2 g of the titled compound as a yellow solid.
$^1$H-NMR (400 MHz, CDCl$_3$) δ 8.27 (brs, 1H), 8.09 (s, 1H), 7.71 (d, 1H), 7.16 (t, 1H), 6.69 (s, 1H), 2.64 (t, 2H), 1.76 (q, 2H), 0.98 (t, 3H)

The synthetic method for the compounds (including the salt thereof) of the present invention is described in the following working examples. And also, the compounds of the following working examples and the NMR spectrum data are shown in the subsequent Tables 1-1 to 1-51.

Example 1

A solution of 4-chloro-N-(4-fluorophenyl)-6-propylpyrimidin-2-amine (20 mg, 0.08 mmol) prepared in Preparation 1 and pyrrolidine (25 mg, 0.35 mmol) in isopropanol (1 ml) was stirred at 100° C. overnight. The reaction mixture was cooled to room temperature and then concentrated under reduced pressure. The resulting residue was purified with silica gel column chromatography (n-hexane/ethyl acetate=4/1) to give 20 mg of the product as a pale yellow solid.

Examples 2 to 24

The products of Examples 2 to 24 were prepared in accordance with the same procedures as in Example 1, using 4-chloro-N-(4-fluorophenyl)-6-propylpyrimidin-2-amine prepared in Preparation 1; and (S)-2-pyrrolidinemethanol, 3-pyrrolidinol, D-prolinol, DL-prolinol, 2-methylpyrrolidine, (S)-2-(methoxymethyl)pyrrolidine, (R)-2-(methoxymethyl)pyrrolidine, (S)-pyrrolidin-2-carboxamide, 3-acetamidopyrrolidine, (3R)-(+)-3-acetamidopyrrolidine, 2,2,2-trifluoro-N-(pyrrolidin-3-yl)acetamide, 3-(ethylamino)pyrrolidine, 3-(dimethylamino)pyrrolidine, (S)-(+)-1-(2-pyrrolidinylmethyl)pyrrolidine, (S)-(+)-2-(anilinomethyl)pyrrolidine, (3S)-(–)-3-acetamidopyrrolidine, (3S)-(–)-3-(ethylamino)pyrrolidine, (3S)-(–)-3-(tert-butoxycarbonylamino)pyrrolidine, 3-aminopyrrolidine, 3-(diethylamino)pyrrolidine, (3S)-(–)-3-(methylamino)pyrrolidine, 3-(N-acetyl-N-methylamino)pyrrolidine, or (S)-3-pyrrolidinol.

Example 25

A solution of 4-chloro-N-(4-fluorophenyl)-6-propylpyrimidin-2-amine (20 mg, 0.08 mmol) prepared in Preparation 1 and 3-(ethylamino)pyrrolidine (0.25 g, 2.25 mmol) in isopropanol (3 ml) was stirred at 100° C. overnight. The reaction mixture was cooled to room temperature and then concentrated under reduced pressure. The resulting residue was purified with silica gel column chromatography (n-hexane/ethyl acetate=1/2) and then dissolved in ethyl acetate (2 ml). Hydrogen chloride gas was added to the resulting solution and then filtered to give 0.33 g of the product as a white solid.

Example 26

A mixture of (S)-2-chloro-4-[2-(methoxymethyl)pyrrolidin-1-yl]-6-propylpyrimidine (0.4 g, 1.4 mmol) prepared in Preparation 2 and 6-aminoindole (0.28 g, 2.1 mmol) in n-butanol (1 ml) was refluxed under stirring overnight. The reaction mixture was cooled to room temperature and then filtered to give 0.25 g of the product as a pale yellow solid.

Example 27

A mixture of (S)-2-chloro-4-[2-(methoxymethyl)pyrrolidin-1-yl]-6-propylpyrimidine (20 mg, 0.07 mmol) prepared in Preparation 2 and 5-aminoindole (30 mg, 0.23 mmol) in n-butanol (1 ml) was refluxed under stirring overnight. The reaction mixture was cooled to room temperature and then concentrated under reduced pressure. The resulting residue was purified with silica gel column chromatography (n-hexane/ethyl acetate=1/1) to give 5.2 mg of the product as a pale yellow solid.

Examples 28 to 46

The products of Examples 28 to 46 were prepared in accordance with the same procedures as in Example 27, using (S)-2-chloro-4-[2-(methoxymethyl)pyrrolidin-1-yl]-6-propylpyrimidine prepared in Preparation 2; and 4-methoxyaniline, 3-methoxyaniline, 3-chloroaniline, 4-fluoro-3-nitroaniline, 3-nitroaniline, 4-chloro-3-nitroaniline, 3-aminobenzonitrile, 3-(methylthio)aniline, 3-(trifluoromethyl)aniline, 7-amino-4-methyl-2H-chromen-2-one, 5-chloro-2-methylaniline, 4-amino-2-chlorotoluene, 4-methyl-3-nitroaniline, 4-fluoro-3-(trifluoromethyl)aniline, 2-(trifluoromethyl)benzene-1,4-diamine, 5-amino-2-fluorobenzonitrile, 5-amino-2-methylbenzonitrile, 2,5-diaminobenzonitrile prepared in Preparation 19, or 2-nitro-1,4-phenylenediamine.

Example 47

(S)-tert-Butyl 1-[2-(4-fluorophenylamino)-6-propylpyrimidin-4-yl]pyrrolidin-3-ylcarbamate (10 mg, 0.02 mmol) prepared in Example 19 was dissolved in ethyl acetate (1 ml) and then hydrogen chloride gas was added thereto. The reaction mixture was stirred at room temperature for 1 hour and then filtered to give 7 mg of the product as a white solid.

Examples 48 to 58

The products of Examples 48 to 58 were prepared in accordance with the same procedures as in Example 1, using 3-(4-chloro-6-propylpyrimidin-2-ylamino)benzonitrile prepared in Preparation 3; and (3S)-(−)-3-(tert-butoxycarbonylamino)pyrrolidine, 3-(diethylamino)pyrrolidine, (3S)-(−)-3-(methylamino)pyrrolidine, 3-(N-acetyl-N-methylamino)pyrrolidine, (S)-3-pyrrolidinol, (R)-(−)-2-methylpyrrolidine, (3S)-(−)-3-acetamidopyrrolidine, (3S)-(−)-3-(ethylamino)pyrrolidine, (3S)-(−)-3-(N-tert-butoxycarbonylaminomethyl)pyrrolidine, (R)-3-hydroxypyrrolidine hydrochloride prepared in Preparation 17, or (S)-3-methoxypyrrolidine prepared in Preparation 18.

Example 59

The product in the form of white solid was prepared in accordance with the same procedures as in Example 25, using 3-(4-chloro-6-propylpyrimidin-2-ylamino)benzonitrile prepared in Preparation 3 and 3-(methylamino)pyrrolidine.

Example 60

The product in the form of white solid was prepared in accordance with the same procedures as in Example 47, using (S)-tert-Butyl 1-[2-(3-cyanophenylamino)-6-propylpyrimidin-4-yl]pyrrolidin-3-ylcarbamate prepared in Example 48.

Example 61

A mixture of (S)-3-[4-(3-aminopyrrolidin-1-yl)-6-propylpyrimidin-2-ylamino]benzonitrile dihydrochloride (20 mg, 0.05 mmol) prepared in Example 60, butyric acid (7 mg, 0.08 mol), (benzotriazole-1-yloxy)-tris-(dimethylamino) phosphonium hexafluorophosphate (31.8 mg, 0.06 mmol), diisopropylethylamine (25.9 mg, 0.2 mmol), and N,N-dimethylformamide (1 ml) was stirred at room temperature overnight. Water was added to the reaction mixture, which was then extracted with ethyl acetate. The organic layer was washed with brine, dried on anhydrous magnesium sulfate, filtered, and then concentrated under reduced pressure. The resulting residue was purified with silica gel column chromatography (n-hexane/ethyl acetate=1/1) to give 10.5 mg of the product as a pale yellow solid.

Examples 62 to 82

The products of Examples 62 to 82 were prepared in accordance with the same procedures as in Example 61, using (S)-3-[4-(3-aminopyrrolidin-1-yl)-6-propylpyrimidin-2-ylamino]benzonitrile dihydrochloride prepared in Example 60; and cyclopentanecarboxylic acid, 1-piperidinepropionic acid, benzoic acid, 4-fluorobenzoic acid, phenylacetic acid, 4-fluorophenylacetic acid, 3-phenoxypropionic acid, 3-isobutoxypropanoic acid, 2-(4-benzylpiperazin-1-yl) acetic acid, 2-(piperidin-1-yl)acetic acid, 3-benzoylpropionic acid, 4-aminophenylacetic acid, cyclopentylacetic acid, methoxyacetic acid, 2-pyridylacetic acid, 3-pyridylacetic acid, 4-pyridylacetic acid, trans-styrylacetic acid, 2-thiopheneacetic acid, isobutanoic acid or 3,3,3-trifluoropropanoic acid.

Example 83

A mixture of 3-(4-chloro-6-propylpyrimidin-2-ylamino) benzonitrile (20 mg, 0.07 mmol) prepared in Preparation 3,2-pyrrolidone (9.4 mg, 0.11 mmol), palladium acetate (0.16 mg, 0.7 µmol), 4,5-bis(diphenylphosphino)-9,9-dimethylxanthene (1.3 mg, 2.1 µmol), cesium carbonate (71.4 mg, 0.22 mmol), and 1,4-dioxane (1 ml) was stirred at 110° C. overnight and then concentrated under reduced pressure. The resulting residue was purified with silica gel column chromatography (n-hexane/ethyl acetate=4/1) to give 5 mg of the product as a pale yellow solid.

Example 84

(S)-3-[4-(3-Aminopyrrolidin-1-yl)-6-propylpyrimidin-2-ylamino]benzonitrile dihydrochloride (20 mg, 0.05 mmol) prepared in Example 60 and hexylaldehyde (5 mg, 0.05 mmol) in methanol (1 ml) was stirred at room temperature for 30 minutes and sodium cyanoborohydride (9.4 mg, 0.15 mmol) was added thereto. The reaction mixture was stirred at room temperature for 3 hours and then an aqueous saturated solution of sodium bicarbonate was added thereto to terminate the reaction. The reaction mixture was extracted with ethyl acetate. The organic layer was dried on anhydrous sodium sulfate, filtered, and then concentrated. The resulting residue was purified with silica gel column chromatography (n-hexane/ethyl acetate=1/1) to give 10 mg of the product as a pale yellow solid.

Examples 85 to 117

The products of Examples 85 to 117 were prepared in accordance with the same procedures as in Example 84, using (S)-3-[4-(3-aminopyrrolidin-1-yl)-6-propylpyrimidin-2-ylamino]benzonitrile dihydrochloride prepared in Example 60; and propionaldehyde, cyclohexanecarboxaldehyde, benzaldehyde, phenylacetaldehyde, 3-phenylpropionaldehyde, 3-fluorobenzaldehyde, 4-hydroxybenzaldehyde, 4-ethylbenzaldehyde, 3-methylbutanal, pentanal, 2-methylbutanal, 2-methylpropanal, 4-methoxybenzaldehyde, 4-fluorobenzaldehyde, cyclopropanecarboxaldehyde, cyclopropanecarboxaldehyde (2 eq.), 2-pyridinecarboxaldehyde, 3-pyridinecarboxaldehyde, 4-pyridinecarboxaldehyde, 2-ethylbutanal, pivaldehyde, 2-fluorobenzaldehyde, 3-(trifluoromethyl)benzaldehyde, 4-(trifluoromethyl)benzaldehyde, 4-acetoxybenzaldehyde, 4-(dimethylamino)benzaldehyde, pyrrole-2-carboxaldehyde, thiophene-2-carboxaldehyde, thiophene-3-carboxaldehyde, butanal (2 eq.), 3-(methylthio)propionaldehyde (2 eq.), butanal, or 3-(methylthio)propionaldehyde.

Example 118

(S)-3-{4-Propyl-6-[3-(propylamino)pyrrolidin-1-yl]pyrimidin-2-ylamino}benzonitrile (20 mg, 0.05 mmol) prepared in Example 85 was dissolved in ethyl acetate (1 ml) and hydrochloric acid was added thereto. The reaction mixture was stirred at room temperature for 1 hour and then filtered to give 15.5 mg of the product as a white solid.

Examples 119

The product in the form of white solid was prepared in accordance with the same procedures as in Example 118, using (S)-3-{4-[3-(cyclopropylmethylamino)pyrrolidin-1-yl]-6-propylpyrimidin-2-ylamino}benzonitrile prepared in Example 99.

Examples 120

The product in the form of white solid was prepared in accordance with the same procedures as in Example 118, using (S)-3-{4-[3-(methylamino)pyrrolidin-1-yl]-6-propylpyrimidin-2-ylamino}benzonitrile prepared in Example 50.

Example 121

The product in the form of pale yellow solid was prepared in accordance with the same procedures as in Example 1, using N-(4-chloro-6-propylpyrimidin-2-yl)-1H-indol-6-amine prepared in Preparation 4 and (3S)-(−)-3-(methylamino)pyrrolidine.

Example 122

A mixture of (S)-1-(2-chloro-6-propylpyrimidin-4-yl)-N-methylpyrrolidin-3-amine (0.4 g, 1.57 mmol) prepared in Preparation 5 and 6-aminoindole (0.21 g, 1.57 mmol) in n-butanol (2 ml) was refluxed under stirring overnight. The reaction mixture was cooled to room temperature and then filtered. The resulting solid was dried to give 0.2 g of the product as a pale yellow solid.

Example 123

A mixture of (S)-1-(2-chloro-6-propylpyrimidin-4-yl)-N-methylpyrrolidin-3-amine (1 g, 3.93 mmol) in prepared in Preparation 5 and 2-(trifluoromethyl)-1,4-phenylenediamine (0.7 g, 3.93 mmol) in n-butanol (10 ml) was refluxed under stirring overnight. The reaction mixture was cooled to room temperature and then concentrated under reduced pressure. The resulting residue was diluted with dichloromethane, washed with an aqueous saturated solution of sodium bicarbonate, dried on anhydrous sodium sulfate, and then concentrated under reduced pressure. The resulting residue was purified with silica gel column chromatography (dichloromethane/methanol=10/1) and then dissolved in ethyl acetate (10 ml). Hydrogen chloride gas was added to the solution and then filtered to give 0.4 g of the product as a white solid.

Example 124

A mixture of (S)-3-[4-(3-aminopyrrolidin-1-yl)-6-propylpyrimidin-2-ylamino]benzonitrile dihydrochloride (20 mg, 0.05 mmol) prepared in Example 60, triethylamine (20 mg, 0.2 mmol), isopropylsulfonyl chloride (8 mg, 0.05 mmol), and N,N-dimethylformamide (1 ml) was stirred at room temperature for 4 hours. Water was added to the reaction mixture, which was then extracted with ethyl acetate. The organic layer was washed with brine, dried on anhydrous magnesium sulfate, filtered, and then concentrated under reduced pressure. The resulting residue was purified with silica gel column chromatography (n-hexane/ethyl acetate=1/1) to give 9.5 mg of the product as a pale yellow solid.

Examples 125 and 126

The products of Examples 125 and 126 were prepared in accordance with the same procedures as in Example 124, using (S)-3-[4-(3-aminopyrrolidin-1-yl)-6-propylpyrimidin-2-ylamino]benzonitrile dihydrochloride prepared in Example 60; and methanesulfonyl chloride or 4-fluorobenzenesulfonyl chloride.

Example 127

A solution of (S)-3-[4-(3-aminopyrrolidin-1-yl)-6-propylpyrimidin-2-ylamino]benzonitrile dihydrochloride (30 mg, 0.08 mmol) prepared in Example 60 and methyl ethyl ketone (18 mg, 0.25 mmol) in methanol (0.8 ml) was stirred at room temperature for 30 minutes. Sodium triacetoxyborohydride (71.2 mg, 0.34 mmol) and a catalytic amount of acetic acid were added thereto. The reaction mixture was stirred at room temperature overnight and then an aqueous saturated solution of sodium bicarbonate was added thereto to terminate the reaction. The reaction mixture was extracted with dichloromethane. The organic layer was dried on anhydrous sodium sulfate, filtered, and then concentrated. The resulting residue was purified with silica gel column chromatography (dichloromethane/methanol=50/1) to give 32 mg of the product as a white solid.

Examples 128 to 145

The products of Examples 128 to 145 were prepared in accordance with the same procedures as in Example 127, using (S)-3-[4-(3-aminopyrrolidin-1-yl)-6-propylpyrimidin-2-ylamino]benzonitrile dihydrochloride prepared in Example 60; and 3-pentanone, 2,6-dimethyl-4-heptanone, 4,4-dimethyl-2-pentanone, 3-hydroxy-3-methyl-2-butanone, 4-heptanone, 2-hexanone, 5-methyl-2-hexanone, cyclohexanone, tert-butyl 2-oxoethylcarbamate, 1-benzyl-4-piperidinone, acetone, 1-benzoyl-4-piperidone, 1-acetyl-4-piperidone, cyclooctanone, cyclobutanone, cyclopentanone, tert-butyl 3-oxoazetidine-1-carboxylate, or 2-benzyloxyacetaldehyde.

Example 146

A mixture of (S)-3-[4-(3-aminopyrrolidin-1-yl)-6-propylpyrimidin-2-ylamino]benzonitrile dihydrochloride (18 mg, 0.05 mmol) prepared in Example 60, propionic acid (4.6 µl, 0.06 mmol), N-(3-dimethylaminopropyl)-N'-ethylcarbodiimide hydrochloride (11.8 mg, 0.06 mmol), 1-hydroxybenzotriazole hydrate (8.3 mg, 0.06 mmol), diisopropylethylamine (19.4 µl, 0.11 mmol), and dichloromethane (1 ml) was stirred at room temperature overnight. The reaction mixture was diluted with dichloromethane, washed with water and an aqueous saturated solution of sodium bicarbonate, dried on anhydrous sodium sulfate, and then concentrated under reduced pressure. The resulting residue was purified with silica gel column chromatography (dichloromethane/methanol=70/1) to give 13.4 mg of the product as a white solid.

Examples 147 to 167

The products of Examples 147 to 167 were prepared in accordance with the same procedures as in Example 146, using (S)-3-[4-(3-aminopyrrolidin-1-yl)-6-propylpyrimidin-2-ylamino]benzonitrile dihydrochloride prepared in Example 60; and pivalic acid, 2,2-dimethylbutyric acid, tiglic acid, hexanoic acid, 3-phenylpropionic acid, indole 3-acetic acid, 2-hydroxyisobutyric acid, 3-(4-methoxyphenyl)propionic acid, 3-(4-hydroxyphenyl)propionic acid, levulinic acid, glycolic acid, benzyloxyacetic acid, phenoxyacetic acid, N,N-dimethylglycine hydrochloride, 3-(dimethylamino)propionic acid hydrochloride, 4-(dimethylamino) butyric acid hydrochloride, ethoxyacetic acid, 2-(2-methoxyethoxy)acetic acid, benzyloxycarbonylaminoacetic acid, N-(tert)-butoxycarbonyl-L-γ-aminobutyric acid, or piperidine-1,4-dicarboxylic acid mono tert-butyl ester.

Example 168

A solution of (R)-2-chloro-4-(2-methylpyrrolidin-1-yl)-6-propylpyrimidine (20 mg, 0.083 mmol) prepared in Preparation 15 and 5-amino-2-methylbenzonitrile (12.6 mg, 0.091 mmol) in n-butanol (0.5 ml) was reacted in a microwave reactor (450 W) for 40 minutes. The reaction mixture was cooled to room temperature and then concentrated under reduced pressure. The resulting residue was purified with silica gel column chromatography (dichloromethane/methanol=50/1) and then dissolved in ethyl acetate (1 ml). Hydrogen chloride gas was added to the solution, which was then stirred at room temperature for 1 hour. The reaction mixture was filtered to give 9 mg of the product as a white solid.

Example 169

The product in the form of white solid was prepared in accordance with the same procedures as in Example 168, using (R)-2-chloro-4-(2-methylpyrrolidin-1-yl)-6-propylpyrimidine prepared in Preparation 15 and 2,5-diaminobenzonitrile prepared in Preparation 19.

Examples 170 and 171

The products of Examples 170 and 171 were prepared in accordance with the same procedures as in Example 1, using 5-(4-chloro-6-propylpyrimidin-2-ylamino)-2-methylbenzonitrile prepared in Preparation 6; and (3S)-(−)-3-(methylamino)pyrrolidine or (3S)-(−)-3-(ethylamino)pyrrolidine.

Example 172

A mixture of 5-(4-chloro-6-propylpyrimidin-2-ylamino)-2-methylbenzonitrile (20 mg, 0.07 mmol) prepared in Preparation 6 and (3S)-(−)-3-(ethylamino)pyrrolidine (8 mg, 0.07 mmol) in isopropanol (1 ml) was refluxed under stirring overnight. The reaction mixture was cooled to room temperature and then filtered. The resulting pale yellow solid was dried to give to 12 mg of the product.

Example 173

The product in the form of pale yellow solid was prepared in accordance with the same procedures as in Example 172, using 5-(4-chloro-6-propylpyrimidin-2-ylamino)-2-methylbenzonitrile prepared in Preparation 6 and 3-(ethylamino) pyrrolidine.

Example 174

A solution of 5-(4-chloro-6-propylpyrimidin-2-ylamino)-2-methylbenzonitrile (200 mg, 0.7 mmol) prepared in Preparation 6 and (3S)-(−)-3-(methylamino)pyrrolidine (69.9 mg, 0.7 mmol) in isopropanol (1.4 ml) was reacted in a microwave reactor (450 W) for 30 minutes. The reaction mixture was cooled to room temperature and then filtered to give 209 mg of the product as a pale gray solid.

Examples 175 and 176

The products of Examples 175 and 176 were prepared in accordance with the same procedures as in Example 1, using $N^1$-(4-chloro-6-propylpyrimidin-2-yl)-3-nitrobenzene-1,4-diamine prepared in Preparation 7; and (3S)-(−)-3-(methylamino)pyrrolidine or (3S)-(−)-3-(ethylamino)pyrrolidine.

Example 177

The product in the form of pale yellow solid was prepared in accordance with the same procedures as in Example 172, using $N^1$-(4-chloro-6-propylpyrimidin-2-yl)-3-nitrobenzene-1,4-diamine prepared in Preparation 7 and (3S)-(−)-3-(ethylamino)pyrrolidine.

Example 178

The product in the form of white solid was prepared in accordance with the same procedures as in Example 172, using 3-(4-chloro-6-propylpyrimidin-2-yl)benzonitrile prepared in Preparation 3 and (3S)-(−)-3-(methylamino)pyrrolidine.

Example 179

The product in the form of white solid was prepared in accordance with the same procedures as in Example 47, using (S)-tert-butyl {1-[2-(3-cyanophenylamino)-6-propylpyrimidin-4-yl]pyrrolidin-3-yl}methylcarbamate prepared in Example 56.

Examples 180 and 181

The products of Examples 180 and 181 were prepared in accordance with the same procedures as in Example 172, using 5-(4-chloro-6-propylpyrimidin-2-ylamino)-2-fluorobenzonitrile prepared in Preparation 8; and (3S)-(−)-3-(methylamino)pyrrolidine or (3S)-(−)-3-(ethylamino)pyrrolidine.

Example 182

A solution of 5-(4-chloro-6-propylpyrimidin-2-ylamino)-2-fluorobenzonitrile (0.2 g, 0.67 mmol) prepared in Preparation 8 and 3-(tert-butoxycarbonylamino)pyrrolidine (0.2 g, 1.0 mmol) in isopropanol (3 ml) was stirred at 100° C. overnight. The reaction mixture was cooled to room temperature and then concentrated under reduced pressure. The resulting residue was purified with silica gel column chromatography (n-hexane/ethyl acetate=1/1) and then dissolved in ethyl acetate (1 ml). Hydrogen chloride gas was added to the solution, which was then stirred at room temperature for 1 hour. The reaction mixture was filtered to give 0.1 g of the product as a white solid.

Example 183

The product in the form of white solid was prepared in accordance with the same procedures as in Example 1, using 4-chloro-N-(4-fluorophenyl)-6-methylpyrimidin-2-amine prepared in Preparation 10 and pyrrolidine.

Example 184

<Step 1> (2S,4R)-1-[2-(4-fluorophenylamino)-6-propylpyrimidin-4-yl]-4-hydroxypyrrolidin-2-carboxylic acid A solution of 4-chloro-N-(4-fluorophenyl)-6-propylpyrimidin-2-amine (50 mg, 0.19 mmol) prepared in Preparation 1, trans-4-hydroxy-L-proline (27.3 mg, 0.21 mmol), and diisopropylethylamine (49 μl, 0.38 mmol) in isopropanol (1.0 ml) was reacted in a microwave reactor (500 W) for 30 minutes. The reaction mixture was cooled to room temperature and then concentrated under reduced pressure. The resulting residue was purified with silica gel column chromatography (dichloromethane/methanol=30/1) to give 30 mg of the titled compound.

<Step 2> (2S,4R)-1-[2-(4-fluorophenylamino)-6-propylpyrimidin-4-yl]-4-hydroxypyrrolidin-2-carboxylic acid methyl ester A solution of (2S,4R)-1-[2-(4-fluorophenylamino)-6-propylpyrimidin-4-yl]-4-hydroxypyrrolidin-2-carboxylic acid (30 mg, 0.08 mmol) prepared in Step 1 and a catalytic amount of sulfuric acid in methanol (3 ml) was refluxed under stirring overnight. The reaction mixture was neutralized with an aqueous saturated solution of sodium bicarbonate and then extracted with dichloromethane. The organic layer was dried on anhydrous sodium sulfate, filtered, and then concentrated to give 30 mg of the titled compound. The resulting product was used in the subsequent reaction without further purification.

<Step 3> (3R,5S)-1-[2-(4-fluorophenyl)-6-propylpyrimidin-4-yl]-5-(hydroxymethyl)pyrrolidin-3-ol A solution of (2S,4R)-1-[2-(4-fluorophenylamino)-6-propylpyrimidin-4-yl]-4-hydroxypyrrolidin-2-carboxylic acid methyl ester (20 mg, 0.05 mmol) prepared in Step 2 and sodium borohydride (12.1 mg, 0.32 mmol) in ethanol (1 ml) was stirred for 3 hours and then an aqueous saturated solution of ammonium chloride was added thereto to terminate the reaction. The reaction mixture was extracted with dichloromethane. The organic layer was dried on anhydrous sodium sulfate, filtered, and then concentrated. The resulting residue was purified with silica gel column chromatography (dichloromethane/methanol=30/1) to give 14 mg of the titled compound as a white solid.

Example 185

A mixture of N-(4-chloro-6-propylpyrimidin-2-yl)-1H-indol-6-amine (13 mg, 0.05 mmol) prepared in Preparation 4, (S)-pyrrolidin-2-ylmethanol (9.1 mg, 0.09 mmol), diisopropylethylamine (17.6 mg, 14 mol) in isopropanol (0.5 ml) was reacted in a microwave reactor (300 W) for 2 hours. The reaction mixture was cooled to room temperature and then concentrated under reduced pressure. The resulting residue was purified with silica gel column chromatography (n-hexane/ethyl acetate=2/1) to give 17.1 mg of the product as a yellow liquid.

Examples 186 to 192

The products of Examples 186 to 192 were prepared in accordance with the same procedures as in Example 185, using N-(4-chloro-6-propylpyrimidin-2-yl)-1H-indol-6-amine prepared in Preparation 4; and (R)-pyrrolidin-2-ylmethanol, pyrrolidin-2-ylmethanol, (R)-2-(methoxymethyl)pyrrolidine, (S)-2-(methoxymethyl)pyrrolidine, 2-methylpyrrolidine, (S)-methylpyrrolidine-2-carboxylate, or N-(pyrrolidin-3-yl)acetamide.

Example 193

The product in the form of white solid was prepared in accordance with the same procedures as in Example 26, using (S)-[1-(2-chloro-6-propylpyrimidin-4-yl)pyrrolidin-2-yl]methanol prepared in Preparation 20 and 6-aminoindole.

Examples 194 to 215

The products of Examples 194 to 215 were prepared in accordance with the same procedures as in Example 27, using (S)-[1-(2-chloro-6-propylpyrimidin-4-yl)pyrrolidin-2-yl]methanol prepared in Preparation 20; and 3-aminobenzonitrile, 3-(methylthio)aniline, 4-chloro-3-nitroaniline, 5-aminoindole, 1H-benzo[d]imidazol-5-amine prepared in Preparation 22, 5-amino-2-(trifluoromethyl)benzimidazole, 4-methoxyaniline, 3-chloroaniline, 3-methoxyaniline, 3-(trifluoromethyl)aniline, 5-chloro-2-methylaniline, 5-methoxy- 2-methylaniline, 4-amino-2-chlorotoluene, 3-nitroaniline, 4-fluoro-3-nitroaniline, 6-aminoquinoline, 4-methyl-3-nitroaniline, 2-(trifluoromethyl)benzene-1,4-diamine, 3-nitro-1,4-phenylenediamine, 5-amino-2-methylbenzonitrile, 5-amino-2-fluorobenzonitrile, or 2,5-diaminobenzonitrile prepared in Preparation 19.

Example 216

3-Aminoquinoline (22 mg, 0.15 mmol) was added to a mixture of (S)-[1-(2-chloro-6-propylpyrimidin-4-yl)pyrrolidin-2-yl]methanol (30 mg, 0.12 mmol) prepared in Preparation 20, palladium acetate (0.5 mg, 2 mol %), 4,5-bis(diphenylphosphino)-9,9-dimethylxanthene (2.1 mg, 3 mol %), cesium carbonate (78 mg, 0.24 mmol), and anhydrous 1,4-dioxane (1 ml). The reaction mixture was stirred in a microwave reactor (600 W) for 1 hour. The reaction mixture was cooled to room temperature, suspended in dichloromethane, and then filtered through a celite pad. The resulting filtrate was concentrated under reduced pressure. The resulting residue was purified with silica gel column chromatography (n-hexane/ethyl acetate=1/1) to give 29.8 mg of the product as a pale yellow solid.

Example 217

<Step 1> (S)-1-(6-{4-[2-(hydroxylmethyl)pyrrolidin-1-yl]-6-propylpyrimidin-2-ylamino}indolin-1-yl)ethanone The titled compound in the form of pale yellow oil was prepared in accordance with the same procedures as in Example 27, using (S)-[1-(2-chloro-6-propylpyrimidin-4-yl)pyrrolidin-2-yl]methanol prepared in Preparation 20 and 1-acetyl-6-aminoindoline. The product was used in the subsequent reaction without further purification.

<Step 2> (S)-2-{1-[2-(indolin-6-ylamino)-6-propylpyrimidin-4-yl]pyrrolidin-2-yl}methanol A mixture of (S)-1-(6-{4-[2-(hydroxylmethyl)pyrrolidin-1-yl]-6-propylpyrimidin-2-ylamino}indolin-1-yl)ethanone (45.7 mg, 0.12 mmol) prepared in Step 1 and 3N hydrochloric acid solution (1.5 ml) was refluxed under stirring for 2 hours. The reaction mixture was cooled to room temperature, basified to pH 8-9 with a 2N sodium hydroxide solution, and then extracted with dichloromethane. The resulting organic layer was dried on anhydrous sodium sulfate, and then concentrated under reduced pressure. The resulting residue was purified with silica gel column chromatography (dichloromethane/methanol=40/1) to give 19.2 mg of the titled compound as colorless oil.

Example 218

The product in the form of white solid was prepared in accordance with the same procedures as in Example 118, using (S)-3-{4-[3-(cyclohexylamino)pyrrolidin-1-yl]-6-propylpyrimidin-2-ylamino}benzonitrile prepared in Example 135.

Example 219

The product in the form of white solid was prepared in accordance with the same procedures as in Example 118, using (S)-3-{4-[3-(isopropylamino)pyrrolidin-1-yl]-6-propylpyrimidin-2-ylamino}benzonitrile prepared in Example 138.

Example 220

The product in the form of white solid was prepared in accordance with the same procedures as in Example 47, using (S)-tert-butyl 2-{1-[2-(3-cyanophenylamino)-6-propylpyrimidin-4-yl]pyrrolidin-3-ylamino}ethylcarbamate prepared in Example 136.

Example 221

A solution of (S)-3-{4-[3-(1-benzylpiperidin-4-ylamino)pyrrolidin-1-yl]-6-propylpyrimidin-2-ylamino}benzonitrile (110 mg, 0.22 mmol) prepared in Example 137 and palladium/charcoal (11 mg, 10 wt %) in methanol (2.2 ml) was stirred at room temperature under hydrogen atmosphere for 5 hours and then filtered through a celite pad. The resulting filtrate was concentrated under reduced pressure. The resulting residue was purified with silica gel column chromatography (dichloromethane/methanol=10/1) to give 28 mg of the product as a white solid.

Example 222

A solution of (S)-3-{4-[3-(piperidin-4-ylamino)pyrrolidin-1-yl]-6-propylpyrimidin-2-ylamino}benzonitrile (15 mg, 0.04 mmol) prepared in Example 221 and butyraldehyde (2.7 mg, 0.04 mmol) in methanol (0.4 ml) was stirred at room temperature for 30 minutes and then sodium triacetoxyborohydride (15.7 mg, 0.08 mmol) was added thereto. The reaction mixture was stirred at room temperature for 1 hour and then an aqueous saturated solution of sodium bicarbonate was added thereto to terminate the reaction. The reaction mixture was extracted with dichloromethane. The resulting organic layer was dried on anhydrous sodium sulfate, filtered, and then concentrated. The resulting residue was purified with silica gel column chromatography (dichloromethane/methanol=50/1) to give 4.0 mg of the product as a white solid.

Example 223

A solution of 3-(4-butyl-6-chloropyrimidin-2-ylamino)benzonitrile (20 mg, 0.07 mmol) prepared in Preparation 11 and (S)—N-(pyrrolidin-3-yl)acetamide (9.8 mg, 0.08 mmol) in isopropanol (0.3 ml) was reacted in a microwave reactor (450 W) for 30 minutes. The reaction mixture was cooled to room temperature and then concentrated under reduced pressure. The resulting residue was purified with silica gel column chromatography (dichloromethane/methanol=50/1) to give 26.7 mg of the product as a white solid.

Examples 224 to 227

The products of Examples 224 to 227 were prepared in accordance with the same procedures as in Example 223, using 3-(4-butyl-6-chloropyrimidin-2-ylamino)benzonitrile prepared in Preparation 11; and (S)-pyrrolidin-2-ylmethanol, (R)-2-methylpyrrolidine, (3S)-(−)-3-(methylamino)pyrrolidine, or (S)-tert-butyl pyrrolidin-3-ylcarbamate.

Examples 228 to 232

The products of Examples 228 to 232 were prepared in accordance with the same procedures as in Example 223, using 5-(4-butyl-6-chloropyrimidin-2-ylamino)-2-methylbenzonitrile prepared in Preparation 12; and (S)—N-(pyrrolidin-3-yl)acetamide, (S)-pyrrolidin-2-ylmethanol, (R)-2-methylpyrrolidine, (3S)-(−)-3-(methylamino)pyrrolidine, or (S)-tert-butyl pyrrolidin-3-ylcarbamate.

Example 233

The product in the form of white solid was prepared in accordance with the same procedures as in Example 47, using (S)-tert-butyl 1-[6-butyl-2-(3-cyanophenylamino)pyrimidin-4-yl]pyrrolidin-3-ylcarbamate prepared in Example 227.

Example 234

The product in the form of white solid was prepared in accordance with the same procedures as in Example 47, using (S)-tert-butyl 1-[6-butyl-2-(3-cyano-4-methylphenylamino)pyrimidin-4-yl]pyrrolidin-3-ylcarbamate prepared in Example 232.

Examples 235 to 237

The products of Examples 235 to 237 were prepared in accordance with the same procedures as in Example 127, using (S)-3-[4-(3-aminopyrrolidin-1-yl)-6-butylpyrimidin-2-ylamino]benzonitrile dihydrochloride prepared in Example 233; and acetone, acetaldehyde (2 eq.), or cyclopropanecarboxaldehyde.

Examples 238 to 240

The products of Examples 238 to 240 were prepared in accordance with the same procedures as in Example 127, using (S)-5-[4-(3-aminopyrrolidin-1-yl)-6-butylpyrimidin-2-ylamino]-2-methylbenzonitrile dihydrochloride prepared in Example 234; and acetone, acetaldehyde (2 eq.), or cyclopropanecarboxaldehyde.

Example 241

A solution of (S)—N-[1-(2-chloro-6-propylpyrimidin-4-yl)pyrrolidin-3-yl]acetamide (20 mg, 0.07 mmol) prepared in Preparation 13 and 4-chloro-3-nitroaniline (13.5 mg, 0.08 mmol) in n-butanol (0.5 ml) was reacted in a microwave reactor (450 W) for 50 minutes. The reaction mixture was cooled to room temperature and then concentrated under reduced pressure. The resulting residue was purified with silica gel column chromatography (dichloromethane/methanol=50/1) to give 26.1 mg of the product as a pale yellow solid.

Examples 242 to 259

The products of Examples 242 to 259 were prepared in accordance with the same procedures as in Example 241, using (S)—N-[1-(2-chloro-6-propylpyrimidin-4-yl)pyrrolidin-3-yl]acetamide prepared in Preparation 13; and 3-(methylthio)aniline, 6-aminoindole, 3-(trifluoromethyl)aniline, 7-amino-4-methyl-2H-chromen-2-one, 2-chloro-4-aminotoluene, 3-nitroaniline, 4-fluoro-3-nitroaniline, 4-methyl-3-nitroaniline, benzyl 5-amino-2-methoxyphenylcarbamate, 5-amino-2-fluorobenzonitrile, 5-amino-2-methylbenzonitrile, 4-fluoro-3-(trifluoromethyl)aniline, 2-nitrobenzene-1,4-diamine, 5-chloro-2-methylaniline, 3-aminobenzamide, 3-amino-N-methylbenzamide, 3-aminobenzylamine, or 3-amino-4-chlorobenzamide.

Example 260

A solution of (S)—N-[1-(2-chloro-6-propylpyrimidin-4-yl)pyrrolidin-3-yl]acetamide (20 mg, 0.08 mmol) prepared in Preparation 13 and 2,5-diaminobenzonitrile (9.5 mg, 0.07 mmol) prepared in Preparation 19 in n-butanol (0.5 ml) was reacted in a microwave reactor (450 W) for 40 minutes. The reaction mixture was cooled to room temperature and then filtered to give 17.1 mg of the product as a yellow solid.

Examples 261 and 262

The products of Examples 261 and 262 were prepared in accordance with the same procedures as in Example 260, using (S)—N-[1-(2-chloro-6-propylpyrimidin-4-yl)pyrrolidin-3-yl]acetamide prepared in Preparation 13; and 2-(trifluoromethyl)-1,4-phenylenediamine or 3,5-diaminobenzonitrile.

Examples 263 to 273

The products of Examples 263 to 273 were prepared in accordance with the same procedures as in Example 26, using (S)—N-[1-(2-chloro-6-propylpyrimidin-4-yl)pyrrolidin-3-yl]acetamide prepared in Preparation 13; and 6-aminoindole, 5-chloro-2-methylaniline, 4-fluoro-3-(trifluoromethyl)aniline, 4-fluoro-1,3-diaminobenzene, 3-(trifluoromethyl)aniline, 5-(trifluoromethyl)-1,3-phenylenediamine, 3-nitroaniline, 1,4-phenylenediamine, 5-amino-2-chlorophenol, 4-aminosalicylic acid, or 5-aminosalicylic acid.

Examples 274 to 282

The products of Examples 274 to 282 were prepared in accordance with the same procedures as in Example 27, using (S)—N-[1-(2-chloro-6-propylpyrimidin-4-yl)pyrrolidin-3-yl]acetamide prepared in Preparation 13; and 5-amino-o-cresol, 4-amino-2-chlorophenol, 4-amino-o-cresol, 4-amino-2-fluorophenol, 3-hydroxy-4-methoxyaniline, 3-methoxy-4-methylaniline, 4-methyl-3-(trifluoromethyl)aniline, 3,4-dimethylaniline, or 3-fluoro-4-methylaniline.

Example 283

The product in the form of white solid was prepared in accordance with the same procedures as in Example 118, using (S)—N-{1-[2-(4-fluoro-3-nitrophenylamino)-6-propylpyrimidin-4-yl]pyrrolidin-3-yl}acetamide prepared in Example 248.

Example 284

The product in the form of white solid was prepared in accordance with the same procedures as in Example 118, using (S)—N-{1-[2-(4-methyl-3-nitrophenylamino)-6-propylpyrimidin-4-yl]pyrrolidin-3-yl}acetamide prepared in Example 249.

Example 285

The product in the form of white solid was prepared in accordance with the same procedures as in Example 118, using (S)—N-{1-[2-(3-cyano-4-methylphenylamino)-6-propylpyrimidin-4-yl]pyrrolidin-3-yl}acetamide prepared in Example 252.

Example 286

The product in the form of white solid was prepared in accordance with the same procedures as in Example 118, using (S)—N-{1-[2-(4-amino-3-nitrophenylamino)-6-propylpyrimidin-4-yl]pyrrolidin-3-yl}acetamide prepared in Example 254.

Example 287

The product in the form of white solid was prepared in accordance with the same procedures as in Example 118, using (S)—N-{1-[2-(3-cyanophenylamino)-6-propylpyrimidin-4-yl]pyrrolidin-3-yl}acetamide prepared in Example 54.

Example 288

The product in the form of white solid was prepared in accordance with the same procedures as in Example 118, using (S)—N-{1-[2-(4-chloro-3-nitrophenylamino)-6-propylpyrimidin-4-yl]pyrrolidin-3-yl}acetamide prepared in Example 241.

Example 289

The product in the form of white solid was prepared in accordance with the same procedures as in Example 221, using (S)-benzyl 5-[4-(3-acetamidopyrrolidin-1-yl)-6-propylpyrimidin-2-ylamino]-2-methoxyphenylcarbamate prepared in Example 250.

Example 290

The product in the form of pale yellow oil was prepared in accordance with the same procedures as in Example 221, using (S)—N-{1-[2-(4-chloro-3-nitrophenylamino)-6-propylpyrimidin-4-yl]pyrrolidin-3-yl}acetamide prepared in Example 241.

Example 291

The product in the form of pale yellow oil was prepared in accordance with the same procedures as in Example 221, using (S)—N-{1-[2-(4-fluoro-3-nitrophenylamino)-6-propylpyrimidin-4-yl]pyrrolidin-3-yl}acetamide prepared in Example 248.

Example 292

The product in the form of pale yellow oil was prepared in accordance with the same procedures as in Example 221, using (S)—N-{1-[2-(4-methyl-3-nitrophenylamino)-6-propylpyrimidin-4-yl]pyrrolidin-3-yl}acetamide prepared in Example 249.

Example 293

The product in the form of pale yellow solid was prepared in accordance with the same procedures as in Example 260, using N-[1-(2-chloro-6-propylpyrimidin-4-yl)pyrrolidin-3-yl]acetamide prepared in Preparation 14 and 2-nitrobenzene-1,4-diamine.

Examples 294 to 309

The products of Examples 294 to 309 were prepared in accordance with the same procedures as in Example 27, using N-[1-(2-chloro-6-propylpyrimidin-4-yl)pyrrolidin-3-yl]acetamide prepared in Preparation 14; and 3-aminobenzonitrile, 3-nitroaniline, 4-fluoro-3-nitroaniline, 4-chloro-3-nitroaniline, 3-methoxyaniline, 5-methoxy-2-methylaniline, 4-methoxyaniline, 3-(trifluoromethyl)aniline, 3-chloroaniline, 5-chloro-2-methylaniline, 2-chloro-4-aminotoluene, 3-(methylthio)aniline, 5-aminoindole, 5-amino-2-(trifluoromethyl)benzimidazole, 6-aminoquinoline, or 7-amino-4-methyl-2H-chromen-2-one.

Example 310

The product in the form of pale yellow solid was prepared in accordance with the same procedures as in Example 216, using N-[1-(2-chloro-6-propylpyrimidin-4-yl)pyrrolidin-3-yl]acetamide prepared in Preparation 14 and 3-aminoquinoline.

Examples 311 and 312

The products of Examples 311 and 312 were prepared in accordance with the same procedures as in Example 26, using N-[1-(2-chloro-6-propylpyrimidin-4-yl)pyrrolidin-3-yl]acetamide prepared in Preparation 14 and 2,5-diaminobenzonitrile prepared in Preparation 19 or 4-fluoro-1,3-phenylenediamine.

Examples 313 to 329

The products of Examples 313 to 329 were prepared in accordance with the same procedures as in Example 241, using (R)-2-chloro-4-(2-methylpyrrolidin-1-yl)-6-propylpyrimidine prepared in Preparation 15; and 4-chloro-3-nitroaniline, 3-(methylthio)aniline, 6-aminoindole, 3-(trifluoromethyl)aniline, 7-amino-4-methyl-2H-chromen-2-one, 2-chloro-4-aminotoluene, 3-nitroaniline, 4-fluoro-3-nitroaniline, 4-methyl-3-nitroaniline, 4-fluoro-3-(trifluoromethyl)aniline, 2-(trifluoromethyl)-1,4-phenylenediamine, benzyl 5-amino-2-methoxyphenylcarbamate, 5-amino-2-fluorobenzonitrile, 5-amino-2-methylbenzonitrile, 2,5-diaminobenzonitrile prepared in Preparation 19, 2-nitrobenzene-1,4-diamine, or 1-(6-aminoindolin-1-yl)ethanone.

Example 330

The product in the form of pale yellow oil was prepared in accordance with the same procedures as in Example 216, using (R)-2-chloro-4-(2-methylpyrrolidin-1-yl)-6-propylpyrimidine prepared in Preparation 15 and 5-chloro-2-methylaniline.

Example 331

The product in the form of pale yellow oil was prepared in accordance with the same procedures as in Example 221, using (R)-benzyl 2-methoxy-5-[4-(2-methylpyrrolidin-1-yl)-6-propylpyrimidin-2-ylamino]phenylcarbamate prepared in Example 324

Example 332

The product in the form of pale yellow oil was prepared in accordance with the same procedures as in Example 221,

Example 333

The product in the form of pale yellow oil was prepared in accordance with the same procedures as in Example 221, using (R)—N-(4-fluoro-3-nitrophenyl)-4-(2-methylpyrrolidin-1-yl)-6-propylpyrimidin-2-amine prepared in Example 320.

Example 334

The product in the form of pale yellow oil was prepared in accordance with the same procedures as in Example 221, using (R)—N-(4-methyl-3-nitrophenyl)-4-(2-methylpyrrolidin-1-yl)-6-propylpyrimidin-2-amine prepared in Example 321.

Example 335

A solution of (S)-3-(4-{3-[2-(benzyloxy)ethylamino]pyrrolidin-1-yl}-6-propylpyrimidin-2-ylamino)benzonitrile (60 mg, 0.13 mmol) prepared in Example 145, palladium/charcoal (12 mg, 10 wt %) and a catalytic amount of conc. HCl in methanol (6.0 ml) was stirred at room temperature under hydrogen atmosphere overnight and then filtered through a celite pad. The resulting filtrate was concentrated under reduced pressure. The resulting residue was dissolved in ethyl acetate (1 ml) and then hydrogen chloride gas was added thereto. The reaction mixture was stirred at room temperature for 1 hour and then filtered to give 39.0 mg of the product as a white solid.

Example 336

The product in the form of white solid was prepared in accordance with the same procedures as in Example 118, using (S)-5-{4-butyl-6-[2-(hydroxymethyl)pyrrolidin-1-yl]pyrimidin-2-ylamino}-2-methylbenzonitrile prepared in Example 229.

Examples 337 and 338

The products of Examples 337 and 338 were prepared in accordance with the same procedures as in Example 223, using $N^1$-(4-butyl-6-chloropyrimidin-2-yl)-3-nitrobenzene-1,4-diamine prepared in Preparation 16; and (S)—N-(pyrrolidin-3-yl)acetamide or (3S)-(−)-3-(methylamino)pyrrolidine.

Example 339

The product in the form of white solid was prepared in accordance with the same procedures as in Example 118, using (S)-3-(4-{3-[(1H-pyrrol-2-yl)methylamino]pyrrolidin-1-yl}-6-propylpyrimidin-2-ylamino)benzonitrile prepared in Example 111.

Example 340

The product in the form of white solid was prepared in accordance with the same procedures as in Example 168, using (S)-2-chloro-4-[2-(methoxymethyl)pyrrolidin-1-yl]-6-propylpyrimidine prepared in Preparation 2 and 2-nitro-1,4-phenylenediamine.

Example 341

The product in the form of pale yellow solid was prepared in accordance with the same procedures as in Example 118, using (S)-{1-[2-(4-fluoro-3-nitrophenylamino)-6-propylpyrimidin-4-yl]pyrrolidin-2-yl}methanol prepared in Example 208.

Example 342

A mixture of (S)-tert-butyl 1-(2-chloro-6-propylpyrimidin-4-yl)pyrrolidin-3-ylcarbamate (30 mg, 0.09 mmol) prepared in Preparation 21, 5-(trifluoromethyl)benzene-1,3-diamine (19.4 mg, 0.11 mmol), and n-butanol (1 ml) was refluxed under stirring overnight. The reaction mixture was cooled to room temperature and then concentrated under reduced pressure. The resulting residue was purified with silica gel column chromatography (dichloromethane/methanol=20/1) and then dissolved in ethyl acetate (2 ml). Hydrogen chloride gas was added to the solution. The reaction mixture was stirred at room temperature for 1 hour and then filtered to give 11.1 mg of the product as a white solid.

Examples 343 to 361

The products of Examples 343 to 361 were prepared in accordance with the same procedures as in Example 342, using (S)-tert-butyl 1-(2-chloro-6-propylpyrimidin-4-yl)pyrrolidin-3-ylcarbamate prepared in Preparation 21; and 2-methylbenzene-1,4-diamine prepared in Preparation 23, 4-chloro-3-nitroaniline, 3-(methylthio)aniline, 6-aminoindole, 3-(trifluoromethyl)aniline, 5-chloro-2-methylaniline, 4-amino-2-chlorotoluene, 3-nitroaniline, 4-methyl-3-nitroaniline, 2-(trifluoromethyl)benzene-1,4-diamine, 5-amino-2-fluorobenzonitrile, 5-amino-2-methylbenzonitrile, 2,5-diaminobenzonitrile prepared in Preparation 19, (5-amino-2-methoxyphenyl)carbamic acid benzyl ester, 4-fluoro-3-(trifluoromethyl)aniline, 4-fluoro-3-nitroaniline, 2-nitro-1,4-phenylenediamine, 3,5-bis(trifluoromethyl)aniline or 3,5-dimethoxyaniline.

Example 362

A solution of (S)-tert-butyl 1-(2-chloro-6-propylpyrimidin-4-yl)pyrrolidin-3-ylcarbamate (30 mg, 0.09 mmol) prepared in Preparation 21, 3,5-diaminobenzonitrile (14.6 mg, 0.11 mmol) in butanol (1 ml) was refluxed under stirring overnight. The reaction mixture was cooled to room temperature and then concentrated under reduced pressure. Hydrochloric acid was added at 0° C. to the resulting residue. The suspension was stirred at room temperature for 2 hours and then filtered. The resulting solid was washed with ethyl acetate. The solid was dissolved in dichloromethane (10 ml) and then an aqueous saturated solution of sodium bicarbonate was added thereto. The solution was stirred for 30 minutes and then extracted with dichloromethane. The organic layer was dried on anhydrous magnesium sulfate and then concentrated under reduced pressure. The resulting residue was purified with silica gel column chromatography (n-hexane/ethyl acetate=1/1) to give 11.7 mg of the titled compound as a white solid.

Example 363

The product in the form of white solid was prepared in accordance with the same procedures as in Example 362, using (S)-tert-butyl 1-(2-chloro-6-propylpyrimidin-4-yl) pyrrolidin-3-ylcarbamate prepared in Preparation 21 and 3-aminobenzenesulfonamide.

Example 364

Palladium/charcoal (25 mg, 10 wt %) was added to a solution of (S)-4-[2-(methoxymethyl)pyrrolidin-1-yl]-N-(3-nitrophenyl)-6-propylpyrimidin-2-amine (20 mg, 0.06 mmol) prepared in Example 32 in methanol (2 ml). The reaction mixture was stirred at room temperature under hydrogen atmosphere (30 bar) for 3 hours and then filtered through a celite pad. The resulting filtrate was concentrated under reduced pressure. The resulting residue was purified with silica gel column chromatography (n-hexane/ethyl acetate=1/1) to give 4.4 mg of the product as a pale yellow solid.

Example 365

The product (4.4 mg) in the form of pale yellow solid was prepared in accordance with the same procedures as in Example 364, using (S)—N-(4-fluoro-3-nitrophenyl)-4-[2-(methoxymethyl)pyrrolidin-1-yl]-6-propylpyrimidin-2-amine prepared in Example 31.

Example 366

The product (7.2 mg) in the form of pale yellow solid was prepared in accordance with the same procedures as in Example 364, using (S)-4-[2-(methoxymethyl)pyrrolidin-1-yl]-N-(4-methyl-3-nitrophenyl)-6-propylpyrimidin-2-amine prepared in Example 40.

Example 367

<Step 1> (S)-benzyl 2-methoxy-5-{4-[2-(methoxymethyl)pyrrolidin-1-yl]-6-propylpyrimidin-2-ylamino}phenylcarbamate The titled compound (15 mg) in the form of pale yellow oil was prepared in accordance with the same procedures as in Example 27, using (S)-2-chloro-4-[2-(methoxymethyl) pyrrolidin-1-yl]-6-propylpyrimidine prepared in Preparation 2 and (5-amino-2-methoxyphenyl)carbamic acid benzyl ester.

<Step 2> (S)-4-methoxy-N$^1$-{4-[2-(methoxymethyl) pyrrolidin-1-yl]-6-propylpyrimidin-2-yl}benzene-1, 3-diamine The titled compound (7.8 mg) in the form of pale yellow solid was prepared in accordance with the same procedures as in Example 364, using (S)-benzyl 2-methoxy-5-{4-[2-(methoxymethyl)pyrrolidin-1-yl]-6-propyl pyrimidin-2-ylamino}phenylcarbamate prepared in Step 1.

Example 368

The titled compound in the form of pale yellow oil was prepared in accordance with the same procedures as in Example 217, using (S)-2-chloro-4-[2-(methoxymethyl)pyrrolidin-1-yl]-6-propylpyrimidine prepared in Preparation 2 and 1-acetyl-6-aminoindoline.

Example 369

The product in the form of pale yellow solid was prepared in accordance with the same procedures as in Example 364, using (S)-4-(3-aminopyrrolidin-1-yl)-N-(4-methyl-3-nitrophenyl)-6-propylpyrimidin-2-amine dihydrochloride prepared in Example 351.

Example 370

<Step 1> (S)—N$^1$-[4-(3-aminopyrrolidin-1-yl)-6-propylpyrimidin-2-yl]-4-fluorobenzene-1,3-diamine The titled compound in the form of pale yellow solid was prepared in accordance with the same procedures as in Example 364, using (S)-4-(3-aminopyrrolidin-1-yl)-N-(4-fluoro-3-nitrophenyl)-6-propylpyrimidin-2-amine dihydrochloride prepared in Example 358.

<Step 2> (S)—N$^1$-[4-(3-aminopyrrolidin-1-yl)-6-propylpyrimidin-2-yl]-4-fluorobenzene-1,3-diamine dihydrochloride The titled compound in the form of pale yellow solid was prepared in accordance with the same procedures as in Example 118, using N$^1$-[4-(3-aminopyrrolidin-1-yl)-6-propylpyrimidin-2-yl]-4-fluorobenzene-1,3-diamine prepared in Step 1.

Example 371

The product in the form of pale yellow solid was prepared in accordance with the same procedures as in Example 118, using (S)-3-amino-5-[4-(3-aminopyrrolidin-1-yl)-6-propylpyrimidin-2-amino]benzonitrile prepared in Example 362.

Example 372

Cyclopropanecarboxaldehyde (6.51 ml, 0.09 mmol) was added to a solution of (S)-4-(3-aminopyrrolidin-1-yl)-N-(4-chloro-3-nitrophenyl)-6-propylpyrimidin-2-amine dihydrochloride (30 mg, 0.07 mmol) prepared in Example 344 in methanol (1 ml). The reaction mixture was stirred at room temperature for 30 minutes and then sodium cyanoborohydride (6.84 mg, 0.11 mmol) was added thereto. The reaction mixture was stirred at room temperature overnight and then a 1N hydrochloric acid solution was added thereto. The reaction mixture was stirred for 30 minutes, neutralized with a 1N sodium hydroxide solution, and then extracted with ethyl acetate. The organic layer was dried on anhydrous magnesium sulfate, filtered, and then concentrated under reduced pressure. The resulting residue was purified with silica gel column chromatography (ethyl acetate/methanol=20/1) to give 5.9 mg of the product as a pale yellow solid.

Example 373

The product in the form of pale yellow solid was prepared in accordance with the same procedures as in Example 372, using (S)-4-(3-aminopyrrolidin-1-yl)-N-(4-fluoro-3-nitrophenyl)-6-propylpyrimidin-2-amine dihydrochloride prepared in Example 358.

Example 374

The product in the form of pale yellow solid was prepared in accordance with the same procedures as in Example 372, using (S)-4-(3-aminopyrrolidin-1-yl)-N-(4-methyl-3-nitrophenyl)-6-propylpyrimidin-2-amine dihydrochloride prepared in Example 351.

Example 375

The product in the form of pale yellow solid was prepared in accordance with the same procedures as in Example 372, using (S)-4-(3-aminopyrrolidin-1-yl)-N-(3-nitrophenyl)-6-propylpyrimidin-2-amine dihydrochloride prepared in Example 350.

Example 376

The product in the form of pale yellow solid was prepared in accordance with the same procedures as in Example 372, using (S)-5-[4-(3-aminopyrrolidin-1-yl)-6-propylpyrimidin-2-ylamino]-2-fluorobenzonitrile dihydrochloride prepared in Example 353.

Example 377

The product in the form of pale yellow solid was prepared in accordance with the same procedures as in Example 372, using (S)-5-[4-(3-aminopyrrolidin-1-yl)-6-propylpyrimidin-2-ylamino]-2-methylbenzonitrile dihydrochloride prepared in Example 354.

Example 378

The product in the form of pale yellow solid was prepared in accordance with the same procedures as in Example 372, using (S)-4-(3-aminopyrrolidin-1-yl)-N-[3-(methylthio)phenyl]-6-propylpyrimidin-2-amine dihydrochloride prepared in Example 345.

Example 379

The product in the form of pale yellow solid was prepared in accordance with the same procedures as in Example 372, using (S)-4-(3-aminopyrrolidin-1-yl)-6-propyl-N-[3-(trifluoromethyl)phenyl]pyrimidin-2-amine dihydrochloride prepared in Example 347.

Example 380

The product in the form of pale yellow solid was prepared in accordance with the same procedures as in Example 372, using (S)-4-(3-aminopyrrolidin-1-yl)-N-(5-chloro-2-methylphenyl)-6-propylpyrimidin-2-amine dihydrochloride prepared in Example 348.

Example 381

The product in the form of pale yellow solid was prepared in accordance with the same procedures as in Example 372, using (S)-4-(3-aminopyrrolidin-1-yl)-N-(3-chloro-4-methylphenyl)-6-propylpyrimidin-2-amine dihydrochloride prepared in Example 349.

Example 382

The product in the form of pale yellow solid was prepared in accordance with the same procedures as in Example 372, using (S)-4-(3-aminopyrrolidin-1-yl)-N-[4-fluoro-3-(trifluoromethyl)phenyl]-6-propylpyrimidin-2-amine dihydrochloride prepared in Example 357.

Example 383

The product in the form of white solid was prepared in accordance with the same procedures as in Example 364, using (S)-4-[3-(cyclopropylmethylamino)pyrrolidin-1-yl]-N-(4-methyl-3-nitrophenyl)-6-propylpyrimidin-2-amine prepared in Example 374.

Example 384

The product in the form of white solid was prepared in accordance with the same procedures as in Example 364, using (S)-4-[3-(cyclopropylmethylamino)pyrrolidin-1-yl]-N-(3-nitrophenyl)-6-propylpyrimidin-2-amine prepared in Example 375.

Example 385

The product in the form of white solid was prepared in accordance with the same procedures as in Example 118, using (S)-5-{4-[3-(cyclopropylmethylamino)pyrrolidin-1-yl]-6-propylpyrimidin-2-ylamino}-2-fluorobenzonitrile prepared in Example 376.

Example 386

The product in the form of pale yellow solid was prepared in accordance with the same procedures as in Example 118, using (S)-4-[3-(cyclopropylmethylamino)pyrrolidin-1-yl]-N-(4-methyl-3-nitrophenyl)-6-propylpyrimidin-2-amine prepared in Example 374.

Example 387

<Step 1> tert-butyl 1-[2-(3-cyanophenylamino)-6-propylpyrimidin-4-yl]pyrrolidin-3-ylcarbamate The titled compound in the form of white solid was prepared in accordance with the same procedures as in Example 1, using 3-(4-chloro-6-propylpyrimidin-2-ylamino)benzonitrile prepared in Preparation 3 and 3-(tert-butoxycarbonylamino)pyrrolidine.

<Step 2> 3-[4-(3-aminopyrrolidin-1-yl)-6-propylpyrimidin-2-ylamino]benzonitrile dihydrochloride The titled compound in the form of white solid was prepared in accordance with the same procedures as in Example 47, using tert-butyl 1-[2-(3-cyanophenylamino)-6-propylpyrimidin-4-yl]pyrrolidin-3-ylcarbamate prepared in Step 1.

<Step 3> 3-{4-[3-(cyclopropylmethylamino)pyrrolidin-1-yl]-6-propylpyrimidin-2-ylamino}benzonitrile The titled compound in the form of white solid was prepared in accordance with the same procedures as in Example 372, using 3-[4-(3-aminopyrrolidin-1-yl)-6-propylpyrimidin-2-ylamino]benzonitrile dihydrochloride prepared in Step 2.

<Step 4> 3-{4-[3-(cyclopropylmethylamino)pyrrolidin-1-yl]-6-propylpyrimidin-2-ylamino}benzonitrile dihydrochloride The titled compound in the form of white solid was prepared in accordance with the same procedures as in Example 118, using 3-{4-[3-(cyclopropylmethylamino)pyrrolidin-1-yl]-6-propylpyrimidin-2-ylamino}benzonitrile prepared in Step 3.

Examples 388 to 392

The products of Examples 388 to 392 were prepared in accordance with the same procedures as in Example 1, using 4-chloro-6-ethyl-N-(4-fluorophenyl)pyrimidin-2-amine prepared in Preparation 9; and L-prolinol, (3S)-(−)-3-acetamidopyrrolidine, (S)-2-(methoxymethyl)pyrrolidine, 2-methylpyrrolidine, or (3S)-(−)-3-(ethylamino)pyrrolidine.

Example 393

A solution of (R)-3-[4-(3-hydroxypyrrolidin-1-yl)-6-propyl pyrimidin-2-ylamino]benzonitrile (30 mg, 0.09 mmol) prepared in Example 57, phenol (13.1 mg, 0.14 mmol), and cyanomethylenetributylphosphorane (37 μl, 0.14 mmol) in toluene (0.5 mol) was stirred in a microwave reactor (400 W) for 1 hour. The reaction mixture was cooled to room temperature and then concentrated under reduced pressure. The resulting residue was purified with silica gel column chromatography (dichloromethane/methanol=100/1) to give 4.0 mg of the product as pale yellow oil.

Example 394

The product was prepared in accordance with the same procedures as in Example 118, using (S)—N-{1-[2-(3-cyanophenylamino)-6-propylpyrimidin-4-yl]pyrrolidin-3-yl}-2-(pyridin-3-yl)acetamide prepared in Example 77.

Example 395

A catalytic amount of palladium/charcoal was added to a solution of (S)-benzyl 2-{1-[2-(3-cyanophenylamino)-6-propylpyrimidin-4-yl]pyrrolidin-3-ylamino}-2-oxoethylcarbamate (120 mg, 0.2 mmol) prepared in Example 165 in methanol (3 ml). The reaction mixture was stirred under hydrogen atmosphere at room temperature overnight. The reaction mixture was filtered through a celite pad. The resulting filtrate was concentrated under reduced pressure to give 21.2 mg of the product as colorless oil.

Example 396

The product was prepared in accordance with the same procedures as in Example 118, using (S)-3-(4-{3-[4-(dimethylamino)benzylamino]pyrrolidin-1-yl}-6-propylpyrimidin-2-ylamino)benzonitrile prepared in Example 110.

Example 397

The product in the form of white solid was prepared in accordance with the same procedures as in Example 118, using (S)-2-fluoro-5-{4-[2-(hydroxymethyl)pyrrolidin-1-yl]-6-propylpyrimidin-2-ylamino}benzonitrile prepared in Example 214.

Example 398

The product in the form of pale red solid was prepared in accordance with the same procedures as in Example 118, using (S)-{1-[2-(4-amino-3-nitrophenylamino)-6-propylpyrimidin-4-yl]pyrrolidin-2-yl}methanol prepared in Example 212.

Example 399

The product in the form of pale red solid was prepared in accordance with the same procedures as in Example 221, using (S)-{1-[2-(4-methyl-3-nitrophenylamino)-6-propylpyrimidin-4-yl]pyrrolidin-2-yl}methanol prepared in Example 210.

Example 400

The product in the form of pale red solid was prepared in accordance with the same procedures as in Example 221, using (S)-{1-[2-(4-fluoro-3-nitrophenylamino)-6-propylpyrimidin-4-yl]pyrrolidin-2-yl}methanol prepared in Example 208.

Example 401

The product in the form of pale red solid was prepared in accordance with the same procedures as in Example 221, using (S)-{1-[2-(4-chloro-3-nitrophenylamino)-6-propylpyrimidin-4-yl]pyrrolidin-2-yl}methanol prepared in Example 196.

Example 402

Dess-Martin periodinane (449 mg, 1.06 mmol) was added at room temperature to a solution of (S)-3-{4-[2-(hydroxymethyl)pyrrolidin-1-yl]-6-propylpyrimidin-2-ylamino}benzonitrile (238 mg, 0.71 mmol) prepared in Example 194 in dichloromethane (3.5 ml), and then stirred for 4 hours. Dess-Martin periodinane (449 mg, 1.06 mmol) was further added at room temperature to the reaction mixture, which was then stirred overnight. The reaction mixture was diluted with ethyl ether, washed with an aqueous saturated solution of sodium bicarbonate, dried on anhydrous sodium sulfate, and then concentrated under reduced pressure. The resulting residue was purified with silica gel column chromatography (n-hexane/ethyl acetate=1/1) to give 154 mg of the product as pale yellow oil.

Example 403

A solution of (S)-3-[4-(2-formylpyrrolidin-1-yl)-6-propylpyrimidin-2-ylamino]benzonitrile (20 mg, 0.06 mmol) prepared in Example 402 and methylamine hydrochloride (4.8 mg, 0.07 mmol) in methanol (0.5 ml) was stirred at room temperature for 30 minutes. Sodium triacetoxyborohydride (25.3 mg, 0.12 mmol) and acetic acid (5.1 μl, 0.09 mmol) were added to the reaction mixture, which was then stirred at room temperature overnight. An aqueous saturated solution of sodium bicarbonate was added to the reaction mixture, which was then extracted with dichloromethane. The organic layer was dried on anhydrous sodium sulfate and then concentrated under reduced pressure. The resulting residue was purified with silica gel column chromatography (ethyl acetate/methanol=1/1) to give 7 mg of the product as colorless oil.

Examples 404 to 407

The products of Examples 404 to 407 were prepared in accordance with the same procedures as in Example 403, using (S)-3-[4-(2-formylpyrrolidin-1-yl)-6-propylpyrimidin-2-ylamino]benzonitrile prepared in Example 402; and cyclobutylamine hydrochloride, 4-fluorobenzylamine, n-propylamine, or ethanolamine.

Example 408

The product in the form of pale yellow solid was prepared in accordance with the same procedures as in Example 118, using Example N-{1-[2-(3-cyanophenylamino)-6-propylpyrimidin-4-yl]pyrrolidin-3-yl}acetamide prepared in Example 294.

Example 409

The product in the form of pale yellow solid was prepared in accordance with the same procedures as in Example 118, using N-{1-[2-(3-nitrophenylamino)-6-propylpyrimidin-4-yl]pyrrolidin-3-yl}acetamide prepared in Example 295.

Example 410

The product in the form of pale yellow solid was prepared in accordance with the same procedures as in Example 118, using N-{1-[2-(4-chloro-3-nitrophenylamino)-6-propylpyrimidin-4-yl]pyrrolidin-3-yl}acetamide prepared in Example 297.

Example 411

The product in the form of pale yellow solid was prepared in accordance with the same procedures as in Example 118, using (R)—N$^1$-[4-(2-methylpyrrolidin-1-yl)-6-propylpyrimidin-2-yl]-3-nitrobenzene-1,4-diamine prepared in Example 328.

Example 412

The product in the form of pale yellow solid was prepared in accordance with the same procedures as in Example 118, using (R)—N$^1$-[4-(2-methylpyrrolidin-1-yl)-6-propylpyrimidin-2-yl]-3-(trifluoromethyl)benzene-1,4-diamine prepared in Example 323.

Example 413

The product in the form of pale yellow solid was prepared in accordance with the same procedures as in Example 118, using (S)-5-{4-[3-(cyclopropylmethylamino)pyrrolidin-1-yl]-6-propylpyrimidin-2-ylamino}-2-methylbenzonitrile prepared in Example 377.

Examples 414 to 421

The products of Examples 414 to 421 were prepared in accordance with the same procedures as in Example 84, using (S)-5-[4-(3-aminopyrrolidin-1-yl)-6-propylpyrimidin-2-ylamino]-2-methylbenzonitrile dihydrochloride prepared in Example 354; and propionaldehyde, 3-(methylthio)propionaldehyde, pyrrole-2-carboxaldehyde, 4-hydroxybenzaldehyde, acetone, cyclobutanone, cyclopentanone, or cyclohexanone.

Example 422

A solution of (S)-5-[4-(3-aminopyrrolidin-1-yl)-6-propylpyrimidin-2-ylamino]-2-methylbenzonitrile dihydrochloride (20 mg, 0.05 mmol) prepared in Example 354 and pentanal (4.3 mg, 0.05 mmol) in methanol (1 ml) was stirred at room temperature for 30 minutes and then sodium cyanoborohydride (9.4 mg, 0.15 mmol) was added thereto. The reaction mixture was stirred at room temperature for 3 hours and then an aqueous saturated solution of sodium bicarbonate was added thereto to terminate the reaction. The reaction mixture was extracted with ethyl acetate. The resulting organic layer was dried on anhydrous sodium sulfate, filtered, and then concentrated. The resulting residue was purified with silica gel column chromatography (n-hexane/ethyl acetate=1/1), and then dissolved in ethyl acetate (1 ml). Hydrogen chloride gas was added to the solution. The reaction mixture was stirred at room temperature for 1 hour and then filtered to give 8 mg of the product as a white solid.

Examples 423 and 424

The products of Examples 423 and 424 were prepared in accordance with the same procedures as in Example 422, using (S)-5-[4-(3-aminopyrrolidin-1-yl)-6-propylpyrimidin-2-ylamino]-2-methylbenzonitrile dihydrochloride prepared in Example 354; and pivaldehyde or 4,5-dimethylfuran-2-carboxaldehyde.

Examples 425 to 430

The products of Examples 425 to 430 were prepared in accordance with the same procedures as in Example 61, using (S)-5-[4-(3-aminopyrrolidin-1-yl)-6-propylpyrimidin-2-ylamino]-2-methylbenzonitrile dihydrochloride prepared in Example 354; and propionic acid, 2-phenylacetic acid, 2-(piperidin-1-yl)acetic acid, 2-(pyridin-3-yl)acetic acid, 2-(pyridin-4-yl)acetic acid, or 2-(thiophene-2-yl)acetic acid.

Example 431

The product in the form of pale yellow solid was prepared in accordance with the same procedures as in Example 124, using (S)-5-[4-(3-aminopyrrolidin-1-yl)-6-propylpyrimidin-2-ylamino]-2-methylbenzonitrile dihydrochloride prepared in Example 354 and methanesulfonyl chloride.

Example 432

The product in the form of white solid was prepared in accordance with the same procedures as in Example 118, using (S)—N-{1-[2-(3-cyano-4-methylphenylamino)-6-propylpyrimidin-4-yl]pyrrolidin-3-yl}methanesulfonamide prepared in Example 431.

Example 433

Ethyl isocyanate (7.1 mg, 0.1 mmol) was slowly added at room temperature to a solution of (S)-5-[4-(3-aminopyrrolidin-1-yl)-6-propylpyrimidin-2-ylamino]-2-methylbenzonitrile dihydrochloride (20 mg, 0.05 mmol) prepared in Example 354 and diisopropylethylamine (0.03 ml, 0.14 mmol) in dichloromethane (1 ml). The reaction mixture was stirred at room temperature for 30 minutes. Water was added to the reaction mixture, which was then extracted with dichloromethane. The separated organic layer was dried on anhydrous sodium sulfate, filtered, and then concentrated under reduced pressure. The resulting residue was purified with silica gel column chromatography (ethyl acetate) and then dissolved in ethyl acetate (2 ml). Hydrogen chloride gas was added to the solution. The reaction mixture was stirred at room temperature for 2 hours and then filtered to give 6 mg of the product as a white solid.

Example 434

The product in the form of pale yellow solid was prepared in accordance with the same procedures as in Example 84, using (R)-3-{4-[3-(aminomethyl)pyrrolidin-1-yl]-6-propylpyrimidin-2-ylamino}benzonitrile dihydrochloride prepared in Example 179 and acetaldehyde.

Example 435

The product in the form of white solid was prepared in accordance with the same procedures as in Example 118, using (S)-5-{4-[3-(isopropylamino)pyrrolidin-1-yl]-6-propylpyrimidin-2-ylamino]-2-methylbenzonitrile prepared in Example 418.

Examples 436 to 446

The products of Examples 436 to 446 were prepared in accordance with the same procedures as in Example 26, using (S)—N-[1-(6-butyl-2-chloropyrimidin-4-yl)pyrrolidin-3-yl]acetamide prepared in Preparation 24; and 4-methyl-3-nitroaniline, 4-fluoro-3-nitroaniline, 4-chloro-3-nitroaniline, 3,5-diaminobenzonitrile, 5-(trifluoromethyl)benzene-1,3-diamine, 2-(trifluoromethyl)benzene-1,4-diamine, 4-fluoro-3-trifluoromethylphenylamine, 5-amino-2-fluorobenzonitrile, 4-fluoro-1,3-phenylenediamine, 4-chloro-1,3-phenylenediamine, or 2,5-diaminobenzonitrile prepared in Preparation 19.

Example 447

A solution of (S)-tert-butyl 1-(6-butyl-2-chloropyrimidin-4-yl)pyrrolidin-3-yl(methyl)carbamate (85 mg, 0.23 mmol) prepared in Preparation 25 and 2,5-diaminobenzonitrile (34 mg, 0.25 mmol) prepared in Preparation 19 in n-butanol (0.5 ml) was stirred at 130° C. for 3 hours. The reaction mixture was cooled to room temperature and then concentrated under reduced pressure. The resulting residue was purified with silica gel column chromatography (dichloromethane/methanol=20/1) and then dissolved in ethyl acetate/methanol (1 ml/1 ml). The resulting solution was saturated with hydrogen chloride gas and then filtered to give 46.7 mg of the product as a white solid.

Examples 448 to 457

The products of Examples 448 to 457 were prepared in accordance with the same procedures as in Example 447, using (S)-tert-butyl 1-(6-butyl-2-chloropyrimidin-4-yl)pyrrolidin-3-yl(methyl)carbamate prepared in Preparation 25; and 4-methyl-3-nitroaniline, 4-fluoro-3-nitroaniline, 4-chloro-3-nitroaniline, 3,5-diaminobenzonitrile, 5-(trifluoromethyl)benzene-1,3-diamine, 2-(trifluoromethyl)benzene-1,4-diamine, 4-fluoro-3-trifluoromethylphenylamine, 5-amino-2-fluorobenzonitrile, 4-fluoro-1,3-phenylenediamine, or 4-chloro-1,3-phenylenediamine.

Examples 458 to 471

The products of Examples 458 to 471 were prepared in accordance with the same procedures as in Example 447, using (S)-tert-butyl 1-(6-butyl-2-chloropyrimidin-4-yl)pyrrolidin-3-yl(ethyl)carbamate prepared in Preparation 26; and 2,5-diaminobenzonitrile prepared in Preparation 19, 3-aminobenzonitrile, 5-amino-2-methylbenzonitrile, 2-nitro-1,4-phenylenediamine, 4-methyl-3-nitroaniline, 4-fluoro-3-nitroaniline, 4-chloro-3-nitroaniline, 3,5-diaminobenzonitrile, 5-(trifluoromethyl)benzene-1,3-diamine, 2-(trifluoromethyl)benzene-1,4-diamine, 4-fluoro-3-trifluoromethylphenylamine, 5-amino-2-fluorobenzonitrile, 4-fluoro-1,3-phenylenediamine, or 4-chloro-1,3-phenylenediamine.

Example 472

A mixture of (S)—N-[1-(2-chloro-6-propylpyrimidin-4-yl)pyrrolidin-3-yl]-2-hydroxyacetamide (20 mg, 0.07 mmol) prepared in Preparation 27 and 5-amino-2-methylbenzonitrile (10.6 mg, 0.08 mmol) in n-butanol (0.5 ml) was stirred in a microwave reactor (600 W) for 1 hour. The reaction mixture was concentrated under reduced pressure. The resulting residue was purified with silica gel column chromatography (dichloromethane/methanol=20/1) to give 5.9 mg of the product as yellow oil.

Examples 473 to 481

The products of Examples 473 to 481 were prepared in accordance with the same procedures as in Example 472, using (S)—N-[1-(2-chloro-6-propylpyrimidin-4-yl)pyrrolidin-3-yl]-2-hydroxyacetamide prepared in Preparation 27; and 5-amino-2-fluorobenzonitrile, 3,5-diaminobenzonitrile, 5-(trifluoromethyl)benzene-1,3-diamine, 2-(trifluoromethyl)benzene-1,4-diamine, 4-fluoro-3-trifluoromethylphenylamine, 4-fluoro-1,3-phenylenediamine, 4-chloro-1,3-phenylenediamine, 2-chloro-4-aminotoluene, or 4-methyl-3-(trifluoromethyl)aniline.

Example 482

The product in the form of white solid was prepared in accordance with the same procedures as in Example 118, using (S)—N-{1-[2-(3-amino-5-cyanophenylamino)-6-propylpyrimidin-4-yl]pyrrolidin-3-yl}-2-hydroxyacetamide prepared in Example 474.

Example 483

The product in the form of white solid was prepared in accordance with the same procedures as in Example 118, using (S)—N-{1-[2-(3-cyano-4-methylphenylamino)-6-propyl pyrimidin-4-yl]pyrrolidin-3-yl}-2-hydroxyacetamide prepared in Example 472.

Example 484

A solution of (S)-tert-butyl 1-(2-chloro-6-propylpyrimidin-4-yl)pyrrolidin-3-yl(methyl)carbamate (0.2 g, 0.56 mmol) prepared in Preparation 28, 4-fluorobenzene-1,3-diamine (0.1 g, 0.61 mmol), and diisopropylethylamine (0.2 ml, 1.12 mmol) in n-butanol (2 ml) was stirred at 130° C. overnight. The reaction mixture was cooled to room temperature and then concentrated under reduced pressure. The resulting residue was purified with silica gel column chromatography (dichloromethane/ethyl acetate=20/1) and then dissolved in ethyl acetate (2 ml). Hydrogen chloride gas was added to the solution. The reaction mixture was stirred at room temperature for 1 hour and then filtered to give 0.1 g of the product as a white solid.

Examples 485 to 487

The products of Examples 485 to 487 were prepared in accordance with the same procedures as in Example 484, using (S)-tert-butyl 1-(2-chloro-6-propylpyrimidin-4-yl)pyrrolidin-3-yl(methyl)carbamate prepared in Preparation 28; and 3,5-diaminobenzonitrile, 2,5-diaminobenzonitrile prepared in Preparation 19, or 5-(trifluoromethyl)-1,3-phenylenediamine.

Examples 488 to 489

The products of Examples 488 to 489 was prepared in accordance with the same procedures as in Example 484, using (S)-tert-butyl 1-(2-chloro-6-propylpyrimidin-4-yl)pyrrolidin-3-yl(ethyl)carbamate prepared in Preparation 29; and 2-(trifluoromethyl)-1,4-phenylenediamine or 2,5-diaminobenzonitrile prepared in Preparation 19.

Examples 490 and 491

The products of Examples 490 and 491 were prepared in accordance with the same procedures as in Example 172, using 4-chloro-N-[4-fluoro-3-(trifluoromethyl)phenyl]-6-propylpyrimidin-2-amine prepared in Preparation 30; and (3S)-(−)-3-(methylamino)pyrrolidine or (3S)-(−)-3-(ethylamino)pyrrolidine.

Example 492

The product in the form of white solid was prepared in accordance with the same procedures as in Example 118, using (S)—N-{1-[6-butyl-2-(3-cyano-4-methylphenylamino)pyrimidin-4-yl]pyrrolidin-3-yl}acetamide prepared in Example 228.

Example 493

The product in the form of white solid was prepared in accordance with the same procedures as in Example 118, using (S)—N-{1-[2-(3-amino-4-methylphenylamino)-6-propylpyrimidin-4-yl]pyrrolidin-3-yl}acetamide prepared in Example 292.

Example 494

The product in the form of pale yellow solid was prepared in accordance with the same procedures as in Example 395, using (S)—N-{1-[2-(4-amino-3-nitrophenylamino)-6-propylpyrimidin-4-yl]pyrrolidin-3-yl}acetamide hydrochloride prepared in Example 286.

The compounds of Examples 1 to 494 and the NMR spectrum data thereof are shown in Tables 1-1 to 1-51 below.

TABLE 1-1

| Example | Compound | NMR Spectrum |
|---|---|---|
| 1 | N-(4-fluorophenyl)-4-propyl-6-(pyrrolidin-1-yl)pyrimidin-2-amine | $^1$H-NMR (400 MHz, CDCl$_3$) δ 7.70-7.60 (m, 2H), 6.97 (t, 2H), 5.68 (s, 1H), 3.70-3.20 (m, 4H), 2.46 (t, 2H), 2.10-1.90 (m, 4H), 1.80-1.60 (m, 2H), 0.97 (t, 3H) |
| 2 | (S)-{1-[2-(4-fluorophenylamino)-6-propylpyrimidin-4-yl]pyrrolidin-2-yl}methanol | $^1$H-NMR (400 MHz, CDCl$_3$) δ 7.60-7.50 (m, 2H), 6.99 (t, 2H), 6.75 (brs, 1H), 5.74 (s, 1H), 4.38 (brs, 1H), 3.80-3.60 (m, 2H), 3.50-3.40 (m, 1H), 3.40-3.30 (m, 1H), 2.48 (t, 2H), 2.10-1.90 (m, 3H), 1.80-1.60 (m, 3H), 0.98 (t, 3H) |
| 3 | 1-[2-(4-fluorophenylamino)-6-propylpyrimidin-4-yl]pyrrolidin-3-ol | $^1$H-NMR (400 MHz, CDCl$_3$) δ 7.60-7.50 (m, 2H), 6.97 (t, 2H), 6.84 (brs, 1H), 5.70 (s, 1H), 4.62 (brs, 1H), 3.63 (brs, 4H), 2.46 (t, 2H), 2.20-2.00 (m, 2H), 1.71 (q, 2H), 0.98 (t, 3H) |
| 4 | (R)-{1-[2-(4-fluorophenylamino)-6-propylpyrimidin-4-yl]pyrrolidin-2-yl}methanol | $^1$H-NMR (400 MHz, CDCl$_3$) δ 7.55-7.45 (m, 2H), 6.98 (t, 2H), 6.83 (brs, 1H), 5.74 (s, 1H), 4.35 (brs, 1H), 3.70-3.55 (m, 2H), 3.50-3.40 (m, 1H), 3.40-3.30 (m, 1H), 2.47 (t, 2H), 2.10-1.90 (m, 3H), 1.80-1.60 (m, 3H), 0.98 (t, 3H) |
| 5 | {1-[2-(4-fluorophenylamino)-6-propylpyrimidin-4-yl]pyrrolidin-2-yl}methanol | $^1$H-NMR (400 MHz, CDCl$_3$) δ 7.55-7.45 (m, 2H), 6.98 (t, 2H), 6.83 (brs, 1H), 5.74 (s, 1H), 4.35 (brs, 1H), 3.70-3.55 (m, 2H), 3.50-3.40 (m, 1H), 3.40-3.30 (m, 1H), 2.47 (t, 2H), 2.10-1.90 (m, 3H), 1.80-1.60 (m, 3H), 0.98 (t, 3H) |
| 6 | N-(4-fluorophenyl)-4-(2-methylpyrrolidin-1-yl)-6-propylpyrimidin-2-amine | $^1$H-NMR (400 MHz, CDCl$_3$) δ 7.65-7.55 (m, 2H), 6.97 (t, 2H), 6.83 (brs, 1H), 5.68 (s, 1H), 4.20 (brs, 1H), 3.55 (brs, 1H), 3.38 (brs, 1H), 2.45 (t, 2H), 2.10-1.90 (m, 3H), 1.80-1.65 (m, 3H), 1.23 (d, 3H), 0.98 (t, 3H) |
| 7 | (S)-N-(4-fluorophenyl)-4-[2-(methoxymethyl)pyrrolidin-1-yl]-6-propylpyrimidin-2-amine | $^1$H-NMR (400 MHz, CDCl$_3$) δ 7.65-7.55 (m, 2H), 6.97 (t, 2H), 6.86 (brs, 1H), 5.73 (s, 1H), 4.30-4.10 (brs, 1H), 3.66 (brs, 1H), 3.49 (brs, 1H), 3.36 (s, 3H), 3.30-3.15 (m, 2H), 2.46 (t, 2H), 2.10-1.85 (m, 4H), 1.71 (q, 2H), 0.98 (t, 3H) |
| 8 | (R)-N-(4-fluorophenyl)-4-[2-(methoxymethyl)pyrrolidin-1-yl]-6-propylpyrimidin-2-amine | $^1$H-NMR (400 MHz, CDCl$_3$) δ 7.65-7.55 (m, 2H), 6.97 (t, 2H), 6.86 (brs, 1H), 5.73 (s, 1H), 4.30-4.10 (brs, 1H), 3.66 (brs, 1H), 3.49 (brs, 1H), 3.36 (s, 3H), 3.30-3.15 (m, 2H), 2.46 (t, 2H), 2.10-1.85 (m, 4H), 1.71 (q, 2H), 0.98 (t, 3H) |
| 9 | (S)-1-[2-(4-fluorophenylamino)-6-propylpyrimidin-4-yl]pyrrolidin-2-carboxamide | $^1$H-NMR (400 MHz, CD$_3$OD) δ 7.65-7.55 (m, 2H), 6.97 (t, 2H), 5.90 (s, 1H), 4.60-4.40 (m, 1H), 3.75-3.60 (m, 1H), 3.55-3.35 (m, 1H), 2.47 (t, 2H), 2.30-2.20 (m, 1H), 2.15-1.95 (m, 3H), 1.72 (q, 2H), 0.98 (t, 3H) |
| 10 | N-{1-[2-(4-fluorophenylamino)-6-propylpyrimidin-4-yl]pyrrolidin-3-yl}acetamide | $^1$H-NMR (400 MHz, CD$_3$OD) δ 7.70-7.60 (m, 2H), 6.98 (t, 2H), 5.81 (s, 1H), 4.44 (t, 1H), 3.80-3.30 (m, 4H), 2.45 (t, 2H), 2.30-2.20 (m, 1H), 2.05-1.95 (m, 1H), 1.94 (s, 3H), 1.71 (q, 2H), 0.97 (t, 3H) |

TABLE 1-2

| Example | Compound | NMR Spectrum |
|---|---|---|
| 11 | (R)-N-{1-[2-(4-fluorophenylamino)-6-propylpyrimidin-4-yl]pyrrolidin-3-yl}acetamide | $^1$H-NMR (400 MHz, CDCl$_3$) δ 7.70-7.60 (m, 2H), 6.98 (t, 2H), 5.79 (brs, 1H), 5.68 (s, 1H), 4.65-4.55 (m, 1H), 3.80-3.70 (m, 1H), 3.65-3.45 (m, 3H), 2.46 (t, 2H), 2.00 (s, 3H), 1.80-1.60 (m, 2H), 0.97 (t, 3H) |
| 12 | 2,2,2-trifluoro-N-{1-[2-(4-fluorophenylamino)-6-propylpyrimidin-4-yl]pyrrolidin-3-yl}acetamide | $^1$H-NMR (400 MHz, CDCl$_3$) δ 7.60-7.50 (m, 2H), 6.99 (t, 2H), 6.80 (brs, 1H), 6.54 (brs, 1H), 5.70 (s, 1H), 4.70-4.60 (m, 1H), 3.85-3.75 (m, 1H), 3.70-3.30 (m, 3H), 2.48 (t, 2H), 2.40-2.30 (m, 1H), 2.15-2.05 (m, 1H), 1.80-1.65 (m, 2H), 0.98 (t, 3H) |
| 13 | 4-[3-(ethylamino)pyrrolidin-1-yl]-N-(4-fluorophenyl)-6-propylpyrimidin-2-amine | $^1$H-NMR (400 MHz, CDCl$_3$) δ 7.65-7.55 (m, 2H), 6.96 (t, 2H), 6.92 (brs, 1H), 5.67 (s, 1H), 3.47 (t, 2H), 2.72 (q, 2H), 2.45 (t, 2H), 2.25-2.10 (m, 1H), 1.90-1.80 (m, 1H), 1.71 (q, 2H), 1.15 (t, 3H), 0.99 (t, 3H) |
| 14 | 4-[3-(dimethylamino)pyrrolidin-1-yl]-N-(4-fluorophenyl)-6-propylpyrimidin-2-amine | $^1$H-NMR (400 MHz, CDCl$_3$) δ 7.65-7.55 (m, 2H), 6.96 (t, 2H), 6.88 (brs, 1H), 5.68 (s, 1H), 4.00-3.50 (m, 2H), 3.50-3.30 (m, 1H), 3.30-3.10 (m, 1H), 2.85-2.70 (m, 1H), 2.46 (t, 2H), 2.31 (s, 6H), 2.20-2.10 (m, 1H), 1.90-1.80 (m, 1H), 1.72 (q, 2H), 0.97 (t, 3H) |
| 15 | (S)-N-(4-fluorophenyl)-4-propyl-6-[2-(pyrrolidin-1-ylmethyl)pyrrolidin-1-yl]pyrimidin-2-amine | $^1$H-NMR (400 MHz, CDCl$_3$) δ 7.70-7.60 (m, 2H), 6.97 (t, 2H), 5.72 (s, 1H), 3.60-3.20 (m, 2H), 3.10-2.60 (m, 6H), 2.51 (t, 2H), 2.40-2.20 (m, 1H), 2.10-2.00 (m, 4H), 2.00-1.80 (m, 4H), 1.75 (q, 2H), 0.99 (t, 3H) |
| 16 | (S)-N-(4-fluorophenyl)-4-{2-[(phenylamino)methyl]pyrrolidin-1-yl}-6-propylpyrimidin-2-amine | $^1$H-NMR (400 MHz, CDCl$_3$) δ 7.60-7.50 (m, 2H), 7.20-7.10 (m, 2H), 6.93 (t, 2H), 6.79 (brs, 1H), 6.65 (t, 1H), 6.50-6.40 (m, 2H), 5.72 (s, 1H), 4.70-4.40 (m, 1H), 3.60-3.20 (m, 3H), 3.20-3.10 (m, 1H), 2.46 (t, 2H), 2.20-1.90 (m, 4H), 1.71 (q, 2H), 0.98 (t, 3H) |
| 17 | (S)-N-{1-[2-(4-fluorophenylamino)-6-propylpyrimidin-4-yl]pyrrolidin-3-yl}acetamide | $^1$H-NMR (400 MHz, CDCl$_3$) δ 7.60-7.50 (m, 2H), 7.05-6.90 (m, 3H), 6.08 (brs, 1H), 5.66 (s, 1H), 4.56 (brs, 1H), 3.80-3.20 (m, 4H), 2.45 (t, 2H), 2.30-2.15 (m, 1H), 1.98 (s, 3H), 2.00-1.90 (m, 1H), 1.70 (q, 2H), 0.96 (t, 3H) |
| 18 | (S)-4-[3-(ethylamino)pyrrolidin-1-yl]-N-(4-fluorophenyl)-6-propylpyrimidin-2-amine | $^1$H-NMR (400 MHz, CDCl$_3$) δ 7.65-7.55 (m, 2H), 6.96 (t, 2H), 6.92 (brs, 1H), 5.67 (s, 1H), 3.47 (t, 2H), 2.72 (q, 2H), 2.45 (t, 2H), 2.25-2.10 (m, 1H), 1.90-1.80 (m, 1H), 1.71 (q, 2H), 1.14 (t, 3H), 0.97 (t, 3H) |
| 19 | (S)-tert-butyl 1-[2-(4-fluorophenylamino)-6-propylpyrimidin-4-yl]pyrrolidin-3-ylcarbamate | $^1$H-NMR (400 MHz, CDCl$_3$) δ 7.65-7.55 (m, 2H), 6.97 (t, 2H), 6.86 (brs, 1H), 5.68 (s, 1H), 4.72 (brs, 1H), 4.34 (brs, 1H), 3.80-3.20 (m, 4H), 2.46 (t, 2H), 2.30-2.20 (m, 1H), 2.05-1.90 (m, 1H), 1.71 (q, 2H), 1.46 (s, 9H), 0.97 (t, 3H) |
| 20 | 4-(3-aminopyrrolidin-1-yl)-N-(4-fluorophenyl)-6-propylpyrimidin-2-amine | $^1$H-NMR (400 MHz, CD$_3$OD) δ 7.70-7.60 (m, 2H), 6.98 (t, 2H), 5.84 (s, 1H), 3.90-3.35 (m, 5H), 2.46 (t, 2H), 2.35-2.25 (m, 1H), 2.00-1.90 (m, 1H), 1.72 (q, 2H), 0.98 (t, 3H) |

TABLE 1-3

| Example | Compound | NMR Spectrum |
|---|---|---|
| 21 | 4-[3-(diethylamino)pyrrolidin-1-yl]-N-(4-fluorophenyl)-6-propylpyrimidin-2-amine | $^1$H-NMR (400 MHz, CDCl$_3$) δ 7.65-7.55 (m, 2H), 7.05-6.90 (m, 3H), 5.68 (s, 1H), 4.00-3.10 (m, 5H), 2.80-2.60 (m, 4H), 2.46 (t, 2H), 2.25-2.15 (m, 1H), 1.90-1.80 (m, 1H), 1.72 (q, 2H), 1.06 (t, 6H), 0.98 (t, 3H) |
| 22 | (S)-N-(4-fluorophenyl)-4-[3-(methylamino)pyrrolidin-1-yl]-6-propylpyrimidin-2-amine | $^1$H-NMR (400 MHz, CDCl$_3$) δ 7.70-7.60 (m, 2H), 7.20 (brs, 1H), 6.97 (t, 2H), 5.68 (s, 1H), 3.80-3.10 (m, 5H), 2.49 (s, 3H), 2.47 (t, 2H), 2.20-2.10 (m, 1H), 1.90-1.80 (m, 1H), 1.71 (q, 2H), 0.98 (t, 3H) |
| 23 | N-{1-[2-(4-fluorophenylamino)-6-propylpyrimidin-4-yl]pyrrolidin-3-yl}-N-methylacetamide | $^1$H-NMR (400 MHz, CDCl$_3$) δ 7.65-7.55 (m, 2H), 6.98 (t, 2H), 6.88 (brs, 1H), 5.69 (s, 1H), 5.39 (t, 1H), 3.80-3.20 (m, 4H), 2.94 (s, 3H), 2.47 (t, 2H), 2.30-2.20 (m, 2H), 2.14 (s, 3H), 1.72 (q, 2H), 0.98 (t, 3H) |
| 24 | (S)-1-[2-(4-fluorophenylamino)-6-propylpyrimidin-4-yl]pyrrolidin-3-ol | $^1$H-NMR (400 MHz, CDCl$_3$) δ 7.65-7.55 (m, 2H), 6.97 (t, 2H), 6.85 (brs, 1H), 5.68 (s, 1H), 4.62 (brs, 1H), 3.80-3.30 (m, 4H), 2.46 (t, 2H), 2.20-2.00 (m, 2H), 1.71 (q, 2H), 0.97 (t, 3H) |
| 25 | 4-[3-(ethylamino)pyrrolidin-1-yl]-N-(4-fluorophenyl)-6-propylpyrimidin-2-amine dihydrochloride | $^1$H-NMR (400 MHz, CD$_3$OD) δ 7.65-7.55 (m, 2H), 7.17 (t, 2H), 6.28 (s, 1H), 4.20-4.00 (m, 2H), 4.00-3.80 (m, 2H), 3.80-3.70 (m, 1H), 3.25-3.10 (m, 2H), 2.68 (t, 2H), 2.60-2.45 (m, 1H), 2.40-2.20 (m, 1H), 1.79 (t, 2H), 1.45-1.30 (m, 3H), 1.07 (t, 3H) |
| 26 | (S)-N-{4-[2-(methoxymethyl)pyrrolidin-1-yl]-6-propylpyrimidin-2-yl}-1H-indol-6-amine hydrochloride | $^1$H-NMR (400 MHz, CD$_3$OD) δ 7.61 (s, 1H), 7.55 (d, 1H), 7.26 (s, 1H), 7.04 (d, 1H), 6.45 (s, 1H), 6.10 (s, 1H), 4.43 (brs, 1H), 3.60 (brs, 1H), 3.48 (brs, 1H), 3.50-3.40 (m, 2H), 3.10 (s, 3H), 2.59 (t, 2H), 2.25-1.95 (m, 4H), 1.74 (q, 2H), 1.04 (t, 3H) |

TABLE 1-3-continued

| Example | Compound | NMR Spectrum |
|---|---|---|
| 27 | (S)—N-{4-[2-(methoxymethyl)pyrrolidin-1-yl]-6-propylpyrimidin-2-yl}-1H-indol-5-amine | $^1$H-NMR (400 MHz, CDCl$_3$) δ 8.10-8.00 (m, 2H), 7.35-7.25 (m, 1H), 7.17 (s, 1H), 6.90-6.80 (m, 1H), 6.49 (s, 1H), 5.69 (brs, 1H), 3.80-3.60 (m, 2H), 3.60-3.40 (m, 2H), 3.33 (s, 3H), 3.30-3.20 (m, 1H), 2.46 (t, 2H), 2.10-1.90 (m, 4H), 1.73 (q, 2H), 0.99 (t, 3H) |
| 28 | (S)-4-[2-(methoxymethyl)pyrrolidin-1-yl]-N-(4-methoxyphenyl)-6-propylpyrimidin-2-amine | $^1$H-NMR (400 MHz, CDCl$_3$) δ 7.60-7.50 (m, 2H), 6.90-6.80 (m, 2H), 6.74 (brs, 1H), 5.70 (s, 1H), 4.35 (brs, 1H), 3.79 (s, 3H), 3.80-3.60 (m, 1H), 3.50-3.40 (m, 1H), 3.36 (s, 3H), 3.30-3.20 (m, 2H), 2.50-2.40 (m, 2H), 2.20-1.90 (m, 4H), 1.80-1.65 (m, 2H), 1.00-0.90 (m, 3H) |
| 29 | (S)-4-[2-(methoxymethyl)pyrrolidin-1-yl]-N-(3-methoxyphenyl)-6-propylpyrimidin-2-amine | $^1$H-NMR (400 MHz, CDCl$_3$) δ 7.50-7.40 (m, 1H), 7.20-7.10 (m, 2H), 6.87 (brs, 1H), 6.51 (d, 1H), 5.74 (s, 1H), 3.81 (s, 3H), 3.80-3.60 (m, 2H), 3.60-3.40 (m, 1H), 3.36 (s, 3H), 3.30-3.20 (m, 2H), 2.46 (t, 2H), 2.10-1.90 (m, 4H), 1.72 (q, 2H), 0.98 (t, 3H) |
| 30 | (S)-N-(3-chlorophenyl)-4-[2-(methoxymethyl)pyrrolidin-1-yl]-6-propylpyrimidin-2-amine | $^1$H-NMR (400 MHz, CDCl$_3$) δ 7.95 (s, 1H), 7.34 (d, 1H), 7.17 (t, 1H), 7.00-6.80 (m, 2H), 5.76 (brs, 1H), 4.50-4.30 (m, 1H), 3.80-3.30 (m, 4H), 3.37 (s, 3H), 2.47 (t, 2H), 2.20-1.90 (m, 4H), 1.72 (q, 2H), 0.98 (t, 3H) |

TABLE 1-4

| Example | Compound | NMR Spectrum |
|---|---|---|
| 31 | (S)-N-(4-fluoro-3-nitrophenyl)-4-[2-(methoxymethyl)pyrrolidin-1-yl]-6-propylpyrimidin-2-amine | $^1$H-NMR (400 MHz, CDCl$_3$) δ 9.00-8.70 (m, 1H), 7.70-7.40 (m, 1H), 7.16 (t, 1H), 7.11 (brs, 1H), 5.83 (brs, 1H), 4.50-4.20 (m, 1H), 3.70-3.35 (m, 4H), 3.36 (s, 3H), 2.48 (t, 2H), 2.20-1.90 (m, 4H), 1.72 (q, 2H), 0.98 (t, 3H) |
| 32 | (S)-4-[2-(methoxymethyl)pyrrolidin-1-yl]-N-(3-nitrophenyl)-6-propylpyrimidin-2-amine | $^1$H-NMR (400 MHz, CDCl$_3$) δ 8.75 (brs, 1H), 7.48 (brs, 2H), 7.37 (d, 1H), 6.05 (brs, 1H), 5.83 (brs, 1H), 4.40 (brs, 1H), 3.65-3.40 (m, 4H), 3.36 (s, 3H), 2.60-2.40 (m, 2H), 2.30-1.90 (m, 4H), 1.71 (q, 2H), 0.98 (t, 3H) |
| 33 | (S)-N-(4-chloro-3-nitrophenyl)-4-[2-(methoxymethyl)pyrrolidin-1-yl]-6-propyl pyrimidin-2-amine | $^1$H-NMR (400 MHz, CDCl$_3$) δ 7.77 (dd, 1H), 7.64 (brs, 1H), 7.38 (t, 1H), 7.19 (brs, 1H), 5.83 (brs, 1H), 4.60-4.30 (m, 1H), 3.70-3.40 (m, 4H), 3.36 (s, 3H), 2.49 (t, 2H), 2.20-1.90 (m, 4H), 1.73 (q, 2H), 0.99 (t, 3H) |
| 34 | (S)-3-{4-[2-(methoxymethyl)pyrrolidin-1-yl]-6-propylpyrimidin-2-ylamino}benzonitrile | $^1$H-NMR (400 MHz, CDCl$_3$) δ 8.23 (brs, 1H), 7.66 (brs, 1H), 7.34 (t, 1H), 7.21 (d, 1H), 7.08 (brs, 1H), 5.81 (brs, 1H), 4.50-4.30 (m, 1H), 3.70-3.40 (m, 4H), 3.31 (s, 3H), 2.48 (t, 2H), 2.20-1.90 (m, 4H), 1.72 (q, 2H), 0.99 (t, 3H) |
| 35 | (S)-4-[2-(methoxymethyl)pyrrolidin-1-yl]-N-[3-(methylthio)phenyl]-6-propylpyrimidin-2-amine | $^1$H-NMR (400 MHz, CDCl$_3$) δ 7.66 (br, 1H), 7.40 (br, 1H), 7.19 (t, 2H), 6.85 (d, 1H), 5.75 (br, 1H), 4.37 (br, 1H), 3.63 (br, 2H), 3.36 (s, 3H), 2.48 (m, 5H), 2.09 (m, 2H), 2.00 (m, 2H), 1.74 (m, 2H), 0.98 (t, 3H) |
| 36 | (S)-4-[2-(methoxymethyl)pyrrolidin-1-yl]-6-propyl-N-[3-(trifluoromethyl)phenyl]pyrimidin-2-amine | $^1$H-NMR (400 MHz, CDCl$_3$) δ 8.89 (br, 1H), 8.45-8.20 (br, 1H), 7.65 (br, 1H), 7.39 (t, 1H), 7.25 (m, 1H), 5.78-5.62 (br, 2H), 4.49-4.05 (br, 1H), 3.54 (br, 3H), 3.33 (br, 4H), 2.55 (t, 2H), 2.04 (br, 2H), 1.81 (m, 2H), 1.00 (t, 3H) |
| 37 | (S)-7-{4-[2-(methoxymethyl)pyrrolidin-1-yl]-6-propylpyrimidin-2-ylamino}-4-methyl-2H-chromen-2-one | $^1$H-NMR (400 MHz, CDCl$_3$) δ 8.03 (br, 1H), 7.69 (br, 1H), 7.46 (d, 1H), 7.35 (br, 1H), 6.12 (s, 1H), 5.80 (br, 1H), 4.53-3.73 (br, 2H), 3.57-3.22 (br, 2H), 3.40 (s, 3H), 2.73 (br, 1H), 2.50 (t, 2H), 2.39 (s, 3H), 2.18 (m, 1H), 2.05 (m, 3H), 1.76 (m, 2H), 0.97 (t, 3H) |
| 38 | (S)-N-(5-chloro-2-methylphenyl)-4-[2-(methoxymethyl)pyrrolidin-1-yl]-6-propylpyrimidin-2-amine | $^1$H-NMR (400 MHz, CDCl$_3$) δ 8.24 (br, 1H), 8.05 (br, 1H), 6.95 (d, 1H), 6.93 (d, 1H), 5.76 (br, 1H), 4.44 (br, 1H), 3.53 (br, 3H), 3.31 (br, 4H), 2.55 (t, 2H), 2.40 (s, 3H), 2.10-2.01 (m, 4H), 1.79 (m, 2H), 1.01 (t, 3H) |
| 39 | (S)-N-(3-chloro-4-methylphenyl)-4-[2-(methoxymethyl)pyrrolidin-1-yl]-6-propylpyrimidin-2-amine | $^1$H-NMR (400 MHz, CDCl$_3$) δ 8.56 (br, 1H), 7.89 (br, 1H), 7.30 (m, 1H), 7.11 (d, 1H), 5.89-5.73 (br, 2H), 3.63-3.48 (br, 3H), 3.35 (m, 4H), 2.53 (t, 2H), 2.30 (s, 3H), 2.10-2.03 (m, 4H), 1.79 (m, 2H), 1.00 (t, 3H) |
| 40 | (S)-4-[2-(methoxymethyl)pyrrolidin-1-yl]-N-(4-methyl-3-nitrophenyl)-6-propylpyrimidin-2-amine | $^1$H-NMR (400 MHz, CDCl$_3$) δ 9.00-8.73 (br, 2H), 7.52 (br, 1H), 7.22 (d, 1H), 5.96 (br, 1H), 5.55 (br, 1H), 4.55-4.10 (br, 1H), 3.59 (br, 3H), 3.33 (m, 4H), 2.55 (m, 4H), 2.60 (m, 4H), 1.79 (m, 2H), 1.00 (t, 3H) |

TABLE 1-5

| Example | Compound | NMR Spectrum |
|---|---|---|
| 41 | (S)-N-[4-fluoro-3-(trifluoromethyl)phenyl]-4-[2-(methoxymethyl)pyrrolidin-1-yl]-6-propylpyrimidin-2-amine | $^1$H-NMR (400 MHz, CDCl$_3$) δ 9.20 (br, 1H), 8.42-8.12 (br, 1H), 7.67 (br, 1H), 7.12 (t, 1H), 5.78 (br, 2H), 4.45-4.07 (br, 1H), 3.50 (br, 3H), 3.32 (m, 4H), 2.56 (t, 2H), 2.06 (m, 4H), 1.81 (m, 2H), 1.00 (t, 3H) |
| 42 | (S)-N$^1$-{4-[2-(methoxymethyl)pyrrolidin-1-yl]-6-propylpyrimidin-2-yl}-3-(trifluoromethyl)benzene-1,4-diamine | $^1$H-NMR (400 MHz, CDCl$_3$) δ 7.93 (br, 1H), 7.41 (br, 1H), 6.76 (br, 1H), 6.69 (d, 1H), 5.72 (br, 1H), 4.36 (br, 1H), 4.00 (s, 2H), 3.55 (br, 2H), 3.33 (m, 5H), 2.45 (t, 2H), 2.09 (m, 2H), 2.00 (m, 2H), 1.72 (m, 2H), 0.97 (t, 3H) |
| 43 | (S)-2-fluoro-5-{4-[2-(methoxymethyl)pyrrolidin-1-yl]-6-propylpyrimidin-2-ylamino}benzonitrile | $^1$H-NMR (400 MHz, CDCl$_3$) δ 8.21 (br, 1H), 8.06 (br, 1H), 7.11 (t, 1H), 5.80 (br, 1H), 4.45 (br, 1H), 3.62 (m, 3H), 3.37 (m, 5H), 2.51 (t, 2H), 2.12-2.04 (m, 4H), 1.75 (m, 2H), 0.99 (t, 3H) |
| 44 | (S)-5-{4-[2-(methoxymethyl)pyrrolidin-1-yl]-6-propylpyrimidin-2-ylamino}-2-methylbenzonitrile | $^1$H-NMR (400 MHz, CDCl$_3$) δ 8.58 (br, 1H), 8.17 (br, 1H), 7.57 (br, 1H), 7.22 (d, 1H), 5.78 (br, 1H), 5.31 (br, 1H), 4.49-4.00 (br, 1H), 3.63 (m, 3H), 3.41 (m, 4H), 2.55 (t, 2H), 2.51 (s, 3H), 2.18-2.05 (m, 4H), 1.77 (m, 2H), 0.99 (t, 3H) |
| 45 | (S)-2-amino-5-{4-[2-(methoxymethyl)pyrrolidin-1-yl]-6-propylpyrimidin-2-ylamino}benzonitrile | $^1$H-NMR (400 MHz, CDCl$_3$) δ 7.92 (br, 1H), 7.43 (m, 1H), 7.12 (br, 1H), 6.71 (d, 1H), 5.75 (br, 1H), 4.40 (br, 1H), 4.19 (s, 2H), 3.53 (br, 3H), 3.36 (s, 5H), 2.47 (t, 2H), 2.21 (br, 2H), 2.05 (m, 2H), 1.97 (m, 2H), 1.72 (m, 2H), 0.98 (t, 3H) |
| 46 | (S)-N$^1$-{4-[2-(methoxymethyl)pyrrolidin-1-yl]-6-propylpyrimidin-2-yl}-3-nitrobenzene-1,4-diamine | $^1$H-NMR (400 MHz, CDCl$_3$) δ 8.72 (br, 1H), 8.35 (br, 1H), 7.41 (br, 1H), 6.80 (d, 1H), 6.06 (s, 2H), 5.78 (br, 1H), 4.60-4.10 (br, 3H), 3.54 (br, 3H), 3.32 (m, 3H), 2.52 (t, 2H), 2.18-2.03 (m, 2H), 1.79 (m, 2H), 0.99 (t, 3H) |
| 47 | (S)-4-(3-aminopyrrolidin-1-yl)-N-(4-fluorophenyl)-6-propylpyrimidin-2-amine dihydrochloride | $^1$H-NMR (400 MHz, CD$_3$OD) δ 7.60-7.45 (m, 2H), 7.15 (t, 2H), 6.30-6.20 (m, 1H), 4.10-3.91 (m, 2H), 3.90-3.70 (m, 3H), 2.66 (t, 2H), 2.60-2.40 (m, 1H), 2.30-2.10 (m, 1H), 1.80-1.65 (m, 2H), 1.05 (t, 3H) |
| 48 | (S)-tert-butyl 1-[2-(3-cyanophenylamino)-6-propylpyrimidin-4-yl]pyrrolidin-3-ylcarbamate | $^1$H-NMR (400 MHz, CDCl$_3$) δ 8.31 (brs, 1H), 7.62 (brs, 1H), 7.34 (t, 1H), 7.21 (d, 1H), 7.01 (brs, 1H), 5.75 (s, 1H), 4.71 (brs, 1H), 4.34 (brs, 1H), 3.80-3.20 (m, 4H), 2.48 (t, 2H), 2.40-2.20 (m, 1H), 2.10-1.90 (m, 1H), 1.72 (q, 2H), 1.46 (s, 9H), 0.98 (t, 3H) |
| 49 | 3-{4-[3-(diethylamino)pyrrolidin-1-yl]-6-propylpyrimidin-2-ylamino}benzonitrile | $^1$H-NMR (400 MHz, CDCl$_3$) δ 8.44 (brs, 1H), 7.55 (d, 1H), 7.32 (t, 1H), 7.20 (d, 1H), 7.13 (brs, 1H), 5.74 (s, 1H), 4.00-3.80 (m, 1H), 3.70-3.10 (m, 4H), 2.71 (d, 4H), 2.48 (t, 2H), 2.25-2.15 (m, 1H), 2.00-1.85 (m, 1H), 1.72 (q, 2H), 1.05 (t, 6H), 0.98 (t, 3H) |
| 50 | (S)-3-{4-[3-(methylamino)pyrrolidin-1-yl]-6-propylpyrimidin-2-ylamino}benzonitrile | $^1$H-NMR (400 MHz, CDCl$_3$) δ 8.40 (s, 1H), 7.57 (dd, 1H), 7.32 (t, 1H), 7.19 (d, 1H), 7.17 (brs, 1H), 5.74 (s, 1H), 3.90-3.10 (m, 5H), 2.50 (s, 3H), 2.48 (t, 2H), 2.30-2.10 (m, 1H), 1.90-1.85 (m, 1H), 1.72 (q, 2H), 0.98 (t, 3H) |

TABLE 1-6

| Example | Compound | NMR Spectrum |
|---|---|---|
| 51 | N-{1-[2-(3-cyanophenylamino)-6-propylpyrimidin-4-yl]pyrrolidin-3-yl}-N-methylacetamide | $^1$H-NMR (400 MHz, CDCl$_3$) δ 8.32 (s, 1H), 7.61 (d, 1H), 7.34 (t, 1H), 7.21 (d, 1H), 7.02 (t, 1H), 5.75 (s, 1H), 5.37 (t, 1H), 3.90-3.20 (m, 4H), 2.96 (s, 3H), 2.49 (t, 2H), 2.20 (m, 2H), 2.15 (s, 3H), 1.73 (q, 2H), 0.98 (t, 3H) |
| 52 | (S)-3-[4-(3-hydroxypyrrolidin-1-yl)-6-propylpyrimidin-2-ylamino]benzonitrile | $^1$H-NMR (400 MHz, CDCl$_3$) δ 8.38 (s, 1H), 7.55 (dd, 1H), 7.32 (t, 1H), 7.20 (d, 1H), 7.00 (brs, 1H), 5.75 (s, 1H), 4.65 (brs, 1H), 3.90-3.30 (m, 4H), 2.48 (t, 2H), 2.20-2.00 (m, 2H), 1.72 (q, 2H), 0.98 (t, 3H) |
| 53 | (R)-3-[4-(2-methylpyrrolidin-1-yl)-6-propylpyrimidin-2-ylamino]benzonitrile | $^1$H-NMR (400 MHz, CDCl$_3$) δ 8.46 (brs, 1H), 7.52 (d, 1H), 7.40-7.25 (m, 2H), 7.18 (d, 1H), 5.75 (s, 1H), 4.50-4.10 (m, 1H), 3.70-3.20 (m, 2H), 2.47 (t, 2H), 2.20-1.90 (m, 3H), 1.80-1.60 (m, 3H), 1.30-1.20 (m, 3H), 0.97 (t, 3H) |
| 54 | (S)-N-{1-[2-(3-cyanophenylamino)-6-propylpyrimidin-4-yl]pyrrolidin-3-yl}acetamide | $^1$H-NMR (400 MHz, CDCl$_3$) δ 8.31 (brs, 1H), 7.60 (brs, 1H), 7.33 (t, 1H), 7.20 (d, 1H), 7.06 (brs, 1H), 5.80 (d, 1H), 5.75 (s, 1H), 4.60 (q, 1H), 3.90-3.20 (m, 4H), 2.48 (t, 2H), 2.40-2.25 (m, 1H), 2.01 (s, 3H), 1.83 (brs, 1H), 1.72 (q, 2H), 0.98 (t, 3H) |
| 55 | (S)-3-{4-[3-(ethylamino)pyrrolidin-1-yl]- | $^1$H-NMR (400 MHz, CDCl$_3$) δ 8.39 (s, 1H), 7.58 (d, 1H), 7.32 (t, 1H), 7.19 (d, 1H), 7.15 (brs, 1H), 5.74 (s, 1H), |

TABLE 1-6-continued

| Example | Compound | NMR Spectrum |
|---|---|---|
|  | 6-propylpyrimidin-2-ylamino}benzonitrile | 3.90-3.10 (m, 5H), 2.74 (q, 2H), 2.48 (t, 2H), 2.25-2.15 (m, 1H), 1.90-1.80 (m, 1H), 1.72 (q, 2H), 1.15 (t, 3H), 0.98 (t, 3H) |
| 56 | (R)-tert-butyl{1-[2-(3-cyanophenylamino)-6-propylpyrimidin-4-yl]pyrrolidin-3-yl}methylcarbamate | $^1$H-NMR (400 MHz, CDCl$_3$) δ 8.39 (s, 1H), 7.60 (d, 1H), 7.37 (brs, 1H), 7.33 (t, 1H), 7.21 (d, 1H), 5.74 (s, 1H), 4.75 (brs, 1H), 3.90-3.00 (m, 6H), 2.53 (brs, 1H), 2.48 (t, 2H), 2.20-2.10 (m, 1H), 1.78 (brs, 1H), 1.72 (q, 2H), 1.46 (s, 9H), 0.98 (t, 3H) |
| 57 | (R)-3-[4-(3-hydroxypyrrolidin-1-yl)-6-propylpyrimidin-2-ylamino]benzonitrile | $^1$H-NMR (400 MHz, CDCl$_3$) δ 8.39 (s, 1H), 7.82 (d, 1H), 7.39 (t, 1H), 7.21 (d, 1H), 5.89 (s, 1H), 4.55 (s, 1H), 3.62 (brs, 4H), 2.51 (t, 2H), 2.13 (m, 2H), 1.73 (m, 2H), 0.97 (t, 3H) |
| 58 | (S)-3-[4-(3-methoxypyrrolidin-1-yl)-6-propylpyrimidin-2-ylamino]benzonitrile | $^1$H-NMR (400 MHz, CD$_3$OD) δ 8.41 (s, 1H), 7.80 (d, 1H), 7.39 (t, 1H), 7.21 (d, 1H), 5.89 (s, 1H), 4.14 (s, 1H), 3.60-3.55 (m, 4H), 3.48 (s, 3H), 2.49 (t, 2H), 2.19-2.11 (m, 2H), 1.75 (m, 2H), 0.98 (t, 3H) |
| 59 | 3-{4-[3-(methylamino)pyrrolidin-1-yl]-6-propylpyrimidin-2-ylamino}benzonitrile dihydrochloride | $^1$H-NMR (400 MHz, CD$_3$OD) δ 8.20-8.10 (m, 1H), 7.90-7.80 (m, 1H), 7.60-7.50 (m, 2H), 6.35 (s, 1H), 4.20-3.70 (m, 5H), 2.81 (s, 3H), 2.69 (t, 2H), 2.60-2.45 (m, 1H), 2.45-2.25 (m, 1H), 1.80 (q, 2H), 1.06 (t, 3H) |
| 60 | (S)-3-[4-(3-aminopyrrolidin-1-yl)-6-propylpyrimidin-2-ylamino]benzonitrile dihydrochloride | $^1$H-NMR (400 MHz, CD$_3$OD) δ 8.09 (d, 1H), 7.90-7.80 (m, 1H), 7.60-7.50 (m, 2H), 6.40-6.30 (m, 1H), 4.20-3.70 (m, 5H), 2.69 (t, 2H), 2.60-2.45 (m, 1H), 2.30-2.15 (m, 1H), 1.80 (q, 2H), 1.06 (t, 3H) |

TABLE 1-7

| Example | Compound | NMR Spectrum |
|---|---|---|
| 61 | (S)-N-{1-[2-(3-cyanophenylamino)-6-propylpyrimidin-4-yl]pyrrolidin-3-yl}butyramide | $^1$H-NMR (400 MHz, CDCl$_3$) δ 8.31 (brs, 1H), 7.60 (brs, 1H), 7.33 (t, 1H), 7.20 (d, 1H), 7.04 (brs, 1H), 5.75 (s, 1H), 5.70 (d, 1H), 4.61 (q, 1H), 3.80-3.20 (m, 4H), 2.48 (t, 2H), 2.40-2.25 (m, 1H), 2.17 (t, 2H), 2.05-1.95 (m, 1H), 1.80-1.60 (m, 4H), 1.00-0.90 (m, 6H) |
| 62 | (S)-N-{1-[2-(3-cyanophenylamino)-6-propylpyrimidin-4-yl]pyrrolidin-3-yl}cyclopentanecarboxamide | $^1$H-NMR (400 MHz, CDCl$_3$) δ 8.31 (brs, 1H), 7.60 (brs, 1H), 7.33 (t, 1H), 7.20 (d, 1H), 7.09 (brs, 1H), 5.75 (s, 1H), 5.71 (d, 1H), 4.65-4.55 (m, 1H), 3.90-3.15 (m, 4H), 2.50-2.40 (m, 3H), 2.35-2.25 (m, 1H), 1.90-1.65 (m, 9H), 1.60-1.50 (m, 2H), 1.00 (t, 3H) |
| 63 | (S)-N-{1-[2-(3-cyanophenylamino)-6-propylpyrimidin-4-yl]pyrrolidin-3-yl}-3-(piperidin-1-yl)propanamide | $^1$H-NMR (400 MHz, CDCl$_3$) δ 9.53 (brs, 1H), 8.38 (brs, 1H), 7.62 (brs, 1H), 7.34 (t, 1H), 7.21 (d, 1H), 7.02 (brs, 1H), 5.77 (s, 1H), 4.59 (brs, 1H), 3.90-3.20 (m, 4H), 2.65 (d, 1H), 2.60-2.15 (m, 10H), 1.90-1.85 (m, 1H), 1.72 (q, 2H), 1.50-1.25 (m, 6H), 0.99 (t, 3H) |
| 64 | (S)-N-{1-[2-(3-cyanophenylamino)-6-propylpyrimidin-4-yl]pyrrolidin-3-yl}benzamide | $^1$H-NMR (400 MHz, CDCl$_3$) δ 8.35 (brs, 1H), 8.16 (d, 1H), 7.79 (d, 1H), 7.72 (brs, 1H), 7.60-7.30 (m, 5H), 7.22 (d, 1H), 6.55 (brs, 1H), 5.75 (s, 1H), 4.80 (q, 1H), 4.00-3.30 (m, 4H), 2.53 (t, 2H), 2.45-2.35 (m, 1H), 2.25-2.15 (m, 1H), 1.73 (q, 2H), 1.00 (t, 3H) |
| 65 | (S)-N-{1-[2-(3-cyanophenylamino)-6-propylpyrimidin-4-yl]pyrrolidin-3-yl}-4-fluorobenzamide | $^1$H-NMR (400 MHz, CDCl$_3$) δ 8.85-8.75 (m, 2H), 8.31 (brs, 1H), 7.60 (brs, 1H), 7.33 (t, 1H), 7.19 (d, 1H), 7.15-7.00 (m, 3H), 6.40 (brs, 1H), 5.77 (s, 1H), 4.78 (q, 1H), 4.00-3.30 (m, 4H), 2.48 (t, 2H), 2.40-2.30 (m, 1H), 2.20-2.10 (m, 1H), 1.72 (q, 2H), 0.98 (t, 3H) |
| 66 | (S)-N-{1-[2-(3-cyanophenylamino)-6-propylpyrimidin-4-yl]pyrrolidin-3-yl}-2-phenylacetamide | $^1$H-NMR (400 MHz, CDCl$_3$) δ 8.28 (brs, 1H), 7.59 (d, 1H), 7.48 (brs, 1H), 7.40-7.20 (m, 7H), 5.69 (s, 1H), 5.66 (d, 1H), 4.57 (q, 1H), 3.58 (s, 2H), 3.85-3.10 (m, 4H), 2.47 (t, 2H), 2.30-2.20 (m, 1H), 1.90-1.80 (m, 1H), 1.70 (q, 2H), 0.97 (t, 3H) |
| 67 | (S)-N-{1-[2-(3-cyanophenylamino)-6-propylpyrimidin-4-yl]pyrrolidin-3-yl}-2-(4-fluorophenyl)acetamide | $^1$H-NMR (400 MHz, CDCl$_3$) δ 8.31 (brs, 1H), 7.57 (d, 1H), 7.33 (t, 1H), 7.30-7.20 (m, 4H), 7.09 (brs, 1H), 7.02 (t, 1H), 5.72 (s, 1H), 4.58 (q, 1H), 3.53 (s, 2H), 3.90-3.20 (m, 4H), 2.48 (t, 2H), 2.30-2.20 (m, 1H), 1.90-1.85 (m, 1H), 1.71 (q, 1H), 0.97 (t, 3H) |
| 68 | (S)-N-{1-[2-(3-cyanophenylamino)-6-propylpyrimidin-4-yl]pyrrolidin-3-yl}-3-phenoxypropanamide | $^1$H-NMR (400 MHz, CDCl$_3$) δ 8.29 (brs, 1H), 7.90-7.80 (m, 2H), 7.61 (d, 1H), 7.33 (t, 1H), 7.30-7.20 (m, 3H), 7.00 (brs, 1H), 6.94 (t, 1H), 6.22 (d, 1H), 5.74 (s, 1H), 4.62 (q, 1H), 4.26 (t, 2H), 3.90-3.20 (m, 4H), 2.67 (t, 2H), 2.49 (t, 2H), 2.35-2.25 (m, 1H), 1.80-1.60 (m, 3H), 0.98 (t, 3H) |
| 69 | (S)—N-{1-[2-(3-cyanophenylamino)-6-propylpyrimidin-4-yl]pyrrolidin-3-yl}-3-isobutoxypropanamide | $^1$H-NMR (400 MHz, CDCl$_3$) δ 8.02 (s, 1H), 7.76 (brs, 1H), 7.36 (t, 1H), 7.30-7.20 (m, 1H), 6.89 (brs, 1H), 5.70 (s, 1H), 4.60 (brs, 1H), 3.90-3.70 (m, 3H), 3.65 (t, 2H), 3.25-3.15 (m, 3H), 2.63 (t, 2H), 2.55-2.45 (m, 3H), 2.40-2.30 (m, 1H), 1.75-1.65 (m, 1H), 0.99 (t, 3H), 0.86 (d, 6H) |

TABLE 1-7-continued

| Example | Compound | NMR Spectrum |
| --- | --- | --- |
| 70 | (S)-2-(4-benzylpiperazin-1-yl)-N-{1-[2-(3-cyanophenylamino)-6-propylpyrimidin-4-yl]pyrrolidin-3-yl}acetamide | $^1$H-NMR (400 MHz, CDCl$_3$) δ 8.40 (brs, 1H), 7.65 (brs, 1H), 7.40-7.15 (m, 8H), 5.75 (s, 1H), 5.30 (s, 1H), 4.65-4.55 (m, 1H), 3.90-3.30 (m, 4H), 3.02 (s, 2H), 2.60-2.30 (m, 11H), 2.10-2.00 (m, 1H), 1.72 (q, 2H), 0.99 (t, 3H) |

TABLE 1-8

| Example | Compound | NMR Spectrum |
| --- | --- | --- |
| 71 | (S)-N-{1-[2-(3-cyanophenylamino)-6-propylpyrimidin-4-yl]pyrrolidin-3-yl}-2-(piperidin-1-yl)acetamide | $^1$H-NMR (400 MHz, CDCl$_3$) δ 8.38 (brs, 1H), 7.68 (brs, 1H), 7.48 (d, 1H), 7.36 (t, 1H), 7.24 (d, 1H), 5.75 (s, 1H), 4.60 (q, 1H), 3.90-3.30 (m, 4H), 3.01 (s, 2H), 2.60-2.25 (m, 7H), 2.10-2.00 (m, 1H), 1.71 (q, 2H), 1.65-1.40 (m, 6H), 0.98 (t, 3H) |
| 72 | (S)-N-{1-[2-(3-cyanophenylamino)-6-propylpyrimidin-4-yl]pyrrolidin-3-yl}-4-oxo-4-phenylbutanamide | $^1$H-NMR (400 MHz, CDCl$_3$) δ 8.35 (brs, 1H), 8.03 (s, 1H), 7.98 (d, 2H), 7.90-7.85 (m, 1H), 7.80 (brs, 1H), 7.58 (t, 1H), 7.50-7.40 (m, 3H), 7.33 (t, 1H), 7.22 (d, 1H), 7.12 (brs, 1H), 5.64 (s, 1H), 4.63 (brs, 1H), 3.90-3.20 (m, 6H), 2.80-2.60 (m, 2H), 2.49 (t, 2H), 2.30-2.20 (m, 1H), 2.10-2.00 (m, 1H), 1.67 (q, 2H), 0.96 (t, 3H) |
| 73 | (S)-2-(4-aminophenyl)-N-{1-[2-(3-cyanophenylamino)-6-propylpyrimidin-4-yl]pyrrolidin-3-yl}acetamide | $^1$H-NMR (400 MHz, CDCl$_3$) δ 8.32 (brs, 1H), 7.60 (brs, 1H), 7.34 (t, 1H), 7.22 (d, 1H), 7.02 (d, 2H), 6.66 (d, 2H), 5.70 (s, 1H), 5.55 (d, 1H), 4.56 (q, 1H), 3.90-3.50 (m, 3H), 3.48 (s, 2H), 3.30-3.10 (m, 1H), 2.48 (d, 2H), 2.30-2.20 (m, 1H), 2.00-1.90 (m, 1H), 1.71 (q, 2H), 0.98 (t, 3H) |
| 74 | (S)-N-{1-[2-(3-cyanophenylamino)-6-propylpyrimidin-4-yl]pyrrolidin-3-yl}-2-cyclopentylacetamide | $^1$H-NMR (400 MHz, CDCl$_3$) δ 8.33 (brs, 1H), 7.61 (brs, 1H), 7.34 (t, 1H), 7.21 (d, 1H), 5.75 (s, 1H), 5.63 (brs, 1H), 4.65-4.55 (m, 1H), 3.90-3.20 (m, 4H), 2.49 (t, 2H), 2.30-2.10 (m, 3H), 2.00-1.90 (m, 1H), 1.90-1.45 (m, 9H), 1.20-1.05 (m, 2H), 0.98 (t, 3H) |
| 75 | (S)-N-{1-[2-(3-cyanophenylamino)-6-propylpyrimidin-4-yl]pyrrolidin-3-yl}-2-methoxyacetamide | $^1$H-NMR (400 MHz, CDCl$_3$) δ 8.40 (brs, 1H), 8.02 (s, 1H), 7.78 (d, 1H), 7.42 (t, 1H), 7.40-7.25 (m, 2H), 6.70 (brs, 1H), 5.77 (s, 1H), 4.70-4.60 (m, 1H), 3.91 (s, 2H), 3.90-3.40 (m, 4H), 3.42 (s, 3H), 2.60 (t, 2H), 2.40-2.30 (m, 1H), 2.10-2.00 (m, 1H), 1.72 (q, 2H), 1.00 (t, 3H) |
| 76 | (S)-N-{1-[2-(3-cyanophenylamino)-6-propylpyrimidin-4-yl]pyrrolidin-3-yl}-2-(pyridin-2-yl)acetamide | $^1$H-NMR (400 MHz, CDCl$_3$) δ 8.49 (s, 1H), 8.40 (brs, 1H), 8.05 (brs, 1H), 7.80-7.60 (m, 2H), 7.40-7.15 (m, 5H), 5.73 (s, 1H), 4.60-4.50 (m, 1H), 3.74 (s, 2H), 3.90-3.20 (m, 4H), 2.55 (t, 2H), 2.35-2.25 (m, 1H), 2.10-2.00 (m, 1H), 1.70 (t, 2H), 0.98 (t, 3H) |
| 77 | (S)-N-{1-[2-(3-cyanophenylamino)-6-propylpyrimidin-4-yl]pyrrolidin-3-yl}-2-(pyridin-3-yl)acetamide | $^1$H-NMR (400 MHz, CDCl$_3$) δ 8.51 (s, 2H), 8.32 (brs, 1H), 7.71 (t, 2H), 7.40-7.20 (m, 4H), 6.45 (brs, 1H), 5.70 (s, 1H), 4.65-4.55 (m, 1H), 3.57 (s, 2H), 3.90-3.30 (m, 4H), 2.55 (t, 2H), 2.30-2.20 (m, 1H), 2.10-2.00 (m, 1H), 1.69 (q, 2H), 0.98 (t, 3H) |
| 78 | (S)-N-{1-[2-(3-cyanophenylamino)-6-propylpyrimidin-4-yl]pyrrolidin-3-yl}-2-(pyridin-4-yl)acetamide | $^1$H-NMR (400 MHz, CDCl$_3$) δ 8.80 (brs, 1H), 8.52 (d, 2H), 8.30 (s, 1H), 7.70-7.65 (m, 1H), 7.40-7.20 (m, 5H), 6.63 (brs, 1H), 5.68 (s, 1H), 4.62 (q, 1H), 3.56 (s, 2H), 3.90-3.30 (m, 4H), 2.53 (t, 2H), 2.35-2.25 (m, 1H), 2.10-2.00 (m, 1H), 1.68 (q, 2H), 0.97 (t, 3H) |
| 79 | (S,E)-N-{1-[2-(3-cyanophenylamino)-6-propylpyrimidin-4-yl]pyrrolidin-3-yl}-4-phenylbut-3-enamide | $^1$H-NMR (400 MHz, CDCl$_3$) δ 8.30 (brs, 1H), 7.60 (brs, 1H), 7.40-7.00 (m, 8H), 6.53 (d, 1H), 6.35-6.25 (m, 1H), 5.91 (brs, 1H), 5.73 (s, 1H), 4.65-4.55 (m, 1H), 3.90-3.25 (m, 4H), 3.17 (d, 2H), 2.47 (t, 2H), 2.35-2.25 (m, 1H), 2.00-1.80 (m, 2H), 1.71 (q, 2H), 0.98 (t, 3H) |
| 80 | (S)-N-{1-[2-(3-cyanophenylamino)-6-propylpyrimidin-4-yl]pyrrolidin-3-yl}-2-(thiophen-2-yl)acetamide | $^1$H-NMR (400 MHz, CDCl$_3$) δ 8.30 (brs, 1H), 7.61 (brs, 1H), 7.40-7.10 (m, 4H), 7.00-6.85 (m, 2H), 5.84 (s, 1H), 5.69 (s, 1H), 4.60-4.50 (m, 1H), 3.79 (s, 2H), 3.80-3.20 (m, 4H), 2.49 (t, 2H), 2.30-2.20 (m, 1H), 2.00-1.85 (m, 1H), 1.80-1.60 (m, 2H), 1.00-0.90 (m, 3H) |

TABLE 1-9

| Example | Compound | NMR Spectrum |
| --- | --- | --- |
| 81 | (S)-N-{1-[2-(3-cyanophenylamino)-6-propylpyrimidin-4-yl]pyrrolidin-3-yl}isobutyramide | $^1$H-NMR (400 MHz, CDCl$_3$) δ 8.34 (brs, 1H), 7.61 (brs, 1H), 7.35 (t, 1H), 7.22 (d, 1H), 5.75 (s, 1H), 5.67 (d, 1H), 4.60 (q, 1H), 3.90-3.20 (m, 4H), 2.49 (t, 2H), 2.20-1.90 (m, 2H), 1.17 (d, 6H), 0.98 (t, 3H) |

TABLE 1-9-continued

| Example | Compound | NMR Spectrum |
|---|---|---|
| 82 | (S)-N-{1-[2-(3-cyanophenylamino)-6-propylpyrimidin-4-yl]pyrrolidin-3-yl}-3,3,3-trifluoropropanamide | $^1$H-NMR (400 MHz, CDCl$_3$) δ 8.29 (brs, 1H), 7.64 (d, 1H), 7.34 (t, 1H), 7.22 (d, 1H), 6.43 (d, 1H), 5.73 (s, 1H), 4.64 (q, 1H), 4.00-3.30 (m, 4H), 3.20-3.00 (m, 2H), 2.51 (t, 2H), 2.40-2.30 (m, 1H), 2.15-2.05 (m, 1H), 1.71 (q, 2H), 0.99 (t, 3H) |
| 83 | 3-[4-(2-oxopyrrolidin-1-yl)-6-propylpyrimidin-2-ylamino]benzonitrile | $^1$H-NMR (400 MHz, CDCl$_3$) δ 8.26 (s, 1H), 7.79 (s, 1H), 7.60 (d, 1H), 7.38 (t, 1H), 7.27 (d, 1H), 7.13 (s, 1H), 4.11 (t, 2H), 2.75-2.55 (m, 4H), 2.18 (t, 2H), 1.77 (q, 2H), 0.99 (t, 3H) |
| 84 | (S)-3-{4-[3-(hexylamino)pyrrolidin-1-yl]-6-propylpyrimidin-2-ylamino}benzonitrile | $^1$H-NMR (400 MHz, CDCl$_3$) δ 8.38 (s, 1H), 7.57 (d, 1H), 7.33 (t, 1H), 7.21 (d, 1H), 5.74 (s, 1H), 3.90-3.20 (m, 5H), 2.67 (t, 2H), 2.48 (t, 2H), 2.25-2.15 (m, 1H), 1.90-1.85 (m, 1H), 1.72 (q, 2H), 1.55-1.45 (m, 2H), 1.40-1.20 (m, 6H), 0.98 (t, 3H), 0.95-0.85 (m, 3H) |
| 85 | (S)-3-{4-propyl-6-[3-(propylamino)pyrrolidin-1-yl]pyrimidin-2-ylamino}benzonitrile | $^1$H-NMR (400 MHz, CDCl$_3$) δ 8.39 (s, 1H), 7.57 (d, 1H), 7.34 (t, 1H), 7.22 (d, 1H), 5.75 (s, 1H), 4.00-3.20 (m, 5H), 2.65 (t, 2H), 2.48 (t, 2H), 2.25-2.15 (m, 1H), 1.90-1.80 (m, 1H), 1.80-1.50 (m, 6H), 1.00-0.90 (m, 6H) |
| 86 | (S)-3-{4-[3-(cyclohexylmethylamino)pyrrolidin-1-yl]-6-propylpyrimidin-2-ylamino}benzonitrile | $^1$H-NMR (400 MHz, CDCl$_3$) δ 8.40 (s, 1H), 7.60 (d, 1H), 7.50 (brs, 1H), 7.33 (t, 1H), 7.21 (d, 1H), 5.73 (s, 1H), 4.00-3.10 (m, 5H), 2.50-2.40 (m, 4H), 2.25-2.15 (m, 1H), 2.00-1.60 (m, 9H), 1.50-1.40 (m, 1H), 1.30-1.10 (m, 4H), 0.98 (t, 3H) |
| 87 | (S)-3-{4-[3-(benzylamino)pyrrolidin-1-yl]-6-propylpyrimidin-2-ylamino}benzonitrile | $^1$H-NMR (400 MHz, CDCl$_3$) δ 8.41 (s, 1H), 7.59 (d, 1H), 7.52 (brs, 1H), 7.40-7.15 (m, 7H), 5.72 (s, 1H), 3.87 (s, 2H), 3.80-3.10 (m, 5H), 2.49 (t, 2H), 2.25-2.15 (m, 1H), 2.00-1.90 (m, 1H), 1.80-1.60 (m, 2H), 0.98 (t, 3H) |
| 88 | (S)-3-{4-[3-(phenethylamino)pyrrolidin-1-yl]-6-propylpyrimidin-2-ylamino}benzonitrile | $^1$H-NMR (400 MHz, CDCl$_3$) δ 8.38 (s, 1H), 7.56 (d, 1H), 7.50-7.00 (m, 7H), 5.73 (s, 1H), 3.95-3.75 (m, 1H), 3.70-3.30 (m, 3H), 3.25-3.10 (m, 1H), 3.00-2.90 (m, 2H), 2.84 (t, 2H), 2.48 (t, 2H), 2.25-2.15 (m, 1H), 1.90-1.85 (m, 1H), 1.72 (q, 2H), 0.98 (t, 3H) |
| 89 | (S)-3-{4-[3-(3-phenylpropylamino)pyrrolidin-1-yl]-6-propylpyrimidin-2-ylamino}benzonitrile | $^1$H-NMR (400 MHz, CDCl$_3$) δ 8.39 (s, 1H), 7.63 (d, 1H), 7.39 (t, 1H), 7.35-7.10 (m, 6H), 5.75 (s, 1H), 4.00-3.20 (m, 5H), 2.80-2.60 (m, 4H), 2.55 (t, 2H), 2.30-2.00 (m, 2H), 2.00-1.90 (m, 2H), 1.80-1.70 (m, 2H), 1.01 (t, 3H) |
| 90 | (S)-3-{4-[3-(3-fluorobenzylamino)pyrrolidin-1-yl]-6-propylpyrimidin-2-ylamino}benzonitrile | $^1$H-NMR (400 MHz, CDCl$_3$) δ 8.43 (s, 1H), 7.53 (d, 1H), 7.40-7.05 (m, 6H), 6.95 (t, 1H), 5.74 (s, 1H), 3.87 (s, 2H), 3.80-3.10 (m, 5H), 2.48 (t, 2H), 2.25-2.15 (m, 1H), 2.00-1.90 (m, 1H), 1.72 (q, 2H), 0.98 (t, 3H) |

TABLE 1-10

| Example | Compound | NMR Spectrum |
|---|---|---|
| 91 | (S)-3-{4-[3-(4-hydroxybenzylamino)pyrrolidin-1-yl]-6-propylpyrimidin-2-ylamino}benzonitrile | $^1$H-NMR (400 MHz, CDCl$_3$) δ 8.37 (s, 1H), 7.52 (d, 1H), 7.32 (t, 1H), 7.25-7.15 (m, 3H), 6.77 (d, 2H), 5.73 (s, 1H), 3.78 (s, 2H), 3.80-3.10 (m, 5H), 2.48 (t, 2H), 1.25-1.15 (m, 1H), 2.00-1.90 (m, 1H), 1.71 (q, 2H), 0.97 (t, 3H) |
| 92 | (S)-3-{4-[3-(4-ethylbenzylamino)pyrrolidin-1-yl]-6-propylpyrimidin-2-ylamino}benzonitrile | $^1$H-NMR (400 MHz, CDCl$_3$) δ 8.40 (s, 1H), 7.59 (d, 1H), 7.40-7.10 (m, 6H), 5.72 (s, 1H), 3.84 (s, 2H), 3.80-3.10 (m, 5H), 2.63 (q, 2H), 2.48 (t, 2H), 2.25-2.15 (m, 1H), 2.00-1.90 (m, 1H), 1.72 (q, 2H), 1.23 (t, 3H), 0.98 (t, 3H) |
| 93 | (S)-3-{4-[3-(isopentylamino)pyrrolidin-1-yl]-6-propylpyrimidin-2-ylamino}benzonitrile | $^1$H-NMR (400 MHz, CDCl$_3$) δ 8.38 (s, 1H), 7.58 (d, 1H), 7.33 (t, 1H), 7.20 (d, 1H), 7.00 (brs, 1H), 5.74 (s, 1H), 3.90-3.00 (m, 5H), 2.68 (t, 2H), 2.48 (t, 2H), 2.25-2.15 (m, 1H), 1.90-1.80 (m, 1H), 1.80-1.50 (m, 3H), 1.40 (q, 2H), 0.98 (t, 3H), 0.92 (d, 6H) |
| 94 | (S)-3-{4-[3-(pentylamino)pyrrolidin-1-yl]-6-propylpyrimidin-2-ylamino}benzonitrile | $^1$H-NMR (400 MHz, CDCl$_3$) δ 8.39 (s, 1H), 7.56 (d, 1H), 7.34 (t, 1H), 7.22 (d, 1H), 7.00 (brs, 1H), 5.75 (s, 1H), 3.90-3.30 (m, 5H), 2.67 (t, 2H), 2.48 (t, 2H), 2.25-2.15 (m, 1H), 2.00-1.60 (m, 3H), 1.52 (t, 2H), 1.40-1.20 (m, 4H), 0.99 (t, 3H), 0.92 (t, 3H) |
| 95 | 3-{4-[(3S)-3-(2-methylbutylamino)pyrrolidin-1-yl]-6-propylpyrimidin-2-ylamino}benzonitrile | $^1$H-NMR (400 MHz, CDCl$_3$) δ 8.39 (s, 1H), 7.58 (d, 1H), 7.33 (t, 1H), 7.20 (d, 1H), 7.03 (brs, 1H), 5.74 (s, 1H), 3.90-3.10 (m, 5H), 2.65-2.55 (m, 1H), 2.50-2.40 (m, 3H), 2.25-2.15 (m, 1H), 1.90-1.80 (m, 1H), 1.72 (q, 2H), 1.50-1.35 (m, 2H), 1.20-1.10 (m, 1H), 0.98 (t, 3H), 0.95-0.85 (m, 6H) |
| 96 | (S)-3-{4-[3-(isobutylamino)pyrrolidin-1-yl]-6-propylpyrimidin-2-ylamino}benzonitrile | $^1$H-NMR (400 MHz, CDCl$_3$) δ 8.39 (s, 1H), 7.55 (d, 1H), 7.35 (t, 1H), 7.23 (d, 1H), 5.75 (s, 1H), 3.90-3.10 (m, 5H), 2.55-2.45 (m, 3H), 2.25-2.15 (m, 1H), 1.90-1.85 (m, 1H), 1.80-1.60 (m, 4H), 0.99 (t, 3H), 0.94 (d, 6H) |
| 97 | (S)-3-{4-[3-(4-methoxybenzylamino)pyrrolidin- | $^1$H-NMR (400 MHz, CDCl$_3$) δ 8.40 (s, 1H), 7.56 (d, 1H), 7.33 (t, 1H), 7.26 (t, 2H), 7.21 (d, 1H), 6.87 (d, 2H), 5.73 (s, |

TABLE 1-10-continued

| Example | Compound | NMR Spectrum |
|---|---|---|
|  | 1-yl]-6-propylpyrimidin-2-ylamino}benzonitrile | 1H), 3.81 (s, 2H), 3.80 (s, 3H), 3.80-3.10 (m, 5H), 2.48 (t, 2H), 2.25-2.15 (m, 1H), 2.00-1.90 (m, 1H), 1.80-1.60 (m, 2H), 0.98 (t, 3H) |
| 98 | (S)-3-{4-[3-(4-fluorobenzylamino)pyrrolidin-1-yl]-6-propylpyrimidin-2-ylamino}benzonitrile | $^1$H-NMR (400 MHz, CDCl$_3$) δ 8.44 (s, 1H), 7.54 (d, 1H), 7.40-7.30 (m, 3H), 7.21 (d, 1H), 7.01 (d, 2H), 5.73 (s, 1H), 3.84 (s, 2H), 3.80-3.10 (m, 5H), 2.48 (t, 2H), 2.25-2.15 (m, 1H), 2.00-1.90 (m, 1H), 1.72 (q, 2H), 0.98 (t, 3H) |
| 99 | (S)-3-{4-[3-(cyclopropylmethylamino)pyrrolidin-1-yl]-6-propylpyrimidin-2-ylamino}benzonitrile | $^1$H-NMR (400 MHz, CDCl$_3$) δ 8.39 (s, 1H), 7.56 (d, 1H), 7.35 (t, 1H), 7.24 (d, 1H), 5.75 (s, 1H), 3.90-3.20 (m, 5H), 2.56 (d, 2H), 2.49 (t, 2H), 2.25-2.15 (m, 1H), 2.00-1.90 (m, 1H), 1.80-1.65 (m, 2H), 1.00-0.90 (m, 4H), 0.53 (d, 2H), 0.17 (d, 2H) |
| 100 | (S)-3-(4-{3-[bis (cyclopropylmethyl)amino]pyrrolidin-1-yl}-6-propylpyrimidin-2-ylamino)benzonitrile | $^1$H-NMR (400 MHz, CDCl$_3$) δ 8.39 (s, 1H), 7.58 (d, 1H), 7.32 (t, 1H), 7.20 (d, 1H), 7.08 (brs, 1H), 5.73 (s, 1H), 4.00-3.10 (m, 5H), 2.70-2.55 (m, 4H), 2.48 (t, 2H), 2.25-2.15 (m, 1H), 2.00-1.90 (m, 1H), 1.80-1.65 (m, 2H), 1.00-0.90 (m, 5H), 0.55 (d, 4H), 0.18 (d, 4H) |

TABLE 1-11

| Example | Compound | NMR Spectrum |
|---|---|---|
| 101 | (S)-3-{4-propyl-6-[3-(pyridin-2-ylmethylamino)pyrrolidin-1-yl]pyrimidin-2-ylamino}benzonitrile | $^1$H-NMR (400 MHz, CDCl$_3$) δ 8.52 (s, 1H), 7.70-7.60 (m, 2H), 7.51 (brs, 1H), 7.33 (t, 1H), 7.21 (d, 1H), 7.15 (t, 2H), 5.68 (s, 1H), 3.95 (s, 2H), 4.00-3.20 (m, 5H), 2.48 (t, 2H), 2.50-2.20 (m, 2H), 1.71 (q, 2H), 0.98 (t, 3H) |
| 102 | (S)-3-{4-propyl-6-[3-(pyridin-3-ylmethylamino)pyrrolidin-1-yl]pyrimidin-2-ylamino}benzonitrile | $^1$H-NMR (400 MHz, CDCl$_3$) δ 8.65-8.45 (m, 3H), 7.70 (t, 1H), 7.55 (d, 1H), 7.40-7.15 (m, 3H), 5.73 (s, 1H), 3.89 (s, 2H), 3.90-3.20 (m, 5H), 2.48 (t, 2H), 2.25-2.15 (m, 1H), 2.00-1.90 (m, 1H), 1.80-1.60 (m, 2H), 0.98 (t, 3H) |
| 103 | (S)-3-{4-propyl-6-[3-(pyridin-4-ylmethylamino)pyrrolidin-1-yl]pyrimidin-2-ylamino}benzonitrile | $^1$H-NMR (400 MHz, CDCl$_3$) δ 8.60-8.40 (m, 3H), 8.10 (brs, 1H), 7.60-7.50 (m, 1H), 7.40-7.15 (m, 4H), 5.73 (s, 1H), 3.90 (s, 2H), 3.90-3.10 (m, 5H), 2.48 (t, 2H), 2.25-2.15 (m, 1H), 2.00-1.90 (m, 1H), 1.72 (q, 2H), 0.99 (t, 3H) |
| 104 | (S)-3-{4-[3-(2-ethylbutylamino)pyrrolidin-1-yl]-6-propylpyrimidin-2-ylamino}benzonitrile | $^1$H-NMR (400 MHz, CDCl$_3$) δ 8.41 (s, 1H), 7.58 (d, 1H), 7.33 (t, 1H), 7.21 (d, 1H), 5.74 (s, 1H), 3.90-3.00 (m, 5H), 2.48 (t, 2H), 2.40 (brs, 2H), 2.25-2.15 (m, 1H), 1.88 (brs, 1H), 1.72 (q, 2H), 0.98 (t, 3H), 0.92 (s, 9H) |
| 105 | (S)-3-{4-[3-(neopentylamino)pyrrolidin-1-yl]-6-propylpyrimidin-2-ylamino}benzonitrile | $^1$H-NMR (400 MHz, CDCl$_3$) δ 8.41 (s, 1H), 7.58 (d, 1H), 7.33 (t, 1H), 7.21 (d, 1H), 5.74 (s, 1H), 3.90-3.00 (m, 5H), 2.48 (t, 2H), 2.40 (brs, 2H), 2.25-2.15 (m, 1H), 1.88 (brs, 1H), 1.72 (q, 2H), 0.98 (t, 3H), 0.92 (s, 9H) |
| 106 | (S)-3-{4-[3-(2-fluorobenzylamino)pyrrolidin-1-yl]-6-propylpyrimidin-2-ylamino}benzonitrile | $^1$H-NMR (400 MHz, CDCl$_3$) δ 8.39 (s, 1H), 7.60 (d, 1H), 7.50-7.20 (m, 4H), 7.12 (t, 1H), 7.05 (t, 1H), 5.73 (s, 1H), 3.92 (s, 2H), 3.90-3.10 (m, 5H), 2.48 (t, 2H), 2.25-2.15 (m, 1H), 2.00-1.90 (m, 1H), 1.72 (q, 2H), 0.98 (t, 3H) |
| 107 | (S)-3-(4-propyl-6-{3-[3-(trifluoromethyl)benzylamino]pyrrolidin-1-yl}pyrimidin-2-ylamino)benzonitrile | $^1$H-NMR (400 MHz, CDCl$_3$) δ 8.45 (s, 1H), 7.64 (s, 1H), 7.60-7.40 (m, 4H), 7.33 (t, 1H), 7.21 (d, 1H), 5.73 (s, 1H), 3.94 (s, 2H), 3.90-3.10 (m, 5H), 2.49 (t, 2H), 2.25-2.15 (m, 1H), 2.00-1.90 (m, 1H), 1.72 (q, 2H), 0.98 (t, 3H) |
| 108 | (S)-3-(4-propyl-6-{3-[4-(trifluoromethyl)benzylamino]pyrrolidin-1-yl}pyrimidin-2-ylamino)benzonitrile | $^1$H-NMR (400 MHz, CDCl$_3$) δ 8.48 (s, 1H), 7.70-7.40 (m, 5H), 7.33 (t, 1H), 7.21 (d, 1H), 5.72 (s, 1H), 3.94 (s, 2H), 3.90-3.10 (m, 5H), 2.48 (t, 2H), 2.25-2.15 (m, 1H), 2.00-1.90 (m, 1H), 1.72 (q, 2H), 0.98 (t, 3H) |
| 109 | (S)-4-({1-[2-(3-cyanophenylamino)-6-propylpyrimidin-4-yl]pyrrolidin-3-ylamino}methyl)phenylacetate | $^1$H-NMR (400 MHz, CDCl$_3$) δ 8.39 (s, 1H), 7.53 (d, 1H), 7.33 (t, 1H), 7.25-7.15 (m, 3H), 6.78 (d, 2H), 5.74 (s, 1H), 3.79 (s, 2H), 3.70-3.10 (m, 5H), 2.49 (s, 2H), 2.25-2.15 (m, 2H), 1.92 (brs, 3H), 1.72 (q, 2H), 0.98 (t, 3H) |
| 110 | (S)-3-(4-{3-[4-(dimethylamino)benzylamino]pyrrolidin-1-yl}-6-propylpyrimidin-2-ylamino)benzonitrile | $^1$H-NMR (400 MHz, CDCl$_3$) δ 8.36 (s, 1H), 7.57 (dd, 1H), 7.35 (t, 1H), 7.30-7.15 (m, 3H), 6.71 (d, 2H), 5.74 (s, 1H), 3.78 (s, 2H), 3.80-3.30 (m, 5H), 2.93 (s, 6H), 2.50 (t, 2H), 2.25-2.15 (m, 1H), 2.00-1.90 (m, 1H), 1.73 (q, 2H), 0.99 (t, 3H) |

TABLE 1-12

| Example | Compound | NMR Spectrum |
|---|---|---|
| 111 | (S)-3-(4-{3-[(1H-pyrrol-2-yl)methylamino]pyrrolidin-1-yl}-6-propylpyrimidin-2-ylamino)benzonitrile | $^1$H-NMR (400 MHz, CDCl$_3$) δ 8.41 (brs, 1 H), 7.52 (brs, 1 H), 7.34 (t, 1H), 7.23 (d, 1H), 6.74 (s, 1H), 6.14 (d, 1H), 6.08 (s, 1H), 5.71 (s, 1H), 3.90 (s, 2H), 3.80-3.10 (m, 5H), 2.49 (t, 2H), 2.25-2.15 (m, 1H), 1.90-1.85 (m, 1H), 1.71 (q, 2H), 0.99 (t, 3H) |
| 112 | (S)-3-{4-propyl-6-[3-(thiophen-2-ylmethylamino)pyrrolidin-1-yl]pyrimidin-2-ylamino}benzonitrile | $^1$H-NMR (400 MHz, CDCl$_3$) δ 8.41 (s, 1H), 7.59 (d, 1H), 7.55 (brs, 1H), 7.33 (t, 1H), 7.30-7.20 (m, 2H), 7.00-6.90 (m, 2H), 5.73 (s, 1H), 4.08 (s, 2H), 3.90-3.10 (m, 5H), 2.48 (t, 2H), 2.25-2.15 (m, 1H), 2.00-1.90 (m, 1H), 1.72 (q, 2H), 0.98 (t, 3H) |
| 113 | (S)-3-{4-propyl-6-[3-(thiophen-3-ylmethylamino)pyrrolidin-1-yl]pyrimidin-2-ylamino}benzonitrile | $^1$H-NMR (400 MHz, CDCl$_3$) δ 8.44 (s, 1H), 7.57 (d, 1H), 7.50 (brs, 1H), 7.40-7.25 (m, 2H), 7.25-7.15 (m, 2H), 7.07 (d, 1H), 5.73 (s, 1H), 3.90 (s, 2H), 3.90-3.10 (m, 5H), 2.48 (t, 2H), 2.25-2.15 (m, 1H), 2.00-1.90 (m, 1H), 1.72 (q, 2H), 0.98 (t, 3H) |
| 114 | (S)-3-{4-[3-(dibutylamino)pyrrolidin-1-yl]-6-propylpyrimidin-2-ylamino}benzonitrile | $^1$H-NMR (400 MHz, CDCl$_3$) δ 8.37 (brs, 1H), 7.60 (brs, 1H), 7.32 (t, 1H), 7.20 (d, 1H), 7.13 (brs, 1H), 5.74 (s, 1H), 3.90 (brs, 1H), 3.60-3.10 (m, 4H), 2.75-2.40 (m, 6H), 2.20-2.10 (m, 1H), 2.00-1.90 (m, 1H), 1.73 (q, 2H), 1.50-1.20 (m, 8H), 1.00-0.90 (m, 9H) |
| 115 | (S)-3-(4-{3-bis[3-(methylthio)propyl]aminopyrrolidin-1-yl}-6-propylpyrimidin-2-ylamino)benzonitrile | $^1$H-NMR (400 MHz, CDCl$_3$) δ 8.42 (brs, 1H), 7.57 (d, 1H), 7.33 (t, 1H), 7.20 (d, 1H), 5.74 (s, 1H), 3.90 (brs, 1H), 3.65-3.10 (m, 4H), 2.70-2.60 (m, 4H), 2.54 (t, 4H), 2.49 (t, 2H), 2.25-2.15 (m, 1H), 2.11 (s, 6H), 2.00-1.90 (m, 1H), 1.80-1.65 (m, 6H), 0.98 (t, 3H) |
| 116 | (S)-3-{4-[3-(butylamino)pyrrolidin-1-yl]-6-propylpyrimidin-2-ylamino}benzonitrile | $^1$H-NMR (400 MHz, CDCl$_3$) δ 8.33 (s, 1H), 7.58 (d, 1H), 7.34 (t, 1H), 7.22 (d, 1H), 5.75 (s, 1H), 3.90-3.10 (m, 5H), 2.73 (t, 2H), 2.49 (t, 2H), 2.30-2.20 (m, 1H), 2.10-1.95 (m, 1H), 1.72 (q, 2H), 1.55-1.45 (m, 2H), 1.45-1.30 (m, 2H), 1.00-0.85 (m, 6H) |
| 117 | (S)-3-(4-{3-[3-(methylthio)propylamino]pyrrolidin-1-yl}-6-propylpyrimidin-2-ylamino)benzonitrile | $^1$H-NMR (400 MHz, CDCl$_3$) δ 8.38 (s, 1H), 7.57 (d, 1H), 7.37 (t, 1H), 7.30-7.20 (m, 1H), 5.77 (s, 1H), 3.90-3.10 (m, 5H), 2.90-2.70 (m, 2H), 2.58 (t, 2H), 2.51 (t, 2H), 2.30-2.20 (m, 1H), 2.11 (s, 3H), 2.00-1.90 (m, 1H), 1.90-1.70 (m, 4H), 1.00 (t, 3H) |
| 118 | (S)-3-{4-propyl-6-[3-(propylamino)pyrrolidin-1-yl]pyrimidin-2-ylamino}benzonitrile dihydrochloride | $^1$H-NMR (400 MHz, CD$_3$OD) δ 8.45 (d, 1 H), 7.77 (t, 1 H), 7.41 (t, 1H), 7.25 (d, 1H), 5.98 (s, 1H), 4.10-3.90 (m, 2H), 3.85-3.50 (m, 3H), 3.10-3.00 (m, 2H), 2.60-2.40 (m, 3H), 2.30-2.20 (m, 1H), 1.80-1.65 (m, 3H), 1.50-1.40 (m, 1H), 1.10-0.90 (m, 6H) |
| 119 | (S)-3-{4-[3-(cyclopropylmethylamino)pyrrolidin-1-yl]-6-propylpyrimidin-2-ylamino}benzonitrile dihydrochloride | $^1$H-NMR (400 MHz, CD$_3$OD) δ 8.15 (d, 1H), 7.90-7.80 (m, 1H), 7.60-7.45 (m, 2H), 6.35 (d, 1H), 4.25-3.65 (m, 5H), 3.15-2.90 (m, 2H), 2.70-2.50 (m, 3H), 2.50-2.25 (m, 1H), 1.90-1.70 (m, 2H), 1.20-1.10 (m, 1H), 1.10-0.95 (m, 3H), 0.80-0.65 (m, 2H), 0.50-0.40 (m, 2H) |
| 120 | (S)-3-{4-[3-(methylamino)pyrrolidin-1-yl]-6-propylpyrimidin-2-ylamino}benzonitrile dihydrochloride | $^1$H-NMR (400 MHz, CD$_3$OD) δ 8.16 (brs, 1H), 7.83 (d, 1H), 7.61-7.53 (m, 2H), 6.34 (s, 1H), 4.12-3.79 (m, 5H), 2.81 (s, 3H), 2.69 (dd, 2H), 2.58 (brs, 1H), 2.38 (brs, 1H), 1.85-1.76 (m, 2H), 1.06 (dd, 3H) |

TABLE 1-13

| Example | Compound | NMR Spectrum |
|---|---|---|
| 121 | (S)-N-{4-[3-(methylamino)pyrrolidin-1-yl]-6-propylpyrimidin-2-yl}-1H-indol-6-amine | $^1$H-NMR (400 MHz, CD$_3$OD) δ 8.03 (s, 1H), 7.41 (d, 1H), 7.12 (d, 1H), 7.04 (d, 1H), 6.35 (d, 1H), 5.82 (s, 1H), 3.90-3.30 (m, 5H), 2.50-2.40 (m, 5H), 2.30-2.20 (m, 1H), 2.00-1.90 (m, 1H), 1.73 (q, 2H), 0.99 (t, 3H) |
| 122 | (S)-N-{4-[3-(methylamino)pyrrolidin-1-yl]-6-propylpyrimidin-2-yl}-1H-indol-6-amine hydrochloride | $^1$H-NMR (400 MHz, CD$_3$OD) δ 7.66 (s, 1H), 7.57 (d, 1H), 7.27 (d, 1H), 7.04 (d, 1H), 6.46 (d, 1H), 6.19 (s, 1H), 4.10-3.60 (m, 5H), 2.78 (s, 3H), 2.62 (t, 2H), 2.55 (brs, 1H), 2.31 (brs, 1H), 1.75 (q, 2H), 1.04 (t, 3H) |
| 123 | (S)-N$^1$-{4-[3-(methylamino)pyrrolidin-1-yl]-6-propylpyrimidin-2-yl}-3-(trifluoromethyl)benzene-1,4-diamine dihydrochloride | $^1$H-NMR (400 MHz, CD$_3$OD) δ 7.97 (d, 1H), 7.65-7.55 (m, 1H), 7.21 (t, 1H), 6.30 (d, 1H), 4.15-3.75 (m, 5H), 2.79 (d, 3H), 2.69 (t, 2H), 2.65-2.50 (m, 1H), 2.50-2.25 (m, 1H), 1.90-1.70 (m, 2H), 1.07 (t, 3H) |
| 124 | (S)-N-{1-[2-(3-cyanophenylamino)-6-propylpyrimidin-4-yl]pyrrolidin-3- | $^1$H-NMR (400 MHz, CDCl$_3$) δ 8.45 (s, 1H), 7.98 (brs, 1H), 7.60-7.50 (m, 1H), 7.34 (t, 1H), 7.22 (d, 1H), 6.27 (brs, 1H), 5.53 (s, 1H), 4.24 (brs, 1H), 3.80-3.20 (m, 5H), 2.50-2.35 (m, 2H), 2.30-2.00 (m, 2H), 1.70-1.50 (m, 2H), 1.46 (d, |

TABLE 1-13-continued

| Example | Compound | NMR Spectrum |
|---|---|---|
| | yl}isopropane-2-sulfonamide | 6H), 0.95 (t, 3H) |
| 125 | (S)-N-{1-[2-(3-cyanophenylamino)-6-propylpyrimidin-4-yl]pyrrolidin-3-yl}methanesulfonamide | $^1$H-NMR (400 MHz, CDCl$_3$) δ 8.43 (s, 1H), 7.61 (d, 1H), 7.35 (t, 1H), 7.24 (d, 1H), 5.66 (s, 1H), 4.24 (brs, 1H), 3.90-3.30 (m, 5H), 3.08 (s, 3H), 2.50-2.20 (m, 4H), 1.67 (q, 2H), 0.98 (t, 3H) |
| 126 | (S)-N-{1-[2-(3-cyanophenylamino)-6-propylpyrimidin-4-yl]pyrrolidin-3-yl}-4-fluorobenzenesulfonamide | $^1$H-NMR (400 MHz, CDCl$_3$) δ 8.35 (s, 1H), 8.00-7.90 (m, 2H), 7.54 (d, 1H), 7.33 (t, 1H), 7.30-7.15 (m, 3H), 5.54 (s, 1H), 4.10 (brs, 1H), 3.70-3.30 (m, 4H), 2.50-2.25 (m, 2H), 2.20-2.00 (m, 2H), 1.58 (q, 2H), 0.91 (t, 3H) |
| 127 | 3-{4-[(3S)-3-(sec-butylamino)pyrrolidin-1-yl]-6-propylpyrimidin-2-ylamino}benzonitrile | $^1$H-NMR (400 MHz, CD$_3$OD) δ 8.36 (s, 1H), 7.58 (d, 1H), 7.33 (dd, 1H), 7.20 (d, 1H), 7.10 (s, 1H), 5.74 (s, 1H), 4.10-3.10 (m, 5H), 2.71-2.67 (m, 1H), 2.48 (dd, 2H), 2.26-2.21 (m, 1H), 1.77-1.67 (m, 3H), 1.52-1.46 (m, 1H), 1.39-1.34 (m, 1H), 1.10-1.07 (m, 3H), 0.98 (t, 3H), 0.94-0.90 (m, 3H) |
| 128 | (S)-3-{4-[3-(pentan-3-ylamino)pyrrolidin-1-yl]-6-propylpyrimidin-2-ylamino}benzonitrile | $^1$H-NMR (400 MHz, CDCl$_3$) δ 10.02 (brs, 1H), 8.42 (s, 1H), 7.70 (d, 1H), 7.35 (dd, 1H), 7.24 (d, 1H), 5.71 (s, 1H), 3.88-3.12 (m, 5H), 2.53-2.45 (m, 3H), 2.26-2.18 (m, 1H), 2.10 (s, 3H), 1.94-1.88 (m, 1H), 1.76-1.67 (m, 2H), 1.52-1.44 (m, 4H), 0.98 (t, 3H), 0.95-0.90 (m, 6H) |
| 129 | (S)-3-{4-[3-(2,6-dimethylheptan-4-ylamino)pyrrolidin-1-yl]-6-propylpyrimidin-2-ylamino}benzonitrile | $^1$H-NMR (400 MHz, CDCl$_3$) δ 8.35 (brs, 1H), 7.65 (brs, 1H), 7.33 (dd, 1H), 7.22-7.20 (m, 2H), 5.74 (s, 1H), 3.88-3.12 (m, 5H), 2.83-2.82 (m, 1H), 2.48 (dd, 2H), 2.24-2.21 (m, 1H), 1.84-1.62 (m, 7H), 1.39-1.36 (m, 1H), 1.26-1.22 (m, 1H), 1.14-1.02 (m, 3H), 0.98 (t, 3H), 0.88-0.81 (m, 9H) |

TABLE 1-14

| Example | Compound | NMR Spectrum |
|---|---|---|
| 130 | (S)-3-{4-[3-(4,4-dimethylpentan-2-ylamino)pyrrolidin-1-yl]-6-propylpyrimidin-2-ylamino}benzonitrile | $^1$H-NMR (400 MHz, CDCl$_3$) δ 8.36 (brs, 1H), 7.62 (brs, 2H), 7.33 (dd, 1H), 7.21 (d, 1H), 5.73 (s, 1H), 3.84-3.07 (m, 5H), 2.85-2.81 (m, 1H), 2.49 (dd, 2H), 2.27-2.20 (m, 1H), 1.77-1.70 (m, 3H), 1.37-1.30 (m, 2H), 1.12 (d, 3H), 1.04-0.81 (m, 12H) |
| 131 | (S)-3-{4-[3-(3-hydroxy-3-methylbutan-2-ylamino)pyrrolidin-1-yl]-6-propylpyrimidin-2-ylamino}benzonitrile | $^1$H-NMR (400 MHz, CDCl$_3$) δ 8.49-8.35 (m, 1H), 7.68 (brs, 1H), 7.37-7.33 (m, 1H), 7.25-7.23 (m, 1H), 5.71 (s, 1H), 3.92-3.22 (m, 5H), 2.54-2.49 (m, 3H), 2.29-2.25 (m, 1H), 2.12-2.06 (m, 1H), 1.75-1.66 (m, 2H), 1.21 (d, 3H), 1.16-1.13 (m, 3H), 1.05 (s, 3H), 1.00 (t, 3H) |
| 132 | (S)-3-{4-[3-(heptan-4-ylamino)pyrrolidin-1-yl]-6-propylyrimidin-2-ylamino}benzonitrile | $^1$H-NMR (400 MHz, CDCl$_3$) δ 8.36 (brs, 1H), 7.62 (brs, 1H), 7.47 (brs, 1H), 7.33 (m, 1H), 7.20 (d, 1H), 5.71 (s, 1H), 3.82-3.06 (m, 5H), 2.58-2.56 (m, 1H), 2.49 (dd, 2H), 2.24-2.16 (m, 1H), 1.94-1.90 (m, 1H), 1.77-1.68 (m, 2H), 1.43-1.36 (m, 8H), 1.00 (t, 3H), 0.95-0.85 (m, 6H) |
| 133 | (S)-3-{4-[3-(n-hexan-2-ylamino)pyrrolidin-1-yl]-6-propylpyrimidin-2-ylamino}benzonitrile | $^1$H-NMR (400 MHz, CDCl$_3$) δ 9.35 (brs, 1H), 8.42 (brs, 1H), 7.34 (dd, 1H), 7.23 (d, 1H), 5.71 (s, 1H), 3.85-3.10 (m, 5H), 2.75-2.71 (m, 1H), 2.50 (dd, 2H), 2.26-2.22 (m, 1H), 1.94-1.87 (m, 1H), 1.74-1.69 (m, 2H), 1.45-1.31 (m, 6H), 1.11-0.88 (m, 9H) |
| 134 | (S)-3-{4-[3-(5-methylhexan-2-ylamino)pyrrolidin-1-yl]-6-propylpyrimidin-2-ylamino}benzonitrile | $^1$H-NMR (400 MHz, CDCl$_3$) δ 8.34 (brs, 2H), 7.63 (d, 1H), 7.33 (dd, 1H), 7.21 (d, 1H), 5.72 (s, 1H), 3.85-3.10 (m, 5H), 2.74-2.70 (m, 1H), 2.49 (dd, 2H), 2.26-2.21 (m, 1H), 1.94-1.87 (m, 1H), 1.74-1.69 (m, 2H), 1.54-1.17 (m, 5H), 1.10-1.08 (m, 3H), 0.98 (t, 3H), 0.90-0.86 (m, 6H) |
| 135 | (S)-3-{4-[3-(cyclohexylamino)pyrrolidin-1-yl]-6-propylpyrimidin-2-ylamino}benzonitrile | $^1$H-NMR (400 MHz, CDCl$_3$) δ 8.45 (s, 1H), 7.72 (d, 1H), 7.35 (dd, 1H), 7.25 (d, 1H), 5.69 (s, 1H), 3.95-3.15 (m, 5H), 2.54-2.52 (m, 3H), 2.27-2.23 (m, 2H), 1.93 (brs, 3H), 1.78-1.63 (m, 5H), 1.32-1.15 (m, 5H), 0.98 (t, 3H) |
| 136 | (S)-tert-butyl 2-{1-[2-(3-cyanophenylamino)-6-propylpyrimidin-4-yl]pyrrolidin-3-ylamino}ethylcarbamate | $^1$H-NMR (400 MHz, CDCl$_3$) δ 8.42 (s, 1H), 7.58 (d, 1H), 7.33 (dd, 1H), 7.20 (d, 1H), 5.73 (s, 1H), 4.97 (brs, 1H), 3.72-3.25 (m, 9H), 2.81 (brs, 1H), 2.48 (dd, 2H), 2.23-2.18 (m, 1H), 1.88 (brs, 1H), 1.76-1.71 (m, 2H), 1.44 (s, 9H), 0.98 (t, 3H) |
| 137 | (S)-3-{4-[3-(1-benzylpiperidin-4-ylamino)pyrrolidin-1-yl]-6-propylpyrimidin-2-ylamino}benzonitrile | $^1$H-NMR (400 MHz, CDCl$_3$) δ 8.39 (s, 1H), 7.57 (d, 1H), 7.35-7.19 (m, 6H), 7.09 (d, 1H), 5.73 (s, 1H), 3.76-3.58 (m, 3H), 3.51 (s, 2H), 3.51-3.05 (m, 2H), 2.87 (d, 2H), 2.61-2.54 (m, 1H), 2.47 (dd, 2H), 2.23-2.19 (m, 1H), 2.05 (dd, 2H), 1.89-1.85 (m, 3H), 1.76-1.67 (m, 2H), 1.46-1.37 (m, 2H), 0.97 (t, 3H) |

TABLE 1-14-continued

| Example | Compound | NMR Spectrum |
|---|---|---|
| 138 | (S)-3-{4-[3-(isopropylamino)pyrrolidin-1-yl]-6-propylpyrimidin-2-ylamino}benzonitrile | $^1$H-NMR (400 MHz, CDCl$_3$) δ 8.38 (s, 1H), 7.59 (d, 1H), 7.32 (dd, 1H), 7.20 (d, 1H), 7.11 (brs, 1H), 5.73 (s, 1H), 4.10-2.99 (m, 5H), 2.99-2.93 (m, 1H), 2.48 (dd, 2H), 2.28-2.21 (m, 1H), 1.84 (brs, 1H), 1.77-1.67 (m, 2H), 1.11 (dd, 6H), 0.97 (t, 3H) |
| 139 | (S)-3-{4-[3-(1-benzoylpiperidin-4-ylamino)pyrrolidin-1-yl]-6-propylpyrimidin-2-ylamino}benzonitrile | $^1$H-NMR (400 MHz, CDCl$_3$) δ 8.54 (brs, 1H), 7.47-7.40 (m, 6H), 7.33 (dd, 1H), 7.21 (d, 1H), 5.73 (s, 1H), 4.63 (brs, 1H), 4.23-2.90 (m, 9H), 2.48 (dd, 2H), 2.27-2.23 (m, 1H), 2.11-1.69 (m, 7H), 0.98 (t, 3H) |

TABLE 1-15

| Example | Compound | NMR Spectrum |
|---|---|---|
| 140 | (S)-3-{4-[3-(1-piperidin-4-acetylpiperidin-4-ylamino)pyrrolidin-1-yl]-6-propylpyrimidin-2-ylamino}benzonitrile | $^1$H-NMR (400 MHz, CDCl$_3$) δ 8.50-8.37 (m, 1H), 7.60-7.49 (m, 1H), 7.32 (dd, 1H), 7.20 (d, 1H), 7.14 (brs, 1H), 5.74 (s, 1H), 4.51 (d, 1H), 3.89-3.38 (m, 6H), 3.15 (dd, 1H), 2.84 (brs, 1H), 2.76 (dd, 1H), 2.48 (dd, 2H), 2.26-2.20 (m, 1H), 2.10 (s, 3H), 1.97-1.89 (m, 3H), 1.76-1.67 (m, 2H), 1.30-1.25 (m, 2H), 0.98 (t, 3H) |
| 141 | (S)-3-{4-[3-(cyclooctylamino)pyrrolidin-1-yl]-6-propylpyrimidin-2-ylamino}benzonitrile | $^1$H-NMR (400 MHz, CDCl$_3$) δ 8.38 (brs, 1H), 7.56 (brs, 1H), 7.33 (dd, 1H), 7.20 (d, 1H), 7.16 (brs, 1H), 5.73 (s, 1H), 3.89-3.38 (m, 5H), 2.79 (brs, 1H), 2.53-2.45 (m, 2H), 2.23-2.09 (m, 3H), 2.01-1.50 (m, 14H), 0.98 (t, 3H) |
| 142 | (S)-3-{4-[3-(cyclobutylamino)pyrrolidin-1-yl]-6-propylpyrimidin-2-ylamino}benzonitrile | $^1$H-NMR (400 MHz, CDCl$_3$) δ 8.37 (brs, 1H), 7.59 (d, 1H), 7.33 (dd, 1H), 7.20 (d, 1H), 7.00 (brs, 1H), 5.73 (s, 1H), 3.83-3.32 (m, 6H), 2.47 (dd, 2H), 2.29-2.15 (m, 3H), 1.85 (brs, 1H), 1.79-1.64 (m, 6H), 0.98 (t, 3H) |
| 143 | (S)-3-{4-[3-cyclopentylamino)pyrrolidin-1-yl]-6-propylpyrimidin-2-ylamino}benzonitrile | $^1$H-NMR (400 MHz, CDCl$_3$) δ 8.37 (brs, 1H), 7.58 (d, 1H), 7.32 (dd, 1H), 7.19 (d, 1H), 7.18 (brs, 1H), 5.73 (s, 1H), 3.99-3.14 (m, 6H), 2.47 (dd, 2H), 2.28-2.20 (m, 1H), 1.93-1.88 (m, 3H), 1.76-1.67 (m, 4H), 1.64-1.51 (m, 2H), 1.38-1.24 (dd, 2H), 0.97 (t, 3H) |
| 144 | (S)-tert-butyl 3-{1-[2-(3-cyanophenylamino)-6-propylpyrimidin-4-yl]pyrrolidin-3-ylamino}azetidine-1-carboxylate | $^1$H-NMR (400 MHz, CDCl$_3$) δ 8.36 (brs, 1H), 7.59 (d, 1H), 7.32 (dd, 1H), 7.21 (brs, 1H), 7.20 (d, 1H), 5.76 (brs, 1H), 4.65 (d, 4H), 3.97-3.40 (m, 6H), 2.48 (dd, 2H), 2.26-2.05 (m, 2H), 1.74-1.69 (m, 2H), 1.49 (s, 9H), 0.97 (t, 3H) |
| 145 | (S)-3-(4-{3-[2-(benzyloxy)ethylamino]pyrrolidin-1-yl}-6-propylpyrimidin-2-ylamino)benzonitrile | $^1$H-NMR (400 MHz, CDCl$_3$) δ 8.44 (s, 1H), 7.70 (d, 1H), 7.37-7.23 (m, 7H), 5.69 (s, 1H), 4.53 (s, 2H), 3.85-3.19 (m, 7H), 2.89 (brs, 2H), 2.52 (dd, 2H), 2.25-2.17 (m, 1H), 2.10 (s, 3H), 1.94 (brs, 1H), 1.76-1.67 (m, 2H), 0.99 (t, 3H) |
| 146 | (S)-N-{1-[2-(3-cyanophenylamino)-6-propylpyrimidin-4-yl]pyrrolidin-3-yl}propionamide | $^1$H-NMR (400 MHz, CDCl$_3$) δ 8.32 (s, 1H), 7.61 (s, 1H), 7.54 (s, 1H), 7.33 (t, 1H), 7.19 (d, 1H), 5.81 (m, 1H), 5.80 (s, 1H), 4.62 (m, 1H), 3.78-3.01 (m, 4H), 2.48 (t, 2H), 2.32 (m, 1H), 2.23 (m, 2H), 2.01 (m, 1H), 1.72 (m, 2H), 1.17 (t, 3H), 0.98 (t, 3H) |
| 147 | (S)-N-{1-[2-(3-cyanophenylamino)-6-propylpyrimidin-4-yl]pyrrolidin-3-yl}pivalamide | $^1$H-NMR (400 MHz, CDCl$_3$) δ 8.45 (s, 1H), 7.71 (s, 1H), 7.35 (t, 1H), 7.23 (d, 1H), 5.77 (s, 1H), 5.71 (s, 1H), 4.59 (m, 1H), 3.81-3.22 (m, 4H), 2.47 (t, 2H), 2.34 (m, 1H), 2.01 (m, 1H), 1.67 (q, 2H), 1.21 (s, 9H), 0.98 (t, 3H) |
| 148 | (S)-N-{1-[2-(3-cyanophenylamino)-6-propylpyrimidin-4-yl]pyrrolidin-3-yl}-2,2-dimethylbutanamide | $^1$H-NMR (400 MHz, CDCl$_3$) δ 8.25 (s, 1H), 7.53 (s, 1H), 7.26 (t, 1H), 7.13 (d, 1H), 7.09 (brs, 1H), 5.69 (s, 1H), 4.53 (m, 1H), 3.75-3.21 (m, 4H), 2.43 (t, 2H), 2.25 (m, 1H), 1.86 (m, 1H), 1.66 (m, 2H), 1.47 (m, 2H), 1.09 (s, 6H), 0.91 (t, 3H), 0.75 (t, 3H) |

TABLE 1-16

| Example | Compound | NMR Spectrum |
|---|---|---|
| 149 | (S,E)-N-{1-[2-(3-cyanophenylamino)-6-propylpyrimidin-4-yl]pyrrolidin-3-yl}-2-methylbut-2-enamide | $^1$H-NMR (400 MHz, CDCl$_3$) δ 8.34 (s, 1H), 7.61 (s, 1H), 7.34 (t, 1H), 7.22 (d, 1H), 7.06 (s, 1H), 6.45 (m, 1H), 5.86 (m, 1H), 5.76 (s, 1H), 4.66 (m, 1H), 3.81-3.37 (m, 4H), 2.48 (t, 2H), 2.34 (m, 1H), 2.05 (m, 1H), 1.85 (s, 3H), 1.71 (m, 5H), 0.98 (t, 3H) |

TABLE 1-16-continued

| Example | Compound | NMR Spectrum |
|---|---|---|
| 150 | (S)-N-{1-[2-(3-cyanophenylamino)-6-propylpyrimidin-4-yl]pyrrolidin-3-yl}hexanamide | $^1$H-NMR (400 MHz, CDCl$_3$) δ 8.32 (s, 1H), 7.60 (s, 1H), 7.34 (t, 1H), 7.20 (d, 1H), 7.06 (s, 1H), 5.75 (s, 1H), 5.67 (m, 1H), 4.60 (m, 1H), 3.77-3.34 (m, 4H), 2.50 (t, 2H), 2.31 (m, 1H), 2.17 (t, 2H), 2.02 (m, 1H), 1.76-1.62 (m, 4H), 1.31 (m, 6H), 0.98 (t, 3H), 0.89 (t, 3H) |
| 151 | (S)-N-{1-[2-(3-cyanophenylamino)-6-propylpyrimidin-4-yl]pyrrolidin-3-yl}-3-phenylpropanamide | $^1$H-NMR (400 MHz, CDCl$_3$) δ 8.30 (s, 1H), 7.59 (s, 1H), 7.35 (t, 1H), 7.27-7.12 (m, 7H), 5.70 (s, 1H), 5.57 (m, 1H), 4.55 (m, 1H), 3.69 (m, 4H), 2.97 (t, 2H), 2.49 (m, 4H), 2.22 (m, 1H), 1.73 (m, 1H), 1.69 (m, 2H), 0.98 (t, 3H) |
| 152 | (S)-N-{1-[2-(3-cyanophenylamino)-6-propylpyrimidin-4-yl]pyrrolidin-3-yl}-2-(1H-indol-3-yl)acetamide | $^1$H-NMR (400 MHz, CDCl$_3$) δ 8.30 (s, 1H), 8.26 (s, 1H), 7.52 (m, 2H), 7.39-7.31 (m, 2H), 7.22-7.16 (m, 2H), 7.09 (m, 1H), 5.80 (m, 1H), 5.65 (s, 1H), 4.58 (m, 1H), 3.76 (s, 2H), 3.34-3.20 (m, 4H), 2.46 (t, 2H), 2.25 (m, 1H), 1.71 (m, 3H), 0.97 (t, 3H) |
| 153 | (S)-N-{1-[2-(3-cyanophenylamino)-6-propylpyrimidin-4-yl]pyrrolidin-3-yl}-2-hydroxy-2-methylpropanamide | $^1$H-NMR (400 MHz, CDCl$_3$) δ 8.37 (s, 1H), 7.58 (d, 1H), 7.32 (t, 1H), 7.20 (d, 2H), 6.97 (m, 1H), 5.75 (s, 1H), 4.59 (m, 1H), 3.83-3.34 (m, 4H), 2.51 (t, 2H), 2.31 (m, 1H), 2.03 (m, 1H), 1.71 (m, 2H), 1.47 (s, 6H), 0.98 (t, 3H) |
| 154 | (S)-N-{1-[2-(3-cyanophenylamino)-6-propylpyrimidin-4-yl]pyrrolidin-3-yl}-3-(4-methoxyphenyl)propanamide | $^1$H-NMR (400 MHz, CDCl$_3$) δ 8.28 (s, 1H), 7.62 (s, 1H), 7.48 (s, 1H), 7.32 (t, 1H), 7.18 (d, 1H), 7.08 (d, 1H), 6.80 (d, 1H), 5.70 (s, 1H), 5.65 (m, 1H), 4.56 (m, 1H), 3.73 (s, 3H), 3.69-3.00 (m, 4H), 2.90 (t, 2H), 2.46 (m, 4H), 2.21 (m, 1H), 1.90 (m, 1H), 1.69 (m, 2H), 0.98 (t, 3H) |
| 155 | (S)-N-{1-[2-(3-cyanophenylamino)-6-propylpyrimidin-4-yl]pyrrolidin-3-yl}-3-(4-hydroxyphenyl)propanamide | $^1$H-NMR (400 MHz, CDCl$_3$) δ 8.01 (s, 1H), 7.50 (s, 1H), 7.37 (t, 1H), 7.20 (d, 1H), 7.04 (d, 2H), 6.78 (d, 2H), 5.69 (s, 1H), 5.47 (m, 1H), 4.55 (m, 1H), 3.75-3.24 (m, 4H), 2.89 (m, 2H), 2.49 (m, 4H), 1.68 (m, 2H), 0.96 (t, 3H) |
| 156 | (S)-N-{1-[2-(3-cyanophenylamino)-6-propylpyrimidin-4-yl]pyrrolidin-3-yl}-4-oxopentanamide | $^1$H-NMR (400 MHz, CDCl$_3$) δ 8.38 (s, 1H), 7.78 (s, 1H), 7.65 (s, 1H), 7.33 (t, 1H), 7.19 (d, 1H), 5.59 (s, 1H), 4.61 (m, 1H), 3.65-3.00 (m, 4H), 2.89 (m, 2H), 2.48 (m, 4H), 2.22 (s, 3H + 1H), 2.06 (m, 1H), 1.64 (m, 2H), 0.95 (t, 3H) |
| 157 | (S)-N-{1-[2-(3-cyanophenylamino)-6-propylpyrimidin-4-yl]pyrrolidin-3-yl}-2-hydroxyacetamide | $^1$H-NMR (400 MHz, CDCl$_3$) δ 8.36 (s, 1H), 7.59 (d, 1H), 7.47 (s, 1H), 7.33 (t, 1H), 7.19 (d, 1H), 6.83 (d, 1H), 5.73 (s, 1H), 4.65 (m, 1H), 4.14 (s, 2H), 3.81-3.43 (m, 4H), 2.48 (t, 2H), 2.33 (m, 1H), 2.05 (m, 1H), 1.70 (m, 2H), 0.98 (t, 3H) |

TABLE 1-17

| Example | Compound | NMR Spectrum |
|---|---|---|
| 158 | (S)-2-benzyloxy-N-{1-[2-(3-cyanophenylamino)-6-propylpyrimidin-4-yl]pyrrolidin-3-yl}acetamide | $^1$H-NMR (400 MHz, CDCl$_3$) δ 8.30 (s, 1H), 7.64 (s, 1H), 7.31 (m, 5H), 7.20 (m, 1H), 6.74 (d, 1H), 5.75 (s, 1H), 4.65 (m, 1H), 4.57 (s, 2H), 3.99 (s, 2H), 3.79-3.37 (m, 4H), 2.51 (t, 2H), 2.32 (m, 1H), 2.02 (m, 1H), 1.70 (m, 2H), 0.98 (t, 3H) |
| 159 | (S)-N-{1-[2-(3-cyanophenylamino)-6-propylpyrimidin-4-yl]pyrrolidin-3-yl}-2-phenoxyacetamide | $^1$H-NMR (400 MHz, CDCl$_3$) δ 8.30 (s, 1H), 7.63 (s, 1H), 7.36-7.20 (m, 4H), 7.02 (t, 1H), 6.90 (d, 2H), 6.71 (m, 1H), 5.75 (s, 1H), 4.69 (m, 1H), 4.51 (s, 2H), 3.83-3.42 (m, 4H), 2.51 (t, 2H), 2.34 (m, 1H), 2.04 (m, 1H), 1.70 (m, 2H), 0.98 (t, 3H) |
| 160 | (S)-N-{1-[2-(3-cyanophenylamino)-6-propylpyrimidin-4-yl]pyrrolidin-3-yl}-2-(dimethylamino)acetamide | $^1$H-NMR (400 MHz, CDCl$_3$) δ 8.35 (s, 1H), 7.60 (s, 1H), 7.33 (m, 2H), 7.21 (d, 1H), 5.76 (s, 1H), 4.65 (m, 1H), 3.93-3.31 (m, 4H), 2.96 (s, 2H), 2.49 (t, 2H), 2.34 (m, 1H), 2.28 (s, 6H), 2.03 (m, 1H), 1.71 (m, 2H), 0.97 (t, 3H) |
| 161 | (S)-N-{1-[2-(3-cyanophenylamino)-6-propylpyrimidin-4-yl]pyrrolidin-3-yl}-3-(dimethylamino)propanamide | $^1$H-NMR (400 MHz, CDCl$_3$) δ 8.91 (s, 1H), 8.37 (s, 1H), 7.62 (s, 1H), 7.35 (t, 1H), 7.23 (d, 1H), 5.75 (s, 1H), 4.57 (m, 1H), 3.74 (m, 2H), 2.96 (m, 2H), 2.60 (m, 2H), 2.50 (m, 2H), 2.41 (m, 2H), 2.28 (m, 7H), 2.00 (m, 1H), 1.71 (q, 2H), 0.98 (t, 3H) |
| 162 | (S)-N-{1-[2-(3-cyanophenylamino)-6-propylpyrimidin-4-yl]pyrrolidin-3-yl}-4-dimethylaminobutanamide | $^1$H-NMR (400 MHz, CDCl$_3$) δ 8.36 (s, 1H), 8.02 (s, 1H), 7.60 (d, 1H), 7.34 (t, 2H), 7.20 (d, 1H), 5.75 (s, 1H), 4.56 (m, 1H), 3.74-3.49 (m, 4H), 2.55-2.41 (m, 8H), 2.35 (s, 6H), 2.00 (m, 1H), 1.86 (m, 1H), 1.69 (m, 2H), 0.96 (t, 3H) |
| 163 | N—(S)-{1-[2-(3-cyanophenylamino)-6-propylpyrimidin-4- | $^1$H-NMR (400 MHz, CDCl$_3$) δ 8.31 (s, 1H), 7.63 (s, 1H), 7.32 (t, 1H), 7.22 (m, 1H), 7.18 (s, 1H), 6.72 (m, 1H), 5.76 (s, 1H), 4.68 (m, 1H), 3.95 (s, 2H), 3.81 (m, 2H), |

TABLE 1-17-continued

| Example | Compound | NMR Spectrum |
|---|---|---|
|  | yl]pyrrolidin-3-yl}-2-ethoxyacetamide | 3.55 (m, 2H), 3.41 (m, 2H), 2.51 (t, 2H), 2.34 (m, 1H), 2.06 (m, 1H), 1.71 (m, 2H), 1.23 (t, 3H), 0.96 (t, 3H) |
| 164 | N—(S)-{1-[2-(3-cyanophenylamino)-6-propylpyrimidin-4-yl]pyrrolidin-3-yl}-2-(2-methoxyethoxy)acetamide | $^1$H-NMR (400 MHz, CDCl$_3$) δ 8.35 (s, 1H), 7.61 (s, 1H), 7.40 (s, 1H), 7.36 (t, 1H), 7.20 (d, 1H), 7.13 (s, 1H), 5.76 (s, 1H), 4.67 (m, 1H), 4.01 (s, 2H), 3.80 (m, 2H), 3.76 (d, 2H), 3.66 (d, 2H), 3.50 (m, 2H), 3.32 (s, 3H), 2.49 (t, 2H), 2.33 (m, 1H), 2.06 (m, 1H), 1.71 (m, 2H), 0.98 (t, 3H) |
| 165 | (S)-benzyl 2-{1-[2-(3-cyanophenylamino)-6-propylpyrimidin-4-yl]pyrrolidin-3-ylamino}-2-oxoethylcarbamate | $^1$H-NMR (400 MHz, CDCl$_3$) δ 8.35 (s, 1H), 7.64 (d, 1H), 7.34 (m, 5H), 7.20 (d, 1H), 6.58 (s, 1H), 5.70 (s, 1H), 5.46 (m, 1H), 5.12 (s, 2H), 4.61 (m, 1H), 3.89 (m, 2H), 3.80-3.25 (m, 4H), 2.48 (t, 2H), 2.28 (m, 1H), 2.01 (m, 1H), 1.70 (m, 2H), 0.98 (t, 3H) |
| 166 | (S)-tert-butyl 3-{1-[2-(3-cyanophenylamino)-6-propylpyrimidin-4-yl]pyrrolidin-3-ylamino}-3-oxobutylcarbamate | $^1$H-NMR (400 MHz, CDCl$_3$) δ 8.32 (s, 1H), 7.64 (s, 1H), 7.31 (t, 1H), 7.20 (d, 1H), 7.11 (s, 1H), 5.75 (s, 1H), 4.75 (m, 1H), 4.61 (m, 1H), 3.76-3.25 (m, 4H), 3.18 (m, 2H), 2.50 (m, 2H), 2.32 (m, 1H), 2.27 (m, 2H), 2.17 (m, 1H), 1.81 (m, 2H), 1.69 (m, 2H), 1.37 (s, 9H), 0.96 (t, 3H) |

TABLE 1-18

| Example | Compound | NMR Spectrum |
|---|---|---|
| 167 | (S)-tert-butyl 4-{1-[2-(3-cyanophenylamino)-6-propylpyrimidin-4-yl]pyrrolidin-3-ylcarbamoyl}piperidine-1-carboxylate | $^1$H-NMR (400 MHz, CDCl$_3$) δ 8.30 (s, 1H), 7.60 (s, 1H), 7.34-7.27 (m, 1H), 7.18 (d, 1H), 5.90 (m, 1H), 5.74 (s, 1H), 4.61 (m, 1H), 4.14 (m, 2H), 3.78-3.34 (m, 4H), 2.72 (m, 2H), 2.23 (t, 2H), 2.11 (m, 2H), 2.01 (m, 1H), 1.81-1.71 (m, 6H), 1.45 (s, 9H), 0.98 (t, 3H) |
| 168 | (R)-2-methyl-5-[4-(2-methylpyrrolidin-1-yl)-6-propylpyrimidin-2-ylamino]benzonitrile hydrochloride | $^1$H-NMR (400 MHz, CD$_3$OD) δ 8.80 (dd, 1H), 7.65 (dd, 1H), 7.44 (d, 1H), 6.24 (d, 1H), 4.35 (m, 1H), 3.90-3.45 (m, 2H), 2.70-2.60 (m, 2H), 2.52 (s, 3H), 2.30-2.00 (m, 3H), 1.90-1.70 (m, 3H), 1.40-1.20 (m, 3H), 1.05 (t, 3H) |
| 169 | (R)-2-amino-5-[4-(2-methylpyrrolidin-1-yl)-6-propylpyrimidin-2-ylamino]benzonitrile hydrochloride | $^1$H-NMR (400 MHz, CD$_3$OD) δ 7.63 (d, 1H), 7.35 (dd, 1H), 6.85 (d, 1H), 6.15 (d, 1H), 4.30 (m, 1H), 3.80-3.40 (m, 2H), 2.60 (t, 2H), 2.30-2.00 (m, 3H), 1.90-1.70 (m, 3H), 1.30-1.20 (m, 3H), 1.04 (t, 3H) |
| 170 | (S)-2-methyl-5-{4-[3-(methylamino)pyrrolidin-1-yl]-6-propylpyrimidin-2-ylamino}benzonitrile | $^1$H-NMR (400 MHz, CDCl$_3$) δ 8.31 (s, 1H), 7.45 (dd, 1H), 7.20-7.10 (m, 2H), 5.72 (s, 1H), 3.90-3.10 (m, 5H), 2.50-2.40 (m, 8H), 2.25-2.10 (m, 1H), 1.90 (brs, 1H), 1.71 (q, 2H), 0.97 (t, 3H) |
| 171 | (S)-5-{4-[3-(ethylamino)pyrrolidin-1-yl]-6-propylpyrimidin-2-ylamino}-2-methylbenzonitrile | $^1$H-NMR (400 MHz, CDCl$_3$) δ 8.32 (s, 1H), 7.63 (brs, 1H), 7.48 (d, 1H), 7.17 (d, 1H), 5.71 (s, 1H), 3.90-3.10 (m, 5H), 2.80-2.70 (m, 2H), 2.60-2.40 (m, 5H), 2.25-2.15 (m, 1H), 2.00-1.80 (m, 1H), 1.71 (q, 2H), 1.15 (t, 3H), 0.98 (t, 3H) |
| 172 | (S)-5-{4-[3-(ethylamino)pyrrolidin-1-yl]-6-propylpyrimidin-2-ylamino}-2-methylbenzonitrile hydrochloride | $^1$H-NMR (400 MHz, CD$_3$OD) δ 8.38 (s, 1H), 7.63 (dd, 1H), 7.27 (d, 1H), 5.96 (s, 1H), 4.10-3.90 (m, 2H), 3.85-3.50 (m, 3H), 3.17 (q, 2H), 2.60-2.45 (m, 3H), 2.45 (s, 3H), 2.30-2.20 (m, 1H), 1.74 (q, 2H), 1.36 (t, 3H), 0.98 (t, 3H) |
| 173 | 5-{4-[3-(ethylamino)pyrrolidin-1-yl]-6-propylpyrimidin-2-ylamino}-2-methylbenzonitrile hydrochloride | $^1$H-NMR (400 MHz, CD$_3$OD) δ 8.38 (s, 1H), 7.63 (dd, 1H), 7.27 (d, 1H), 5.96 (s, 1H), 4.10-3.90 (m, 2H), 3.85-3.50 (m, 3H), 3.17 (q, 2H), 2.60-2.45 (m, 3H), 2.45 (s, 3H), 2.30-2.20 (m, 1H), 1.74 (q, 2H), 1.36 (t, 3H), 0.98 (t, 3H) |
| 174 | (S)-2-methyl-5-{4-[3-(methylamino)pyrrolidin-1-yl]-6-propylpyrimidin-2-ylamino}benzonitrile hydrochloride | $^1$H-NMR (400 MHz, CD$_3$OD) δ 8.32 (s, 1H), 7.63 (dd, 1H), 7.27 (d, 2H), 5.97 (s, 1H), 3.95-3.62 (m, 5H), 2.78 (s, 3H), 2.54-2.49 (m, 3H), 2.44 (s, 3H), 2.28-2.23 (m, 1H), 1.76-1.70 (m, 2H), 0.97 (t, 3H) |
| 175 | (S)-N$^1$-{4-[3-(methylamino)pyrrolidin-1-yl]-6-propylpyrimidin-2-yl}-3-nitrobenzene-1,4-diamine | $^1$H-NMR (400 MHz, CDCl$_3$) δ 8.65 (s, 1H), 7.70 (d, 1H), 7.37 (d, 1H), 5.77 (s, 1H), 4.00-3.30 (m, 5H), 2.60-2.40 (m, 5H), 2.25-2.15 (m, 1H), 2.05-1.95 (m, 1H), 1.70-1.60 (m, 2H), 0.99 (t, 3H) |

TABLE 1-19

| Example | Compound | NMR Spectrum |
|---|---|---|
| 176 | (S)-N$^1$-{4-[3-(ethylamino)pyrrolidin-1-yl]-6-propylpyrimidin-2-yl}-3-nitrobenzene-1,4-diamine | $^1$H-NMR (400 MHz, CDCl$_3$) δ 8.64 (s, 1H), 7.70 (d, 1H), 7.28 (d, 1H), 5.77 (s, 1H), 4.00-3.30 (m, 5H), 2.80-2.70 (m, 2H), 2.51 (t, 2H), 2.30-2.20 (m, 1H), 2.00-1.90 (m, 1H), 1.72 (q, 2H), 1.17 (t, 3H), 0.99 (t, 3H) |
| 177 | (S)-N$^1$-{4-[3-(ethylamino)pyrrolidin-1-yl]-6-propylpyrimidin-2-yl}-3-nitrobenzene-1,4-diamine hydrochloride | $^1$H-NMR (400 MHz, CDCl$_3$) δ 8.66 (s, 1H), 7.76 (d, 1H), 7.47 (d, 1H) 6.05 (s, 1H), 4.10-3.90 (m, 2H), 3.80-3.50 (m, 3H), 3.25-3.10 (m, 2H), 2.60-2.45 (m, 3H), 2.30-2.20 (m, 1H), 1.78 (q, 2H), 1.37 (t, 3H), 1.00 (t, 3H) |
| 178 | (S)-3-{4-[3-(methylamino)pyrrolidin-1-yl]-6-propylpyrimidin-2-ylamino}benzonitrile hydrochloride | $^1$H-NMR (400 MHz, CD$_3$OD) δ 8.44 (s, 1H), 7.79 (d, 1H), 7.39 (t, 1H), 7.24 (d, 1H), 5.99 (s, 1H), 3.96 (m, 2H), 3.75-3.65 (m, 3H), 2.80 (s, 3H), 2.53 (m, 1H + 2H), 2.26 (m, 1H), 1.73 (m, 2H), 0.99 (s, 3H) |
| 179 | (R)-3-{4-[3-(aminomethyl)pyrrolidin-1-yl]-6-propylpyrimidin-2-ylamino}benzonitrile dihydrochloride | $^1$H-NMR (400 MHz, CD$_3$OD) δ 8.13 (d, 1H), 7.87 (dd, 1H), 7.60-7.45 (m, 2H), 6.27 (d, 1H), 4.20-3.60 (m, 3H), 3.50-3.35 (m, 1H), 3.20-3.00 (m, 2H), 2.80-2.60 (m, 3H), 2.45-2.25 (m, 1H), 2.00-1.90 (m, 1H), 1.79 (q, 2H), 1.05 (t, 3H) |
| 180 | (S)-2-fluoro-5-{4-[3-(methylamino)pyrrolidin-1-yl]-6-propylpyrimidin-2-ylamino}benzonitrile hydrochloride | $^1$H-NMR (400 MHz, CD$_3$OD) δ 8.90-8.80 (m, 1H), 8.45-8.35 (m, 1H), 7.24 (t, 1H), 5.98 (s, 1H), 4.00-3.80 (m, 2H), 3.80-3.55 (m, 3H), 2.79 (s, 3H), 2.55-2.45 (m, 3H), 2.30-2.20 (m, 1H), 1.74 (q, 2H), 0.98 (t, 3H) |
| 181 | (S)-2-fluoro-5-{4-[3-(ethylamino)pyrrolidin-1-yl]-6-propylpyrimidin-2-ylamino}benzonitrile hydrochloride | $^1$H-NMR (400 MHz, CD$_3$OD) δ 8.40 (brs, 1H), 7.90-7.75 (m, 1H), 7.24 (t, 1H), 5.98 (s, 1H), 4.10-3.85 (m, 2H), 3.85-3.50 (m, 3H), 3.18 (q, 2H), 2.60-2.40 (m, 3H), 2.30-2.20 (m, 1H), 1.74 (q, 2H), 1.36 (t, 3H), 0.98 (t, 3H) |
| 182 | 5-[4-(3-aminopyrrolidin-1-yl)-6-propylpyrimidin-2-ylamino]-2-fluorobenzonitrile dihydrochloride | $^1$H-NMR (400 MHz, CD$_3$OD) δ 8.20-8.00 (m, 1H), 7.95-7.85 (m, 1H), 7.42 (t, 1H), 6.32 (s, 1H), 4.20-3.60 (m, 5H), 2.68 (t, 2H), 2.60-2.40 (m, 1H), 2.30-2.15 (m, 1H), 1.90-1.70 (m, 2H), 1.06 (t, 3H) |
| 183 | N-(4-fluorophenyl)-4-methyl-6-(pyrrolidin-1-yl)pyrimidin-2-amine | $^1$H-NMR (400 MHz, CDCl$_3$) δ 7.63-7.58 (m, 2H), 7.00-6.95 (m, 3H), 5.59 (s, 1H), 3.53-3.41 (m, 4H), 2.25 (s, 3H), 1.99 (brs, 4H) |
| 184 | (3R,5S)-1-[2-(4-fluorophenyl)-6-propylpyrimidin-4-yl]-5-(hydroxymethyl)pyrrolidin-3-ol | $^1$H-NMR (400 MHz, CDCl$_3$) δ 7.48 (dd, 2H), 6.97 (dd, 2H), 5.66 (s, 1H), 4.56 (s, 1H), 4.41 (d, 1H), 3.78 (d, 1H), 3.62-3.45 (m, 4H), 2.43 (dd, 2H), 2.13 (brs, 1H), 1.97 (brs, 1H), 1.71-1.65 (m, 2H), 0.96 (t, 3H) |
| 185 | (S)-{1-[2-(1H-indol-6-ylamino)-6-propylpyrimidin-4-yl]pyrrolidin-2-yl}methanol | $^1$H-NMR (400 MHz, CDCl$_3$) δ 8.40 (brs, 1H), 8.05 (s, 1H), 7.49 (d, 1H), 7.04 (dd, 1H), 6.97 (dd, 1H), 6.90 (brs, 1H), 6.43 (d, 1H), 5.70 (s, 1H), 4.39 (brs, 1H), 3.75 (dd, 1H), 3.59 (dd, 1H), 3.46 (brs, 1H), 3.35-3.27 (m, 1H), 2.48 (dd, 2H), 2.04-1.96 (m, 3H), 1.78-1.69 (m, 3H), 0.97 (t, 3H) |

TABLE 1-20

| Example | Compound | NMR Spectrum |
|---|---|---|
| 186 | (R)-{1-[2-(1H-indol-6-ylamino)-6-propylpyrimidin-4-yl]pyrrolidin-2-yl}methanol | $^1$H-NMR (400 MHz, CDCl$_3$) δ 8.49 (brs, 1H), 8.03 (s, 1H), 7.48 (d, 1H), 7.01-6.80 (m, 3H), 6.42 (s, 1H), 5.69 (s, 1H), 4.86 (brs, 1H), 4.38 (brs, 1H), 3.74 (dd, 1H), 3.57 (dd, 1H), 3.44 (brs, 1H), 3.29 (brs, 1H), 2.48 (dd, 2H), 2.04-1.96 (m, 3H), 1.77-1.68 (m, 3H), 0.96 (t, 3H) |
| 187 | {1-[2-(1H-indol-6-ylamino)-6-propylpyrimidin-4-yl]pyrrolidin-2-yl}methanol | $^1$H-NMR (400 MHz, CDCl$_3$) δ 8.49 (brs, 1H), 8.02 (s, 1H), 7.47 (dd, 1H), 7.02-6.89 (m, 3H), 6.42 (d, 1H), 5.69 (s, 1H), 4.86 (brs, 1H), 4.38 (brs, 1H), 3.75 (dd, 1H), 3.57 (dd, 1H), 3.43 (brs, 1H), 3.29 (brs, 1H), 2.47 (dd, 2H), 2.04-1.96 (m, 3H), 1.77-1.68 (m, 3H), 0.98 (t, 3H) |
| 188 | (R)-N-{4-[2-(methoxymethyl)pyrrolidin-1-yl]-6-propylpyrimidin-2-yl}-1H-indol-6-amine | $^1$H-NMR (400 MHz, CDCl$_3$) δ 8.49 (brs, 1H), 8.19 (brs, 1H), 7.48 (d, 1H), 7.10 (dd, 1H), 7.01-6.92 (m, 2H), 6.45 (d, 1H), 5.69 (s, 1H), 4.53 (brs, 1H), 3.94 (brs, 1H), 3.47 (d, 1H), 3.37 (s, 3H), 3.31-3.16 (m, 2H), 2.47 (dd, 2H), 2.11-2.00 (m, 4H), 1.76-1.69 (m, 2H), 0.99 (t, 3H) |
| 189 | (S)-N-{4-[2-(methoxymethyl)pyrrolidin-1-yl]-6-propylpyrimidin-2-yl}-1H-indol-6-amine | $^1$H-NMR (400 MHz, CDCl$_3$) δ 8.48 (brs, 1H), 8.22 (brs, 1H), 7.48 (d, 1H), 7.10 (dd, 1H), 7.01-6.92 (m, 2H), 6.46 (d, 1H), 5.69 (s, 1H), 4.53 (brs, 1H), 3.94 (brs, 1H), 3.47 (d, 1H), 3.36 (s, 3H), 3.31-3.16 (m, 2H), 2.47 (dd, 2H), 2.11-2.00 (m, 4H), 1.76-1.69 (m, 2H), 0.99 (t, 3H) |
| 190 | N-[4-(2-methylpyrrolidin-1-yl)-6-propylpyrimidin-2-yl]-1H-indol-6-amine | $^1$H-NMR (400 MHz, CDCl$_3$) δ 8.14 (brs, 1H), 8.04 (brs, 1H), 7.49 (d, 1H), 7.11-7.08 (m, 3H), 6.47 (dd, 1H), 5.67 (s, 1H), 4.28 (brs, 1H), 3.59 (brs, 1H), 3.42 (brs, 1H), 2.47 (dd, 2H), |

TABLE 1-20-continued

| Example | Compound | NMR Spectrum |
|---|---|---|
|  |  | 2.12-1.98 (m, 4H), 1.79-1.72 (m, 2H), 1.27 (dd, 3H), 0.99 (t, 3H) |
| 191 | (S)-methyl 1-[2-(1H-indol-6-ylamino)-6-propylprimidin-4-yl]pyrrolidine-2-carboxylate | $^1$H-NMR (400 MHz, CDCl$_3$) δ 8.56 (brs, 1H), 8.31 (brs, 1H), 7.45 (dd, 1H), 7.12 (dd, 1H), 7.00 (s, 1H), 6.45 (dd, 1H), 5.74 (brs, 1H), 4.75 (brs, 1H), 3.63 (s, 3H), 3.65-3.45 (d, 1H), 2.48 (dd, 2H), 2.32-2.02 (m, 4H), 1.75-1.70 (m, 2H), 0.99 (dd, 3H) |
| 192 | N-{1-[2-(1H-indol-6-ylamino)-6-propylpyrimidin-4-yl]pyrrolidin-3-yl}acetamide | $^1$H-NMR (400 MHz, CDCl$_3$) δ 8.68 (brs, 1H), 8.10 (brs, 1H), 7.47 (d, 1H), 7.11 (s, 1H), 7.04 (s, 1H), 6.46 (s, 1H), 5.48 (brs, 1H), 4.55 (s, 1H), 3.82-3.44 (m, 5H), 2.38-2.23 (m, 3H), 2.03 (s, 3H), 2.05-1.95 (m, 1H), 1.75-1.68 (m, 2H), 0.99 (dd, 3H) |
| 193 | (S)-{1-[2-(1H-indol-6-ylamino)-6-propylpyrimidin-4-yl]pyrrolidin-2-yl}methanol hydrochloride | $^1$H-NMR (400 MHz, CDCl$_3$) δ 12.25 (brs, 1H), 9.81-9.78 (m, 2H), 8.22 (s, 1H), 7.37 (d, 1H), 7.16 (dd, 1H), 6.80 (d, 1H), 6.37 (s, 1H), 5.10 (s, 1H), 4.70 (brs, 1H), 4.50 (brs, 1H), 4.06 (d, 1H), 3.69 (dd, 1H), 3.31 (dd, 1H), 3.20-3.13 (m, 1H), 2.30-1.98 (m, 6H), 1.58-1.50 (m, 2H), 0.93 (t, 3H) |
| 194 | (S)-3-{4-[2-(hydroxymethyl)pyrrolidin-1-yl]-6-propylpyrimidin-2-ylamino}benzonitrile | $^1$H-NMR (400 MHz, CDCl$_3$) δ 8.31 (s, 1H), 7.58 (dd, 1H), 7.34 (t, 1H), 7.24 (d, 1H), 7.22 (brs, 1H), 5.81 (s, 1H), 4.41 (br, 1H), 3.73 (m, 2H), 3.52 (br, 1H), 3.39 (m, 1H), 2.51 (t, 2H), 2.11-2.00 (m, 3H), 1.88 (br, 1H), 1.75 (m, 2H), 0.99 (t, 3H) |
| 195 | (S)-(1-{2-[3-(methylthio)phenylamino]-6-propylpyrimidin-4-yl}pyrrolidin-2-yl)methanol | $^1$H-NMR (400 MHz, CDCl$_3$) δ 10.30-10.13 (br, 1H), 7.84 (s, 1H), 7.25 (m, 2H), 6.98 (s, 1H), 5.71 (brs, 1H), 4.45 (br, 1H), 3.89 (br, 1H), 3.68 (br, 2H), 3.43 (br, 1H), 2.70 (br, 2H), 2.49 (s, 3H), 2.18 (br, 1H), 2.08 (m, 3H), 1.77 (m, 2H), 1.00 (m, 3H) |

TABLE 1-21

| Example | Compound | NMR Spectrum |
|---|---|---|
| 196 | (S)-{1-[2-(4-chloro-3-nitrophenylamino)-6-propylpyrimidin-4-yl]pyrrolidin-2-yl}methanol | $^1$H-NMR (400 MHz, CDCl$_3$) δ 8.87 (s, 1H), 7.37 (m, 2H), 7.34 (br, 1H), 5.82 (s, 1H), 4.44 (br, 1H), 3.77 (m, 2H), 3.52 (br, 1H), 3.39 (br, 1H), 2.50 (t, 2H), 2.07 (m, 3H), 1.94 (m, 1H), 1.74 (m, 2H), 1.00 (t, 3H) |
| 197 | (S)-{1-[2-(1H-indol-5-ylamino)-6-propylpyrimidin-4-yl]pyrrolidin-2-yl}methanol | $^1$H-NMR (400 MHz, CDCl$_3$) δ 8.29 (brs, 1H), 7.80 (s, 1H), 7.27 (m, 3H), 7.13 (m, 1H), 6.47 (s, 1H), 5.69 (s, 1H), 3.59 (m, 2H), 3.48 (br, 1H), 3.38 (br, 1H), 2.49 (t, 2H), 1.97 (m, 3H), 1.75 (m, 3H), 1.99 (t, 3H) |
| 198 | (S)-{1-[2-(1H-benzo[d]imidazol-5-ylamino)-6-propylpyrimidin-4-yl]pyrrolidin-2-yl}methanol | $^1$H-NMR (400 MHz, CDCl$_3$) δ 8.84 (s, 1H), 8.24 (m, 2H), 8.01 (s, 1H), 7.56 (d, 1H), 6.71 (d, 1H), 6.06 (s, 1H), 4.57 (br, 1H), 3.95 (br, 1H), 3.72 (m, 1H), 3.56 (m, 1H), 3.40 (br, 1H), 2.63 (m, 2H), 2.10 (m, 3H), 1.82 (m, 3H), 1.03 (t, 3H) |
| 199 | (S)-(1-{6-propyl-2-[2-(trifluoromethyl)-1H-benzo[d]imidazol-5-ylamino]pyrimidin-4-yl}pyrrolidin-2-yl)methanol | $^1$H-NMR (400 MHz, CDCl$_3$) δ 8.42 (brs, 1H), 7.59 (d, 1H), 7.44 (d, 1H), 7.38 (d, 1H), 6.88 (d, 1H), 6.84 (s, 1H), 5.93 (brs, 1H), 3.76 (br, 1H), 3.55 (br, 1H), 3.35 (s, 2H), 2.50 (t, 2H), 2.11 (m, 2H), 2.02 (m, 2H), 1.77 (m, 2H), 1.02 (t, 3H) |
| 200 | (S)-{1-[2-(4-methoxyphenylamino)-6-propylpyrimidin-4-yl]pyrrolidin-2-yl}methanol | $^1$H-NMR (400 MHz, CDCl$_3$) δ 9.98 (br, 1H), 7.45 (br, 2H), 6.84 (d, 2H), 6.10-5.67 (br, 1H), 4.38 (br, 1H), 3.78 (s, 3H), 3.73 (m, 2H), 3.59 (br, 1H), 3.42 (br, 1H), 2.52 (m, 2H), 2.15 (br, 1H), 2.05 (m, 3H), 1.75 (m, 2H), 0.97 (t, 3H) |
| 201 | (S)-{1-[2-(3-chlorophenylamino)-6-propylpyrimidin-4-yl]pyrrolidin-2-yl}methanol | $^1$H-NMR (400 MHz, CDCl$_3$) δ 10.45 (br, 1H), 7.92 (s, 1H), 7.36 (br, 1H), 7.22 (m, 1H), 7.03 (m, 1H), 5.73 (br, 1H), 4.47 (br, 1H), 4.13 (m, 1H), 3.83 (br, 1H), 3.43 (br, 1H), 2.51 (m, 2H), 2.09 (m, 4H), 1.75 (m, 2H), 0.97 (t, 3H) |
| 202 | (S)-{1-[2-(3-methoxyphenylamino)-6-propylpyrimidin-4-yl]pyrrolidin-2-yl}methanol | $^1$H-NMR (400 MHz, CDCl$_3$) δ 10.17 (br, 1H), 7.61 (brs, 1H), 7.21 (m, 1H), 7.04 (br, 1H), 6.63 (m, 1H), 5.70 (brs, 1H), 4.42 (br, 1H), 3.90 (br, 1H), 3.81 (s, 3H), 3.75 (m, 2H), 3.40 (m, 1H), 2.53 (m, 2H), 2.09 (m, 4H), 1.76 (m, 2H), 0.97 (t, 3H) |
| 203 | (S)-(1-{6-propyl-2-[3-(trifluoromethyl)phenylamino]pyrimidin-4-yl}pyrrolidin-2-yl)methanol | $^1$H-NMR (400 MHz, CDCl$_3$) δ 10.62 (br, 1H), 8.32 (m, 1H), 7.57 (d, 1H), 7.41 (m, 1H), 7.33 (m, 1H), 6.22-5.78 (br, 1H), 4.50 (br, 1H), 4.13 (m, 1H), 3.93 (m, 2H), 3.46 (br, 1H), 2.53 (br, 2H), 2.28-2.05 (m, 4H), 1.77 (m, 2H), 0.97 (t, 3H) |
| 204 | (S)-{1-[2-(5-chloro-2-methylphenylamino)-6-propylpyrimidin-4-yl]pyrrolidin-2-yl}methanol | $^1$H-NMR (400 MHz, CDCl$_3$) δ 8.08 (s, 1H), 7.09 (d, 1H), 6.95 (d, 1H), 5.76 (s, 1H), 4.33 (br, 1H), 3.71-3.61 (m, 2H), 3.40 (br, 1H), 3.39 (br, 1H), 2.52 (m, 2H), 2.30 (s, 3H), 2.11-2.00 (m, 4H), 1.77 (m, 2H), 1.00 (t, 3H) |
| 205 | (S)-{1-[2-(5-methoxy-2-methylphenylamino)-6- | $^1$H-NMR (400 MHz, CDCl$_3$) δ 9.31 (br, 1H), 7.64 (s, 1H), 7.09 (d, 1H), 6.62 (m, 1H), 5.72 (s, 1H), 4.27 (br, 1H), |

TABLE 1-21-continued

| Example | Compound | NMR Spectrum |
|---|---|---|
| | propylpyrimidin-4-yl]pyrrolidin-2-yl}methanol | 3.82 (s, 3H), 3.77 (m, 1H), 3.46 (m, 2H), 3.36 (m, 1H), 2.56 (m, 2H), 2.31 (s, 3H), 2.06-1.99 (m, 4H), 1.80 (m, 2H), 1.02 (t, 3H) |

TABLE 1-22

| Example | Compound | NMR Spectrum |
|---|---|---|
| 206 | (S)-{1-[2-(3-chloro-4-methylphenylamino)-6-propylpyrimidin-4-yl]pyrrolidin-2-yl}methanol | $^1$H-NMR (400 MHz, CDCl$_3$) δ 10.11 (br, 1H), 7.91 (d, 1H), 7.23 (br, 1H), 7.13 (m, 1H), 6.14-5.73 (br, 1H), 4.46 (br, 1H), 3.81 (m, 2H), 3.63 (br, 1H), 3.38 (br, 1H), 2.52 (m, 2H), 2.32 (s, 3H), 2.10 (m, 4H), 1.78 (m, 2H), 0.98 (t, 3H) |
| 207 | (S)-{1-[2-(3-nitrophenylamino)-6-propylpyrimidin-4-yl]pyrrolidin-2-yl}methanol | $^1$H-NMR (400 MHz, CDCl$_3$) δ 9.15 (s, 1H), 8.37 (br, 1H), 7.83 (d, 1H), 7.81 (d, 1H), 7.41 (t, 1H), 5.83 (s, 1H), 4.67 (br, 1H), 4.13 (m, 1H), 3.80 (m, 1H), 3.56 (br, 1H), 3.42 (br, 1H), 2.53 (m, 2H), 2.17-2.05 (m, 4H), 1.79 (m, 2H), 1.00 (t, 3H) |
| 208 | (S)-{1-[2-(4-fluoro-3-nitrophenylamino)-6-propylpyrimidin-4-yl]pyrrolidin-2-yl}methanol | $^1$H-NMR (400 MHz, CDCl$_3$) δ 8.95 (s, 1H), 7.85 (br, 1H), 7.50 (m, 1H), 7.16 (t, 1H), 5.81 (s, 1H), 4.49 (br, 1H), 4.45 (br, 1H), 3.76 (m, 1H), 3.53-3.39 (m, 2H), 2.48 (m, 2H), 2.13 (m, 3H), 1.75 (m, 2H), 0.97 (t, 3H) |
| 209 | (S)-{1-[6-propyl-2-(quinolin-6-ylamino)pyrimidin-4-yl]pyrrolidin-2-yl}methanol | $^1$H-NMR (400 MHz, CDCl$_3$) δ 8.75 (d, 1H), 8.38 (d, 1H), 8.09 (d, 1H), 8.00 (d, 1H), 7.72 (dd, 1H), 7.33 (m, 1H), 5.81 (s, 1H), 4.49 (br, 1H), 3.75 (m, 2H), 3.55 (m, 1H), 3.42 (m, 1H), 2.54 (m, 2H), 2.07 (m, 3H), 1.91 (m, 1H), 1.78 (m, 2H), 1.02 (t, 3H) |
| 210 | (S)-{1-[2-(4-methyl-3-nitrophenylamino)-6-propylpyrimidin-4-yl]pyrrolidin-2-yl}methanol | $^1$H-NMR (400 MHz, CD$_3$OD) δ 8.65 (s, 1H), 7.56 (s, 1H), 7.28 (d, 1H), 6.01 (s, 1H), 4.43-3.50 (m, 5H), 2.53 (m, 5H), 2.12-2.02 (m, 4H), 1.73 (m, 2H), 1.00 (t, 3H) |
| 211 | (S)-(1-{2-[4-amino-3-(trifluoromethyl)phenylamino]-6-propylpyrimidin-4-yl}pyrrolidin-2-yl)methanol | $^1$H-NMR (400 MHz, CD$_3$OD) δ 7.77 (brs, 1H), 7.34 (d, 1H), 6.85 (d, 1H), 6.12 (brs, 1H), 4.13 (m, 1H), 3.93-3.50 (m, 4H), 2.57 (t, 2H), 2.09-1.98 (m, 4H), 1.74 (m, 2H), 1.03 (t, 3H) |
| 212 | (S)-{1-[2-(4-amino-3-nitrophenylamino)-6-propylpyrimidin-4-yl]pyrrolidin-2-yl}methanol | $^1$H-NMR (400 MHz, CDCl$_3$) δ 8.82 (s, 1H), 7.25 (m, 1H), 6.82 (brs, 1H), 6.74 (d, 1H), 5.94 (s, 2H), 5.74 (s, 1H), 4.52 (s, 1H), 3.75 (m, 1H), 3.63 (m, 1H), 3.49 (m, 1H), 3.37 (s, 1H), 2.47 (t, 2H), 2.02 (m, 3H), 1.90 (m, 1H), 1.72 (m, 2H), 0.98 (t, 3H) |
| 213 | (S)-5-{4-[2-(hydroxymethyl)pyrrolidin-1-yl]-6-propylpyrimidin-2-ylamino}-2-methylbenzonitrile | $^1$H-NMR (400 MHz, CDCl$_3$) δ 8.21 (s, 1H), 7.45 (d, 1H), 7.18 (d, 1H), 6.97 (brs, NH) 5.79 (s, 1H), 4.41 (s, 1H), 3.71 (m, 2H), 3.51 (m, 1H), 3.38 (s, 1H), 2.48 (m, 5H), 2.02 (m, 3H), 1.86 (s, 1H), 1.70 (m, 2H), 0.99 (t, 3H) |
| 214 | (S)-2-fluoro-5-{4-[2-(hydroxymethyl)pyrrolidin-1-yl]-6-propylpyrimidin-2-ylamino}benzonitrile | $^1$H-NMR (400 MHz, CDCl$_3$) δ 8.22 (m, 1H), 7.58 (m, 1H), 7.12 (s, 1H), 7.07 (t, 1H), 5.81 (s, 1H), 4.39 (s, 1H), 3.73 (m, 2H), 3.51 (s, 1H), 3.38 (s, 1H), 2.52 (t, 2H), 2.02 (m, 3H), 1.84 (s, 1H), 1.74 (m, 2H), 0.99 (t, 3H) |
| 215 | (S)-2-amino-5-{4-[2-(hydroxymethyl)pyrrolidin-1-yl]-6-propylpyrimidin-2-ylamino}benzonitrile | $^1$H-NMR (400 MHz, CDCl$_3$) δ 7.83 (s, 1H), 7.33 (d, 1H), 6.76 (d, 1H), 5.80 (s, 1H), 4.42 (m, 3H), 3.75 (m, 3H), 2.55 (m, 2H), 2.07 (m, 4H), 1.78 (m, 2H), 1.00 (t, 3H) |

TABLE 1-23

| Example | Compound | NMR Spectrum |
|---|---|---|
| 216 | (S)-{1-[6-propyl-2-(quinolin-3-ylamino)pyrimidin-4-yl]pyrrolidin-2-yl}methanol | $^1$H-NMR (400 MHz, CDCl$_3$) δ 8.94 (s, 1H), 8.66 (d, 1H), 7.99 (d, 1H), 7.72 (d, 1H), 7.55-7.45 (m, 2H), 7.25 (br, 1H), 5.80 (s, 1H), 4.40 (br, 1H), 3.75 (m, 2H), 3.51 (m, 1H), 3.40 (m, 1H), 2.51 (m, 2H), 2.04 (m, 3H), 1.95 (m, 1H), 1.77 (m, 2H), 0.98 (t, 3H) |
| 217 | (S)-{1-[2-(indolin-6-ylamino)-6-propylpyrimidin-4-yl]pyrrolidin-2-yl}methanol | $^1$H-NMR (400 MHz, CDCl$_3$) δ 7.21 (s, 1H), 7.00 (d, 1H), 6.83 (brs, 1H), 6.69 (d, 1H), 5.69 (s, 1H), 4.37 (s, 1H), 3.76 (m, 1H), 3.62 (m, 1H), 3.55 (m, 1H), 3.46 (m, 1H), 3.32 (m, 1H), 2.96 (t, 2H), 2.46 (t, 2H), 2.00 (m, 3H), 1.83 (m, 1H), 1.69 (m, 2H), 0.97 (t, 3H) |
| 218 | (S)-3-{4-[3-(cyclohexylamino)pyrrolidin-1-yl]-6-propylpyrimidin-2- | $^1$H-NMR (400 MHz, CD$_3$OD) δ 8.19 (d, 1H), 7.82-7.75 (m, 1H), 7.61-7.54 (m, 2H), 6.35 (s, 1H), 4.23-3.74 (m, 5H), 3.23 (brs, 1H), 2.69 (dd, 2H), 2.60 (brs, 1H), 2.35-2.20 (m, |

TABLE 1-23-continued

| Example | Compound | NMR Spectrum |
|---|---|---|
|  | ylamino}benzonitrile dihydrochloride | 1H), 1.90 (d, 2H), 1.85-1.72 (m, 5H), 1.47-1.25 (m, 5H), 1.06 (t, 3H) |
| 219 | (S)-3-{4-[3-(isopropylamino)pyrrolidin-1-yl]-6-propylpyrimidin-2-ylamino}benzonitrile dihydrochloride | $^1$H-NMR (400 MHz, CD$_3$OD) δ 8.25 (brs, 1H), 7.79 (brs, 1H), 7.60-7.52 (m, 2H), 6.32 (s, 1H), 4.21-3.75 (m, 5H), 3.58-3.52 (m, 1H), 2.68 (dd, 2H), 2.60 (brs, 1H), 2.32 (brs, 1H), 1.85-1.75 (m, 2H), 1.42 (dd, 6H), 1.06 (t, 3H) |
| 220 | (S)-3-{4-[3-(aminoethylamino)pyrrolidin-1-yl]-6-propylpyrimidin-2-ylamino}benzonitrile dihydrochloride | $^1$H-NMR (400 MHz, CD$_3$OD) δ 8.15 (d, 1H), 7.82 (s, 1H), 7.60-7.54 (m, 2H), 6.35 (s, 1H), 4.18-3.75 (m, 5H), 3.44-3.40 (m, 2H), 3.31-3.25 (m, 2H), 2.69 (dd, 2H), 2.67-2.49 (m, 1H), 2.40-2.25 (m, 1H), 1.83-1.76 (m, 2H), 1.06 (t, 3H) |
| 221 | (S)-3-{4-[3-(piperidin-4-ylamino)pyrrolidin-1-yl]-6-propylpyrimidin-2-ylamino}benzonitrile | $^1$H-NMR (400 MHz, CD$_3$OD) δ 8.20 (brs, 1H), 7.57 (brs, 1H), 7.38 (dd, 1H), 7.22 (d, 1H), 5.87 (s, 1H), 4.15-3.31 (m, 7H), 3.01-2.94 (m, 3H), 2.48 (dd, 2H), 2.31-2.18 (m, 2H), 2.11 (d, 1H), 1.91 (brs, 1H), 1.75-1.68 (m, 2H), 1.57-1.46 (m, 2H), 0.97 (t, 3H) |
| 222 | (S)-3-{4-[3-(1-butylpiperidin-4-ylamino)pyrrolidin-1-yl]-6-propylpyrimidin-2-ylamino}benzonitrile | $^1$H-NMR (400 MHz, CD$_3$OD) δ 8.55-8.45 (m, 1H), 7.32-7.26 (m, 1H), 7.39 (dd, 1H), 7.23 (d, 1H), 5.89 (s, 1H), 3.99-3.44 (m, 6H), 2.99 (d, 2H), 2.65 (brs, 1H), 2.49 (dd, 2H), 2.39-2.28 (m, 3H), 2.10-1.94 (m, 4H), 1.85-1.69 (m, 2H), 1.55-1.28 (m, 6H), 1.00-0.87 (m, 6H) |
| 223 | (S)-N-{1-[6-butyl-2-(3-cyanophenylamino)pyrimidin-4-yl]pyrrolidin-3-yl}acetamide | $^1$H-NMR (400 MHz, CDCl$_3$) δ 8.25 (brs, 1H), 7.61 (brs, 1H), 7.33-7.28 (m, 2H), 7.17 (d, 1H), 6.17 (brs, 1H), 5.73 (s, 1H), 4.58 (brs, 1H), 3.92-3.33 (m, 4H), 2.49 (dd, 2H), 2.30-2.25 (m, 1H), 2.04-2.00 (m, 1H), 2.00 (s, 3H), 1.69-1.61 (m, 2H), 1.43-1.33 (m, 2H), 0.94 (t, 3H) |
| 224 | (S)-3-{4-butyl-6-[2-(hydroxymethyl)pyrrolidin-1-yl]pyrimidin-2-ylamino}benzonitrile | $^1$H-NMR (400 MHz, CDCl$_3$) δ 8.31 (s, 1H), 7.58 (dd, 1H), 7.34 (dd, 1H), 7.22 (d, 1H), 7.17 (brs, 1H), 5.81 (s, 1H), 4.88-4.30 (m, 2H), 3.75-3.69 (m, 2H), 3.51 (brs, 1H), 3.38 (brs, 1H), 2.53 (dd, 2H), 2.11-2.00 (m, 3H), 1.86 (brs, 1H), 1.73-1.65 (m, 2H), 1.45-1.37 (m, 2H), 0.94 (t, 3H) |
| 225 | (R)-3-[4-butyl-6-(2-methylpyrrolidin-1-yl)pyrimidin-2-ylamino]benzonitrile | $^1$H-NMR (400 MHz, CDCl$_3$) δ 8.48 (brs, 1H), 7.51 (d, 1H), 7.33-7.25 (m, 2H), 7.19 (d, 1H), 5.74 (s, 1H), 4.37-3.38 (m, 3H), 2.49 (dd, 2H), 2.08-2.01 (m, 3H), 1.78-1.75 (m, 1H), 1.71-1.63 (m, 2H), 1.44-1.36 (m, 2H), 1.29 (brs, 3H), 0.94 (t, 3H) |

TABLE 1-24

| Example | Compound | NMR Spectrum |
|---|---|---|
| 226 | (S)-3-{4-butyl-6-[3-(methylamino)pyrrolidin-1-yl]pyrimidin-2-ylamino}benzonitrile | $^1$H-NMR (400 MHz, CDCl$_3$) δ 8.40 (s, 1H), 7.56 (dd, 1H), 7.33-7.28 (m, 2H), 7.17 (d, 1H), 5.74 (s, 1H), 3.78-3.16 (m, 5H), 2.50 (s, 3H), 2.48 (dd, 2H), 2.22-2.17 (m, 1H), 1.91 (brs, 1H), 1.70-1.62 (m, 2H), 1.43-1.34 (m, 2H), 0.94 (t, 3H) |
| 227 | (S)-tert-butyl 1-[6-butyl-2-(3-cyanophenylamino)pyrimidin-4-yl]pyrrolidin-3-ylcarbamate | $^1$H-NMR (400 MHz, CDCl$_3$) δ 8.30 (brs, 1H), 7.61 (brs, 1H), 7.33 (dd, 1H), 7.20 (d, 1H), 7.13 (brs, 1H), 5.74 (s, 1H), 4.80 (brs, 1H), 4.34 (brs, 1H), 3.82-3.33 (m, 4H), 2.50 (dd, 2H), 2.29-2.23 (m, 1H), 1.99 (brs, 1H), 1.70-1.63 (m, 2H), 1.46 (s, 9H), 1.42-1.34 (m, 2H), 0.95 (t, 3H) |
| 228 | (S)-N-{1-[6-butyl-2-(3-cyano-4-methylphenylamino)pyrimidin-4-yl]pyrrolidin-3-yl}acetamide | $^1$H-NMR (400 MHz, CDCl$_3$) δ 8.19 (brs, 1H), 7.48 (brs, 1H), 7.16 (d, 1H), 7.06 (brs, 1H), 6.01 (brs, 1H), 5.71 (s, 1H), 4.60-4.56 (m, 1H), 3.75-3.38 (m, 4H), 2.48 (dd, 2H), 2.45 (s, 3H), 2.32-2.24 (m, 1H), 2.04-2.00 (m, 1H), 2.00 (s, 3H), 1.69-1.61 (m, 2H), 1.43-1.34 (m, 2H), 0.94 (t, 3H) |
| 229 | (S)-5-{4-butyl-6-[2-(hydroxymethyl)pyrrolidin-1-yl]pyrimidin-2-ylamino}-2-methylbenzonitrile | $^1$H-NMR (400 MHz, CDCl$_3$) δ 8.20 (dd, 1H), 7.45 (dd, 1H), 7.18 (d, 1H), 7.11 (brs, 1H), 5.78 (s, 1H), 4.40 (brs, 1H), 3.74-3.69 (m, 2H), 3.50 (brs, 1H), 3.37 (brs, 1H), 2.51 (dd, 2H), 2.47 (s, 3H), 2.08-1.99 (m, 3H), 1.86 (brs, 1H), 1.72-1.64 (m, 2H), 1.42-1.37 (m, 2H), 0.94 (t, 3H) |
| 230 | (R)-5-[4-butyl-6-(2-methylpyrrolidin-1-yl)pyrimidin-2-ylamino]-2-methylbenzonitrile | $^1$H-NMR (400 MHz, CDCl$_3$) δ 8.40 (brs, 1H), 7.40 (brs, 1H), 7.16 (d, 1H), 7.03 (brs, 1H), 5.72 (s, 1H), 4.40-3.36 (m, 3H), 2.48 (dd, 2H), 2.47 (s, 3H), 2.12-2.00 (m, 3H), 1.77-1.75 (m, 1H), 1.70-1.62 (m, 2H), 1.44-1.36 (m, 2H), 1.29 (brs, 3H), 0.94 (t, 3H) |
| 231 | (S)-5-{4-butyl-6-[3-(methylamino)pyrrolidin-1-yl]pyrimidin-2-ylamino}-2-methylbenzonitrile | $^1$H-NMR (400 MHz, CDCl$_3$) δ 8.32 (d, 1H), 7.44 (dd, 1H), 7.16 (d, 1H), 7.11 (brs, 1H), 5.72 (s, 1H), 3.78-3.16 (m, 5H), 2.50 (s, 3H), 2.48 (dd, 2H), 2.47 (s, 3H), 2.22-2.16 (m, 1H), 1.90 (brs, 1H), 1.70-1.62 (m, 2H), 1.43-1.34 (m, 2H), 0.94 (t, 3H) |
| 232 | (S)-tert-butyl 1-[6-butyl-2-(3-cyano-4-methylphenylamino)pyrimidin- | $^1$H-NMR (400 MHz, CDCl$_3$) δ 8.20 (brs, 1H), 7.50 (brs, 1H), 7.17 (d, 1H), 7.16 (brs, 1H), 5.70 (s, 1H), 4.90 (brs, 1H), 4.33 (brs, 1H), 3.82-3.33 (m, 4H), 2.49 (dd, 2H), 2.47 (s, |

TABLE 1-24-continued

| Example | Compound | NMR Spectrum |
|---|---|---|
|  | 4-yl]pyrrolidin-3-ylcarbamate | 3H), 2.27-2.23 (m, 1H), 1.99 (brs, 1H), 1.69-1.62 (m, 2H), 1.46 (s, 9H), 1.43-1.33 (m, 2H), 0.95 (t, 3H) |
| 233 | (S)-3-[4-(3-aminopyrrolidin-1-yl)-6-butylpyrimidin-2-ylamino]benzonitrile dihydrochloride | $^1$H-NMR (400 MHz, CDCl$_3$) δ 8.19 (brs, 1H), 7.48 (brs, 1H), 7.16 (d, 1H), 7.06 (brs, 1H), 6.01 (brs, 1H), 5.71 (s, 1H), 4.60-4.56 (m, 1H), 3.75-3.38 (m, 4H), 2.48 (dd, 2H), 2.45 (s, 3H), 2.32-2.24 (m, 1H), 2.04-2.00 (m, 1H), 2.00 (s, 3H), 1.69-1.61 (m, 2H), 1.43-1.34 (m, 2H), 0.94 (t, 3H) |
| 234 | (S)-5-[4-(3-aminopyrrolidin-1-yl)-6-butylpyrimidin-2-ylamino]-2-methylbenzonitrile dihydrochloride | $^1$H-NMR (400 MHz, CDCl$_3$) δ 8.19 (brs, 1H), 7.48 (brs, 1H), 7.16 (d, 1H), 7.06 (brs, 1H), 6.01 (brs, 1H), 5.71 (s, 1H), 4.60-4.56 (m, 1H), 3.75-3.38 (m, 4H), 2.48 (dd, 2H), 2.45 (s, 3H), 2.32-2.24 (m, 1H), 2.04-2.00 (m, 1H), 2.00 (s, 3H), 1.69-1.61 (m, 2H), 1.43-1.34 (m, 2H), 0.94 (t, 3H) |
| 235 | (S)-3-{4-butyl-6-[3-(isopropylamino)pyrrolidin-1-yl]pyrimidin-2-ylamino}benzonitrile | $^1$H-NMR (400 MHz, CDCl$_3$) δ 8.38 (s, 1H), 7.58 (d, 1H), 7.33 (dd, 1H), 7.20 (d, 1H), 7.17 (brs, 1H), 5.73 (s, 1H), 3.90-3.38 (m, 5H), 2.99-2.93 (m, 1H), 2.50 (dd, 2H), 2.28-2.21 (m, 1H), 1.85 (brs, 1H), 1.71-1.63 (m, 2H), 1.44-1.37 (m, 2H), 1.11 (t, 6H), 0.97 (t, 3H) |

TABLE 1-25

| Example | Compound | NMR Spectrum |
|---|---|---|
| 236 | (S)-3-{4-butyl-6-[3-(diethylamino)pyrrolidin-1-yl]pyrimidin-2-ylamino}benzonitrile | $^1$H-NMR (400 MHz, CDCl$_3$) δ 8.45 (brs, 1H), 7.53 (brs, 1H), 7.32 (dd, 1H), 7.21 (d, 1H), 7.09 (brs, 1H), 5.74 (s, 1H), 4.04-3.35 (m, 5H), 2.72 (brs, 4H), 2.51 (dd, 2H), 2.24 (brs, 1H), 1.93 (brs, 1H), 1.71-1.64 (m, 2H), 1.44-1.35 (m, 2H), 1.05 (t, 3H), 1.11 (t, 6H), 0.97 (t, 3H) |
| 237 | (S)-3-{4-butyl-6-[3-(cyclopropylmethylamino)pyrrolidin-1-yl]pyrimidin-2-ylamino}benzonitrile | $^1$H-NMR (400 MHz, CDCl$_3$) δ 8.40 (s, 1H), 7.57 (d, 1H), 7.33 (dd, 1H), 7.21 (d, 1H), 7.11 (brs, 1H), 5.74 (s, 1H), 3.91-3.14 (m, 6H), 2.63-2.48 (m. 4H), 2.26-2.18 (m, 1H), 1.90 (brs, 1H), 1.71-1.63 (m, 2H), 1.44-1.35 (m, 2H), 1.25-0.93 (m, 4H), 0.53 (dd, 2H), 0.15 (d, 2H) |
| 238 | (S)-5-{4-butyl-6-[3-(isopropylamino)pyrrolidin-1-yl]pyrimidin-2-ylamino}-2-methylbenzonitrile | $^1$H-NMR (400 MHz, CDCl$_3$) δ 8.30 (s, 1H), 7.47 (d, 1H), 7.17 (d, 1H), 7.08 (brs, 1H), 5.71 (s, 1H), 3.90-3.05 (m, 5H), 2.99-2.93 (m, 1H), 2.49 (dd, 2H), 2.47 (s, 3H), 2.28-2.20 (m, 1H), 1.84 (brs, 1H), 1.70-1.63 (m, 2H), 1.44-1.34 (m, 2H), 1.11 (dd, 6H), 0.97 (t, 3H) |
| 239 | (S)-5-{4-butyl-6-[3-(diethylamino)pyrrolidin-1-yl]pyrimidin-2-ylamino}-2-methylbenzonitrile | $^1$H-NMR (400 MHz, CDCl$_3$) δ 8.36 (brs, 1H), 7.42 (brs, 1H), 7.16 (d, 1H), 7.05 (brs, 1H), 5.71 (s, 1H), 4.04-3.18 (m, 5H), 2.71 (brs. 4H), 2.49 (dd, 2H), 2.47 (s, 3H), 2.23-1.92 (m, 2H), 1.71-1.63 (m, 2H), 1.44-1.35 (m, 2H), 1.07 (dd, 6H), H), 0.97 (t, 3H) |
| 240 | (S)-5-{4-butyl-6-[3-(cyclopropylmethylamino)pyrrolidin-1-yl]pyrimidin-2-ylamino}-2-methylbenzonitrile | $^1$H-NMR (400 MHz, CDCl$_3$) δ 8.32 (s, 1H), 7.45 (d, 1H), 7.17 (d, 1H), 7.09 (brs, 1H), 5.71 (s, 1H), 3.90-3.05 (m, 5H), 2.56-2.48 (m, 7H), 2.25-2.18 (m, 1H), 1.89 (brs, 1H), 1.70-1.63 (m, 2H), 1.44-1.36 (m, 2H), 1.25-0.93 (m, 4H), 0.53 (dd, 2H), 0.15 (d, 2H) |
| 241 | (S)-N-{1-[2-(4-chloro-3-nitrophenylamino)-6-propylpyrimidin-4-yl]pyrrolidin-3-yl}acetamide | $^1$H-NMR (400 MHz, CDCl$_3$) δ 8.89 (brs, 1H), 8.10 (brs, 1H), 7.35 (s, 2H), 6.21 (brs, 1H), 5.74 (s, 1H), 4.63-4.59 (m, 1H), 4.10-3.38 (m, 4H), 2.47 (dd, 2H), 2.34-2.28 (m, 1H), 2.09-2.04 (m, 1H), 2.03 (s, 3H), 1.74-1.68 (m, 2H), 0.97 (t, 3H) |
| 242 | (S)-N-(1-{2-[3-(methylthio)phenylamino]-6-propylpyrimidin-4-yl}pyrrolidin-3-yl)acetamide | $^1$H-NMR (400 MHz, CDCl$_3$) δ 7.78 (s, 1H), 7.29 (dd, 1H), 7.18 (dd, 1H), 7.01 (brs, 1H), 6.84 (d, 1H), 5.96 (d, 1H), 5.67 (s, 1H), 4.59-4.56 (m, 1H), 4.73-3.48 (m, 4H), 2.68 (s, 3H), 2.46 (dd, 2H), 2.44-2.21 (m, 1H), 2.06-2.00 (m, 1H), 2.03 (s, 3H), 1.76-1.66 (m, 2H), 0.97 (t, 3H) |
| 243 | (S)-N-{1-[2-1H-indol-6-ylamino)-6-propylpyrimidin-4-yl]pyrrolidin-3-yl}acetamide | $^1$H-NMR (400 MHz, CDCl$_3$) δ 8.15 (s, 1H), 7.49 (d, 1H), 7.11 (dd, 1H), 7.00 (d, 1H), 6.47 (s, 1H), 5.95 (brs, 1H), 5.62 (s, 1H), 4.55 (brs, 1H), 3.75-3.49 (m, 4H), 2.45 (dd, 2H), 2.29-2.23 (m, 1H), 2.06-2.00 (m, 1H), 2.03 (s, 3H), 1.75-1.66 (m, 2H), 0.96 (t, 3H) |
| 244 | (S)-N-(1-{6-propyl-2-[3-(trifluoromethyl)phenylamino]pyrimidin-4-yl}pyrrolidin-3-yl)acetamide | $^1$H-NMR (400 MHz, CDCl$_3$) δ 8.44 (brs, 1H), 7.46 (d, 1H), 7.35 (dd, 1H), 7.19 (d, 1H), 5.88 (d, 1H), 5.72 (s, 1H), 4.62-4.58 (m, 1H), 3.75-3.49 (m, 4H), 2.47 (dd, 2H), 2.24-2.33 (m, 1H), 2.06-2.00 (m, 1H), 2.00 (s, 3H), 1.76-1.67 (m, 2H), 0.95 (t, 3H) |
| 245 | (S)-N-{1-[2-(4-methyl-2-oxo-2H-chromen-7-ylamino)-6-propylpyrimidin-4-yl]pyrrolidin-3-yl}acetamide | $^1$H-NMR (400 MHz, CDCl$_3$) δ 8.08 (brs, 1H), 7.38 (d, 1H), 7.35 (dd, 1H), 6.99 (brs, 1H), 6.98 (d, 1H), 5.94 (brs, 1H), 5.72 (s, 1H), 4.69 (brs, 1H), 3.72-3.49 (m, 4H), 2.45 (dd, 2H), 2.33 (s, 3H), 2.33-2.24 (m, 1H), 2.06-2.00 (m, 1H), 2.03 (s, 3H), 1.75-1.67 (m, 2H), 0.99 (t, 3H) |

TABLE 1-26

| Example | Compound | NMR Spectrum |
| --- | --- | --- |
| 246 | (S)-N-{1-[2-(3-chloro-4-methylphenylamino)-6-propylpyrimidin-4-yl]pyrrolidin-3-yl}acetamide | $^1$H-NMR (400 MHz, CDCl$_3$) δ 7.97 (brs, 1H), 7.20 (d, 1H), 7.09 (d, 1H), 7.00 (brs, 1H), 6.15 (d, 1H), 5.65 (s, 1H), 4.59 (brs, 1H), 3.70-3.48 (m, 4H), 2.45 (dd, 2H), 2.30 (s, 3H), 2.28-2.23 (m, 2H), 2.00 (s, 3H), 1.72-1.66 (m, 2H), 0.96 (t, 3H) |
| 247 | (S)-N-{1-[2-(3-nitrophenylamino)-6-propylpyrimidin-4-yl]pyrrolidin-3-yl}acetamide | $^1$H-NMR (400 MHz, CDCl$_3$) δ 9.27 (brs, 1H), 7.76 (dd, 1H), 7.45 (brs, 1H), 7.37 (brs, 1H), 7.24 (brs, 1H), 5.89 (s, 1H), 5.76 (s, 1H), 4.64-4.60 (m, 1H), 3.86-3.32 (m, 4H), 2.48 (dd, 2H), 2.36-2.28 (m, 1H), 2.08-2.02 (m, 1H), 2.02 (s, 3H), 1.75-1.68 (m, 2H), 0.98 (t, 3H) |
| 248 | (S)-N-{1-[2-(4-fluoro-3-nitrophenylamino)-6-propylpyrimidin-4-yl]pyrrolidin-3-yl}acetamide | $^1$H-NMR (400 MHz, CDCl$_3$) δ 9.05 (brs, 1H), 7.43 (brs, 1H), 7.13 (dd, 1H), 6.56 (brs, 1H), 5.74 (s, 1H), 4.64-4.61 (m, 1H), 3.83-3.43 (m, 4H), 2.47 (dd, 2H), 2.32 (brs, 1H), 2.12-2.05 (m, 1H), 2.05 (s, 3H), 1.75-1.67 (m, 2H), 0.98 (t, 3H) |
| 249 | (S)-N-{1-[2-(4-methyl-3-nitrophenylamino)-6-propylpyrimidin-4-yl]pyrrolidin-3-yl}acetamide | $^1$H-NMR (400 MHz, CDCl$_3$) δ 8.93 (brs, 1H), 7.82 (brs, 1H), 7.33 (d, 1H), 7.17 (d, 1H), 6.38 (brs, 1H), 5.69 (s, 1H), 4.62-4.58 (m, 1H), 3.76-3.48 (m, 4H), 2.51 (s, 3H), 2.45 (dd, 2H), 2.32-2.26 (m, 1H), 2.08-2.02 (m, 1H), 2.02 (s, 3H), 1.73-1.67 (m, 2H), 0.96 (t, 3H) |
| 250 | (S)-benzyl 5-[4-(3-acetamidopyrrolidin-1-yl)-6-propylpyrimidin-2-ylamino]-2-methoxyphenylcarbamate | $^1$H-NMR (400 MHz, CDCl$_3$) δ 8.52 (brs, 1H), 7.41-7.33 (m, 5H), 7.18 (d, 1H), 7.10 (brs, 1H), 6.78 (d, 1H), 5.93 (s, 1H), 5.64 (s, 1H), 5.18 (s, 2H), 4.55 (brs, 1H), 3.82 (s, 3H), 3.76-3.48 (m, 4H), 2.45 (dd, 2H), 2.26-2.20 (m, 1H), 2.04-1.96 (m, 1H), 1.97 (s, 3H), 1.73-1.66 (m, 2H), 0.97 (t, 3H) |
| 251 | (S)-N-{1-[2-(3-cyano-4-fluorophenylamino)-6-propylpyrimidin-4-yl]pyrrolidin-3-yl}acetamide | $^1$H-NMR (400 MHz, CDCl$_3$) δ 8.21 (brs, 1H), 7.61 (brs, 2H), 7.09 (dd, 1H), 6.07 (brs, 1H), 5.74 (s, 1H), 4.60 (d, 1H), 3.76-3.39 (m, 4H), 2.48 (dd, 2H), 2.33-2.28 (m, 1H), 2.08-2.02 (m, 1H), 2.02 (s, 3H), 1.76-1.67 (m, 2H), 0.98 (t, 3H) |
| 252 | (S)-N-{1-[2-(3-cyano-4-methylphenylamino)-6-propylpyrimidin-4-yl]pyrrolidin-3-yl}acetamide | $^1$H-NMR (400 MHz, CDCl$_3$) δ 8.20 (brs, 1H), 7.49 (brs, 2H), 7.27 (brs, 1H), 7.18 (d, 1H), 5.99 (d, 1H), 5.71 (s, 1H), 4.62-4.58 (m, 1H), 3.75-3.41 (m, 4H), 2.47 (dd, 2H), 2.46 (s, 3H), 2.32-2.27 (m, 1H), 2.08-2.02 (m, 1H), 2.01 (s, 3H), 1.74-1.68 (m, 2H), 0.97 (t, 3H) |
| 253 | (S)-N-(1-{2-[4-fluoro-3-(trifluoromethyl)phenylamino]-6-propylpyrimidin-4-yl}pyrrolidin-3-yl)acetamide | $^1$H-NMR (400 MHz, CDCl$_3$) δ 8.40 (brs, 1H), 7.44 (brs, 2H), 7.08 (dd, 1H), 5.91 (brs, 1H), 5.72 (s, 1H), 4.62-4.58 (m, 1H), 3.75-3.39 (m, 4H), 2.47 (dd, 2H), 2.32-2.25 (m, 1H), 2.08-2.01 (m, 1H), 2.01 (s, 3H), 1.76-1.66 (m, 2H), 0.97 (t, 3H) |
| 254 | (S)-N-{1-[2-(4-amino-3-nitrophenylamino)-6-proylpyrimidin-4-yl]pyrrolidin-3-yl}acetamide | $^1$H-NMR (400 MHz, CDCl$_3$) δ 8.97 (brs, 1H), 7.24 (brs, 1H), 6.98 (brs, 1H), 6.73 (d, 1H), 6.06 (d, 1H), 5.92 (brs, 2H), 5.67 (s, 1H), 4.61-4.57 (m, 1H), 3.79-3.44 (m, 4H), 2.44 (dd, 2H), 2.32-2.27 (m, 1H), 2.08-2.01 (m, 1H), 2.00 (s, 3H), 1.75-1.65 (m, 2H), 0.97 (t, 3H) |
| 255 | (S)-N-{1-[2-(5-chloro-2-methylphenylamino)-6-propylpyrimidin-4-yl]pyrrolidin-3-yl}acetamide | $^1$H-NMR (400 MHz, CDCl$_3$) δ 8.59 (brs, 1H), 7.07 (d, 1H), 6.86 (dd, 1H), 6.68 (brs, 1H), 6.22 (s, 1H), 5.68 (s, 1H), 4.58 (s, 1H), 3.71-3.33 (m, 5H), 2.47 (dd, 2H), 2.30-2.20 (m, 2H), 2.27 (s, 3H), 2.00 (s, 3H), 1.73-1.68 (m, 2H), 0.98 (t, 3H) |

TABLE 1-27

| Example | Compound | NMR Spectrum |
| --- | --- | --- |
| 256 | (S)-3-[4-(3-acetamidopyrrolidin-1-yl)-6-propylpyrimidin-2-ylamino]benzamide | $^1$H-NMR (400 MHz, CD$_3$OD) δ 8.33 (s, 1H), 7.82 (d, 1H), 7.42 (d, 1H), 7.35 (t, 1H), 5.89 (s, 1H), 4.50-4.40 (m, 1H), 3.90-3.30 (m, 4H), 2.49 (t, 2H), 2.30-2.20 (m, 1H), 2.10-1.90 (m, 4H), 1.73 (q, 2H), 0.99 (t, 3H) |
| 257 | (S)-3-{[4-(3-acetamidopyrrolidin-1-yl)-6-propylpyrimidin-2-yl]amino}-N-methylbenzamide | $^1$H-NMR (400 MHz, CD$_3$OD) δ 8.29 (s, 1H), 7.80 (s, 1H), 7.33 (d, 2H), 5.87 (s, 1H), 4.47 (t, 1H), 3.90-3.30 (m, 4H), 2.91 (s, 3H), 2.48 (t, 2H), 2.35-2.20 (m, 1H), 2.10-2.00 (m, 1H), 1.95 (s, 3H), 1.72 (q, 2H), 1.00 (t, 3H) |
| 258 | (S)-N-[1-(2-{3-(aminomethyl)phenyl]amino}-6-propylpyrimidin-4-yl)pyrrolidin-3-yl]acetamide | $^1$H-NMR (400 MHz, CD$_3$OD) δ 7.03 (t, 1H), 6.80-6.55 (m, 3H), 5.85 (s, 1H), 4.50-4.35 (m, 3H), 3.80-3.40 (m, 4H), 2.47 (t, 2H), 2.30-2.15 (m, 1H), 2.05-1.95 (m, 1H), 1.94 (s, 3H), 1.68 (q, 2H), 0.98 (t, 3H) |
| 259 | (S)-3-{[4-(3-acetamidopyrrolidin-1-yl)-6-propylpyrimidin-2-yl]amino}-4-chlorobenzamide | $^1$H-NMR (400 MHz, CD$_3$OD) δ 7.35-7.20 (m, 2H), 7.07 (d, 1H), 6.28 (brs, 1H), 4.55-4.35 (m, 1H), 3.85-3.40 (m, 4H), 2.51 (t, 2H), 2.40-2.15 (m, 1H), 2.15-1.90 (m, 1H), 1.94 (s, 3H), 1.68 (q, 2H), 0.95 (t, 3H) |
| 260 | (S)-N-{1-[2-(4-amino-3-cyanophenylamino)-6-propylpyrimidin-4-yl]pyrrolidin-3-yl}acetamide hydrochloride | $^1$H-NMR (400 MHz, CD$_3$OD) δ 7.48 (d, 1H), 7.44-7.40 (m, 1H), 6.84 (d, 1H), 6.13 (s, 1H), 4.52-4.43 (m, 1H), 3.86-3.44 (m, 4H), 2.63-2.59 (m, 2H), 2.33-2.25 (m, 1H), 2.10-2.02 (m, 1H), 1.96 (d, 3H), 1.78-1.73 (m, 2H), 1.03 (t, 3H) |

TABLE 1-27-continued

| Example | Compound | NMR Spectrum |
|---|---|---|
| 261 | (S)-N-(1-{2-[4-amino-3-(trifluoromethyl)phenylamino]-6-propylpyrimidin-4-yl}pyrrolidin-3-yl)acetamide hydrochloride | $^1$H-NMR (400 MHz, CDCl$_3$) δ 8.05-7.91 (m, 2H), 7.33 (dd, 1H), 6.72 (dd, 1H), 5.53 (d, 1H), 4.72 (brs, 1H), 4.19 (brs, 2H), 4.03-3.50 (m, 4H), 2.37-2.23 (m, 4H), 2.11 (s, 3H), 1.68-1.53 (m, 2H), 0.98 (t, 3H) |
| 262 | (S)-N-{1-[2-(3-amino-5-cyanophenylamino)-6-propylpyrimidin-4-yl]pyrrolidin-3-yl}acetamide hydrochloride | $^1$H-NMR (400 MHz, CD$_3$OD) δ 7.15 (d, 1H), 7.13 (s, 1H), 6.67 (s, 1H), 6.15 (d, 1H), 4.54-4.47 (m, 1H), 3.97-3.46 (m, 4H), 2.65-2.60 (m, 2H), 2.41-2.30 (m, 1H), 2.16-2.08 (m, 1H), 1.97 (s, 3H), 1.81-1.74 (m, 2H), 1.04 (t, 3H) |
| 263 | (S)-N-{1-[2-(1H-indol-6-ylamino)-6-propylpyrimidin-4-yl]pyrrolidin-3-yl}acetamide hydrochloride | $^1$H-NMR (400 MHz, CD$_3$OD) δ 7.75 (s, 1H), 7.54 (d, 1H), 7.26 (s, 1H), 7.01 (t, 1H), 6.45 (s, 1H), 6.09 (d, 1H), 4.47 (d, 1H), 4.00-3.50 (m, 4H), 2.59 (q, 2H), 2.40-2.20 (m, 1H), 2.20-2.00 (m, 1H), 1.96 (s, 3H), 1.80-1.60 (m, 2H), 1.03 (t, 3H) |
| 264 | (S)-N-{1-[2-(5-chloro-2-methylphenylamino)-6-propylpyrimidin-4-yl]pyrrolidin-3-yl}acetamide hydrochloride | $^1$H-NMR (400 MHz, CD$_3$OD) δ 7.76 (d, 1H), 7.35-7.15 (m, 2H), 6.21 (d, 1H), 4.45 (d, 1H), 3.90-3.50 (m, 4H), 2.62 (t, 2H), 2.40-2.15 (m, 4H), 2.15-1.85 (m, 4H), 1.76 (q, 2H), 1.05 (t, 3H) |
| 265 | (S)-N-(1-{2-[4-fluoro-3-(trifluoromethyl)phenylamino]-6-propylpyrimidin-4-yl}pyrrolidin-3-yl)acetamide hydrochloride | $^1$H-NMR (400 MHz, CD$_3$OD) δ 8.16 (d, 1H), 7.77 (brs, 1H), 7.38 (t, 1H), 6.26 (d, 1H), 4.48 (d, 1H), 3.90-3.45 (m, 4H), 2.65 (t, 2H), 2.40-2.20 (m, 1H), 2.20-2.00 (m, 1H), 1.95 (s, 3H), 1.76 (q, 2H), 1.05 (t, 3H) |

TABLE 1-28

| Example | Compound | NMR Spectrum |
|---|---|---|
| 266 | (S)-N-{1-[2-(3-amino-4-fluorophenylamino)-6-propylpyrimidin-4-yl]pyrrolidin-3-yl}acetamide hydrochloride | $^1$H-NMR (400 MHz, CD$_3$OD) δ 7.05 (brs, 1H), 6.94 (t, 1H), 6.76 (t, 1H), 6.13 (d, 1H), 4.47 (d, 1H), 4.00-3.40 (m, 4H), 2.65-2.50 (m, 2H), 2.40-2.20 (m, 1H), 2.20-2.00 (m, 1H), 1.95 (s, 3H), 1.75 (q, 2H), 1.03 (t, 3H) |
| 267 | (S)-N-(1-{6-propyl-2-[3-(trifluoromethyl)phenylamino]pyrimidin-4-yl}pyrrolidin-3-yl)acetamide hydrochloride | $^1$H-NMR (400 MHz, CD$_3$OD) δ 8.17 (d, 1H), 7.80-7.70 (m, 1H), 7.59 (t, 1H), 7.47 (d, 1H), 6.26 (d, 1H), 4.60-4.40 (m, 1H), 4.00-3.40 (m, 4H), 2.66 (t, 2H), 2.40-2.20 (m, 1H), 2.20-2.00 (m, 1H), 1.95 (s, 3H), 1.78 (q, 2H), 1.05 (t, 3H) |
| 268 | (S)-N-{1-{2-[3-amino-5-(trifluoromethyl)phenylamino]-6-propylpyrimidin-4-yl}pyrrolidin-3-yl}acetamide hydrochloride | $^1$H-NMR (400 MHz, CD$_3$OD) δ 7.29 (d, 1H), 7.01 (d, 1H), 6.74 (s, 1H), 6.21 (d, 1H), 4.60-4.40 (m, 1H), 4.00-3.40 (m, 4H), 2.63 (t, 2H), 2.40-2.20 (m, 1H), 2.20-2.00 (m, 1H), 1.95 (s, 3H), 1.77 (q, 2H), 1.04 (t, 3H) |
| 269 | (S)-N-{1-[2-(3-nitrophenylamino)-6-propylpyrimidin-4-yl]pyrrolidin-3-yl}acetamide hydrochloride | $^1$H-NMR (400 MHz, CD$_3$OD) δ 8.92 (d, 1H), 8.04 (d, 1H), 7.81 (t, 1H), 7.63 (t, 1H), 6.30 (d, 1H), 4.60-4.45 (m, 1H), 4.10-3.40 (m, 4H), 2.75-2.60 (m, 2H), 2.45-2.25 (m, 1H), 2.20-2.00 (m, 1H), 1.96 (s, 3H), 1.90-1.70 (m, 2H), 1.06 (t, 3H) |
| 270 | (S)-N-(1-{2-[(4-aminophenyl)amino]-6-propylpyrimidin-4-yl}pyrrolidin-3-yl)acetamide hydrochloride | $^1$H-NMR (400 MHz, CD$_3$OD) δ 7.90-7.75 (m, 2H), 7.50-7.40 (m, 2H), 6.26 (d, 1H), 4.50-4.35 (m, 1H), 4.00-3.40 (m, 4H), 2.66 (q, 2H), 2.40-2.20 (m, 1H), 2.20-2.00 (m, 1H), 1.96 (s, 3H), 1.90-1.70 (m, 2H), 1.05 (t, 3H) |
| 271 | (S)-N-(1-{2-[(4-chloro-3-hydroxyphenyl)amino]-6-propylpyrimidin-4-yl}pyrrolidin-3-yl)acetamide hydrochloride | $^1$H-NMR (400 MHz, CD$_3$OD) δ 7.28 (d, 1H), 7.24 (d, 1H), 7.01 (s, 1H), 6.20 (d, 1H), 4.49 (d, 1H), 4.00-3.40 (m, 4H), 2.63 (t, 2H), 2.40-2.20 (m, 1H), 2.20-2.00 (m, 1H), 1.96 (s, 3H), 1.76 (q, 2H), 1.03 (t, 3H) |
| 272 | (S)-4-{[4-(3-acetamidopyrrolidin-1-yl)-6-propylpyrimidin-2-yl]amino}-2-hydroxybenzoic acid hydrochloride | $^1$H-NMR (400 MHz, CD$_3$OD) δ 7.18 (t, 1H), 6.98 (d, 1H), 6.62 (d, 1H), 6.17 (d, 1H), 4.49 (d, 1H), 4.00-3.40 (m, 4H), 2.62 (t, 2H), 2.40-2.20 (m, 1H), 2.20-2.00 (m, 1H), 1.95 (s, 3H), 1.76 (q, 2H), 1.04 (t, 3H) |
| 273 | (S)-5-{[4-(3-acetamidopyrrolidin-1-yl)-6-propylpyrimidin-2-yl]amino}-2-hydroxybenzoic acid hydrochloride | $^1$H-NMR (400 MHz, CD$_3$OD) δ 8.15 (d, 1H), 7.71 (s, 1H), 6.93 (d, 1H), 6.14 (d, 1H), 4.47 (d, 1H), 4.10-3.40 (m, 4H), 2.62 (t, 2H), 2.55-2.30 (m, 1H), 2.30-2.00 (m, 1H), 1.95 (s, 3H), 1.04 (q, 3H) |
| 274 | (S)-N-(1-{2-[(3-hydroxy-4-methylphenyl)amino]-6-propylpyrimidin-4-yl}pyrrolidin-3-yl)acetamide | $^1$H-NMR (400 MHz, CD$_3$OD) δ 7.50 (s, 1H), 7.10 (brs, 1H), 6.95 (d, 1H), 6.70 (brs, 1H), 6.61 (s, 1H), 5.59 (s, 1H), 4.12 (brs, 1H), 3.80-3.30 (m, 4H), 2.44 (t, 2H), 2.18 (s, 3H), 2.15-1.95 (m, 2H), 1.91 (s, 3H), 1.66 (q, 2H), 0.92 (t, 3H) |

TABLE 1-28-continued

| Example | Compound | NMR Spectrum |
| --- | --- | --- |
| 275 | (S)-N-(1-{2-[(3-chloro-4-hydroxyphenyl)amino]-6-propylpyrimidin-4-yl}pyrrolidin-3-yl)acetamide | $^1$H-NMR (400 MHz, CDCl$_3$) δ 7.96 (s, 1H), 7.21 (d, 1H), 6.92 (d, 1H), 5.72 (brs, 1H), 5.68 (s, 1H), 4.12 (d, 1H), 3.80-3.20 (m, 4H), 2.46 (t, 2H), 2.35-2.20 (m, 1H), 2.00-1.90 (m, 4H), 1.70 (q, 2H), 0.97 (t, 3H) |

TABLE 1-29

| Example | Compound | NMR Spectrum |
| --- | --- | --- |
| 276 | (S)-N-(1-{2-[(4-hydroxy-3-methylphenyl)amino]-6-propylpyrimidin-4-yl}pyrrolidin-3-yl)acetamide | $^1$H-NMR (400 MHz, CDCl$_3$) δ 7.24 (s, 1H), 6.85 (brs, 1H), 6.70 (d, 1H), 6.26 (d, 1H), 5.59 (s, 1H), 4.52 (brs, 1H), 3.80-3.20 (m, 4H), 2.43 (t, 2H), 2.25-2.10 (m, 1 + 3H), 2.00-1.85 (m, 1 + 3H), 1.67 (q, 2H), 0.94 (t, 3H) |
| 277 | (S)-N-(1-{2-[(3-fluoro-4-hydroxyphenyl)amino]-6-propylpyrimidin-4-yl}pyrrolidin-3-yl)acetamide | $^1$H-NMR (400 MHz, CDCl$_3$) δ 7.75 (d, 1H), 6.95 (d, 1H), 6.89 (t, 1H), 6.10 (brs, 1H), 5.63 (s, 1H), 4.59 (brs, 1H), 3.90-3.30 (m, 4H), 2.45 (t, 2H), 2.35-2.15 (m, 1H), 2.10-2.00 (m, 1H), 1.99 (s, 3H), 1.68 (q, 2H), 0.96 (t, 3H) |
| 278 | (S)-N-(1-{2-[(3-hydroxy-4-methoxyphenyl)amino]-6-propylpyrimidin-4-yl}pyrrolidin-3-yl)acetamide | $^1$H-NMR (400 MHz, CDCl$_3$) δ 7.43 (s, 1H), 7.10-7.00 (m, 1H), 6.78 (d, 1H), 5.62 (s, 1H), 4.59 (s, 1H), 3.86 (s, 3H), 3.80-3.20 (m, 4H), 2.45 (t, 2H), 2.35-2.20 (m, 1H), 2.10-2.00 (m, 1H), 2.01 (s, 3H), 1.67 (q, 2H), 0.96 (t, 3H) |
| 279 | (S)-N-(1-{2-[(3-methoxy-4-methylphenyl)amino]-6-propylpyrimidin-4-yl}pyrrolidin-3-yl)acetamide | $^1$H-NMR (400 MHz, CDCl$_3$) δ 7.56 (s, 1H), 7.38 (brs, 1H), 7.00 (d, 1H), 6.89 (d, 1H), 5.78 (brs, 1H), 5.65 (s, 1H), 4.59 (brs, 1H), 3.83 (s, 3H), 3.80-3.20 (m, 4H), 2.46 (t, 2H), 2.40-2.20 (m, 2H), 2.16 (s, 3H), 1.99 (s, 3H), 1.71 (q, 2H), 0.97 (t, 3H) |
| 280 | (S)-N-[1-(2-{[4-methyl-3-(trifluoromethyl)phenyl]amino}-6-propylpyrimidin-4-yl)pyrrolidin-3-yl]acetamide | $^1$H-NMR (400 MHz, CDCl$_3$) δ 8.40 (brs, 1H), 7.37 (d, 1H), 7.21 (brs, 1H), 7.16 (d, 1H), 5.70 (s, 1H), 4.60 (brs, 1H), 3.85-3.20 (m, 4H), 2.46 (t, 2H), 2.41 (s, 3H), 2.35-2.20 (m, 1H), 2.15-2.00 (m, 1H), 1.98 (s, 3H), 1.71 (q, 2H), 0.97 (t, 3H) |
| 281 | (S)-N-(1-{2-[(3,4-dimethylphenyl)amino]-6-propylpyrimidin-4-yl}pyrrolidin-3-yl)acetamide | $^1$H-NMR (400 MHz, CDCl$_3$) δ 7.50-7.40 (m, 2H), 7.04 (d, 1H), 5.73 (brs, 1H), 5.65 (s, 1H), 4.62 (brs, 1H), 3.85-3.20 (m, 4H), 2.46 (t, 2H), 2.40-2.25 (m, 1H), 2.24 (s, 3H), 2.21 (s, 3H), 2.15-2.00 (m, 1H), 2.00 (s, 3H), 1.71 (q, 2H), 0.97 (t, 3H) |
| 282 | (S)-N-(1-{2-[(3-fluoro-4-methylphenyl)amino]-6-propylpyrimidin-4-yl}pyrrolidin-3-yl)acetamide | $^1$H-NMR (400 MHz, CDCl$_3$) δ 7.73 (d, 1H), 7.16 (brs, 1H), 7.10-7.00 (m, 2H), 5.74 (brs, 1H), 5.68 (s, 1H), 4.61 (brs, 1H), 3.85-3.20 (m, 4H), 2.47 (t, 2H), 2.40-2.25 (m, 1H), 2.21 (s, 3H), 2.10-1.90 (m, 4H), 1.71 (q, 2H), 0.97 (t, 3H) |
| 283 | (S)-N-{1-[2-(4-fluoro-3-nitrophenylamino)-6-propylpyrimidin-4-yl]pyrrolidin-3-yl}acetamide hydrochloride | $^1$H-NMR (400 MHz, CDCl$_3$) δ 11.06 (d, 1H), 8.98 (d, 1H), 7.55 (d, 1H), 7.22 (d, 1H), 6.78 (s, 1H), 5.79 (s, 1H), 4.68 (s, 1H), 4.05-3.59 (m, 4H), 2.56-2.51 (m, 2H), 2.40-2.21 (m, 2H), 2.05 (s, 3H), 1.82-1.76 (m, 2H), 0.98-0.94 (m, 3H) |
| 284 | (S)-N-{1-[2-(4-methyl-3-nitrophenylamino)-6-propylpyrimidin-4-yl]pyrrolidin-3-yl}acetamide hydrochloride | $^1$H-NMR (400 MHz, CDCl$_3$) δ 8.78 (d, 1H), 7.70-7.60 (m, 1H), 7.38-7.34 (m, 1H), 7.24-7.21 (m, 1H), 5.73 (d, 1H), 4.73 (brs, 1H), 4.08-3.70 (m, 4H), 2.53 (s, 3H), 2.46-2.27 (m, 4H), 2.11 (s, 3H), 1.78-1.68 (m, 2H), 0.98-0.94 (m, 3H) |
| 285 | (S)-N-{1-[2-(3-cyano-4-methylphenylamino)-6-propylpyrimidin-4-yl]pyrrolidin-3-yl}acetamide hydrochloride | $^1$H-NMR (400 MHz, CDCl$_3$) δ 12.85 (d, 1H), 10.66 (d, 1H), 8.10-7.88 (m, 2H), 7.61-7.54 (m, 1H), 7.29-7.24 (m, 1H), 5.73 (s, 1H), 4.73 (s, 1H), 4.06-3.73 (m, 4H), 2.63 (brs, 1H), 2.48 (s, 3H), 2.44-2.28 (m, 4H), 2.12 (s, 3H), 1.73-1.65 (m, 2H), 0.97-0.93 (m, 3H) |

TABLE 1-30

| Example | Compound | NMR Spectrum |
| --- | --- | --- |
| 286 | (S)-N-{1-[2-(4-amino-3-nitrophenylamino)-6-propylpyrimidin-4-yl]pyrrolidin-3-yl}acetamide hydrochloride | $^1$H-NMR (400 MHz, CD$_3$OD) δ 8.66 (s, 0.5H), 8.57 (s, 0.5H), 7.46-7.42 (m, 1H), 7.03 (d, 1H), 6.18 (s, 0.5H), 6.14 (s, 0.5H), 4.54-4.48 (m, 1H), 3.92-3.60 (m, 4H), 2.65-2.60 (m, 2H), 2.30-2.22 (m, 1H), 2.13-2.05 (m, 1H), 2.00 (s, 1.5H), 1.99 (s, 1.5H), 1.80-1.74 (m, 2H), 1.07-1.02 (m, 3H) |
| 287 | (S)-N-{1-[2-(3-cyanophenylamino)-6-propylpyrimidin-4- | $^1$H-NMR (400 MHz, CDCl$_3$) δ 8.34 (brs, 1H), 7.59 (brs, 1H), 7.34 (dd, 1H), 7.22 (d, 1H), 6.98 (brs, 1H), 5.76 (s, 1H), 5.66 (d, 1H), 4.64-4.57 (m, 1H), 3.77-3.35 (m, 4H), |

TABLE 1-30-continued

| Example | Compound | NMR Spectrum |
|---|---|---|
|  | yl]pyrrolidin-3-yl}acetamide hydrochloride | 2.48 (dd, 2H), 2.36-2.29 (m, 1H), 2.05-2.01 (m, 1H), 2.01 (s, 3H), 1.75-1.69 (m, 2H), 0.98 (t, 3H) |
| 288 | (S)-N-{1-[2-(4-chloro-3-nitrophenylamino)-6-propylpyrimidin-4-yl]pyrrolidin-3-yl}acetamide hydrochloride | $^1$H-NMR (400 MHz, CD$_3$OD) δ 8.66 (s, 0.5H), 8.55 (s, 0.5H), 7.73-7.64 (m, 2H), 6.32 (s, 0.5H), 6.28 (s, 0.5H), 4.53-4.50 (m, 1H), 3.90-3.52 (m, 4H), 2.70-2.65 (m, 2H), 2.33-2.25 (m, 1H), 2.15-2.07 (m, 1H), 1.97 (s, 3H), 1.82-1.76 (m, 2H), 1.07-1.03 (m, 3H) |
| 289 | (S)-N-{1-[2-(3-amino-4-methoxyphenylamino)-6-propylpyrimidin-4-yl]pyrrolidin-3-yl}acetamide | $^1$H-NMR (400 MHz, CDCl$_3$) δ 7.10 (d, 1H), 6.97 (dd, 1H), 6.72 (d, 1H), 5.95 (brs, 1H), 5.62 (s, 1H), 4.58 (brs, 1H), 3.82 (s, 3H), 3.84-3.60 (m, 6H), 2.44 (dd, 2H), 2.28-2.23 (m, 1H), 2.02-1.95 (m, 1H), 2.00 (s, 3H), 1.74-1.65 (m, 2H), 0.97 (t, 3H) |
| 290 | (S)-N-{1-[2-(3-amino-4-chlorophenylamino)-6-propylpyrimidin-4-yl]pyrrolidin-3-yl}acetamide | $^1$H-NMR (400 MHz, CDCl$_3$) δ 7.24 (d, 1H), 7.12-7.04 (m, 2H), 6.93-6.89 (m, 1H), 5.98 (brs, 1H), 5.69 (s, 1H), 4.58 (brs, 1H), 3.97 (s, 2H), 3.75-3.36 (m, 4H), 2.46 (dd, 2H), 2.30-2.24 (m, 1H), 2.06-1.96 (m, 1H), 1.99 (s, 3H), 1.74-1.68 (m, 2H), 1.00 (t, 3H) |
| 291 | (S)-N-{1-[2-(3-amino-4-fluorophenylamino)-6-propylpyrimidin-4-yl]pyrrolidin-3-yl}acetamide | $^1$H-NMR (400 MHz, CDCl$_3$) δ 7.25 (d, 1H), 6.91-6.87 (m, 2H), 5.72 (d, 1H), 5.67 (s, 1H), 5.60-4.55 (m, 1H), 3.72 (s, 2H), 3.84-3.36 (m, 4H), 2.46 (dd, 2H), 2.31-2.26 (m, 1H), 2.06-1.96 (m, 1H), 2.00 (s, 3H), 1.75-1.66 (m, 2H), 0.97 (t, 3H) |
| 292 | (S)-N-{1-[2-(3-amino-4-methylphenylamino)-6-propylpyrimidin-4-yl]pyrrolidin-3-yl}acetamide | $^1$H-NMR (400 MHz, CDCl$_3$) δ 7.14 (d, 1H), 6.95-6.89 (m, 3H), 5.96 (d, 1H), 5.63 (s, 1H), 5.60-4.55 (m, 1H), 3.84-3.36 (m, 6H), 2.44 (dd, 2H), 2.28-2.23 (m, 1H), 2.12 (s, 3H), 2.02-1.95 (m, 1H), 2.00 (s, 3H), 1.72-1.67 (m, 2H), 0.97 (t, 3H) |
| 293 | N-{1-[2-(4-amino-3-nitrophenylamino)-6-propylpyrimidin-4-yl]pyrrolidin-3-yl}acetamide hydrochloride | $^1$H-NMR (400 MHz, CD$_3$OD) δ 8.62 (s, 0.5H), 8.51 (s, 0.5H), 7.41 (brs, 1H), 6.99 (d, 1H), 6.16 (s, 1H), 4.49 (d, 1H), 3.83-3.44 (m, 4H), 2.62 (brs, 2H), 2.34-2.27 (m, 1H), 2.11-2.01 (m, 1H), 1.96 (s, 3H), 1.78-1.74 (m, 2H), 1.04 (t, 3H) |
| 294 | N-{1-[2-(3-cyanophenylamino)-6-propylpyrimidin-4-yl]pyrrolidin-3-yl}acetamide | $^1$H-NMR (400 MHz, CD$_3$OD) δ 8.73 (brs, NH), 8.32 (s, 1H), 7.65 (m, 1H), 7.33 (m, 1H), 7.20 (m, 1H), 6.14 (brs, NH), 5.70 (s, 1H), 4.61 (m, 1H), 3.76 (m, 4H), 2.47 (t, 2H), 2.30 (m, 1H), 2.02 (m, 4H), 1.69 (m, 2H), 0.98 (t, 3H) |
| 295 | N-{1-[2-(3-nitrophenylamino)-6-propylpyrimidin-4-yl]pyrrolidin-3-yl}acetamide | $^1$H-NMR (400 MHz, CDCl$_3$) δ 9.18 (s, 1H), 8.10 (brs, NH), 7.76 (d, 1H), 7.47 (m, 1H), 7.34 (m, 1H), 6.24 (brs, NH), 5.72 (s, 1H), 4.63 (m, 1H), 3.80-3.64 (m, 4H), 2.47 (t, 2H), 2.33 (m, 1H), 2.03 (m, 4H), 1.71 (m, 2H), 0.98 (t, 3H) |

TABLE 1-31

| Example | Compound | NMR Spectrum |
|---|---|---|
| 296 | N-{1-[2-(4-fluoro-3-nitrophenylamino)-6-propylpyrimidin-4-yl]pyrrolidin-3-yl}acetamide | $^1$H-NMR (400 MHz, CDCl$_3$) δ 9.08 (s, 1H), 8.10 (brs, NH), 7.45 (m, 1H), 7.13 (m, 1H), 5.98 (brs, NH), 5.75 (s, 1H), 4.62 (m, 1H), 3.79-3.44 (m, 4H), 2.49 (t, 2H), 2.33 (m, 1H), 2.03 (m, 4H), 1.70 (m, 2H), 0.98 (t, 3H) |
| 297 | N-{1-[2-(4-chloro-3-nitrophenylamino)-6-propylpyrimidin-4-yl]pyrrolidin-3-yl}acetamide | $^1$H-NMR (400 MHz, CDCl$_3$) δ 8.95 (s, 1H), 7.81 (brs, NH), 7.35 (m, 2H), 5.94 (brs, NH), 5.74 (s, 1H), 4.60 (m, 1H), 3.76-3.40 (m, 4H), 2.47 (t, 2H), 2.31 (m, 1H), 2.06 (m, 4H), 1.70 (m, 2H), 0.95 (t, 3H) |
| 298 | N-{1-[2-(3-methoxyphenylamino)-6-propylpyrimidin-4-yl]pyrrolidin-3-yl}acetamide | $^1$H-NMR (400 MHz, CDCl$_3$) δ 8.15 (brs, NH), 7.51 (s, 1H), 7.16 (t, 1H), 7.02 (d, 1H), 6.72 (brs, NH), 6.53 (d, 1H), 5.53 (s, 1H), 4.63 (m, 1H), 3.80 (s, 3H), 3.70 (m, 4H), 2.39 (t, 2H), 2.25 (m, 1H), 2.04 (m, 4H), 1.65 (m, 2H), 0.95 (t, 3H) |
| 299 | N-{1-[2-(5-methoxy-2-methylphenylamino)-6-propylpyrimidin-4-yl]pyrrolidin-3-yl}acetamide | $^1$H-NMR (400 MHz, CDCl$_3$) δ 7.91 (s, 1H), 7.05 (d, 1H), 6.54 (d, 1H), 5.63 (s, 1H), 4.62 (m, 1H), 3.78 (s, 3H), 3.72-3.60 (m, 4H), 2.46 (4t, 2H), 2.30 (s, 3H), 2.21 (m, 1H), 2.05 (m, 4H), 1.67 (m, 2H), 0.95 (t, 3H) |
| 300 | N-{1-[2-(4-methoxyphenylamino)-6-propylpyrimidin-4-yl]pyrrolidin-3-yl}acetamide | $^1$H-NMR (400 MHz, CDCl$_3$) δ 8.29 (brs, NH), 7.53 (d, 2H), 6.85 (m, 2H + NH), 5.53 (s, 1H), 4.66 (m, 1H), 3.77 (s, 3H), 3.71-3.51 (m, 4H), 2.39 (t, 2H), 2.25 (m, 1H), 2.05 (m, 4H), 1.62 (m, 2H), 0.94 (t, 3H) |
| 301 | N-(1-{6-propyl-2-[3-(trifluoromethyl)phenylamino]pyrimidin-4-yl}pyrrolidin-3-yl)acetamide | $^1$H-NMR (400 MHz, CDCl$_3$) δ 8.60 (brs, NH), 8.37 (s, 1H), 7.50 (m, 1H), 7.37 (t, 1H), 7.22 (m, 1H), 6.85 (brs, NH), 5.65 (s, 1H), 4.66 (m, 1H), 3.75-3.60 (m, 4H), 2.39 (t, 2H), 2.26 (m, 1H), 2.11 (m, 1H), 2.04 (s, 3H), 1.66 (m, 2H), 0.94 (t, 3H) |
| 302 | N-{1-[2-(3-chlorophenylamino)-6-propylpyrimidin-4- | $^1$H-NMR (400 MHz, CDCl$_3$) δ 8.42 (brs, NH), 7.91 (s, 1H), 7.33 (d, 1H), 7.18 (t, 1H), 6.94 (d, 1H), 6.74 (brs, NH), 5.58 (s, 1H), 4.66 (m, 1H), 3.73-3.70 (m, 4H), 2.42 (t, 2H), |

TABLE 1-31-continued

| Example | Compound | NMR Spectrum |
|---|---|---|
| | yl]pyrrolidin-3-yl}acetamide | 2.29 (m, 1H), 2.11 (m, 1H), 2.06 (s, 3H), 1.64 (m, 2H), 0.96 (t, 3H) |
| 303 | N-{1-[2-(5-chloro-2-methylphenylamino)-6-propylpyrimidin-4-yl]pyrrolidin-3-yl}acetamide | $^1$H-NMR (400 MHz, CDCl$_3$) δ 8.43 (s, 1H), 7.06 (d, 1H), 6.90 (d, 1H), 6.31 (brs, NH), 5.68 (s, 1H), 4.62 (m, 1H), 3.73-3.44 (m, 4H), 2.48 (t, 2H), 2.31 (s, 3H), 2.24 (m, 1H), 2.01 (m, 4H), 1.70 (m, 2H), 0.98 (t, 3H) |
| 304 | N-{1-[2-(3-chloro-4-methylphenylamino)-6-propylpyrimidin-4-yl]pyrrolidin-3-yl}acetamide | $^1$H-NMR (400 MHz, CDCl$_3$) δ 8.52 (brs, NH), 7.86 (s, 1H), 7.27 (m, 1H), 7.10 (d, 1H), 7.05 (brs, NH), 5.52 (s, 1H), 4.65 (m, 1H), 3.70 (m, 4H), 2.37 (m, 2H), 2.28 (s, 3H), 2.26 (m, 1H), 2.13 (m, 1H), 2.07 (s, 3H), 1.63 (m, 2H), 0.95 (t, 3H) |
| 305 | N-(1-{2-[3-(methylthio)phenylamino]-6-propylpyrimidin-4-yl}pyrrolidin-3-yl)acetamide | $^1$H-NMR (400 MHz, CDCl$_3$) δ 8.13 (brs. NH), 7.73 (s, 1H), 7.30 (d, 1H), 7.18 (t, 1H), 6.85 (d, 1H), 6.57 (brs, NH), 5.57 (s, 1H), 4.63 (m, 1H), 3.72 (m, 4H), 2.48 (s, 3H), 2.39 (t, 2H), 2.26 (m, 1H), 2.04 (m, 4H), 1.64 (m, 2H), 0.94 (t, 3H) |

TABLE 1-32

| Example | Compound | NMR Spectrum |
|---|---|---|
| 306 | N-{1-[2-(1H-indol-5-ylamino)-6-propylpyrimidin-4-yl]pyrrolidin-3-yl}acetamide | $^1$H-NMR (400 MHz, CDCl$_3$) δ 8.11 (s, NH), 7.98 (s, 1H), 7.37 (d, 1H), 7.35 (m, 1H), 7.30 (m, 1H), 7.17 (m, 1H), 6.99 (brs, NH), 6.49 (s, 1H), 5.75 (brs, NH), 5.64 (s, 1H), 4.60 (m, 1H), 3.81-3.43 (m, 4H), 2.48 (t, 2H), 2.25 (m, 1H), 1.98 (m, 4H), 1.71 (m, 2H), 0.98 (t, 3H) |
| 307 | N-(1-{6-propyl-2-[2-(trifluoromethyl)-1H-benzo[d]imidazol-5-ylamino]pyrimidin-4-yl}pyrrolidin-3-yl)acetamide | $^1$H-NMR (400 MHz, CDCl$_3$) δ 8.60 (brs, 1H), 7.64 (s, 1H), 7.53 (brs, 1H), 7.10 (s, 1H), 6.12 (s, 1H), 5.68 (s, 1H), 4.47 (m, 1H), 3.92-3.54 (m, 4H), 2.48 (m, 2H), 2.27 (m, 1H), 2.01 (m, 4H), 1.71 (m, 2H), 0.98 (t, 3H) |
| 308 | N-{1-[6-propyl-2-(quinolin-6-ylamino)pyrimidin-4-yl]pyrrolidin-3-yl}acetamide | $^1$H-NMR (400 MHz, CDCl$_3$) δ 8.67 (s, 1H), 8.28 (s, 1H), 7.91 (m, 2H), 7.64 (m, 1H), 7.31 (brs, NH), 7.24 (m, 1H), 6.80 (brs, NH), 5.65 (s, 1H), 4.63 (m, 1H), 3.71-3.54 (m, 4H), 2.50 (t, 2H), 2.23 (m, 1H), 2.04 (m, 4H), 1.70 (m, 2H), 0.98 (t, 3H) |
| 309 | N-{1-[2-(4-methyl-2-oxo-2H-chromen-7-ylamino)-6-propylpyrimidin-4-yl]pyrrolidin-3-yl}acetamide | $^1$H-NMR (400 MHz, CD$_3$OD) δ 8.22 (m, 1H), 7.65 (d, 1H), 7.46 (m, 1H), 6.13 (s, 1H), 5.93 (s, 1H), 4.49 (m, 1H), 3.80-3.55 (m, 4H), 2.53 (t, 2H), 2.49 (s, 3H), 2.29 (m, 1H), 2.10 (m, 1H), 1.96 (s, 3H), 1.73 (m, 2H), 0.99 (t, 3H) |
| 310 | N-{1-[6-propyl-2-(quinolin-3-ylamino)pyrimidin-4-yl]pyrrolidin-3-yl}acetamide | $^1$H-NMR (400 MHz, CDCl$_3$) δ 8.98 (s, 1H), 8.58 (s, 1H), 7.97 (d, 1H), 7.66 (m, 2H), 7.52-7.46 (m, 2H), 5.80 (brs, NH), 5.53 (s, 1H), 4.63 (m, 1H), 3.71-3.57 (m, 4H), 2.44 (t, 2H), 2.27 (m, 1H), 2.05 (m, 4H), 1.68 (m, 2H), 0.97 (t, 3H) |
| 311 | N-{1-[2-(4-amino-3-cyanophenylamino)-6-propylpyrimidin-4-yl]pyrrolidin-3-yl}acetamide hydrochloride | $^1$H-NMR (400 MHz, CD$_3$OD) δ 8.33 (m, 1H), 7.59-7.50 (d, 1H), 7.39 (m, 1H), 6.84 (d, 1H), 6.13 (d, 1H), 4.49 (m, 1H), 3.86 (m, 1H), 3.68 (m, 2H), 3.45 (m, 1H), 2.61 (m, 2H), 2.27 (m, 1H), 2.04 (m, 1H), 1.94 (s, 3H), 1.73 (m, 2H), 1.05 (m, 3H) |
| 312 | N-{1-[2-(3-amino-4-fluorophenylamino)-6-propylpyrimidin-4-yl]pyrrolidin-3-yl}acetamide hydrochloride | $^1$H-NMR (400 MHz, CD$_3$OD) δ 7.04 (m, 1H), 6.96 (t, 1H), 6.75 (m, 1H), 6.17 (d, 1H), 4.51-4.43 (m, 1H), 3.92-3.40 (m, 4H), 2.60 (m, 2H), 2.37 (m, 1H), 2.10 (m, 1H), 1.95 (s, 3H), 1.75 (q, 2H), 1.03 (t, 3H) |
| 313 | (R)-N-(4-chloro-3-nitrophenyl)-4-(2-methylpyrrolidin-1-yl)-6-propylpyrimidin-2-amine | $^1$H-NMR (400 MHz, CDCl$_3$) δ 8.91 (s, 1H), 7.54 (d, 1H), 7.44 (d, 1H), 5.83 (brs, 1H), 4.56-3.44 (m, 3H), 2.62 (dd, 2H), 2.26-2.03 (m, 3H), 1.88-1.79 (m, 3H), 1.31 (brs, 3H), 1.02 (t, 3H) |
| 314 | (R)-4-(2-methylpyrrolidin-1-yl)-N-[3-(methylthio)phenyl]-6-propylpyrimidin-2-ylamine | $^1$H-NMR (400 MHz, CDCl$_3$) δ 8.57 (s, 1H), 7.80 (s, 1H), 7.34 (dd, 1H), 7.20 (dd, 1H), 6.89 (d, 1H), 5.70 (brs, 1H), 4.56-3.37 (m, 3H), 2.53 (dd, 2H), 2.48 (s, 3H), 2.10-2.04 (m, 3H), 1.82-1.73 (m, 3H), 1.28 (d, 3H), 0.99 (t, 3H) |
| 315 | (R)-N-[4-(2-methylpyrrolidin-1-yl)-6-propylpyrimidin-2-yl]-1H-indol-6-amine | $^1$H-NMR (400 MHz, CDCl$_3$) δ 9.16 (brs, 1H), 8.96 (brs, 1H), 8.02 (s, 1H), 7.44 (d, 1H), 7.13-7.11 (m, 1H), 6.41 (s, 1H), 5.46 (s, 1H), 4.56-3.29 (m, 3H), 2.39 (dd, 2H), 2.10-2.04 (m, 3H), 1.72-1.66 (m, 3H), 1.21 (brs, 3H), 0.93 (t, 3H) |

TABLE 1-33

| Example | Compound | NMR Spectrum |
| --- | --- | --- |
| 316 | (R)-4-(2-methylpyrrolidin-1-yl)-6-propyl-N-[3-(trifluoromethyl)phenyl]pyrimidin-2-amine | $^1$H-NMR (400 MHz, CDCl$_3$) δ 9.03 (brs, 1H), 8.48 (s, 1H), 7.51 (d, 1H), 7.38 (dd, 1H), 7.26 (d, 1H), 5.75 (s, 1H), 4.48-3.43 (m, 3H), 2.55 (dd, 2H), 2.18-2.04 (m, 3H), 1.84-1.74 (m, 3H), 1.28 (d, 3H), 1.00 (t, 3H) |
| 317 | (R)-4-methyl-7-[4-(2-methylpyrrolidin-1-yl)-6-propylpyrimidin-2-ylamino]-2H-chromen-2-one | $^1$H-NMR (400 MHz, CDCl$_3$) δ 8.20 (s, 1H), 7.69 (brs, 1H), 7.46 (d, 1H), 7.21 (dd, 1H), 6.11 (s, 1H), 5.77 (s, 1H), 4.14-3.32 (m, 3H), 2.50 (dd, 2H), 2.39 (s, 3H), 2.12-2.03 (m, 3H), 1.79-1.71 (m, 3H), 1.30 (brs, 3H), 1.00 (t, 3H) |
| 318 | (R)-N-(3-chloro-4-methylphenyl)-4-(2-methylpyrrolidin-1-yl)-6-propylpyrimidin-2-amine | $^1$H-NMR (400 MHz, CDCl$_3$) δ 8.78 (brs, 1H), 8.06 (s, 1H), 7.23 (d, 1H), 7.11 (d, 1H), 5.70 (s, 1H), 4.52-3.35 (m, 3H), 2.53 (dd, 2H), 2.31 (s, 3H), 2.12-2.03 (m, 3H), 1.81-1.75 (m, 3H), 1.30 (brs, 3H), 1.00 (t, 3H) |
| 319 | (R)-4-(2-methylpyrrolidin-1-yl)-N-(3-nitrophenyl)-6-propylpyrimidin-2-ylamine | $^1$H-NMR (400 MHz, CDCl$_3$) δ 9.23 (dd, 1H), 7.85 (dd, 1H), 7.58 (dd, 1H), 7.41 (dd, 1H), 5.78 (s, 1H), 4.67-3.40 (m, 3H), 2.56 (dd, 2H), 2.12-2.03 (m, 3H), 1.85-1.75 (m, 3H), 1.32 (brs, 3H), 1.01 (t, 3H) |
| 320 | (R)-N-(4-fluoro-3-nitrophenyl)-4-(2-methylpyrrolidin-1-yl)-6-propylpyrimidin-2-amine | $^1$H-NMR (400 MHz, CDCl$_3$) δ 9.08 (d, 1H), 7.61-7.57 (m, 1H), 7.22 (dd, 1H), 5.81 (s, 1H), 4.63-3.44 (m, 3H), 2.60 (dd, 2H), 2.22-2.08 (m, 3H), 1.88-1.78 (m, 3H), 1.32 (brs, 3H), 1.02 (t, 3H) |
| 321 | (R)-N-(4-methyl-3-nitrophenyl)-4-(2-methylpyrrolidin-1-yl)-6-propylpyrimidin-2-amine | $^1$H-NMR (400 MHz, CDCl$_3$) δ 9.39 (brs, 1H), 8.99 (d, 1H), 7.43 (dd, 1H), 7.23 (d, 1H), 5.77 (s, 1H), 4.60-3.38 (m, 3H), 2.56 (dd, 2H), 2.55 (s, 3H), 2.17-2.03 (m, 3H), 1.85-1.77 (m, 3H), 1.30 (brs, 3H), 1.01 (t, 3H) |
| 322 | (R)-N-[4-fluoro-3-(trifluoromethyl)phenyl]-4-(2-methylpyrrolidin-1-yl)-6-propylpyrimidin-2-ylamine | $^1$H-NMR (400 MHz, CDCl$_3$) δ 9.02 (brs, 1H), 8.42 (dd, 1H), 7.53-7.50 (m, 1H), 7.11 (dd, 1H), 5.75 (s, 1H), 4.47-3.34 (m, 3H), 2.55 (dd, 2H), 2.55 (s, 3H), 2.17-2.03 (m, 3H), 1.83-1.76 (m, 3H), 1.26 (d, 3H), 1.00 (t, 3H) |
| 323 | (R)-N$^1$-[4-(2-methylpyrrolidin-1-yl)-6-propylpyrimidin-2-yl]-3-(trifluoromethyl)benzene-1,4-diamine | $^1$H-NMR (400 MHz, CDCl$_3$) δ 8.72 (brs, 1H), 8.14 (s, 1H), 7.30-7.27 (m, 1H), 6.72 (d, 1H), 5.68 (s, 1H), 4.33-3.38 (m, 3H), 4.09 (s, 2H), 2.52 (dd, 2H), 2.17-2.03 (m, 3H), 1.82-1.72 (m, 3H), 1.23 (d, 3H), 0.99 (t, 3H) |
| 324 | (R)-benzyl 2-methoxy-5-[4-(2-methylpyrrolidin-1-yl)-6-propylpyrimidin-2-ylamino]phenylcarbamate | $^1$H-NMR (400 MHz, CDCl$_3$) δ 8.32 (brs, 1H), 7.46-7.26 (m, 6H), 6.78 (d, 1H), 5.65 (s, 1H), 5.19 (s, 2H), 3.81 (s, 3H), 4.44-3.34 (m, 3H), 2.46 (dd, 2H), 2.10-1.95 (m, 3H), 1.76-1.68 (m, 3H), 1.21 (d, 3H), 0.98 (t, 3H) |
| 325 | (R)-2-fluoro-5-[4-(2-methylpyrrolidin-1-yl)-6-propylpyrimidin-2-ylamino]benzonitrile | $^1$H-NMR (400 MHz, CDCl$_3$) δ 8.36 (brs, 1H), 7.60 (brs, 1H), 7.12 (dd, 1H), 5.77 (s, 1H), 4.45-3.36 (m, 3H), 2.54 (dd, 2H), 2.18-2.03 (m, 3H), 1.83-1.73 (m, 3H), 1.31 (brs, 3H), 1.00 (t, 3H) |

TABLE 1-34

| Example | Compound | NMR Spectrum |
| --- | --- | --- |
| 326 | (R)-2-methyl-5-[4-(2-methylpyrrolidin-1-yl)-6-propylpyrimidin-2-ylamino]benzonitrile | $^1$H-NMR (400 MHz, CDCl$_3$) δ 8.91 (brs, 1H), 8.37 (brs, 1H), 7.48 (d, 1H), 7.21 (d, 1H), 5.75 (s, 1H), 4.45-3.41 (m, 3H), 2.54 (dd, 2H), 2.49 (s, 3H), 2.18-2.03 (m, 3H), 1.83-1.75 (m, 3H), 1.32 (brs, 3H), 1.00 (t, 3H) |
| 327 | (R)-2-amino-5-[4-(2-methylpyrrolidin-1-yl)-6-propylpyrimidin-2-ylamino]benzonitrile | $^1$H-NMR (400 MHz, CDCl$_3$) δ 8.12 (brs, 1H), 7.31 (d, 1H), 7.16 (brs, 1H), 6.69 (d, 1H), 4.20 (s, 2H), 4.45-3.54 (m, 3H), 2.45 (dd, 2H), 2.09-2.01 (m, 3H), 1.76-1.66 (m, 3H), 1.26 (d, 3H), 0.98 (t, 3H) |
| 328 | (R)-N$^1$-[4-(2-methylpyrrolidin-1-yl)-6-propylpyrimidin-2-yl]-3-nitrobenzene-1,4-diamine | $^1$H-NMR (400 MHz, CDCl$_3$) δ 8.97 (s, 1H), 8.87 (brs, 1H), 7.29 (dd, 1H), 6.73 (d, 1H), 6.23 (s, 2H), 5.71 (s, 1H), 4.63-3.33 (m, 3H), 2.53 (dd, 2H), 2.09-2.01 (m, 3H), 1.82-1.73 (m, 3H), 1.28 (brs, 3H), 0.99 (t, 3H) |
| 329 | (R)-1-{6-[4-(2-methylpyrrolidin-1-yl)-6-propylpyrimidin-2-ylamino]indolin-1-yl}ethanone | $^1$H-NMR (400 MHz, CDCl$_3$) δ 8.65 (brs, 1H), 7.44 (brs, 1H), 7.07 (d, 1H), 5.68 (s, 1H), 4.04 (dd, 2H), 4.63-3.33 (m, 3H), 3.13 (dd, 2H), 2.50 (dd, 2H), 2.20 (s, 3H), 2.10-2.01 (m, 3H), 1.79-1.73 (m, 3H), 1.22 (d, 3H), 0.99 (t, 3H) |
| 330 | (R)-N-(5-chloro-2-methylphenyl)-4-(2-methylpyrrolidin-1-yl)-6-propylpyrimidin-2-amine | $^1$H-NMR (400 MHz, CDCl$_3$) δ 8.69 (s, 1H), 7.04 (d, 1H), 6.84 (dd, 1H), 6.68 (brs, 1H), 5.71 (s, 1H), 4.46-3.27 (m, 3H), 2.46 (dd, 2H), 2.28 (s, 3H), 2.20-2.03 (m, 3H), 1.75-1.67 (m, 3H), 1.28 (brs, 3H), 0.99 (t, 3H) |
| 331 | (R)-4-methoxy-N$^1$-[4-(2-methylpyrrolidin-1-yl)-6-propylpyrimidin-2-yl]benzene-1,3-diamine | $^1$H-NMR (400 MHz, CDCl$_3$) δ 7.18 (s, 1H), 6.96 (dd, 1H), 6.71 (d, 1H), 5.64 (s, 1H), 4.56-3.33 (m, 3H), 3.82 (s, 3H), 3.76 (s, 2H), 2.46 (dd, 2H), 2.09-1.99 (m, 3H), 1.77-1.66 (m, 3H), 1.26 (d, 3H), 0.98 (t, 3H) |
| 332 | (R)-4-chloro-N$^1$-[4-(2-methylpyrrolidin-1-yl)-6- | $^1$H-NMR (400 MHz, CDCl$_3$) δ 7.37 (s, 1H), 7.10 (d, 1H), 6.90 (dd, 1H), 5.68 (s, 1H), 4.56-3.33 (m, 3H), 3.96 (s, 2H), |

TABLE 1-34-continued

| Example | Compound | NMR Spectrum |
|---|---|---|
| | propylpyrimidin-2-yl]benzene-1,3-diamine | 2.45 (dd, 2H), 2.07-2.00 (m, 3H), 1.76-1.66 (m, 3H), 1.26 (d, 3H), 0.99 (t, 3H) |
| 333 | (R)-4-fluoro-$N^1$-[4-(2-methylpyrrolidin-1-yl)-6-propylpyrimidin-2-yl]benzene-1,3-diamine | $^1$H-NMR (400 MHz, CDCl$_3$) δ 7.31 (d, 1H), 6.97 (s, 1H), 6.87 (d, 2H), 5.67 (s, 1H), 4.56-3.33 (m, 3H), 3.67 (s, 2H), 2.45 (dd, 2H), 2.12-1.98 (m, 3H), 1.75-1.68 (m, 3H), 1.26 (d, 3H), 0.98 (t, 3H) |
| 334 | (R)-4-methyl-$N^1$-[4-(2-methylpyrrolidin-1-yl)-6-propylpyrimidin-2-yl]benzene-1,3-diamine | $^1$H-NMR (400 MHz, CDCl$_3$) δ 9.56 (s, 1H), 7.08 (d, 1H), 7.02 (s, 1H), 6.96 (d, 3H), 5.66 (s, 1H), 4.55-3.36 (m, 5H), 2.56 (dd, 2H), 2.15-2.07 (m, 2H), 2.12 (s, 3H), 1.85-1.76 (m, 2H), 1.29 (brs, 3H), 1.00 (t, 3H) |
| 335 | (S)-3-{4-[3-(2-hydroxyethylamino)pyrrolidin-1-yl]-6-propylpyrimidin-2-ylamino}benzonitrile dihydrochloride | $^1$H-NMR (400 MHz, CD$_3$OD) δ 7.81-7.70 (m, 2H), 7.49 (d, 1H), 7.30 (d, 1H), 6.30 (s, 1H), 4.21-3.77 (m, 9H), 2.69-2.30 (m, 4H), 1.82 (brs, 2H), 1.05 (t, 3H) |

TABLE 1-35

| Example | Compound | NMR Spectrum |
|---|---|---|
| 336 | (S)-5-{4-butyl-6-[2-(hydroxymethyl)pyrrolidin-1-yl]pyrimidin-2-ylamino}-2-methylbenzonitrile hydrochloride | $^1$H-NMR (400 MHz, CD$_3$OD) δ 7.99 (d, 1H), 7.70 (d, 1H), 7.44 (d, 1H), 6.31 (d, 1H), 4.28 (d, 1H), 3.84-3.56 (m, 4H), 2.66 (dd, 2H), 2.51 (s, 3H), 2.12-2.02 (m, 4H), 1.76-1.68 (m, 2H), 1.48-1.43 (m, 2H), 1.03 (t, 3H) |
| 337 | (S)-N-{1-[2-(4-amino-3-nitrophenylamino)-6-butylpyrimidin-4-yl]pyrrolidin-3-yl}acetamide | $^1$H-NMR (400 MHz, CD$_3$OD) δ 8.86 (brs, 1H), 7.42 (d, 1H), 6.90 (d, 1H), 5.83 (s, 1H), 4.48 (s, 1H), 3.78-3.40 (m, 4H), 2.49 (dd, 2H), 2.28-2.23 (m, 1H), 2.04-1.99 (m, 1H), 1.95 (s, 3H), 1.71-1.64 (m, 2H), 1.45-1.35 (m, 2H), 0.98 (t, 3H) |
| 338 | (S)-$N^1$-{4-butyl-6-[3-(methylamino)pyrrolidin-1-yl]pyrimidin-2-yl}-3-nitrobenzene-1,4-diamine | $^1$H-NMR (400 MHz, CDCl$_3$) δ 9.06 (brs, 1H), 7.34 (d, 1H), 6.90 (d, 1H), 5.85 (s, 1H), 3.96-3.44 (m, 5H), 2.64 (s, 3H), 2.49 (dd, 2H), 2.39 (brs, 1H), 2.08 (brs, 1H), 1.71-1.64 (m, 2H), 1.44-1.36 (m, 2H), 0.96 (t, 3H) |
| 339 | (S)-3-(4-{3-[(1H-pyrrol-2-yl)methylamino]pyrrolidin-1-yl}-6-propylpyrimidin-2-ylamino)benzonitrile dihydrochloride | $^1$H-NMR (400 MHz, CD$_3$OD) δ 10.59-10.51 (m, 1H), 8.12 (s, 1H), 7.83 (d, 1H), 7.60-7.56 (m, 2H), 6.87-6.83 (m, 1H), 6.36-6.30 (m, 2H), 6.16-6.12 (m, 1H), 4.36-4.33 (m, 2H), 4.12-3.75 (m, 5H), 2.71-2.58 (m, 3H), 2.41-2.30 (m, 1H), 1.83-1.77 (m, 2H), 1.06 (dd, 3H) |
| 340 | (S)-$N^1$-{4-[2-(methoxymethyl)pyrrolidin-1-yl]-6-propylpyrimidin-2-yl}-3-nitrobenzene-1,4-diamine hydrochloride | $^1$H-NMR (400 MHz, CDCl$_3$) δ 10.71 (s, 1H), 8.96 (d, 1H), 7.38 (s, 1H), 6.85 (s, 1H), 6.15-6.13 (m, 2H), 5.89 (d, 1H), 4.68-3.43 (m, 5H), 3.31 (d, 3H), 2.62 (brs, 2H), 2.33-2.05 (m, 4H), 1.88-1.84 (m, 2H), 1.00 (m, 3H) |
| 341 | (S)-{1-[2-(4-fluoro-3-nitrophenylamino)-6-propylpyrimidin-4-yl]pyrrolidin-2-yl}methanol hydrochloride | $^1$H-NMR (400 MHz, CDCl$_3$) δ 13.50 (s, 1H), 13.18 (s, 1H), 11.25 (s, 1H), 11.04 (s, 1H), 9.05 (m, 1H), 8.97 (m, 1H), 7.63 (m, 2H), 7.26 (m, 2H), 6.34 (s, 1H), 5.84 (s, 1H), 4.62 (m, 1H), 4.20 (m, 1H), 3.83 (m, 2H), 3.81 (m, 3H), 3.76 (m, 3H), 3.47 (m, 2H), 2.65 (m, 3H), 2.31 (m, 3H), 2.13 (m, 4H), 1.86 (m, 4H), 1.01 (m, 6H) |
| 342 | (S)-$N^1$-[4-(3-aminopyrrolidin-1-yl)-6-propylpyrimidin-2-yl]-5-(trifluoromethyl)benzene-1,3-diamine dihydrochloride | $^1$H-NMR (400 MHz, CD$_3$OD) δ 7.97 (d, 1H), 7.75 (d, 1H), 7.30 (d, 1H), 6.37 (s, 1H), 4.17-3.75 (m, 5H), 2.71 (t, 2H), 2.58 (m, 1H), 2.33 (m, 1H), 1.82 (m, 2H), 1.06 (t, 3H) |
| 343 | (S)-$N^1$-[4-(3-aminopyrrolidin-1-yl)-6-propylpyrimidin-2-yl]-3-methylbenzene-1,4-diamine dihydrochloride | $^1$H-NMR (400 MHz, CD$_3$OD) δ 7.63 (br, 1H), 7.60 (s, 1H), 7.38 (m, 1H), 6.31 (s, 1H), 4.15-3.75 (m, 5H), 2.68 (t, 2H), 2.53 (m, 1H), 2.43 (d, 3H), 2.29 (m, 1H), 1.82 (m, 2H), 1.07 (t, 3H) |
| 344 | (S)-4-(3-aminopyrrolidin-1-yl)-N-(4-chloro-3-nitrophenyl)-6-propylpyrimidin-2-amine dihydrochloride | $^1$H-NMR (400 MHz, CD$_3$OD) δ 8.59 (d, 1H), 7.75-7.64 (m, 2H), 7.41 (d, 1H), 6.57 (d, 1H), 4.11-3.78 (m, 5H), 2.72 (m, 2H), 2.65 (m, 1H), 2.04 (m, 1H), 1.78 (m, 2H), 1.06 (m, 3H) |
| 345 | (S)-4-(3-aminopyrrolidin-1-yl)-N-[3-(methylthio)phenyl]-6-propylpyrimidin-2-amine dihydrochloride | $^1$H-NMR (400 MHz, CD$_3$OD) δ 7.51 (d, 1H), 7.33 (m, 2H), 7.01 (m, 1H), 6.28 (brs, 1H), 4.15-3.75 (m, 5H), 2.67 (m, 2H), 2.56 (m, 1H), 2.50 (s, 3H), 2.24 (m, 1H), 1.79 (m, 2H), 1.29 (m, 3H) |

TABLE 1-36

| Example | Compound | NMR Spectrum |
| --- | --- | --- |
| 346 | (S)-N-[4-(3-aminopyrrolidin-1-yl)-6-propylpyrimidin-2-yl]-1H-indol-6-amine dihydrochloride | $^1$H-NMR (400 MHz, CD$_3$OD) δ 7.67 (d, 1H), 7.56 (d, 1H), 7.28 (s, 2H), 7.05 (d, 1H), 6.17 (d, 1H), 4.14-3.71 (m, 5H), 2.62 (m, 2H), 2.57 (m, 1H), 2.29 (m, 1H), 1.78 (m, 2H), 1.04 (t, 3H) |
| 347 | (S)-4-(3-aminopyrrolidin-1-yl)-6-propyl-N-[3-(trifluoromethyl)phenyl]pyrimidin-2-amine dihydrochloride | $^1$H-NMR (400 MHz, CD$_3$OD) δ 8.20-8.05 (d, 1H), 7.81-7.30 (dd, 1H), 7.62 (m, 1H), 7.50 (m, 1H), 6.34 (d, 1H), 4.17-3.74 (m, 5H), 2.70 (m, 2H), 2.57 (m, 1H), 2.25 (m, 1H), 1.83 (m, 2H), 1.06 (t, 3H) |
| 348 | (S)-4-(3-aminopyrrolidin-1-yl)-N-(5-chloro-2-methylphenyl)-6-propylpyrimidin-2-amine dihydrochloride | $^1$H-NMR (400 MHz, CD$_3$OD) δ 7.77-7.67 (d, 1H), 7.29 (d, 1H), 7.21 (m, 1H), 6.28 (d, 1H), 4.11-3.70 (m, 5H), 2.67 (m, 2H), 2.55 (m, 1H), 2.30 (d, 3H), 2.20 (m, 1H), 1.79 (m, 2H), 1.05 (t, 3H) |
| 349 | (S)-4-(3-aminopyrrolidin-1-yl)-N-(3-chloro-4-methylphenyl)-6-propylpyrimidin-2-amine dihydrochloride | $^1$H-NMR (400 MHz, CD$_3$OD) δ 7.78-7.71 (d, 1H), 7.37-7.30 (m, 2H), 6.28 (s, 1H), 4.08-3.81 (m, 5H), 2.66 (m, 2H), 2.52 (m, 1H), 2.35 (s, 3H), 2.20 (m, 1H), 1.80 (m, 2H), 1.05 (t, 3H) |
| 350 | (S)-4-(3-aminopyrrolidin-1-yl)-N-(3-nitrophenyl)-6-propylpyrimidin-2-amine dihydrochloride | $^1$H-NMR (400 MHz, CD$_3$OD) δ 8.94 (d, 1H), 8.05 (m, 1H), 7.82 (m, 1H), 7.64 (m, 1H), 6.60 (d, 1H), 4.16-3.76 (m, 5H), 2.71 (m, 2H), 2.55 (m, 1H), 2.30 (m, 1H), 1.84 (m, 2H), 1.07 (t, 3H) |
| 351 | (S)-4-(3-aminopyrrolidin-1-yl)-N-(4-methyl-3-nitrophenyl)-6-propylpyrimidin-2-amine dihydrochloride | $^1$H-NMR (400 MHz, CD$_3$OD) δ 8.64 (d, 1H), 7.64 (m, 1H), 7.47 (m, 1H), 6.64 (d, 1H), 4.16-3.71 (m, 5H), 2.70 (m, 2H), 2.56 (s, 3H), 2.54 (m, 1H), 2.31 (m, 1H), 1.81 (m, 2H), 1.06 (t, 3H) |
| 352 | (S)-N$^1$-[4-(3-aminopyrrolidin-1-yl)-6-propylpyrimidin-2-yl]-3-(trifluoromethyl)benzene-1,4-diamine dihydrochloride | $^1$H-NMR (400 MHz, CD$_3$OD) δ 8.18 (d, 1H), 7.92-7.85 (dd, 1H), 7.52 (m, 1H), 6.35 (s, 1H), 6.78-4.18 (m, 5H), 2.68 (m, 2H), 2.58 (m, 1H), 2.35 (m, 1H), 1.82 (m, 2H), 1.05 (t, 3H) |
| 353 | (S)-5-[4-(3-aminopyrrolidin-1-yl)-6-propylpyrimidin-2-ylamino]-2-fluorobenzonitrile dihydrochloride | $^1$H-NMR (400 MHz, CD$_3$OD) δ 8.07 (d, 1H), 7.87 (m, 1H), 7.43 (t, 1H), 6.33 (s, 1H), 4.14-3.84 (m, 5H), 2.69 (m, 2H), 2.56 (m, 1H), 2.23 (m, 1H), 1.80 (m, 2H), 1.06 (t, 3H) |
| 354 | (S)-5-[4-(3-aminopyrrolidin-1-yl)-6-propylpyrimidin-2-ylamino]-2-methylbenzonitrile dihydrochloride | $^1$H-NMR (400 MHz, CD$_3$OD) δ 8.02 (d, H), 7.68 (d, 1H), 7.45 (d, 1H), 6.31 (s, 1H), 4.08-3.82 (m, 5H), 2.68 (m, 2H), 2.58 (m, 1H), 2.52 (s, 3H), 2.28 (m, 1H), 1.80 (m, 2H), 1.06 (t, 3H) |
| 355 | (S)-2-amino-5-[4-(3-aminopyrrolidin-1-yl)-6-propylpyrimidin-2-ylamino]benzonitrile dihydrochloride | $^1$H-NMR (400 MHz, CD$_3$OD) δ 7.64 (d, 1H), 7.45 (m, 1H), 6.94 (m, 1H), 6.25 (s, 1H), 4.13-3.70 (m, 5H), 2.65 (m, 2H), 2.55 (m, 1H), 2.28 (m, 1H), 1.78 (m, 2H), 1.05 (t, 3H) |

TABLE 1-37

| Example | Compound | NMR Spectrum |
| --- | --- | --- |
| 356 | (S)-benzyl 5-[4-(3-aminopyrrolidin-1-yl)-6-propylpyrimidin-2-ylamino]-2-methoxyphenylcarbamate dihydrochloride | $^1$H-NMR (400 MHz, CD$_3$OD) δ 8.34 (d, 1H), 7.44-7.31 (m, 5H), 7.09-7.00 (dd, 2H), 6.21 (d, 1H), 5.20 (d, 2H), 4.01-3.72 (m, 5H), 3.80 (s, 3H), 2.64 (m, 2H), 2.62 (m, 1H), 2.54-2.29 (m, 1H), 1.78 (m, 2H), 1.04 (t, 3H) |
| 357 | (S)-4-(3-aminopyrrolidin-1-yl)-N-[4-fluoro-3-(trifluoromethyl)phenyl]-6-propylpyrimidin-2-amine dihydrochloride | $^1$H-NMR (400 MHz, CD$_3$OD) δ 8.12 (d, 1H), 7.85 (m, 1H), 7.41 (m, 1H), 6.30 (s, 1H), 4.09-3.88 (m, 5H), 2.71 (m, 2H), 2.64 (m, 1H), 2.30 (m, 1H), 1.82 (m, 2H), 1.07 (t, 3H) |
| 358 | (S)-4-(3-aminopyrrolidin-1-yl)-N-(4-fluoro-3-nitrophenyl)-6-propylpyrimidin-2-amine dihydrochloride | $^1$H-NMR (400 MHz, CD$_3$OD) δ 8.81-8.68 (m, 1H), 7.83 (m, 1H), 7.49 (m, 1H), 6.36 (s, 1H), 4.18-3.76 (m, 5H), 2.70 (m, 2H), 2.58 (m, 1H), 2.32 (m, 1H), 1.82 (m, 2H), 1.06 (t, 3H) |
| 359 | (S)-N$^1$-[4-(3-aminopyrrolidin-1-yl)-6-propylpyrimidin-2-yl]-3-nitrobenzene-1,4-diamine dihydrochloride | $^1$H-NMR (400 MHz, CD$_3$OD) δ 8.54 (m, 1H), 7.43 (m, 1H), 7.02 (m, 1H), 6.25 (d, 1H), 4.15-3.71 (m, 5H), 2.66 (m, 2H), 2.57 (m, 1H), 2.30 (m, 1H), 1.79 (m, 2H), 1.05 (t, 3H) |

TABLE 1-37-continued

| Example | Compound | NMR Spectrum |
|---|---|---|
| 360 | (S)-4-(3-aminopyrrolidin-1-yl)-N-[3,5-bis(trifluoromethyl)phenyl]-6-propylpyrimidin-2-amine dihydrochloride | $^1$H-NMR (400 MHz, CD$_3$OD) δ 8.34-8.30 (d, 2H), 7.78 (s, 1H), 6.40 (s, 1H), 4.16-3.77 (m, 5H), 2.73 (t, 2H), 2.54 (m, 1H), 2.26 (m, 1H), 1.82 (m, 2H), 0.90 (t, 3H) |
| 361 | (S)-4-(3-aminopyrrolidin-1-yl)-N-(3,5-dimethoxyphenyl)-6-propylpyrimidin-2-amine dihydrochloride | $^1$H-NMR (400 MHz, CD$_3$OD) δ 6.81-6.78 (m, 2H), 6.35 (s, 1H), 6.28 (s, 1H), 4.15-3.99 (m, 4H), 3.85 (s, 6H), 3.84-3.79 (m, 1H), 2.66 (t, 2H), 2.59 (m, 1H), 2.50 (m, 1H), 1.81 (m, 2H), 1.05 (t, 3H) |
| 362 | (S)-3-amino-5-{[4-(3-aminopyrrolidin-1-yl)-6-propylpyrimidin-2-yl]amino}benzonitrile | $^1$H-NMR (400 MHz, CD$_3$OD) δ 6.53 (s, 1H), 6.26 (m, 2H), 5.83 (s, 1H), 3.82 (br, 1H), 3.65 (m, 2H), 3.48 (br, 1H), 3.30 (br, 1H), 2.46 (m, 2H), 2.21 (m, 1H), 1.89 (m, 1H), 1.71 (m, 2H), 0.97 (t, 3H) |
| 363 | (S)-3-[4-(3-aminopyrrolidin-1-yl)-6-propylpyrimidin-2-ylamino]benzenesulfonamide | $^1$H-NMR (400 MHz, CD$_3$OD) δ 8.76 (s, 1H), 7.62 (m, 1H), 7.41 (m, 2H), 5.86 (s, 1H), 3.88-3.77 (br, 1H), 3.65 (m, 2H), 3.53 (br, 2H), 2.48 (m, 2H), 2.21 (m, 1H), 1.87 (m, 1H), 1.74 (m, 2H), 0.98 (t, 3H) |
| 364 | (S)-N$^1$-{4-[2-(methoxymethyl)pyrrolidin-1-yl]-6-propylpyrimidin-2-yl}benzene-1,3-diamine | $^1$H-NMR (400 MHz, CDCl$_3$) δ 7.73 (br, 1H), 7.04 (t, 1H), 6.97 (br, 1H), 6.63 (br, 1H), 6.30 (m, 1H), 5.68 (br, 1H), 4.63 (br, 1H), 3.92 (m, 3H), 3.45 (br, 1H), 3.39 (s, 3H), 3.18 (br, 1H), 3.14 (m, 1H), 2.45 (t, 2H), 2.10-1.96 (m, 4H), 1.68 (m, 3H), 0.99 (m, 3H) |
| 365 | (S)-4-fluoro-N$^1$-{4-[2-(methoxymethyl)pyrrolidin-1-yl]-6-propylpyrimidin-2-yl}benzene-1,3-diamine | $^1$H-NMR (400 MHz, CDCl$_3$) δ 7.82 (br, 1H), 6.97 (br, 1H), 6.85 (m, 1H), 6.51 (br, 1H), 5.68 (s, 1H), 4.46 (br, 1H), 3.89 (br, 2H), 3.45 (br, 1H), 3.39 (s, 3H), 3.34 (m, 1H), 3.12 (m, 1H), 2.45 (t, 2H), 2.09-1.98 (m, 4H), 1.68 (m, 3H), 0.97 (t, 3H) |

TABLE 1-38

| Example | Compound | NMR Spectrum |
|---|---|---|
| 366 | (S)-N$^1$-{4-[2-(methoxymethyl)pyrrolidin-1-yl]-6-propylpyrimidin-2-yl}-4-methylbenzene-1,3-diamine | $^1$H-NMR (400 MHz, CDCl3) δ 7.72 (br, 1H), 6.90 (m, 2H), 6.57 (br, 1H), 5.67 (s, 1H), 4.51 (br, 1H), 3.93-3.78 (br, 2H), 3.45 (br, 1H), 3.40 (s, 3H), 3.22 (m, 1H), 3.13 (m, 1H), 2.45 (m, 2H), 2.11 (s, 3H), 1.99 (m, 4H), 1.69 (m, 3H), 0.98 (t, 3H) |
| 367 | (S)-4-methoxy-N$^1$-{4-[2-(methoxymethyl)pyrrolidin-1-yl]-6-propylpyrimidin-2-yl}benzene-1,3-diamine | $^1$H-NMR (400 MHz, CDCl$_3$) δ 7.62 (br, 1H), 7.00 (br, 1H), 6.70 (m, 2H), 5.66 (s, 1H), 4.72 (br, 1H), 3.92 (br, 2H), 3.81 (s, 3H), 3.40 (m, 1H), 3.39 (s, 3H), 3.29 (m, 1H), 3.17 (m, 1H), 2.44 (t, 2H), 2.02 (m, 4H), 1.71 (m, 2H), 0.97 (t, 3H) |
| 368 | (S)-N-{4-[2-(methoxymethyl)pyrrolidin-1-yl]-6-propylpyrimidin-2-yl}indolin-6-amine | $^1$H-NMR (400 MHz, CDCl$_3$) δ 7.40 (br, 1H), 6.99 (m, 1H), 6.78 (m, 1H), 6.68 (s, 1H), 4.40 (br, 1H), 3.75 (br, 1H), 3.59 (t, 2H), 3.53 (br, 1H), 3.38 (s, 3H), 3.36 (m, 1H), 3.26 (t, 1H), 2.99 (t, 2H), 2.46 (t, 2H), 2.09-1.95 (m, 4H), 1.72 (m, 2H), 0.96 (m, 3H) |
| 369 | (S)-N$^1$-[4-(3-aminopyrrolidin-1-yl)-6-propylpyrimidin-2-yl]-4-methylbenzene-1,3-diamine | $^1$H-NMR (400 MHz, CDCl$_3$) δ 7.17 (s, 1H), 6.94 (s, 1H), 6.81 (br, 1H), 5.65 (s, 1H), 3.71 (m, 2H), 3.56 (br, 1H), 2.45 (m, 2H), 2.19 (m, 1H), 2.12 (s, 3H), 1.81 (m, 1H), 1.70 (m, 2H), 1.26 (br, 2H), 0.97 (t, 3H) |
| 370 | (S)-N$^1$-[4-(3-aminopyrrolidin-1-yl)-6-propylpyrimidin-2-yl]-4-fluorobenzene-1,3-diamine dihydrochloride | $^1$H-NMR (400 MHz, CD$_3$OD) δ 7.90 (m, 1H), 7.65 (m, 1H), 7.41 (t, 1H), 6.32 (s, 1H), 4.16-3.77 (m, 5H), 2.69 (m, 2H), 2.57 (m, 1H), 2.51 (m, 1H), 1.81 (m, 2H), 1.00 (t, 3H) |
| 371 | (S)-3-amino-5-{[4-(3-aminopyrrolidin-1-yl)-6-propylpyrimidin-2-yl]amino}benzonitrile dihydrochloride | $^1$H-NMR (400 MHz, CD$_3$OD) δ 7.85 (d, 1H), 7.78 (s, 1H), 7.28 (m, 1H), 6.36 (s, 1H), 4.17-3.76 (m, 5H), 2.70 (m, 2H), 2.60 (m, 1H), 2.33 (m, 1H), 1.82 (m, 2H), 1.06 (t, 3H) |
| 372 | (S)-N-(4-chloro-3-nitrophenyl)-4-[3-(cyclopropylmethylamino)pyrrolidin-1-yl]-6-propylpyrimidin-2-amine | $^1$H-NMR (400 MHz, CDCl$_3$) δ 9.05 (brs, 1H), 7.37 (d, 1H), 7.30 (br, 1H), 7.15 (br, 1H), 5.75 (s, 1H), 3.86-3.30 (m, 5H), 2.55 (d, 2H), 2.47 (t, 2H), 2.23 (m, 1H), 1.90 (br, 1H), 1.72 (m, 3H), 1.00 (t, 4H), 0.55 (d, 2H), 0.15 (m, 2H) |
| 373 | (S)-4-[3-(cyclopropylmethylamino)pyrrolidin-1-yl]-N-(4-fluoro-3-nitrophenyl)-6-propylpyrimidin-2-amine | $^1$H-NMR (400 MHz, CDCl$_3$) δ 9.16 (brs, 1H), 7.40 (br, 1H), 7.17 (br, 1H), 7.12 (t, 2H), 5.74 (s, 1H), 3.90-3.15 (m, 5H), 2.56 (m, 2H), 2.47 (t, 2H), 2.23 (m, 1H), 1.90 (br, 1H), 1.74 (m, 3H), 0.97 (t, 4H), 0.51 (d, 2H), 0.16 (d, 2H) |
| 374 | (S)-4-[3-(cyclopropylmethylamino)pyrrolidin- | $^1$H-NMR (400 MHz, CDCl$_3$) δ 9.06 (brs, 1H), 7.30 (m, 1H), 7.17 (d, 1H), 7.10 (br, 1H), 5.72 (s, 1H), 3.91-3.40 (m, 5H), |

TABLE 1-38-continued

| Example | Compound | NMR Spectrum |
|---|---|---|
|  | 1-yl]-N-(4-methyl-3-nitrophenyl)-6-propylpyrimidin-2-amine | 2.57 (m, 2H), 2.54 (s, 3H), 2.47 (t, 2H), 2.23 (m, 1H), 1.90 (br, 1H), 1.75 (m, 3H), 0.98 (t, 3H), 0.52 (d, 2H), 0.15 (m, 2H) |
| 375 | (S)-4-[3-(cyclopropylmethylamino)pyrrolidin-1-yl]-N-(3-nitrophenyl)-6-propylpyrimidin-2-amine | $^1$H-NMR (400 MHz, CDCl$_3$) δ 9.26 (brs, 1H), 7.77 (d, 1H), 7.44 (m, 1H), 7.37 (m, 1H), 5.74 (s, 1H), 3.92-3.60 (m, 5H), 2.64 (m, 2H), 2.48 (t, 2H), 2.29 (m, 1H), 2.02 (m, 1H), 1.72 (m, 3H), 1.00 (m, 4H), 0.56 (m, 4H), 0.22 (m, 2H) |

TABLE 1-39

| Example | Compound | NMR Spectrum |
|---|---|---|
| 376 | (S)-5-{4-[3-(cyclopropylmethylamino)pyrrolidin-1-yl]-6-propylpyrimidin-2-ylamino}-2-fluorobenzonitrile | $^1$H-NMR (400 MHz, CDCl$_3$) δ 8.34 (m, 1H), 7.56 (m, 1H), 7.09 (m, 2H), 5.73 (s, 1H), 3.84-3.16 (m, 5H), 2.60 (m, 2H), 2.47 (t, 2H), 2.22 (m, 1H), 1.88 (br, 1H), 1.70 (m, 3H), 0.99 (m, 4H), 0.50 (m, 2H), 0.15 (m, 2H) |
| 377 | (S)-5-{4-[3-(cyclopropylmethylamino)pyrrolidin-1-yl]-6-propylpyrimidin-2-ylamino}-2-methylbenzonitrile | $^1$H-NMR (400 MHz, CDCl$_3$) δ 8.32 (d, 1H), 7.46 (d, 1H), 7.18 (d, 1H), 7.02 (br, 1H), 5.71 (s, 1H), 3.80-3.00 (m, 5H), 2.54 (d, 2H), 2.48-2.45 (m, 5H), 2.21 (m, 1H), 1.88 (br, 1H), 1.74 (m, 3H), 0.98 (t, 4H), 0.54 (m, 2H), 0.17 (m, 2H) |
| 378 | (S)-4-[3-(cyclopropylmethylamino)pyrrolidin-1-yl]-N-[3-(methylthio)phenyl]-6-propylpyrimidin-2-amine | $^1$H-NMR (400 MHz, CDCl$_3$) δ 7.86 (s, 1H), 7.28 (d, 1H), 7.17 (t, 1H), 6.96 (br, 1H), 6.84 (d, 1H), 5.69 (s, 1H), 4.00-3.20 (m, 5H), 2.54 (d, 2H), 2.49 (s, 3H), 2.44 (m, 2H), 2.20 (m, 1H), 1.86 (br, 1H), 1.73 (m, 3H), 0.97 (m, 4H), 0.50 (m, 2H), 0.15 (m, 2H) |
| 379 | (S)-4-[3-(cyclopropylmethylamino)pyrrolidin-1-yl]-6-propyl-N-[3-(trifluoromethyl)phenyl]pyrimidin-2-amine | $^1$H-NMR (400 MHz, CDCl$_3$) δ 8.54 (s, 1H), 7.40 (m, 1H), 7.33 (m, 1H), 7.18 (m, 2H), 5.71 (s, 1H), 4.10-3.00 (m, 5H), 2.53 (m, 2H), 2.46 (t, 2H), 2.21 (m, 1H), 1.88 (br, 1H), 1.72 (m, 3H), 0.97 (t, 4H), 0.50 (m, 2H), 0.15 (m, 2H) |
| 380 | (S)-N-(5-chloro-2-methylphenyl)-4-[3-(cyclopropylmethylamino)pyrrolidin-1-yl]-6-propylpyrimidin-2-amine | $^1$H-NMR (400 MHz, CDCl$_3$) δ 8.64 (s, 1H), 7.03 (d, 1H), 6.86 (d, 1H), 6.70 (brs, 1H), 5.71 (s, 1H), 3.84-3.15 (m, 5H), 2.55 (m, 2H), 2.47 (t, 2H), 2.27 (s, 3H), 2.23 (m, 1H), 1.87 (br, 1H), 1.71 (m, 3H), 0.98 (m, 4H), 0.50 (m, 2H), 0.15 (m, 2H) |
| 381 | (S)-N-(3-chloro-4-methylphenyl)-4-[3-(cyclopropylmethylamino)pyrrolidin-1-yl]-6-propylpyrimidin-2-amine | $^1$H-NMR (400 MHz, CDCl$_3$) δ 8.03 (s, 1H), 7.27 (br, 1H), 7.18 (m, 1H), 7.09 (m, 1H), 5.68 (s, 1H), 4.00-3.15 (m, 5H), 2.55 (m, 2H), 2.47 (m, 2H), 2.31 (s, 3H), 2.23 (m, 1H), 1.91 (br, 1H), 1.68 (m, 3H), 0.98 (m, 4H), 0.52 (m, 2H), 0.15 (m, 2H) |
| 382 | (S)-4-[3-(cyclopropylmethylamino)pyrrolidin-1-yl]-N-[4-fluoro-3-(trifluoromethyl)phenyl]-6-propylpyrimidin-2-amine | $^1$H-NMR (400 MHz, CDCl$_3$) δ 8.48 (brs, 1H), 7.39 (brs, 1H), 7.06 (m, 2H), 5.71 (s, 1H), 4.00-3.00 (m, 5H), 2.53 (m, 2H), 2.46 (m, 2H), 2.21 (m, 1H), 1.88 (m, 1H), 1.72 (m, 3H), 0.97 (m, 4H), 0.52 (m, 2H), 0.14 (m, 2H) |
| 383 | (S)-N$^1$-{4-[3-(cyclopropylmethylamino)pyrrolidin-1-yl]-6-propylpyrimidin-2-yl}-4-methylbenzene-1,3-diamine | $^1$H-NMR (400 MHz, CDCl$_3$) δ 7.16 (s, 1H), 6.96 (m, 2H), 5.64 (s, 1H), 3.71-3.31 (m, 7H), 2.54 (dd, 2H), 2.46 (m, 2H), 2.19 (m, 1H), 2.12 (s, 3H), 1.87 (br, 1H), 1.71 (m, 3H), 0.98 (t, 4H), 0.51 (m, 2H), 0.14 (m, 2H) |
| 384 | (S)-N$^1$-{4-[3-(cyclopropylmethylamino)pyrrolidin-1-yl]-6-propylpyrimidin-2-yl}benzene-1,3-diamine | $^1$H-NMR (400 MHz, CDCl$_3$) δ 7.17 (s, 1H), 7.09-6.99 (m, 2H), 6.32 (d, 1H), 5.66 (s, 1H), 3.59-3.41 (m, 7H), 2.53 (m, 2H), 2.32 (m, 2H), 2.20 (m, 1H), 1.87 (br, 1H), 1.68 (m, 3H), 0.96 (m, 4H), 0.51 (m, 2H), 0.14 (m, 2H) |
| 385 | (S)-5-{4-[3-(cyclopropylmethylamino)pyrrolidin-1-yl]-6-propylpyrimidin-2-ylamino}-2-fluorobenzonitrile dihydrochloride | $^1$H-NMR (400 MHz, CDCl$_3$) δ 8.16 (br, 1H), 7.85 (br, 1H), 7.42 (t, 1H), 6.31 (s, 1H), 4.12-3.74 (m, 5H), 3.05 (m, 2H), 2.69 (t, 2H), 2.58 (br, 1H), 2.35 (br, 1H), 1.80 (m, 2H), 1.14 (m, 1H), 1.05 (t, 3H), 0.75 (m, 2H), 0.48 (m, 2H) |

TABLE 1-40

| Example | Compound | NMR Spectrum |
|---|---|---|
| 386 | (S)-4-[3-(cyclopropylmethylamino)pyrrolidin- | $^1$H-NMR (400 MHz, CD$_3$OD) δ 8.77 (d, 1H), 7.60 (m, 1H), 7.46 (d, 1H), 6.33 (s, 1H), 4.24-3.93 (m, 5H), 3.05 (m, 2H), |

TABLE 1-40-continued

| Example | Compound | NMR Spectrum |
|---|---|---|
| | 1-yl]-N-(4-methyl-3-nitrophenyl)-6-propylpyrimidin-2-amine dihydrochloride | 2.70 (t, 2H), 2.63 (m, 1H), 2.57 (s, 3H), 2.37 (br, 1H), 1.79 (m, 2H), 1.22 (m, 1H), 1.18 (t, 3H), 0.76 (m, 2H), 0.46 (m, 2H) |
| 387 | 3-{4-[3-(cyclopropylmethylamino)pyrrolidin-1-yl]-6-propylpyrimidin-2-ylamino}benzonitrile dihydrochloride | $^1$H-NMR (400 MHz, CD$_3$OD) δ 8.16 (d, 1H), 7.85-7.78 (m, 1H), 7.59 (m, 2H), 6.35 (s, 1H), 4.19-3.73 (m, 5H), 3.07-3.00 (m, 2H), 2.67 (t, 2H), 2.63-2.60 (m, 2H), 1.79 (m, 2H), 1.22 (m, 1H), 1.16 (t, 3H), 0.74 (m, 2H), 0.48 (m, 2H) |
| 388 | (S)-{1-[6-ethyl-2-(4-fluorophenylamino)pyrimidin-4-yl]pyrrolidin-2-yl}methanol | $^1$H-NMR (400 MHz, CD$_3$OD) δ 7.45 (t, 2H), 7.18 (t, 2H), 6.28-6.11 (m, 1H), 4.35-4.09 (d, 1H), 3.70-3.45 (m, 4H), 2.60 (q, 2H), 2.10 (m, 4H), 1.27 (t, 3H) |
| 389 | (S)-N-{1-[6-ethyl-2-(4-fluorophenylamino)pyrimidin-4-yl]pyrrolidin-3-yl}acetamide | $^1$H-NMR (400 MHz, CD$_3$OD) δ 7.42 (m, 2H), 7.19 (t, 2H), 6.14-6.10 (m, 1H), 4.50 (m, 1H), 3.86-3.40 (m, 4H), 2.60 (m, 2H), 2.31 (m, 1H), 2.10 (m, 1H), 1.95 (s, 3H), 1.27 (t, 3H) |
| 390 | (S)-4-ethyl-N-(4-fluorophenyl)-6-(2-methoxymethylpyrrolidin-1-yl)pyrimidin-2-amine | $^1$H-NMR (400 MHz, CD$_3$OD) δ 7.43 (m, 2H), 7.19 (t, 2H), 6.28-6.11 (m, 1H), 4.44-4.21 (d, 1H), 3.59-3.54 (m, 4H), 3.24 (d, 3H), 2.61 (q, 2H), 2.04 (m, 4H), 1.26 (t, 3H) |
| 391 | 4-ethyl-N-(4-fluorophenyl)-6-(2-methylpyrrolidin-1-yl)pyrimidin-2-amine | $^1$H-NMR (400 MHz, CD$_3$OD) δ 7.43 (t, 2H), 7.16 (t, 2H), 6.13-6.07 (m, 1H), 4.37-4.18 (d, 1H), 3.69-3.44 (m, 2H), 3.35 (s, 3H), 2.63 (q, 2H), 2.14 (m, 3H), 1.82 (m, 1H), 1.27 (t, 3H) |
| 392 | (S)-4-ethyl-6-[3-(ethylamino)pyrrolidin-1-yl]-N-(4-fluorophenyl)pyrimidin-2-amine | $^1$H-NMR (400 MHz, CD$_3$OD) δ 7.45 (m, 2H), 7.19 (m, 2H), 6.14 (s, 1H), 3.87-3.58 (m, 5H), 2.84 (m, 2H), 2.63 (m, 2H), 2.36 (m, 1H), 2.06 (m, 1H), 1.27-1.22 (m, 6H) |
| 393 | (S)-3-[4-(3-phenoxypyrrolidin-1-yl)-6-propylpyrimidin-2-ylamino]benzonitrile | $^1$H-NMR (400 MHz, CDCl$_3$) δ 8.40 (s, 1H), 7.58 (m, 1H), 7.38 (brs, 1H), 7.20 (m, 3H), 7.20 (d, 1H), 7.00 (t, 1H), 6.90 (m, 2H), 5.77 (s, 1H), 5.08 (s, 1H), 3.77 (m, 4H), 2.51 (t, 2H), 2.40 (m, 1H), 2.27 (m, 1H), 1.73 (q, 2H), 0.98 (t, 3H) |
| 394 | (S)-N-{1-[2-(3-cyanophenylamino)-6-propylpyrimidin-4-yl]pyrrolidin-3-yl}-2-(pyridin-3-yl)acetamide dihydrochloride | $^1$H-NMR (400 MHz, CD$_3$OD) δ 8.80 (s, 1H), 8.77 (t, 1H), 8.58 (d, 1H), 8.17 (d, 1H), 8.07 (m, 1H), 7.82-7.75 (m, 1H), 7.59-7.51 (m, 2H), 6.32 (d, 1H), 4.58-4.50 (m, 1H), 3.99 (m, 1H), 3.82 (m, 3H), 3.78-3.56 (m, 3H), 2.66 (m, 2H), 2.39 (m, 1H), 2.14 (m, 1H), 1.80 (m, 2H), 1.06 (t, 3H) |

TABLE 1-41

| Example | Compound | NMR Spectrum |
|---|---|---|
| 395 | (S)-2-amino-N-{1-[2-(3-cyanophenylamino)-6-propylpyrimidin-4-yl]pyrrolidin-3-yl}acetamide | $^1$H-NMR (400 MHz, CDCl$_3$) δ 8.33 (s, 1H), 7.61 (m, 2H), 7.34 (t, 1H), 7.20 (d, 1H), 5.75 (s, 1H), 4.63 (m, 1H), 3.81 (m, 3H), 3.38 (s, 4H), 2.51 (t, 2H), 2.33 (m, 1H), 2.05 (m, 1H), 1.71 (m, 2H), 0.98 (t, 3H) |
| 396 | (S)-3-(4-{3-[4-(dimethylamino)benzylamino]pyrrolidin-1-yl}-6-propylpyrimidin-2-ylamino)benzonitrile dihydrochloride | $^1$H-NMR (400 MHz, CD$_3$OD) δ 8.38 (s, 1H), 7.77 (d, 1H), 7.45 (t, 1H), 7.34 (m, 3H), 6.81 (d, 2H), 6.06 (s, 1H), 4.21 (s, 2H), 4.04 (m, 2H), 3.81-3.64 (m, 3H), 2.96 (s, 6H), 2.56 (t, 3H), 2.31 (m, 1H), 1.77 (q, 2H), 1.00 (t, 3H) |
| 397 | (S)-2-fluoro-5-{4-[2-(hydroxymethyl)pyrrolidin-1-yl]-6-propylpyrimidin-2-ylamino}benzonitrile hydrochloride | $^1$H-NMR (400 MHz, CD$_3$OD) δ 8.08-8.01 (d, 1H), 7.86 (m, 1H), 7.41 (m, 1H), 6.41-6.23 (d, 1H), 4.34-4.18 (d, 1H), 3.71-3.55 (m, 4H), 2.63 (t, 2H), 2.11 (m, 4H), 1.77 (m, 2H), 1.05 (t, 3H) |
| 398 | (S)-{1-[2-(4-amino-3-nitrophenylamino)-6-propylpyrimidin-4-yl]pyrrolidin-2-yl}methanol hydrochloride | $^1$H-NMR (400 MHz, CD$_3$OD) δ 8.58-8.38 (d, 1H), 7.41 (m, 1H), 7.03 (m, 1H), 6.34-7.17 (d, 1H), 4.40-4.17 (d, 1H), 3.88-3.62 (m, 4H), 2.61 (t, 2H), 2.25-2.01 (m, 4H), 1.76 (m, 2H), 1.04 (t, 3H) |
| 399 | (S)-{1-[2-(3-amino-4-methylphenylamino)-6-propylpyrimidin-4-yl]pyrrolidin-2-yl}methanol | $^1$H-NMR (400 MHz, CDCl$_3$) δ 7.32 (s, 1H), 6.92 (d, 1H), 6.78 (brs, NH), 6.67 (d, 1H), 5.69 (s, 1H), 4.41 (brs, 1H), 3.80 (m, 1H), 3.70 (brs, 1H), 3.59 (m, 1H), 3.46 (m, 1H), 3.30 (m, 1H), 2.44 (t, 2H), 2.11 (s, 3H), 2.02 (m, 3H), 1.85 (m, 1H), 1.71 (m, 2H), 0.98 (t, 3H) |
| 400 | (S)-{1-[2-(3-amino-4-fluorophenylamino)-6-propylpyrimidin-4- | $^1$H-NMR (400 MHz, CDCl$_3$) δ 7.43 (d, 1H), 6.86 (m, 2H), 6.63 (brs, 1H), 5.70 (s, 1H), 4.38 (s, 1H), 3.86 (s, 1H), 3.76 (m, 1H), 3.58 (m, 1H), 3.45 (m, 1H), 3.29 (brs, 1H), |

TABLE 1-41-continued

| Example | Compound | NMR Spectrum |
|---|---|---|
|  | yl]pyrrolidin-2-yl}methanol | 2.45 (t, 3H), 2.01 (m, 3H), 1.85 (m, 1H), 1.70 (m, 2H), 0.97 (t, 3H) |
| 401 | (S)-{1-[2-(3-amino-4-chlorophenylamino)-6-propylpyrimidin-4-yl]pyrrolidin-2-yl}methanol | $^1$H-NMR (400 MHz, CDCl$_3$) δ 7.52 (s, 1H), 7.00 (d, 1H), 6.68 (m, 1H), 5.73 (s, 1H), 4.43 (m, 1H), 4.22 (m, 1H), 3.82 (m, 1H), 3.62 (m, 1H), 3.49 (m, 1H), 3.34 (m, 1H), 2.49 (t, 2H), 2.05 (m, 2H), 1.63 (m, 4H), 0.98 (t, 3H) |
| 402 | (S)-3-[4-(2-formylpyrrolidin-1-yl)-6-propylpyrimidin-2-ylamino]benzonitrile | $^1$H-NMR (400 MHz, CDCl$_3$) δ 9.61 (s, 1H), 8.12 (s, 1H), 7.57 (d, 1H), 7.34 (t, 1H), 7.24 (t, 1H), 7.13 (s, 1H), 5.84 (s, 1H), 4.54 (s, 1H), 3.62-3.52 (m, 2H), 2.53 (t, 2H), 2.22 (s, 1H), 2.09 (m, 3H), 1.73 (m, 2H), 0.99 (t, 3H) |
| 403 | (S)-3-(4-{2-[(methylamino)methyl]pyrrolidin-1-yl}-6-propylpyrimidin-2-ylamino)benzonitrile | $^1$H-NMR (400 MHz, CD$_3$OD) δ 8.32 (s, 1H), 7.83 (d, 1H), 7.41 (t, 1H), 7.22 (d, 1H), 5.94 (s, 1H), 4.30 (brs, 1H), 3.56-3.38 (m, 2H), 2.86 (s, 1H), 2.62 (m, 1H), 2.48 (t, 2H), 2.40 (s, 3H), 2.04 (m, 4H), 1.74 (m, 2H), 0.99 (t, 3H) |

TABLE 1-42

| Example | Compound | NMR Spectrum |
|---|---|---|
| 404 | (S)-3-(4-{2-[(cyclobutylamino)methyl]pyrrolidin-1-yl}-6-propylpyrimidin-2-ylamino)benzonitrile | $^1$H-NMR (400 MHz, CDCl$_3$) δ 8.75 (s, 1H), 8.45 (s, 1H), 7.87 (s, 1H), 7.31 (m, 1H), 7.19 (d, 1H), 5.80 (s, 1H), 4.52 (s, 1H), 3.45-3.31 (m, 2H), 2.92-2.81 (m, 2H), 2.53 (m, 2H), 2.23-2.01 (m, 7H), 1.75 (m, 4H), 0.88 (t, 3H) |
| 405 | (S)-3-(4-{2-[(4-fluorobenzylamino)methyl]pyrrolidin-1-yl}-6-propylpyrimidin-2-ylamino)benzonitrile | $^1$H-NMR (400 MHz, CDCl$_3$) δ 8.37 (s, 1H), 7.64 (s, 1H), 7.33-7.19 (m, 4H), 6.94 (m, 2H), 5.75 (s, 1H), 4.44 (s, 1H), 3.85 (s, 2H), 3.45-3.31 (m, 2H), 2.87-2.76 (m, 2H), 2.48 (m, 2H), 2.02 (m, 4H), 1.71 (m, 2H), 0.98 (t, 3H) |
| 406 | (S)-3-(4-propyl-6-{2-[(propylamino)methyl]pyrrolidin-1-yl}pyrimidin-2-ylamino)benzonitrile | $^1$H-NMR (400 MHz, CDCl$_3$) δ 9.44 (s, 1H), 8.56 (s, 1H), 7.99 (m, 1H), 7.30 (m, 1H), 7.18 (d, 1H), 5.80 (s, 1H), 4.69 (s, 1H), 3.48-3.32 (m, 3H), 3.02 (m, 1H), 2.82 (m, 2H), 2.54 (t, 2H), 2.16 (m, 1H), 1.98 (m, 2H), 1.88-1.75 (m, 5H), 0.98 (t, 3H), 0.89 (t, 3H) |
| 407 | (S)-3-(4-{2-[(2-hydroxyethylamino)methyl]pyrrolidin-1-yl}-6-propylpyrimidin-2-ylamino)benzonitrile | $^1$H-NMR (400 MHz, CDCl$_3$) δ 9.11 (s, 1H), 8.48 (s, 1H), 7.89 (d, 1H), 7.31 (m, 1H), 7.17 (d, 1H), 5.78 (s, 1H), 4.30 (m, 1H), 4.10 (m, 1H), 3.92 (m, 1H), 3.45 (m, 1H), 3.37 (m, 2H), 3.14-3.04 (m, 2H), 2.92 (m, 1H), 2.55 (t, 2H), 2.23 (m, 1H), 1.97 (m, 2H), 1.80-1.75 (m, 3H), 1.01 (t, 3H) |
| 408 | N-{1-[2-(3-cyanophenylamino)-6-propylpyrimidin-4-yl]pyrrolidin-3-yl}acetamide hydrochloride | $^1$H-NMR (400 MHz, CD$_3$OD) δ 8.14-8.02 (d, 1H), 7.85 (m, 1H), 7.58-7.52 (m, 2H), 6.29 (d, 1H), 4.52 (m, 1H), 3.95-3.48 (m, 4H), 2.66 (m, 2H), 2.33 (m, 1H), 2.10 (m, 1H), 1.95 (s, 3H), 1.77 (m, 2H), 1.05 (m, 3H) |
| 409 | N-{1-[2-(3-nitrophenylamino)-6-propylpyrimidin-4-yl]pyrrolidin-3-yl}acetamide hydrochloride | $^1$H-NMR (400 MHz, CD$_3$OD) δ 8.97 (d, 1H), 8.03 (m, 1H), 7.79 (m, 1H), 7.60 (m, 1H), 6.27 (m, 1H), 4.53 (m, 1H), 3.99-3.48 (m, 4H), 2.66 (m, 2H), 2.33 (m, 1H), 2.10 (m, 1H), 1.96 (s, 3H), 1.78 (m, 2H), 1.06 (m, 3H) |
| 410 | N-{1-[2-(4-chloro-3-nitrophenylamino)-6-propylpyrimidin-4-yl]pyrrolidin-3-yl}acetamide hydrochloride | $^1$H-NMR (400 MHz, CD$_3$OD) δ 8.64-8.52 (d, 1H), 7.71-7.66 (m, 2H), 6.32 (d, 1H), 4.52 (m, 1H), 4.10-3.62 (m, 4H), 2.69 (m, 2H), 2.34 (m, 1H), 2.13 (m, 1H), 1.99 (s, 3H), 1.77 (m, 2H), 1.04 (m, 3H) |
| 411 | (R)-N$^1$-[4-(2-methylpyrrolidin-1-yl)-6-propylpyrimidin-2-yl]-3-nitrobenzene-1,4-diamine hydrochloride | $^1$H-NMR (400 MHz, CD$_3$OD) δ 8.56 (s, 1H), 7.41 (m, 1H), 6.99 (d, 1H), 6.21 (m, 1H), 4.52-4.23 (m, 2H), 3.81-3.48 (m, 2H), 2.63 (t, 2H), 2.15 (m, 3H), 1.74 (m, 2H), 1.25 (m, 3H), 1.03 (t, 3H) |
| 412 | (R)-N$^1$-[4-(2-methylpyrrolidin-1-yl)-6-propylpyrimidin-2-yl]-3-(trifluoromethyl)benzene-1,4-diamine hydrochloride | $^1$H-NMR (400 MHz, CD$_3$OD) δ 8.15-8.10 (m, 1H), 7.66-7.65 (m, 1H), 7.30-7.25 (m, 1H), 6.29-6.17 (d, 1H), 4.45-4.24 (m, 1H), 3.78-3.47 (m, 2H), 2.63 (m, 2H), 2.21-2.07 (m, 3H), 1.78 (m, 3H), 1.27 (m, 3H), 1.05 (t, 3H) |
| 413 | (S)-5-{4-[3-(cyclopropylmethylamino)pyrrolidin-1-yl]-6-propylpyrimidin-2-ylamino}-2-methylbenzonitrile dihydrochloride | $^1$H-NMR (400 MHz, CD$_3$OD) δ 8.12-8.03 (d, 1H), 7.65 (m, 1H), 7.44 (d, 1H), 6.32 (s, 1H), 4.14 (m, 2H), 3.94-3.75 (m, 3H), 3.06-3.00 (m, 2H), 2.68 (t, 2H), 2.61 (m, 1H), 2.52 (s, 3H), 2.38-2.36 (m, 1H), 1.82-1.76 (m, 2H), 1.15 (m, 3H), 1.05 (t, 3H), 0.74 (m, 2H), 0.48 (m, 2H) |

TABLE 1-43

| Example | Compound | NMR Spectrum |
| --- | --- | --- |
| 414 | (S)-2-methyl-5-{4-propyl-6-[3-(propylamino)pyrrolidin-1-yl]pyrimidin-2-ylamino}benzonitrile | ¹H-NMR (400 MHz, CD₃OD) δ 8.37 (d, 1H), 7.64 (d, 1H), 7.26 (d, 1H), 5.87 (d, 1H), 4.00-3.30 (m, 5H), 2.90-2.60 (m, 2H), 2.48 (t, 2H), 2.44 (s, 3H), 2.40-2.25 (m, 1H), 2.05-1.90 (m, 1H), 1.80-1.50 (m, 4H), 1.00-0.90 (m, 6H) |
| 415 | (S)-2-methyl-5-(4-{3-[3-(methylthio)propylamino]pyrrolidin-1-yl}-6-propylpyrimidin-2-ylamino)benzonitrile | ¹H-NMR (400 MHz, CD₃OD) δ 8.36 (s, 1H), 7.66 (d, 1H), 7.26 (d, 1H), 5.87 (s, 1H), 3.90-3.30 (m, 5H), 2.81 (t, 2H), 2.57 (t, 2H), 2.48 (t, 2H), 2.45 (s, 3H), 2.30-2.20 (m, 1H), 2.09 (s, 3H), 2.00-1.90 (m, 1H), 1.84 (t, 2H), 1.75 (q, 2H), 0.98 (t, 3H) |
| 416 | (S)-5-(4-{3-[(1H-pyrrol-2-yl)methylamino]pyrrolidin-1-yl}-6-propylpyrimidin-2-ylamino)-2-methylbenzonitrile | ¹H-NMR (400 MHz, CD₃OD) δ 8.35 (s, 1H), 7.66 (dd, 1H), 7.26 (d, 1H), 6.69 (s, 1H), 6.10-6.00 (m, 2H), 5.84 (s, 1H), 3.86 (s, 2H), 3.80-3.30 (m, 5H), 2.47 (t, 2H), 2.45 (s, 3H), 2.25-2.15 (m, 1H), 2.00-1.90 (m, 1H), 1.72 (q, 2H), 0.98 (t, 3H) |
| 417 | (S)-5-{4-[3-(4-hydroxybenzylamino)pyrrolidin-1-yl]-6-propylpyrimidin-2-ylamino}-2-methylbenzonitrile | ¹H-NMR (400 MHz, CD₃OD) δ 8.36 (s, 1H), 7.65 (d, 1H), 7.30-7.20 (m, 3H), 6.77 (d, 1H), 5.85 (s, 1H), 3.82 (s, 2H), 3.80-3.30 (m, 5H), 2.48 (t, 2H), 2.44 (s, 3H), 2.30-2.20 (m, 1H), 2.00-1.90 (m, 1H), 1.72 (q, 2H), 0.98 (t, 3H) |
| 418 | (S)-5-{4-[3-(isopropylamino)pyrrolidin-1-yl]-6-propylpyrimidin-2-ylamino}-2-methylbenzonitrile | ¹H-NMR (400 MHz, CD₃OD) δ 8.35 (s, 1H), 7.66 (d, 1H), 7.25 (d, 1H), 5.86 (s, 1H), 4.00-3.35 (m, 5H), 3.01 (t, 1H), 2.47 (t, 2H), 2.44 (s, 3H), 2.35-2.25 (m, 1H), 1.90-1.85 (m, 1H), 1.73 (q, 2H), 1.20-1.10 (m, 6H), 0.98 (t, 3H) |
| 419 | (S)-5-{4-[3-(cyclobutylamino)pyrrolidin-1-yl]-6-propylpyrimidin-2-ylamino}-2-methylbenzonitrile | ¹H-NMR (400 MHz, CD₃OD) δ 8.33 (s, 1H), 7.67 (d, 1H), 7.25 (d, 1H), 5.84 (s, 1H), 3.90-3.30 (m, 6H), 2.47 (t, 2H), 2.44 (s, 3H), 2.30-2.15 (m, 3H), 2.00-1.60 (m, 7H), 0.98 (t, 3H) |
| 420 | (S)-5-{4-[3-(cyclopentylamino)pyrrolidin-1-yl]-6-propylpyrimidin-2-ylamino}-2-methylbenzonitrile | ¹H-NMR (400 MHz, CD₃OD) δ 8.36 (s, 1H), 7.64 (d, 1H), 7.25 (d, 1H), 5.85 (s, 1H), 4.00-3.35 (m, 5H), 3.21 (t, 1H), 2.47 (t, 2H), 2.44 (s, 3H), 2.35-2.25 (m, 1H), 2.05-1.80 (m, 3H), 1.80-1.50 (m, 6H), 1.40-1.30 (m, 2H), 0.99 (t, 3H) |
| 421 | (S)-5-{4-[3-(cyclohexylamino)pyrrolidin-1-yl]-6-propylpyrimidin-2-ylamino}-2-methylbenzonitrile | ¹H-NMR (400 MHz, CD₃OD) δ 8.35 (s, 1H), 7.63 (d, 1H), 7.23 (d, 1H), 5.83 (s, 1H), 4.00-3.10 (m, 5H), 2.60 (t, 1H), 2.46 (t, 2H), 2.43 (s, 3H), 2.30-2.20 (m, 1H), 2.00-1.60 (m, 7H), 1.45-1.05 (m, 6H), 0.98 (t, 3H) |
| 422 | (S)-2-methyl-5-{4-[3-(pentylamino)pyrrolidin-1-yl]-6-propylpyrimidin-2-ylamino}benzonitrile dihydrochloride | ¹H-NMR (400 MHz, CD₃OD) δ 8.20-8.00 (m, 1H), 7.70-7.61 (m, 1H), 7.45 (d, 1H), 6.32 (s, 1H), 4.20-3.60 (m, 5H), 3.20-3.00 (m, 2H), 2.68 (t, 2H), 2.65-2.55 (m, 1H), 2.52 (s, 3H), 2.40-2.25 (m, 1H), 1.90-1.70 (m, 4H), 1.50-1.30 (m, 4H), 1.05 (t, 3H), 1.00-0.90 (m, 3H) |
| 423 | (S)-2-methyl-5-{4-[3-(neopentylamino)pyrrolidin-1-yl]-6-propylpyrimidin-2-ylamino}benzonitrile dihydrochloride | ¹H-NMR (400 MHz, CD₃OD) δ 8.08 (d, 1H), 7.75-7.55 (m, 1H), 7.50-7.40 (m, 1H), 6.32 (s, 1H), 4.30-3.60 (m, 5H), 3.10-2.90 (m, 2H), 2.80-2.60 (m, 3H), 2.52 (s, 3H), 2.50-2.30 (m, 1H), 1.80 (q, 2H), 1.12 (s, 9H), 1.05 (t, 3H) |

TABLE 1-44

| Example | Compound | NMR Spectrum |
| --- | --- | --- |
| 424 | (S)-5-(4-{3-[(4,5-dimethylfuran-2-yl)methylamino]pyrrolidin-1-yl}-6-propylpyrimidin-2-ylamino)-2-methylbenzonitrile dihydrochloride | ¹H-NMR (400 MHz, CD₃OD) δ 8.10-8.00 (m, 1H), 7.73 (d, 1H), 7.45 (d, 1H), 6.48 (s, 1H), 6.31 (s, 1H), 4.40-4.20 (m, 2H), 4.20-3.60 (m, 5H), 2.68 (t, 2H), 2.60-2.50 (m, 1H), 2.52 (s, 3H), 2.40-2.30 (m, 1H), 2.25-2.15 (m, 3H), 1.93 (s, 3H), 1.80 (q, 2H), 1.05 (t, 3H) |
| 425 | (S)-N-{1-[2-(3-cyano-4-methylphenylamino)-6-propylpyrimidin-4-yl]pyrrolidin-3-yl}propionamide | ¹H-NMR (400 MHz, CD₃OD) δ 8.24 (brs, 1H), 7.71 (d, 1H), 7.27 (d, 1H), 5.89 (s, 1H), 4.47 (t, 1H), 3.90-3.30 (m, 4H), 2.49 (t, 2H), 2.44 (s, 3H), 2.30-2.15 (m, 3H), 2.10-2.00 (m, 1H), 1.73 (q, 2H), 1.12 (t, 3H), 0.98 (t, 3H) |
| 426 | (S)-N-{1-[2-(3-cyano-4-methylphenylamino)-6-propylpyrimidin-4-yl]pyrrolidin-3-yl}-2-phenylacetamide | ¹H-NMR (400 MHz, CD₃OD) δ 7.97 (brs, 1H), 7.72 (d, 1H), 7.35-7.15 (m, 6H), 5.92 (s, 1H), 4.50-4.40 (m, 1H), 3.90-3.40 (m, 6H), 2.50 (t, 2H), 2.46 (s, 3H), 2.30-2.20 (m, 1H), 2.10-2.00 (m, 1H), 1.73 (q, 2H), 0.99 (t, 3H) |
| 427 | (S)-N-{1-[2-(3-cyano-4-methylphenylamino)-6-propylpyrimidin-4- | ¹H-NMR (400 MHz, CD₃OD) δ 8.28 (s, 1H), 7.69 (dd, 1H), 7.25 (d, 1H), 5.88 (s, 1H), 4.51 (t, 1H), 3.90-3.35 (m, 4H), 3.09 (s, 2H), 2.60-2.45 (m, 6H), 2.44 (s, 3H), 2.35-2.25 (m, |

TABLE 1-44-continued

| Example | Compound | NMR Spectrum |
| --- | --- | --- |
| | yl]pyrrolidin-3-yl}-2-(piperidin-1-yl)acetamide | 1H), 2.10-2.00 (m, 1H), 1.80-1.65 (m, 2H), 1.60-1.50 (m, 4H), 1.50-1.40 (m, 2H), 0.98 (t, 3H) |
| 428 | (S)-N-{1-[2-(3-cyano-4-methylphenylamino)-6-propylpyrimidin-4-yl]pyrrolidin-3-yl}-2-(pyridin-3-yl)acetamide | $^1$H-NMR (400 MHz, CD$_3$OD) δ 8.84 (s, 1H), 8.80-8.70 (m, 1H), 8.56 (d, 1H), 8.10-8.00 (m, 2H), 7.70-7.60 (m, 1H), 7.43 (t, 1H), 6.25 (d, 1H), 4.55-4.45 (m, 1H), 4.10-3.50 (m, 6H), 2.70-2.60 (m, 2H), 2.51 (d, 3H), 2.40-2.25 (m, 1H), 2.20-2.05 (m, 1H), 1.80-1.65 (m, 2H), 1.10-1.00 (m, 3H) |
| 429 | (S)-N-{1-[2-(3-cyano-4-methylphenylamino)-6-propylpyrimidin-4-yl]pyrrolidin-3-yl}-2-(pyridin-4-yl)acetamide | $^1$H-NMR (400 MHz, CD$_3$OD) δ 8.50-8.40 (m, 2H), 8.29 (s, 1H), 7.70 (dd, 1H), 7.36 (d, 2H), 7.26 (d, 1H), 5.87 (s, 1H), 4.48 (t, 1H), 3.90-3.30 (m, 6H), 2.50-2.40 (m, 5H), 2.30-2.20 (m, 1H), 2.10-2.00 (m, 1H), 1.73 (q, 2H), 0.98 (t, 3H) |
| 430 | (S)-N-{1-[2-(3-cyano-4-methylphenylamino)-6-propylpyrimidin-4-yl]pyrrolidin-3-yl}-2-(thiophen-2-yl)acetamide | $^1$H-NMR (400 MHz, CD$_3$OD) δ 8.24 (brs, 1H), 7.72 (d, 1H), 7.30-7.20 (m, 2H), 7.00-6.90 (m, 2H), 5.86 (s, 1H), 4.47 (t, 1H), 3.90-3.30 (m, 6H), 2.48 (t, 2H), 2.44 (s, 3H), 2.20 (m, 1H), 2.10-2.00 (m, 1H), 1.73 (q, 2H), 0.98 (t, 3H) |
| 431 | (S)-N-{1-[2-(3-cyano-4-methylphenylamino)-6-propylpyrimidin-4-yl]pyrrolidin-3-yl}methanesulfonamide | $^1$H-NMR (400 MHz, CD$_3$OD) δ 8.29 (s, 1H), 7.70 (dd, 1H), 5.88 (s, 1H), 4.15 (t, 1H), 3.90-3.30 (m, 4H), 3.02 (s, 3H), 2.49 (t, 2H), 2.44 (s, 3H), 2.35-2.25 (m, 1H), 2.10-2.00 (m, 1H), 1.73 (q, 2H), 0.98 (t, 3H) |
| 432 | (S)-N-{1-[2-(3-cyano-4-methylphenylamino)-6-propylpyrimidin-4-yl]pyrrolidin-3-yl}methanesulfonamide hydrochloride | $^1$H-NMR (400 MHz, CD$_3$OD) δ 8.02 (d, 1H), 7.70 (d, 1H), 7.44 (d, 1H), 6.26 (s, 1H), 4.30-4.10 (m, 1H), 4.00-3.40 (m, 4H), 3.03 (s, 3H), 2.65 (t, 2H), 2.52 (s, 3H), 2.45-2.30 (m, 1H), 2.20-2.00 (m, 1H), 1.77 (q, 2H), 1.05 (t, 3H) |

TABLE 1-45

| Example | Compound | NMR Spectrum |
| --- | --- | --- |
| 433 | (S)-1-(1-{2-[(3-cyano-4-methylphenyl)amino]-6-propylpyrimidin-4-yl}pyrrolidin-3-yl)-3-ethylurea hydrochloride | $^1$H-NMR (400 MHz, CD$_3$OD) δ 8.00 (d, 1H), 7.80-7.60 (m, 1H), 7.44 (d, 1H), 6.24 (d, 1H), 4.45-4.30 (m, 1H), 4.00-3.30 (m, 4H), 3.20-3.00 (m, 2H), 2.70-2.60 (m, 2H), 2.51 (s, 3H), 2.40-2.20 (m, 1H), 2.15-2.00 (m, 1H), 1.90-1.70 (m, 2H), 1.20-1.00 (m, 6H) |
| 434 | (R)-3-(4-{3-[(diethylamino)methyl]pyrrolidin-1-yl}-6-propylpyrimidin-2-ylamino)benzonitrile | $^1$H-NMR (400 MHz, CD$_3$OD) δ 8.40 (s, 1H), 7.81 (d, 1H), 7.39 (t, 1H), 7.22 (d, 1H), 5.87 (s, 1H), 3.90-3.20 (m, 4H), 2.80-2.50 (m, 6H), 2.48 (t, 2H), 2.20-2.10 (m, 1H), 1.80-1.65 (m, 3H), 1.10 (t, 6H), 0.98 (t, 3H) |
| 435 | (S)-5-{4-[3-(isopropylamino)pyrrolidin-1-yl]-6-propylpyrimidin-2-ylamino}-2-methylbenzonitrile dihydrochloride | $^1$H-NMR (400 MHz, CD$_3$OD) δ 8.03 (d, 1H), 7.64 (brs, 1H), 7.45 (d, 1H), 6.32 (s, 1H), 4.20-3.74 (m, 5H), 3.56-3.51 (m, 1H), 2.67 (dd, 2H), 2.60 (brs, 1H), 2.36-2.31 (m, 1H), 1.84-1.74 (m, 2H), 1.42 (dd, 6H), 1.05 (t, 3H) |
| 436 | (S)-N-{1-[6-butyl-2-(4-methyl-3-nitrophenylamino)pyrimidin-4-yl]pyrrolidin-3-yl}acetamide hydrochloride | $^1$H-NMR (400 MHz, CD$_3$OD) δ 8.68-8.56 (d, 1H), 7.60 (t, 1H), 7.44 (d, 1H), 6.24 (d, 1H), 4.49 (m, 1H), 4.00-3.48 (m, 4H), 2.68 (m, 2H), 2.56 (s, 3H), 2.33 (m, 1H), 2.11 (m, 1H), 1.96 (s, 3H), 1.73 (m, 2H), 1.45 (m, 2H), 0.98 (t, 3H) |
| 437 | (S)-N-{1-[6-butyl-2-(4-fluoro-3-nitrophenylamino)pyrimidin-4-yl]pyrrolidin-3-yl}acetamide hydrochloride | $^1$H-NMR (400 MHz, CD$_3$OD) δ 8.78-8.66 (d, 1H), 7.79 (m, 1H), 7.47 (t, 1H), 6.30-6.27 (d, 1H), 4.52 (m, 1H), 4.48-3.48 (m, 4H), 2.69 (m, 2H), 2.36 (m, 1H), 2.10 (m, 1H), 1.95 (s, 3H), 1.73 (s, 3H), 1.45 (m, 2H), 0.98 (t, 3H) |
| 438 | (S)-N-{1-[6-butyl-2-(4-chloro-3-nitrophenylamino)pyrimidin-4-yl]pyrrolidin-3-yl}acetamide hydrochloride | $^1$H-NMR (400 MHz, CD$_3$OD) δ 8.65-8.54 (d, 1H), 8.40-8.37 (m, 1H), 7.72-7.65 (m, 2H), 6.31-6.28 (d, 1H), 4.51 (m, 1H), 3.96-3.48 (m, 4H), 2.69 (m, 2H), 2.32 (m, 1H), 2.13 (m, 1H), 1.96 (s, 3H), 1.72 (m, 2H), 1.45 (m, 2H), 1.00 (t, 3H) |
| 439 | (S)-N-{1-[2-(3-amino-5-cyanophenylamino)-6-butylpyrimidin-4-yl]pyrrolidin-3-yl}acetamide hydrochloride | $^1$H-NMR (400 MHz, CD$_3$OD) δ 8.06-7.83 (m, 2H), 7.36 (d, 1H), 6.33 (d, 1H), 4.53-4.47 (m, 1H), 4.00-3.49 (m, 4H), 2.70 (m, 2H), 2.40 (m, 1H), 2.16 (m, 1H), 1.97 (s, 3H), 1.73 (m, 2H), 1.44 (m, 2H), 1.02 (t, 3H) |
| 440 | (S)-N-(1-{2-[3-amino-5-(trifluoromethyl)phenylamino]-6-butylpyrimidin-4-yl}pyrrolidin-3-yl)acetamide hydrochloride | $^1$H-NMR (400 MHz, CD$_3$OD) δ 8.14-8.02 (d, 1H), 7.30 (d, 1H), 6.33 (d, 1H), 4.53-4.47 (m, 1H), 3.97-3.49 (m, 4H), 2.71 (m, 2H), 2.31 (m, 1H), 2.15 (m, 1H), 1.96 (s, 3H), 1.74 (m, 2H), 1.47 (m, 2H), 0.99 (t, 3H) |
| 441 | (S)-N-(1-{2-[4-amino-3-(trifluoromethyl)phenylamino]- | $^1$H-NMR (400 MHz, CD$_3$OD) δ 7.74-7.65 (d, 1H), 7.34 (d, 1H), 6.86 (d, 1H), 6.13 (d, 1H), 4.49 (m, 1H), 3.83-3.43 (m, |

TABLE 1-45-continued

| Example | Compound | NMR Spectrum |
| --- | --- | --- |
|  | 6-butylpyrimidin-4-yl}pyrrolidin-3-yl)acetamide hydrochloride | 4H), 2.63 (m, 2H), 2.30 (m, 1H), 2.08 (m, 1H), 1.94 (s, 3H), 1.69 (m, 2H), 1.45 (m, 2H), 0.99 (t, 3H) |
| 442 | (S)-N-(1-{6-butyl-2-[4-fluoro-3-(trifluoromethyl)phenylamino]pyrimidin-4-yl}pyrrolidin-3-yl)acetamide hydrochloride | $^1$H-NMR (400 MHz, CD$_3$OD) δ 8.19-8.10 (d, 1H), 7.76 (m, 1H), 7.38 (t, 1H), 6.27 (d, 1H), 4.51 (m, 1H), 3.89-3.48 (m, 4H), 2.68 (m, 2H), 2.31 (m, 1H), 2.11 (m, 1H), 1.95 (s, 3H), 1.72 (m, 2H), 1.45 (m, 2H), 1.00 (t, 3H) |

TABLE 1-46

| Example | Compound | NMR Spectrum |
| --- | --- | --- |
| 443 | (S)-N-{1-[6-butyl-2-(3-cyano-4-fluorophenylamino)pyrimidin-4-yl]pyrrolidin-3-yl}acetamide hydrochloride | $^1$H-NMR (400 MHz, CD$_3$OD) δ 8.09-7.99 (d, 1H), 7.87 (m, 1H), 7.41 (t, 1H), 6.24 (d, 1H), 4.51-4.45 (m, 1H), 3.89-3.48 (m, 4H), 2.69 (m, 2H), 2.28 (m, 1H), 2.11 (m, 1H), 1.95 (s, 3H), 1.72 (m, 2H), 1.45 (m, 2H), 1.00 (t, 3H) |
| 444 | (S)-N-{1-[2-(3-amino-4-fluorophenylamino)-6-butylpyrimidin-4-yl]pyrrolidin-3-yl}acetamide hydrochloride | $^1$H-NMR (400 MHz, CD$_3$OD) δ 7.03 (m, 1H), 6.98 (t, 1H), 6.74 (m, 1H), 6.17 (d, 1H), 4.50-4.44 (m, 1H), 2.63 (m, 2H), 2.33 (m, 1H), 2.09 (m, 1H), 1.95 (s, 3H), 1.67 (m, 2H), 1.43 (m, 2H), 0.99 (t, 3H) |
| 445 | (S)-N-{1-[2-(3-amino-4-chlorophenylamino)-6-butylpyrimidin-4-yl]pyrrolidin-3-yl}acetamide hydrochloride | $^1$H-NMR (400 MHz, CD$_3$OD) δ 7.18 (d, 1H), 7.07 (s, 1H), 6.79 (m, 1H), 6.16 (d, 1H), 4.51-4.45 (m, 1H), 3.93-3.47 (m, 4H), 2.64 (m, 2H), 2.34 (m, 1H), 2.10 (m, 1H), 1.95 (s, 3H), 1.69 (m, 2H), 1.45 (m, 2H), 0.99 (t, 3H) |
| 446 | (S)-N-{1-[2-(4-amino-3-cyanophenylamino)-6-butylpyrimidin-4-yl]pyrrolidin-3-yl}acetamide hydrochloride | $^1$H-NMR (400 MHz, CD$_3$OD) δ 7.59 (d, 1H), 7.40 (s, 1H), 6.84 (m, 1H), 6.13 (m, 1H), 4.49 (m, 1H), 3.84-3.44 (m, 4H), 2.63 (m, 2H), 2.32 (m, 1H), 2.25 (m, 1H), 1.94 (s, 3H), 1.69 (m, 2H), 1.44 (m, 2H), 0.99 (m, 3H) |
| 447 | (S)-2-amino-5-{4-butyl-6-[3-(methylamino)pyrrolidin-1-yl]pyrimidin-2-ylamino}benzonitrile dihydrochloride | $^1$H-NMR (400 MHz, CD$_3$OD) δ 7.65 (s, 1H), 7.42 (t, 1H), 6.94 (d, 1H), 6.25 (d, 1H), 4.04-3.73 (m, 5H), 2.78 (d, 3H), 2.59 (t, 2H), 2.49 (m, 1H), 2.36 (m, 1H), 1.71 (m, 2H), 1.45 (m, 2H), 1.00 (t, 3H) |
| 448 | (S)-4-butyl-N-(4-methyl-3-nitrophenyl)-6-[3-(methylamino)pyrrolidin-1-yl]pyrimidin-2-amine dihydrochloride | $^1$H-NMR (400 MHz, CD$_3$OD) δ 8.81-8.79 (m, 1H), 7.56 (m, 1H), 7.46 (m, 1H), 6.33 (s, 1H), 4.19-3.81 (m, 5H), 2.84 (s, 3H), 2.71 (t, 2H), 2.57 (s, 3H + 1H), 2.34 (m, 1H), 1.75 (m, 2H), 1.46 (m, 2H), 1.01 (t, 3H) |
| 449 | (S)-4-butyl-N-(4-fluoro-3-nitrophenyl)-6-[3-(methylamino)pyrrolidin-1-yl]pyrimidin-2-amine dihydrochloride | $^1$H-NMR (400 MHz, CD$_3$OD) δ 8.88 (m, 1H), 7.72 (m, 1H), 7.48 (m, 1H), 6.36 (s, 1H), 4.16-3.78 (m, 5H), 2.83 (s, 3H), 2.70 (m, 2H), 2.59 (m, 1H), 2.33 (m, 1H), 1.75 (m, 2H), 1.46 (m, 2H), 1.01 (m, 3H) |
| 450 | (S)-4-butyl-N-(4-chloro-3-nitrophenyl)-6-[3-(methylamino)pyrrolidin-1-yl]pyrimidin-2-amine dihydrochloride | $^1$H-NMR (400 MHz, CD$_3$OD) δ 8.73-8.63 (m, 1H), 7.68 (m, 2H), 6.38 (s, 1H), 4.19-3.74 (m, 5H), 2.84 (s, 3H), 2.75 (m, 2H), 2.60 (m, 1H), 2.36 (m, 1H), 1.73 (m, 2H), 1.46 (m, 2H), 1.01 (m, 3H) |
| 451 | (S)-3-amino-5-{4-butyl-6-[3-(methylamino)pyrrolidin-1-yl]pyrimidin-2-ylamino}benzonitrile dihydrochloride | $^1$H-NMR (400 MHz, CD$_3$OD) δ 7.77-7.74 (d, 1H), 7.58 (s, 1H), 7.16 (s, 1H), 6.35 (s, 1H), 4.09-3.77 (m, 5H), 2.83 (d, 3H), 2.72 (t, 2H), 2.41 (m, 1H), 2.36 (m, 1H), 1.74 (m, 2H), 1.02 (m, 2H), 0.99 (t, 3H) |
| 452 | (S)-N$^1$-{4-butyl-6-[3-(methylamino)pyrrolidin-1-yl]pyrimidin-2-yl}-5-(trifluoromethyl)benzene-1,3-diamine dihydrochloride | $^1$H-NMR (400 MHz, CD$_3$OD) δ 7.89-7.78 (d, 1H), 7.54 (m, 1H), 7.17 (m, 1H), 6.36 (s, 1H), 4.14-3.79 (m, 5H), 2.83 (d, 3H), 2.65 (t, 2H), 2.54 (m, 1H), 2.37 (m, 1H), 1.75 (m, 2H), 1.46 (m, 2H), 0.99 (t, 3H) |

TABLE 1-47

| Example | Compound | NMR Spectrum |
| --- | --- | --- |
| 453 | (S)-N$^1$-{4-butyl-6-[3-(methylamino)pyrrolidin-1-yl]pyrimidin-2-yl}-3-(trifluoromethyl)benzene-1,4-diamine dihydrochloride | $^1$H-NMR (400 MHz, CD$_3$OD) δ 7.77 (d, 1H), 7.47 (m, 1H), 7.02 (t, 1H), 6.27 (d, 1H), 4.04-3.75 (m, 5H), 2.81 (d, 3H), 2.58 (t, 2H), 2.38 (m, 1H), 2.35 (m, 1H), 1.70 (m, 2H), 1.45 (m, 2H), 0.98 (t, 3H) |

TABLE 1-47-continued

| Example | Compound | NMR Spectrum |
|---|---|---|
| 454 | (S)-4-butyl-N-[4-fluoro-3-(trifluoromethyl)phenyl]-6-[3-(methylamino)pyrrolidin-1-yl]pyrimidin-2-amine dihydrochloride | $^1$H-NMR (400 MHz, CD$_3$OD) δ 8.13 (s, 1H), 7.79 (m, 1H), 7.40 (t, 1H), 6.33 (s, 1H), 5.06-3.79 (m, 5H), 2.78 (s, 3H), 2.69 (t, 2H), 2.34 (m, 1H), 2.27 (m, 1H), 1.74 (m, 2H), 1.46 (m, 2H), 1.00 (t, 3H) |
| 455 | (S)-5-{4-butyl-6-[3-(methylamino)pyrrolidin-1-yl]pyrimidin-2-ylamino}-2-fluorobenzonitrile dihydrochloride | $^1$H-NMR (400 MHz, CD$_3$OD) δ 8.12 (s, 1H), 7.83 (m, 1H), 7.42 (t, 1H), 4.04-3.82 (m, 5H), 2.81 (s, 3H), 2.68 (t, 2H), 2.35 (m, 1H), 2.32 (m, 1H), 1.73 (m, 2H), 1.46 (m, 2H), 1.00 (t, 3H) |
| 456 | (S)-N$^1$-{4-butyl-6-[3-(methylamino)pyrrolidin-1-yl]pyrimidin-2-yl}-4-fluorobenzene-1,3-diamine dihydrochloride | $^1$H-NMR (400 MHz, CD$_3$OD) δ 7.49 (s, 1H), 7.34 (m, 2H), 6.29 (d, 1H), 4.11-3.76 (m, 5H), 2.82 (d, 3H), 2.69 (t, 2H), 2.60 (m, 1H), 2.38 (m, 1H), 1.73 (m, 2H), 1.45 (m, 2H), 0.98 (t, 3H) |
| 457 | (S)-N$^1$-{4-butyl-6-[3-(methylamino)pyrrolidin-1-yl]pyrimidin-2-yl}-4-chlorobenzene-1,3-diamine dihydrochloride | $^1$H-NMR (400 MHz, CD$_3$OD) δ 7.67 (m, 1H), 7.50 (m, 1H), 7.38 (m, 1H), 6.33 (d, 1H), 4.16-3.77 (m, 5H), 2.81 (d, 3H), 2.69 (t, 2H), 2.52 (m, 1H), 2.31 (m, 1H), 1.74 (m, 2H), 1.48 (m, 2H), 1.00 (t, 3H) |
| 458 | (S)-2-amino-5-{4-butyl-6-[3-(ethylamino)pyrrolidin-1-yl]pyrimidin-2-ylamino}benzonitrile dihydrochloride | $^1$H-NMR (400 MHz, CD$_3$OD) δ 7.66 (d, 1H), 7.40 (m, 1H), 6.91 (d, 1H), 6.24 (s, 1H), 4.06-3.70 (m, 5H), 3.14 (m, 2H), 2.69 (m, 2H), 2.59-2.56 (m, 1H), 2.36 (m, 1H), 1.69 (m, 2H), 1.48 (m, 2H), 1.37 (t, 3H), 0.98 (t, 3H) |
| 459 | (S)-3-{4-butyl-6-[3-(ethylamino)pyrrolidin-1-yl]pyrimidin-2-ylamino}benzonitrile dihydrochloride | $^1$H-NMR (400 MHz, CD$_3$OD) δ 8.19-8.13 (m, 1H), 7.80 (m, 1H), 7.56 (m, 2H), 6.35 (s, 1H), 4.07-3.77 (m, 5H), 3.19 (m, 2H), 2.73 (t, 2H), 2.60 (m, 1H), 2.36 (m, 1H), 1.75 (m, 2H), 1.48 (m, 2H), 1.37 (m, 3H), 0.99 (t, 3H) |
| 460 | (S)-5-{4-butyl-6-[3-(ethylamino)pyrrolidin-1-yl]pyrimidin-2-ylamino}-2-methylbenzonitrile dihydrochloride | $^1$H-NMR (400 MHz, DMSO-d$_6$) δ 13.30 (brs, 1H), 10.6 (brs, 1H), 9.53-9.36 (m, 2H), 8.09 (m, 1H), 7.76 (m, 1H), 7.48 (m, 1H), 6.34 (s, 1H), 3.94 (m, 7H), 3.04 (m, 2H), 2.62 (m, 3H), 2.38 (m, 2H), 1.70 (m, 2H), 1.35 (m, 2H), 0.95 (m, 3H), 0.91 (m, 3H) |
| 461 | (S)-N$^1$-{4-butyl-6-[3-(ethylamino)pyrrolidin-1-yl]pyrimidin-2-yl}-3-nitrobenzene-1,4-diamine dihydrochloride | $^1$H-NMR (400 MHz, CD$_3$OD) δ 8.76-8.60 (m, 1H), 7.38 (m, 1H), 7.02 (m, 1H), 6.28 (s, 1H), 4.20-3.73 (m, 5H), 3.21 (m, 2H), 2.62 (m, 2H), 2.60 (m, 1H), 2.25 (m, 1H), 1.47 (m, 2H), 1.40 (m, 2H), 1.36 (m, 3H), 1.00 (m, 3H) |
| 462 | (S)-4-butyl-6-[3-(ethylamino)pyrrolidin-1-yl]-N-(4-methyl-3-nitrophenyl)pyrimidin-2-amine dihydrochloride | $^1$H-NMR (400 MHz, DMSO-d$_6$) δ 13.19 (brs, 1H), 10.79 (brs, 1H), 9.52-9.38 (m, 2H), 8.68 (s, 1H), 7.67 (s, 1H), 7.51 (m, 1H), 6.35 (s, 1H), 3.99-3.63 (m, 5H), 3.05 (m, 2H), 2.65 (m, 2H), 2.39 (m, 2H), 1.71 (m, 2H), 1.36 (m, 2H), 1.27 (m, 3H), 0.94 (m, 3H) |

TABLE 1-48

| Example | Compound | NMR Spectrum |
|---|---|---|
| 463 | (S)-4-butyl-6-[3-(ethylamino)pyrrolidin-1-yl]-N-(4-fluoro-3-nitrophenyl)pyrimidin-2-amine dihydrochloride | $^1$H-NMR (400 MHz, DMSO-d$_6$) δ 13.00 (brs, 1H), 10.77 (brs, 1H), 9.34 (m, 2H), 8.82 (s, 1H), 7.83 (s, 1H), 7.62 (m, 1H), 6.35 (s, 1H), 3.93 (m, 5H), 3.05 (m, 2H), 2.65 (m, 2H), 2.34 (m, 2H), 1.71 (m, 2H), 1.37 (m, 2H), 1.25 (m, 3H), 0.94 (m, 3H) |
| 464 | (S)-4-butyl-N-(4-chloro-3-nitrophenyl)-6-[3-(ethylamino)pyrrolidin-1-yl]pyrimidin-2-amine dihydrochloride | $^1$H-NMR (400 MHz, CD$_3$OD) δ 8.74-8.64 (m, 1H), 7.68 (m, 2H), 6.38 (s, 1H), 4.18-3.77 (m, 5H), 3.22 (m, 2H), 2.73 (m, 2H), 2.61 (m, 1H), 2.35 (m, 1H), 1.75 (m, 2H), 1.40 (m, 2H), 1.39 (m, 3H), 1.00 (m, 3H) |
| 465 | (S)-3-amino-5-{4-butyl-6-[3-(ethylamino)pyrrolidin-1-yl]pyrimidin-2-ylamino}benzonitrile dihydrochloride | $^1$H-NMR (400 MHz, CD$_3$OD) δ 8.17-7.87 (m, 2H), 7.39 (s, 1H), 6.38 (d, 1H), 4.21-3.78 (m, 5H), 3.19 (m, 2H), 2.75 (m, 2H), 2.59 (m, 1H), 1.34 (m, 1H), 1.76 (m, 2H), 1.40 (m, 2H), 1.39 (m, 3H), 1.01 (m, 3H) |
| 466 | (S)-N$^1$-{4-butyl-6-[3-(ethylamino)pyrrolidin-1-yl]pyrimidin-2-yl}-5-(trifluoromethyl)benzene-1,3-diamine dihydrochloride | $^1$H-NMR (400 MHz, CD$_3$OD) δ 8.18-8.03 (m, 1H), 7.98-7.88 (m, 1H), 7.40 (m, 1H), 6.40 (m, 1H), 4.20-3.78 (m, 5H), 3.20 (m, 2H), 2.71 (m, 2H), 2.62 (m, 1H), 2.31 (m, 1H), 1.75 (m, 2H), 1.46 (m, 2H), 1.37 (m, 3H), 0.99 (m, 3H) |
| 467 | (S)-N$^1$-{4-butyl-6-[3-(ethylamino)pyrrolidin-1-yl]pyrimidin-2-yl}-3-(trifluoromethyl)benzene-1,4-diamine dihydrochloride | $^1$H-NMR (400 MHz, CD$_3$OD) δ 8.01-7.89 (m, 1H), 7.59 (m, 1H), 7.20 (t, 1H), 6.28 (d, 1H), 4.08-3.75 (m, 5H), 3.21-3.11 (m, 2H), 2.69 (m, 2H), 2.58-2.52 (m, 1H), 2.38-2.27 (m, 1H), 1.73 (m, 2H), 1.45 (m, 2H), 1.37 (m, 3H), 1.00 (m, 3H) |

TABLE 1-48-continued

| Example | Compound | NMR Spectrum |
|---|---|---|
| 468 | (S)-4-butyl-6-[3-(ethylamino)pyrrolidin-1-yl]-N-[4-fluoro-3-(trifluoromethyl)phenyl]pyrimidin-2-amine dihydrochloride | $^1$H-NMR (400 MHz, CD$_3$OD) δ 8.16-8.10 (m, 1H), 7.78 (m, 1H), 7.41 (m, 1H), 6.33 (s, 1H), 4.07-3.76 (m, 5H), 3.21-3.19 (m, 2H), 2.73 (m, 2H), 2.56 (m, 1H), 2.28 (m, 1H), 1.72 (m, 2H), 1.44 (m, 2H), 1.36 (m, 3H), 1.00 (m, 3H) |
| 469 | (S)-5-{4-butyl-6-[3-(ethylamino)pyrrolidin-1-yl]pyrimidin-2-ylamino}-2-fluorobenzonitrile dihydrochloride | $^1$H-NMR (400 MHz, CD$_3$OD) δ 8.14 (m, 1H), 7.87 (m, 1H), 7.44 (m, 1H), 6.34 (s, 1H), 4.08 (m, 2H), 3.90-3.76 (m, 3H), 3.19 (m, 2H), 2.71 (m, 2H), 2.59 (m, 1H), 2.30 (m, 1H), 1.74 (m, 2H), 1.48 (m, 2H), 1.37 (m, 3H), 1.00 (m, 3H) |
| 470 | (S)-N$^1$-{4-butyl-6-[3-(ethylamino)pyrrolidin-1-yl]pyrimidin-2-yl}-4-fluorobenzene-1,3-diamine dihydrochloride | $^1$H-NMR (400 MHz, CD$_3$OD) δ 7.78-7.72 (m, 1H), 7.45 (m, 1H), 7.35-7.32 (m, 1H), 6.31 (s, 1H), 4.12-3.76 (m, 5H), 3.20 (m, 2H), 2.72 (m, 2H), 2.52 (m, 1H), 2.30 (m, 1H), 1.74 (m, 2H), 1.39 (m, 2H), 1.37 (m, 3H), 1.00 (m, 3H) |
| 471 | (S)-N$^1$-{4-butyl-6-[3-(ethylamino)pyrrolidin-1-yl]pyrimidin-2-yl}-4-chlorobenzene-1,3-diamine dihydrochloride | $^1$H-NMR (400 MHz, CD$_3$OD) δ 7.62 (m, 1H), 7.47 (m, 1H), 7.33 (m, 1H), 6.30 (s, 1H), 4.17-3.76 (m, 5H), 3.20 (m, 2H), 2.70 (m, 2H), 2.40 (m, 1H), 2.30 (m, 1H), 1.74 (m, 2H), 1.47 (m, 2H), 1.39 (m, 3H), 1.00 (m, 3H) |
| 472 | (S)-N-{1-[2-(3-cyano-4-methylphenylamino)-6-propylpyrimidin-4-yl]pyrrolidin-3-yl}-2-hydroxyacetamide | $^1$H-NMR (400 MHz, CDCl$_3$) δ 9.25 (brs, NH), 8.27 (s, 1H), 7.51 (d, 1H), 7.16 (d, 1H), 6.94 (brs, NH), 5.67 (s, 1H), 4.66 (m, 1H), 4.14 (s, 2H), 3.81-3.44 (m, 4H), 2.47 (m, 5H), 2.33 (m, 1H), 2.10 (m, 1H), 1.68 (m, 2H), 0.98 (t, 3H) |

TABLE 1-49

| Example | Compound | NMR Spectrum |
|---|---|---|
| 473 | (S)-N-{1-[2-(3-cyano-4-fluorophenylamino)-6-propylpyrimidin-4-yl]pyrrolidin-3-yl}-2-hydroxyacetamide | $^1$H-NMR (400 MHz, CDCl$_3$) δ 8.29 (s, 1H), 7.58 (d, 1H), 7.10 (m, 1H), 6.76 (brs, NH), 5.74 (s, 1H), 4.67 (m, 1H), 4.14 (s, 2H), 3.81-3.42 (m, 4H), 2.47 (t, 2H), 2.34 (m, 1H), 2.04 (m, 1H), 1.72 (m, 2H), 0.98 (t, 3H) |
| 474 | (S)-N-{1-[2-(3-amino-5-cyanophenylamino)-6-propylpyrimidin-4-yl]pyrrolidin-3-yl}-2-hydroxyacetamide | $^1$H-NMR (400 MHz, CDCl$_3$) δ 7.56 (s, NH), 7.10-7.02 (m, 2H), 6.69 (m, 1H), 6.51 (s, 1H), 5.73 (s, 1H), 4.64 (m, 1H), 4.14 (s, 2H), 3.85 (brs, 2NH), 3.81-3.49 (m, 4H), 2.49 (t, 2H), 2.35 (m, 1H), 2.06 (m, 1H), 1.72 (m, 2H), 0.98 (t, 3H) |
| 475 | (S)-N-(1-{2-[3-amino-5-(trifluoromethyl)phenylamino]-6-propylpyrimidin-4-yl}pyrrolidin-3-yl)-2-hydroxyacetamide | $^1$H-NMR (400 MHz, CDCl$_3$) δ 7.63 (s, NH), 7.10-6.98 (m, 2H), 6.78 (m, 1H), 6.51 (s, 1H), 5.68 (s, 1H), 4.64 (m, 1H), 4.13 (s, 2H), 3.83 (brs, 2NH), 3.49 (m, 4H), 2.45 (t, 2H), 2.30 (m, 1H), 2.04 (m, 1H), 1.68 (m, 2H), 0.96 (t, 3H) |
| 476 | (S)-N-(1-{2-[4-amino-3-(trifluoromethyl)phenylamino]-6-propylpyrimidin-4-yl}pyrrolidin-3-yl)-2-hydroxyacetamide | $^1$H-NMR (400 MHz, CDCl$_3$) δ 8.11 (brs, NH), 7.26 (m, 2H), 6.94 (brs, NH), 6.68 (m, 1H), 5.63 (s, 1H), 4.66 (m, 1H), 4.15 (s, 2H), 4.00 (brs, 2NH), 3.76-3.63 (m, 4H), 2.43 (t, 2H), 2.31 (m, 1H), 2.08 (m, 1H), 1.70 (m, 2H), 0.96 (t, 3H) |
| 477 | (S)-N-(1-{2-[4-fluoro-3-(trifluoromethyl)phenylamino]-6-propylpyrimidin-4-yl}pyrrolidin-3-yl)-2-hydroxyacetamide | $^1$H-NMR (400 MHz, CDCl$_3$) δ 8.40 (brs, NH), 7.45 (m, 1H), 7.08 (m, 2H), 6.70 (m, 1H), 5.72 (s, 1H), 4.66 (m, 1H), 4.15 (s, 2H), 3.78-3.41 (m, 4H), 2.46 (t, 2H), 2.34 (m, 1H), 2.04 (m, 1H), 1.70 (m, 2H), 0.97 (t, 3H) |
| 478 | (S)-N-{1-[2-(3-amino-4-fluorophenylamino)-6-propylpyrimidin-4-yl]pyrrolidin-3-yl}-2-hydroxyacetamide | $^1$H-NMR (400 MHz, CDCl$_3$) δ 7.21 (m, 1H), 6.86 (m, 2H), 6.80 (brs, NH), 5.64 (s, 1H), 4.64 (m, 1H), 4.15 (s, 2H), 3.76 (brs, 2NH), 3.63-3.59 (m, 4H), 2.44 (t, 2H), 2.31 (m, 1H), 2.05 (m, 1H), 1.70 (m, 2H), 0.97 (t, 3H) |
| 479 | (S)-N-{1-[2-(3-amino-4-chlorophenylamino)-6-propylpyrimidin-4-yl]pyrrolidin-3-yl}-2-hydroxyacetamide | $^1$H-NMR (400 MHz, CD$_3$OD) δ 7.25 (s, 1H), 7.06 (m, 1H), 6.92 (m, 1H), 5.89 (s, 1H), 4.55 (m, 1H), 3.99 (s, 2H), 3.87-3.62 (m, 4H), 2.49 (t, 2H), 2.31 (m, 1H), 2.10 (m, 1H), 1.71 (m, 2H), 0.99 (t, 3H) |
| 480 | (S)-N-{1-[2-(3-chloro-4-methylphenylamino)-6-propylpyrimidin-4-yl]pyrrolidin-3-yl}-2-hydroxyacetamide | $^1$H-NMR (400 MHz, CDCl$_3$) δ 7.96 (brs, NH), 7.21 (m, 1H), 7.09 (m, 1H), 6.92 (brs, NH), 6.76 (m, 1H), 5.67 (s, 1H), 4.67 (m, 1H), 4.14 (s, 2H), 3.77-3.43 (m, 4H), 2.45 (t, 2H), 2.31 (m, 4H), 2.04 (m, 1H), 1.69 (m, 2H), 0.97 (t, 3H) |
| 481 | (S)-2-hydroxy-N-(1-{2-[4-methyl-3-(trifluoromethyl)phenylamino]- | $^1$H-NMR (400 MHz, CDCl$_3$) δ 8.36 (brs, NH), 7.38 (m, 1H), 7.16 (m, 2H), 6.78 (m, 1H), 5.67 (s, 1H), 4.66 (m, 1H), 4.14 (s, 2H), 3.76-3.61 (m, 4H), 2.47 (m, 5H), 2.30 (m, 1H), |

TABLE 1-49-continued

| Example | Compound | NMR Spectrum |
| --- | --- | --- |
|  | 6-propylpyrimidin-4-yl}pyrrolidin-3-yl)acetamide | 2.04 (m, 1H), 1.70 (m, 2H), 0.96 (t, 3H) |

TABLE 1-50

| Example | Compound | NMR Spectrum |
| --- | --- | --- |
| 482 | (S)-N-{1-[2-(3-amino-5-cyanophenylamino)-6-propylpyrimidin-4-yl]pyrrolidin-3-yl}-2-hydroxyacetamide hydrochloride | $^1$H-NMR (400 MHz, CD$_3$OD) δ 7.73 (m, 2H), 7.22 (d, 1H), 6.31 (d, 1H), 4.57 (m, 1H), 4.05 (s, 2H), 3.95-3.54 (m, 4H), 2.67 (m, 2H), 2.38 (m, 1H), 2.19 (m, 2H), 1.80 (m, 2H), 1.05 (m, 3H) |
| 483 | (S)-N-{1-[2-(3-cyano-4-methylphenylamino)-6-propylpyrimidin-4-yl]pyrrolidin-3-yl}-2-hydroxyacetamide hydrochloride | $^1$H-NMR (400 MHz, CD$_3$OD) δ 8.02 (d, 1H), 7.71 (m, 1H), 7.43 (d, 1H), 6.27 (d, 1H), 4.56 (m, 1H), 3.99 (s, 2H), 3.90-3.47 (m, 4H), 2.64 (m, 2H), 2.52 (s, 3H), 2.17 (m, 1H), 2.01 (m, 1H), 1.78 (m, 2H), 1.05 (m, 3H) |
| 484 | (S)-4-fluoro-N$^1$-{4-[3-(methylamino)pyrrolidin-1-yl]-6-propylpyrimidin-2-yl}benzene-1,3-diamine dihydrochloride | $^1$H-NMR (400 MHz, CD$_3$OD) δ 7.67-7.62 (m, 1H), 7.44-7.28 (m, 2H), 6.30 (d, 1H), 4.12-3.76 (m, 5H), 2.81 (d, 3H), 2.67 (dd, 2H), 2.60-2.01 (m, 2H), 1.82-1.62 (m, 2H), 1.05 (t, 3H) |
| 485 | (S)-3-amino-5-({4-[3-(methylamino)pyrrolidin-1-yl]-6-propylpyrimidin-2-yl}amino)benzonitrile dihydrochloride | $^1$H-NMR (400 MHz, CD$_3$OD) δ 7.79 (d, 1H), 7.67 (d, 1H), 7.21 (s, 1H), 6.36 (d, 1H), 4.19-3.77 (m, 5H), 2.82 (d, 3H), 2.70 (dd, 2H), 2.64-2.36 (m, 2H), 1.84-1.77 (m, 2H), 1.05 (t, 3H) |
| 486 | (S)-2-amino-5-({4-[3-(methylamino)pyrrolidin-1-yl]-6-propylpyrimidin-2-yl}amino)benzonitrile dihydrochloride | $^1$H-NMR (400 MHz, CD$_3$OD) δ 7.63-7.62 (m, 1H), 7.43-7.39 (m, 1H), 6.90 (d, 1H), 6.24 (d, 1H), 4.12-3.73 (m, 5H), 2.79 (d, 3H), 2.64 (dd, 2H), 2.59-2.25 (m, 2H), 1.79-1.73 (m, 2H), 1.04 (t, 3H) |
| 487 | (S)-N$^1$-{4-[3-(methylamino)pyrrolidin-1-yl]-6-propylpyrimidin-2-yl}-5-(trifluoromethyl)benzene-1,3-diamine dihydrochloride | $^1$H-NMR (400 MHz, CD$_3$OD) δ 7.74 (d, 1H), 7.47 (d, 1H), 7.10 (s, 1H), 6.35 (s, 1H), 4.20-3.70 (m, 5H), 2.81 (d, 3H), 2.69 (t, 2H), 2.69-2.50 (m, 1H), 2.45-2.25 (m, 1H), 1.90-1.70 (m, 2H), 1.06 (t, 3H) |
| 488 | (S)-N$^1$-{4-[3-(ethylamino)pyrrolidin-1-yl]-6-propylpyrimidin-2-yl}-3-(trifluoromethyl)benzene-1,4-diamine dihydrochloride | $^1$H-NMR (400 MHz, CD$_3$OD) δ 7.79 (d, 1H), 7.50-7.40 (m, 1H), 7.02 (t, 1H), 6.30-6.20 (m, 1H), 4.20-3.60 (m, 5H), 3.25-3.00 (m, 2H), 2.65 (t, 2H), 2.60-2.40 (m, 1H), 2.40-2.20 (m, 1H), 1.78 (q, 2H), 1.40-1.30 (m, 3H), 1.05 (t, 3H) |
| 489 | (S)-2-amino-5-({4-[3-(ethylamino)pyrrolidin-1-yl]-6-propylpyrimidin-2-yl}amino)benzonitrile dihydrochloride | $^1$H-NMR (400 MHz, CD$_3$OD) δ 7.69 (d, 1H), 7.55-7.45 (m, 1H), 6.96 (d, 1H), 6.25 (d, 1H), 4.15-3.60 (m, 5H), 3.25-3.05 (m, 2H), 2.65 (t, 2H), 2.65-2.45 (m, 1H), 2.40-2.20 (m, 1H), 1.75 (q, 2H), 1.37 (t, 3H), 1.04 (t, 3H) |
| 490 | (S)-N-[4-fluoro-3-(trifluoromethyl)phenyl]-4-[3-(methylamino)pyrrolidin-1-yl]-6-propylpyrimidin-2-amine hydrochloride | $^1$H-NMR (400 MHz, CD$_3$OD) δ 8.47 (d, 1H), 7.75-7.65 (m, 1H), 7.20 (t, 1H), 5.97 (s, 1H), 4.00-3.85 (m, 2H), 3.85-3.50 (m, 3H), 2.78 (s, 3H), 2.60-2.40 (m, 3H), 2.30-2.20 (m, 1H), 1.74 (q, 2H), 0.98 (t, 3H) |

TABLE 1-51

| Example | Compound | NMR Spectrum |
| --- | --- | --- |
| 491 | (S)-4-[3-(ethylamino)pyrrolidin-1-yl]-N-[4-fluoro-3-(trifluoromethyl)phenyl]-6-propylpyrimidin-2-amine hydrochloride | $^1$H-NMR (400 MHz, CD$_3$OD) δ 8.45 (d, 1H), 7.71 (d, 1H), 7.20 (t, 1H), 5.97 (s, 1H), 4.10-3.85 (m, 2H), 3.85-3.50 (m, 3H), 3.16 (t, 2H), 2.60-2.40 (m, 3H), 2.30-2.15 (m, 1H), 1.75 (q, 2H), 1.36 (t, 3H), 0.98 (t, 3H) |
| 492 | (S)-N-{1-[6-butyl-2-(3-cyano-4-methylphenylamino)pyrimidin- | $^1$H-NMR (400 MHz, CD$_3$OD) δ 7.97 (d, 1H), 7.71 (t, 1H), 7.44 (d, 1H), 6.24 (d, 1H), 4.48 (d, 1H), 4.00-3.40 (m, 4H), 2.67 (t, 2H), 2.52 (s, 3H), 2.40-2.20 (m, 1H), 2.15-2.00 (m, |

TABLE 1-51-continued

| Example | Compound | NMR Spectrum |
|---|---|---|
| | 4-yl]pyrrolidin-3-yl}acetamide hydrochloride | 1H), 1.95 (s, 3H), 1.80-1.60 (m, 2H), 1.45 (q, 2H), 0.98 (t, 3H) |
| 493 | (S)-N-{1-[2-(3-amino-4-methylphenylamino)-6-propylpyrimidin-4-yl]pyrrolidin-3-yl}acetamide hydrochloride | $^1$H-NMR (400 MHz, CD$_3$OD) δ 7.00 (d, 1H), 6.92 (s, 1H), 6.76 (t, 1H), 6.14 (d, 1H), 4.47 (d, 1H), 4.00-3.35 (m, 4H), 2.60 (t, 2H), 2.40-2.20 (m, 1H), 2.13 (s, 3H), 2.15-2.00 (m, 1H), 1.95 (s, 3H), 1.74 (q, 2H), 1.03 (t, 3H) |
| 494 | (S)-N-(1-{2-[(3,4-diaminophenyl)amino]-6-propylpyrimidin-4-yl}pyrrolidin-3-yl)acetamide | $^1$H-NMR (400 MHz, CD$_3$OD) δ 6.88 (s, 1H), 6.70 (m, 2H), 6.02 (s, 1H), 4.45 (brs, 1H), 3.83-3.63 (m, 3H), 2.55 (m, 2H), 2.28 (br, 1H), 2.03 (br, 1H), 1.97 (s, 3H), 1.72 (m, 2H), 1.01 (t, 3H) |

Test Example 1: Evaluation of Agonistic Activity in CHO-K1 Cells Expressing Human 5-HT$_{4(a)}$ As CHO-K1 cells stably expressing human 5-HT$_{4(a)}$, we used the GeneBlAzer HTR4-CRE-bla CHO-K1 cells (Invitrogen Corp.). The cells were cultured, under the condition of 37□ and 5% CO$_2$, in a DMEM supplemented with 10% fetal bovine serum (FBS), 25 mM HEPES (pH7.4), 600 μg/ml hygromycin B, 0.1 mM non-essential amino acids, 100 unit/ml penicillin and 100 μg/ml streptomycin. Subcultures were performed three times per one week, each being at less than 80% confluence. At the previous day before treating test compounds, the cells were collected using 0.5% trypsin/EDTA and then diluted with a DMEM supplemented with 1% FBS, 25 mM HEPES, and 0.1 mM non-essential amino acids into 3.125×10$^5$ cells/ml. 32 μl of the diluted cells were added into 384-well plate (10$^4$ cells per well) and then incubated overnight. After the overnight culture, 8 μl of the medium having 1% of DMSO was added into the cell-free control well and the non-stimulating control well, respectively. 8 μl of the respective test compound dilutions (which had been prepared by diluting by 100-times with the medium as mentioned in the above) having 1% of DMSO were added to the respective remaining wells. After being cultured in the incubator for 5 hours, the wells of the 384-plate were treated with the substrate solution (8 μl per well) prepared according to the vendor's instruction (i.e., Invitrogen's instruction), and then incubated in the dark room for additional two hours. Agonistic activities on 5-HT$_4$ receptor were evaluated, on the basis of fluorescence values of the cleavage-products by beta-lactamase. After exciting to 410 nm of wavelength using a fluorescence detector (Genios Pro), we measured the fluorescence values at two emission wavelengths (first wavelength: 465 nm, second wavelength: 535 nm). Data were analyzed on the basis of the ratio of fluorescence intensities of each well at the respective wavelengths. Each EC$_{50}$ value was calculated by non-linear regression analysis using the "GraphPad Prism" program, based on the activities according to 8-different concentrations of the test compounds. The results are shown in Table 2-1 to 2-3 below.

TABLE 2-1

| Example | EC$_{50}$(nM) |
|---|---|
| 13 | 0.12 |
| 17 | 0.35 |
| 18 | 0.14 |
| 22 | 0.33 |
| 31 | 0.13 |
| 32 | 0.23 |
| 33 | 0.059 |

TABLE 2-1-continued

| Example | EC$_{50}$(nM) |
|---|---|
| 34 | 0.16 |
| 36 | 0.243 |
| 40 | 0.03 |
| 41 | 0.15 |
| 42 | 0.033 |
| 43 | 0.178 |
| 44 | 0.022 |
| 45 | 0.036 |
| 46 | 0.0097 |
| 47 | 0.38 |
| 50 | 0.012 |
| 52 | 0.33 |
| 53 | 0.098 |
| 54 | 0.032 |
| 55 | 0.016 |
| 56 | 0.312 |
| 57 | 0.389 |
| 59 | 0.028 |
| 60 | 0.047 |
| 61 | 0.15 |
| 62 | 0.36 |
| 63 | 0.13 |
| 66 | 0.1 |
| 67 | 0.19 |
| 71 | 0.25 |
| 73 | 0.27 |
| 75 | 0.22 |
| 77 | 0.15 |
| 78 | 0.28 |
| 79 | 0.44 |
| 80 | 0.17 |
| 81 | 0.205 |
| 82 | 0.048 |
| 84 | 0.031 |
| 85 | 0.003 |
| 86 | 0.039 |
| 87 | 0.048 |
| 88 | 0.041 |
| 89 | 0.08 |
| 90 | 0.091 |
| 91 | 0.014 |
| 92 | 0.057 |
| 93 | 0.01 |
| 94 | 0.041 |
| 95 | 0.081 |
| 96 | 0.017 |
| 97 | 0.046 |
| 98 | 0.094 |
| 99 | 0.0015 |
| 100 | 0.31 |
| 102 | 0.39 |
| 103 | 0.067 |
| 104 | 0.073 |
| 105 | 0.005 |
| 106 | 0.13 |
| 107 | 0.42 |
| 108 | 0.21 |
| 109 | 0.012 |
| 110 | 0.018 |

TABLE 2-1-continued

| Example | EC$_{50}$(nM) |
|---|---|
| 111 | 0.008 |
| 112 | 0.045 |
| 113 | 0.016 |
| 116 | 0.0035 |
| 117 | 0.014 |
| 121 | 0.005 |
| 123 | 0.0019 |
| 125 | 0.159 |
| 127 | 0.0062 |
| 128 | 0.039 |
| 129 | 0.323 |
| 131 | 0.091 |
| 133 | 0.039 |
| 134 | 0.214 |
| 135 | 0.011 |
| 136 | 0.045 |
| 137 | 0.072 |
| 138 | 0.012 |
| 139 | 0.034 |
| 140 | 0.028 |
| 141 | 0.085 |
| 142 | 0.01 |
| 143 | 0.0066 |
| 144 | 0.036 |
| 145 | 0.046 |
| 146 | 0.084 |
| 149 | 0.277 |
| 150 | 0.41 |
| 151 | 0.334 |
| 153 | 0.228 |
| 155 | 0.417 |
| 156 | 0.219 |
| 157 | 0.044 |
| 158 | 0.436 |
| 160 | 0.121 |
| 161 | 0.119 |
| 162 | 0.193 |
| 165 | 0.2 |
| 166 | 0.103 |
| 170 | 0.0013 |
| 171 | 0.00064 |
| 173 | 0.004 |
| 175 | 0.229 |
| 176 | 0.018 |
| 177 | 0.02 |
| 180 | 0.0087 |
| 181 | 0.00088 |
| 182 | 0.036 |
| 185 | 0.015 |
| 186 | 0.382 |
| 187 | 0.037 |
| 189 | 0.028 |
| 190 | 0.05 |
| 191 | 0.29 |
| 192 | 0.02 |
| 194 | 0.2 |
| 195 | 0.25 |
| 196 | 0.1 |
| 203 | 0.3 |
| 204 | 0.47 |
| 206 | 0.16 |
| 207 | 0.083 |
| 208 | 0.06 |
| 210 | 0.016 |
| 211 | 0.019 |
| 212 | 0.0089 |
| 213 | 0.017 |
| 214 | 0.029 |
| 215 | 0.018 |
| 217 | 0.23 |
| 220 | 0.07 |
| 221 | 0.149 |
| 222 | 0.082 |
| 223 | 0.011 |
| 224 | 0.0043 |
| 225 | 0.052 |

TABLE 2-1-continued

| Example | EC$_{50}$(nM) |
|---|---|
| 226 | 0.052 |
| 228 | 0.014 |

TABLE 2-2

| Example | EC$_{50}$(nM) |
|---|---|
| 229 | 0.00098 |
| 230 | 0.047 |
| 231 | 0.0067 |
| 232 | 0.13 |
| 233 | 0.019 |
| 234 | 0.0012 |
| 235 | 0.0023 |
| 236 | 0.209 |
| 237 | 0.0013 |
| 238 | 0.00039 |
| 239 | 0.115 |
| 240 | 0.0025 |
| 241 | 0.012 |
| 242 | 0.058 |
| 243 | 0.011 |
| 244 | 0.028 |
| 245 | 0.053 |
| 246 | 0.04 |
| 247 | 0.012 |
| 248 | 0.016 |
| 249 | 0.0018 |
| 251 | 0.01 |
| 252 | 0.0052 |
| 253 | 0.014 |
| 254 | 0.0015 |
| 255 | 0.023 |
| 260 | 0.015 |
| 261 | 0.0071 |
| 262 | 0.0039 |
| 268 | 0.011 |
| 270 | 0.204 |
| 274 | 0.087 |
| 279 | 0.078 |
| 280 | 0.026 |
| 281 | 0.196 |
| 282 | 0.103 |
| 286 | 0.0047 |
| 289 | 0.062 |
| 290 | 0.013 |
| 291 | 0.0074 |
| 292 | 0.038 |
| 293 | 0.0043 |
| 294 | 0.076 |
| 295 | 0.048 |
| 296 | 0.039 |
| 297 | 0.028 |
| 301 | 0.11 |
| 302 | 0.42 |
| 303 | 0.12 |
| 304 | 0.07 |
| 305 | 0.18 |
| 307 | 0.24 |
| 309 | 0.076 |
| 310 | 0.37 |
| 311 | 0.019 |
| 312 | 0.023 |
| 313 | 0.078 |
| 314 | 0.18 |
| 315 | 0.028 |
| 316 | 0.21 |
| 317 | 0.14 |
| 318 | 0.16 |
| 319 | 0.08 |
| 320 | 0.041 |
| 321 | 0.044 |
| 322 | 0.15 |
| 323 | 0.027 |
| 325 | 0.085 |

TABLE 2-2-continued

| Example | EC$_{50}$(nM) |
|---|---|
| 326 | 0.028 |
| 327 | 0.025 |
| 328 | 0.017 |
| 329 | 0.18 |
| 331 | 0.138 |
| 332 | 0.046 |
| 333 | 0.024 |
| 334 | 0.085 |
| 337 | 0.0026 |
| 338 | 0.0032 |
| 342 | 0.0055 |
| 344 | 0.0092 |
| 345 | 0.062 |
| 346 | 0.014 |
| 347 | 0.03 |
| 348 | 0.019 |
| 349 | 0.016 |
| 350 | 0.012 |
| 351 | 0.0035 |
| 352 | 0.0027 |
| 353 | 0.01 |
| 354 | 0.003 |
| 355 | 0.007 |
| 357 | 0.0065 |
| 358 | 0.014 |
| 359 | 0.0021 |
| 362 | 0.0021 |
| 364 | 0.122 |
| 365 | 0.027 |
| 366 | 0.078 |
| 367 | 0.153 |
| 368 | 0.182 |
| 369 | 0.049 |
| 370 | 0.015 |
| 372 | 0.0046 |
| 373 | 0.0043 |
| 374 | 0.0027 |
| 375 | 0.0033 |
| 376 | 0.0037 |
| 377 | 0.0013 |
| 378 | 0.015 |
| 379 | 0.0098 |
| 380 | 0.009 |
| 381 | 0.0043 |
| 382 | 0.0051 |
| 383 | 0.0057 |
| 384 | 0.077 |
| 387 | 0.007 |
| 395 | 0.082 |
| 399 | 0.13 |
| 400 | 0.033 |
| 401 | 0.073 |
| 402 | 0.236 |
| 403 | 0.414 |
| 405 | 0.399 |
| 406 | 0.402 |
| 407 | 0.254 |
| 414 | 0.0034 |
| 415 | 0.015 |
| 416 | 0.0074 |
| 417 | 0.0051 |
| 418 | 0.0022 |
| 419 | 0.0032 |
| 420 | 0.0029 |
| 421 | 0.0079 |
| 422 | 0.011 |
| 423 | 0.0084 |
| 424 | 0.02 |
| 425 | 0.056 |
| 426 | 0.079 |
| 427 | 0.024 |
| 428 | 0.066 |
| 429 | 0.025 |
| 430 | 0.027 |
| 431 | 0.029 |
| 433 | 0.055 |

TABLE 2-3

| Example | EC$_{50}$ (nM) |
|---|---|
| 434 | 0.111 |
| 436 | 0.01 |
| 437 | 0.02 |
| 438 | 0.015 |
| 439 | 0.0075 |
| 440 | 0.017 |
| 441 | 0.0095 |
| 442 | 0.041 |
| 443 | 0.0099 |
| 444 | 0.012 |
| 445 | 0.0098 |
| 446 | 0.0077 |
| 447 | 0.0023 |
| 448 | 0.0025 |
| 449 | 0.0044 |
| 450 | 0.0078 |
| 451 | 0.003 |
| 452 | 0.0033 |
| 453 | 0.0016 |
| 454 | 0.014 |
| 455 | 0.0038 |
| 456 | 0.0026 |
| 457 | 0.003 |
| 458 | 0.0017 |
| 459 | 0.0034 |
| 460 | 0.0019 |
| 461 | 0.0019 |
| 462 | 0.0026 |
| 463 | 0.0021 |
| 464 | 0.0039 |
| 465 | 0.0022 |
| 466 | 0.0058 |
| 467 | 0.0014 |
| 468 | 0.0062 |
| 469 | 0.0021 |
| 470 | 0.0025 |
| 471 | 0.0033 |
| 472 | 0.0075 |
| 473 | 0.022 |
| 474 | 0.0066 |
| 475 | 0.011 |
| 476 | 0.014 |
| 477 | 0.0096 |
| 478 | 0.024 |
| 479 | 0.0064 |
| 480 | 0.032 |
| 481 | 0.0093 |
| 484 | 0.0058 |
| 485 | 0.0024 |
| 486 | 0.0014 |
| 487 | 0.0021 |
| 488 | 0.00077 |
| 489 | 0.0015 |
| 490 | 0.0048 |
| 491 | 0.0029 |
| 492 | 0.019 |
| 493 | 0.024 |

As shown in Table 2-1 to 2-3, the compounds of the present invention have excellent activities as a 5-HT$_4$ receptor agonist, and therefore they can be usefully applied for preventing or treating the dysfunction in gastrointestinal motility.

The invention claimed is:
1. A compound or its pharmaceutically acceptable salt selected from the group consisting of:
  N-(4-fluorophenyl)-4-propyl-6-(pyrrolidin-1-yl)pyrimidin-2-amine;
  (S)-{1-[2-(4-fluorophenylamino)-6-propylpyrimidin-4-yl]pyrrolidin-2-yl}methanol;
  1-[2-(4-fluorophenylamino)-6-propylpyrimidin-4-yl]pyrrolidin-3-ol;
  (R)-{1-[2-(4-fluorophenylamino)-6-propylpyrimidin-4-yl]pyrrolidin-2-yl}methanol;

{1-[2-(4-fluorophenylamino)-6-propylpyrimidin-4-yl]
  pyrrolidin-2-yl}methanol;
N-(4-fluorophenyl)-4-(2-methylpyrrolidin-1-yl)-6-propy-
  lpyrimidin-2-amine;
(S)-N-(4-fluorophenyl)-4-[2-(methoxymethyl)pyrrolidin-
  1-yl]-6-propylpyrimidin-2-amine;
(R)-N-(4-fluorophenyl)-4-[2-(methoxymethyl)pyrrolidin-
  1-yl]-6-propylpyrimidin-2-amine;
(S)-1-[2-(4-fluorophenylamino)-6-propylpyrimidin-4-yl]
  pyrrolidin-2-carboxamide;
N-{1-[2-(4-fluorophenylamino)-6-propylpyrimidin-4-yl]
  pyrrolidin-3-yl}acetamide;
(R)-N-{1-[2-(4-fluorophenylamino)-6-propylpyrimidin-
  4-yl]pyrrolidin-3-yl}acetamide;
2,2,2-trifluoro-N-{1-[2-(4-fluorophenylamino)-6-propy-
  lpyrimidin-4-yl]pyrrolidin-3-yl}acetamide;
4-[3-(ethylamino)pyrrolidin-1-yl]-N-(4-fluorophenyl)-6-
  propylpyrimidin-2-amine;
4-[3-(dimethylamino)pyrrolidin-1-yl]-N-(4-fluorophe-
  nyl)-6-propylpyrimidin-2-amine;
(S)-N-(4-fluorophenyl)-4-propyl-6-[2-(pyrrolidin-1-ylm-
  ethyl)pyrrolidin-1-yl]pyrimidin-2-amine;
(S)-N-(4-fluorophenyl)-4-{2-[(phenylamino)methyl]pyr-
  rolidin-1-yl}-6-propylpyrimidin-2-amine;
(S)-N-{1-[2-(4-fluorophenylamino)-6-propylpyrimidin-
  4-yl]pyrrolidin-3-yl}acetamide;
(S)-4-[3-(ethylamino)pyrrolidin-1-yl]-N-(4-fluorophe-
  nyl)-6-propylpyrimidin-2-amine;
(S)-tert-butyl 1-[2-(4-fluorophenylamino)-6-propylpy-
  rimidin-4-yl]pyrrolidin-3-ylcarbamate;
4-(3-aminopyrrolidin-1-yl)-N-(4-fluorophenyl)-6-propy-
  lpyrimidin-2-amine;
4-[3-(diethylamino)pyrrolidin-1-yl]-N-(4-fluorophenyl)-
  6-propylpyrimidin-2-amine;
(S)-N-(4-fluorophenyl)-4-[3-(methylamino)pyrrolidin-1-
  yl]-6-propylpyrimidin-2-amine;
N-{1-[2-(4-fluorophenylamino)-6-propylpyrimidin-4-yl]
  pyrrolidin-3-yl}-N-methylacetamide;
(S)-1-[2-(4-fluorophenylamino)-6-propylpyrimidin-4-yl]
  pyrrolidin-3-ol;
(S)-N-{4-[2-(methoxymethyl)pyrrolidin-1-yl]-6-propy-
  lpyrimidin-2-yl}-1H-indol-6-amine;
(S)-N-{4-[2-(methoxymethyl)pyrrolidin-1-yl]-6-propy-
  lpyrimidin-2-yl}-1H-indol-5-amine;
(S)-4-[2-(methoxymethyl)pyrrolidin-1-yl]-N-(4-
  methoxyphenyl)-6-propylpyrimidin-2-amine;
(S)-4-[2-(methoxymethyl)pyrrolidin-1-yl]-N-(3-
  methoxyphenyl)-6-propylpyrimidin-2-amine;
(S)-N-(3-chlorophenyl)-4-[2-(methoxymethyl)pyrrolidin-
  1-yl]-6-propylpyrimidin-2-amine;
(S)-N-(4-fluoro-3-nitrophenyl)-4-[2-(methoxymethyl)
  pyrrolidin-1-yl]-6-propylpyrimidin-2-amine;
(S)-4-[2-(methoxymethyl)pyrrolidin-1-yl]-N-(3-nitrophe-
  nyl)-6-propylpyrimidin-2-amine;
(S)-N-(4-chloro-3-nitrophenyl)-4-[2-(methoxymethyl)
  pyrrolidin-1-yl]-6-propylpyrimidin-2-amine;
(S)-3-{4-[2-(methoxymethyl)pyrrolidin-1-yl]-6-propy-
  lpyrimidin-2-ylamino}benzonitrile;
(S)-4-[2-(methoxymethyl)pyrrolidin-1-yl]-N-[3-(methyl-
  thio)phenyl]-6-propylpyrimidin-2-amine;
(S)-4-[2-(methoxymethyl)pyrrolidin-1-yl]-6-propyl-N-
  [3-(trifluoromethyl)phenyl]pyrimidin-2-amine;
(S)-7-{4-[2-(methoxymethyl)pyrrolidin-1-yl]-6-propy-
  lpyrimidin-2-ylamino}-4-methyl-2H-chromen-2-one;
(S)-N-(5-chloro-2-methylphenyl)-4-[2-(methoxymethyl)
  pyrrolidin-1-yl]-6-propylpyrimidin-2-amine;
(S)-N-(3-chloro-4-methylphenyl)-4-[2-(methoxymethyl)
  pyrrolidin-1-yl]-6-propylpyrimidin-2-amine;
(S)-4-[2-(methoxymethyl)pyrrolidin-1-yl]-N-(4-methyl-
  3-nitrophenyl)-6-propylpyrimidin-2-amine;
(S)-N-[4-fluoro-3-(trifluoromethyl)phenyl]-4-[2-
  (methoxymethyl)pyrrolidin-1-yl]-6-propylpyrimidin-
  2-amine;
(S)-$N^1$-{4-[2-(methoxymethyl)pyrrolidin-1-yl]-6-propy-
  lpyrimidin-2-yl}-3-(trifluoromethyl)benzene-1,4-di-
  amine;
(S)-2-fluoro-5-{4-[2-(methoxymethyl)pyrrolidin-1-yl]-6-
  propylpyrimidin-2-ylamino}benzonitrile;
(S)-5-{4-[2-(methoxymethyl)pyrrolidin-1-yl]-6-propy-
  lpyrimidin-2-ylamino}-2-methylbenzonitrile;
(S)-2-amino-5-{4-[2-(methoxymethyl)pyrrolidin-1-yl]-6-
  propylpyrimidin-2-ylamino}benzonitrile;
(S)-$N^1$-{4-[2-(methoxymethyl)pyrrolidin-1-yl]-6-propy-
  lpyrimidin-2-yl}-3-nitrobenzene-1,4-diamine;
(S)-4-(3-aminopyrrolidin-1-yl)-N-(4-fluorophenyl)-6-
  propylpyrimidin-2-amine;
(S)-tert-butyl 1-[2-(3-cyanophenylamino)-6-propylpy-
  rimidin-4-yl]pyrrolidin-3-ylcarbamate;
3-{4-[3-(diethylamino)pyrrolidin-1-yl]-6-propylpyrimi-
  din-2-ylamino}benzonitrile;
(S)-3-{4-[3-(methylamino)pyrrolidin-1-yl]-6-propylpy-
  rimidin-2-ylamino}benzonitrile;
N-{1-[2-(3-cyanophenylamino)-6-propylpyrimidin-4-yl]
  pyrrolidin-3-yl}-N-methylacetamide;
(S)-3-[4-(3-hydroxypyrrolidin-1-yl)-6-propylpyrimidin-
  2-ylamino]benzonitrile;
(R)-3-[4-(2-methylpyrrolidin-1-yl)-6-propylpyrimidin-2-
  ylamino]benzonitrile;
(S)-N-{1-[2-(3-cyanophenylamino)-6-propylpyrimidin-
  4-yl]pyrrolidin-3-yl}acetamide;
(S)-3-{4-[3-(ethylamino)pyrrolidin-1-yl]-6-propylpy-
  rimidin-2-ylamino}benzonitrile;
(R)-tert-butyl {1-[2-(3-cyanophenylamino)-6-propylpy-
  rimidin-4-yl]pyrrolidin-3-yl}methylcarbamate;
(R)-3-[4-(3-hydroxypyrrolidin-1-yl)-6-propylpyrimidin-
  2-ylamino]benzonitrile;
(S)-3-[4-(3-methoxypyrrolidin-1-yl)-6-propylpyrimidin-
  2-ylamino]benzonitrile;
3-{4-[3-(methylamino)pyrrolidin-1-yl]-6-propylpyrimi-
  din-2-ylamino}benzonitrile;
(S)-3-[4-(3-aminopyrrolidin-1-yl)-6-propylpyrimidin-2-
  ylamino]benzonitrile;
(S)-N-{1-[2-(3-cyanophenylamino)-6-propylpyrimidin-
  4-yl]pyrrolidin-3-yl}butyramide;
(S)-N-{1-[2-(3-cyanophenylamino)-6-propylpyrimidin-
  4-yl]pyrrolidin-3-yl}cyclopentanecarboxamide;
(S)-N-{1-[2-(3-cyanophenylamino)-6-propylpyrimidin-
  4-yl]pyrrolidin-3-yl}-3-(piperidin-1-yl)propanamide;
(S)-N-{1-[2-(3-cyanophenylamino)-6-propylpyrimidin-
  4-yl]pyrrolidin-3-yl}benzamide;
(S)-N-{1-[2-(3-cyanophenylamino)-6-propylpyrimidin-
  4-yl]pyrrolidin-3-yl}-4-fluorobenzamide;
(S)-N-{1-[2-(3-cyanophenylamino)-6-propylpyrimidin-
  4-yl]pyrrolidin-3-yl}-2-phenylacetamide;
(S)-N-{1-[2-(3-cyanophenylamino)-6-propylpyrimidin-
  4-yl]pyrrolidin-3-yl}-2-(4-fluorophenyl)acetamide;
(S)-N-{1-[2-(3-cyanophenylamino)-6-propylpyrimidin-
  4-yl]pyrrolidin-3-yl}-3-phenoxypropanamide;
(S)-N-{1-[2-(3-cyanophenylamino)-6-propylpyrimidin-
  4-yl]pyrrolidin-3-yl}-3-isobutoxypropanamide;
(S)-2-(4-benzylpiperazin-1-yl)-N-{1-[2-(3-cyanophe-
  nylamino)-6-propylpyrimidin-4-yl]pyrrolidin-3-
  yl}acetamide;

(S)-N-{1-[2-(3-cyanophenylamino)-6-propylpyrimidin-4-yl]pyrrolidin-3-yl}-2-(piperidin-1-yl)acetamide;
(S)-N-{1-[2-(3-cyanophenylamino)-6-propylpyrimidin-4-yl]pyrrolidin-3-yl}-4-oxo-4-phenylbutanamide;
(S)-2-(4-aminophenyl)-N-{1-[2-(3-cyanophenylamino)-6-propylpyrimidin-4-yl]pyrrolidin-3-yl}acetamide;
(S)-N-{1-[2-(3-cyanophenylamino)-6-propylpyrimidin-4-yl]pyrrolidin-3-yl}-2-cyclopentylacetamide;
(S)-N-{1-[2-(3-cyanophenylamino)-6-propylpyrimidin-4-yl]pyrrolidin-3-yl}-2-methoxyacetamide;
(S)-N-{1-[2-(3-cyanophenylamino)-6-propylpyrimidin-4-yl]pyrrolidin-3-yl}-2-(pyridin-2-yl)acetamide;
(S)-N-{1-[2-(3-cyanophenylamino)-6-propylpyrimidin-4-yl]pyrrolidin-3-yl}-2-(pyridin-3-yl)acetamide;
(S)-N-{1-[2-(3-cyanophenylamino)-6-propylpyrimidin-4-yl]pyrrolidin-3-yl}-2-(pyridin-4-yl)acetamide;
(S,E)-N-{1-[2-(3-cyanophenylamino)-6-propylpyrimidin-4-yl]pyrrolidin-3-yl}-4-phenylbut-3-enamide;
(S)-N-{1-[2-(3-cyanophenylamino)-6-propylpyrimidin-4-yl]pyrrolidin-3-yl}-2-(thiophen-2-yl)acetamide;
(S)-N-{1-[2-(3-cyanophenylamino)-6-propylpyrimidin-4-yl]pyrrolidin-3-yl}isobutyramide;
(S)-N-{1-[2-(3-cyanophenylamino)-6-propylpyrimidin-4-yl]pyrrolidin-3-yl}-3,3,3-trifluoropropanamide;
3-[4-(2-oxopyrrolidin-1-yl)-6-propylpyrimidin-2-ylamino]benzonitrile;
(S)-3-{4-[3-(hexylamino)pyrrolidin-1-yl]-6-propylpyrimidin-2-ylamino}benzonitrile;
(S)-3-{4-propyl-6-[3-(propylamino)pyrrolidin-1-yl]pyrimidin-2-ylamino}benzonitrile;
(S)-3-{4-[3-(cyclohexylmethylamino)pyrrolidin-1-yl]-6-propylpyrimidin-2-ylamino}benzonitrile;
(S)-3-{4-[3-(benzylamino)pyrrolidin-1-yl]-6-propylpyrimidin-2-ylamino}benzonitrile;
(S)-3-{4-[3-(phenethylamino)pyrrolidin-1-yl]-6-propylpyrimidin-2-ylamino}benzonitrile;
(S)-3-{4-[3-(3-phenylpropylamino)pyrrolidin-1-yl]-6-propylpyrimidin-2-ylamino}benzonitrile;
(S)-3-{4-[3-(3-fluorobenzylamino)pyrrolidin-1-yl]-6-propylpyrimidin-2-ylamino}benzonitrile;
(S)-3-{4-[3-(4-hydroxybenzylamino)pyrrolidin-1-yl]-6-propylpyrimidin-2-ylamino}benzonitrile;
(S)-3-{4-[3-(4-ethylbenzylamino)pyrrolidin-1-yl]-6-propylpyrimidin-2-ylamino}benzonitrile;
(S)-3-{4-[3-(isopentylamino)pyrrolidin-1-yl]-6-propylpyrimidin-2-ylamino}benzonitrile;
(S)-3-{4-[3-(pentylamino)pyrrolidin-1-yl]-6-propylpyrimidin-2-ylamino}benzonitrile;
3-{4-[(3S)-3-(2-methylbutylamino)pyrrolidin-1-yl]-6-propylpyrimidin-2-ylamino}benzonitrile;
(S)-3-{4-[3-(isobutylamino)pyrrolidin-1-yl]-6-propylpyrimidin-2-ylamino}benzonitrile;
(S)-3-{4-[3-(4-methoxybenzylamino)pyrrolidin-1-yl]-6-propylpyrimidin-2-ylamino}benzonitrile;
(S)-3-{4-[3-(4-fluorobenzylamino)pyrrolidin-1-yl]-6-propylpyrimidin-2-ylamino}benzonitrile;
(S)-3-{4-[3-(cyclopropylmethylamino)pyrrolidin-1-yl]-6-propylpyrimidin-2-ylamino}benzonitrile;
(S)-3-(4-{3-[bis(cyclopropylmethyl)amino]pyrrolidin-1-yl}-6-propylpyrimidin-2-ylamino)benzonitrile;
(S)-3-{4-propyl-6-[3-(pyridin-2-ylmethylamino)pyrrolidin-1-yl]pyrimidin-2-ylamino}benzonitrile;
(S)-3-{4-propyl-6-[3-(pyridin-3-ylmethylamino)pyrrolidin-1-yl]pyrimidin-2-ylamino}benzonitrile;
(S)-3-{4-propyl-6-[3-(pyridin-4-ylmethylamino)pyrrolidin-1-yl]pyrimidin-2-ylamino}benzonitrile;
(S)-3-{4-[3-(2-ethylbutylamino)pyrrolidin-1-yl]-6-propylpyrimidin-2-ylamino}benzonitrile;
(S)-3-{4-[3-(neopentylamino)pyrrolidin-1-yl]-6-propylpyrimidin-2-ylamino}benzonitrile;
(S)-3-{4-[3-(2-fluorobenzylamino)pyrrolidin-1-yl]-6-propylpyrimidin-2-ylamino}benzonitrile;
(S)-3-(4-propyl-6-{3-[3-(trifluoromethyl)benzylamino]pyrrolidin-1-yl}pyrimidin-2-ylamino)benzonitrile;
(S)-3-(4-propyl-6-{3-[4-(trifluoromethyl)benzylamino]pyrrolidin-1-yl}pyrimidin-2-ylamino)benzonitrile;
(S)-4-({1-[2-(3-cyanophenylamino)-6-propylpyrimidin-4-yl]pyrrolidin-3-ylamino}methyl)phenylacetate;
(S)-3-(4-{3-[4-(dimethylamino)benzylamino]pyrrolidin-1-yl}-6-propylpyrimidin-2-ylamino)benzonitrile;
(S)-3-(4-{3-[(1H-pyrrol-2-yl)methylamino]pyrrolidin-1-yl}-6-propylpyrimidin-2-ylamino)benzonitrile;
(S)-3-{4-propyl-6-[3-(thiophen-2-ylmethylamino)pyrrolidin-1-yl]pyrimidin-2-ylamino}benzonitrile;
(S)-3-{4-propyl-6-[3-(thiophen-3-ylmethylamino)pyrrolidin-1-yl]pyrimidin-2-ylamino}benzonitrile;
(S)-3-{4-[3-(dibutylamino)pyrrolidin-1-yl]-6-propylpyrimidin-2-ylamino}benzonitrile;
(S)-3-(4-{3-bis[3-(methylthio)propyl]aminopyrrolidin-1-yl}-6-propylpyrimidin-2-ylamino)benzonitrile;
(S)-3-{4-[3-(butylamino)pyrrolidin-1-yl]-6-propylpyrimidin-2-ylamino}benzonitrile;
(S)-3-(4-{3-[3-(methylthio)propylamino]pyrrolidin-1-yl}-6-propylpyrimidin-2-ylamino)benzonitrile;
(S)-N-{4-[3-(methylamino)pyrrolidin-1-yl]-6-propylpyrimidin-2-yl}-1H-indol-6-amine;
(S)-N$^1$-{4-[3-(methylamino)pyrrolidin-1-yl]-6-propylpyrimidin-2-yl}-3-(trifluoromethyl)benzene-1,4-diamine;
(S)-N-{1-[2-(3-cyanophenylamino)-6-propylpyrimidin-4-yl]pyrrolidin-3-yl}isopropane-2-sulfonamide;
(S)-N-{1-[2-(3-cyanophenylamino)-6-propylpyrimidin-4-yl]pyrrolidin-3-yl}methanesulfonamide;
(S)-N-{1-[2-(3-cyanophenylamino)-6-propylpyrimidin-4-yl]pyrrolidin-3-yl}-4-fluorobenzenesulfonamide;
3-{4-[(3S)-3-(sec-butylamino)pyrrolidin-1-yl]-6-propylpyrimidin-2-ylamino}benzonitrile;
(S)-3-{4-[3-(pentan-3-ylamino)pyrrolidin-1-yl]-6-propylpyrimidin-2-ylamino}benzonitrile;
(S)-3-{4-[3-(2,6-dimethylheptan-4-ylamino)pyrrolidin-1-yl]-6-propylpyrimidin-2-ylamino}benzonitrile;
(S)-3-{4-[3-(4,4-dimethylpentan-2-ylamino)pyrrolidin-1-yl]-6-propylpyrimidin-2-ylamino}benzonitrile;
(S)-3-{4-[3-(3-hydroxy-3-methylbutan-2-ylamino)pyrrolidin-1-yl]-6-propylpyrimidin-2-ylamino}benzonitrile;
(S)-3-{4-[3-(heptan-4-ylamino)pyrrolidin-1-yl]-6-propylpyrimidin-2-ylamino}benzonitrile;
(S)-3-{4-[3-(n-hexan-2-ylamino)pyrrolidin-1-yl]-6-propylpyrimidin-2-ylamino}benzonitrile;
(S)-3-{4-[3-(5-methylhexan-2-ylamino)pyrrolidin-1-yl]-6-propylpyrimidin-2-ylamino}benzonitrile;
(S)-3-{4-[3-(cyclohexylamino)pyrrolidin-1-yl]-6-propylpyrimidin-2-ylamino}benzonitrile;
(S)-tert-butyl 2-{1-[2-(3-cyanophenylamino)-6-propylpyrimidin-4-yl]pyrrolidin-3-ylamino}ethylcarbamate;
(S)-3-{4-[3-(1-benzylpiperidin-4-ylamino)pyrrolidin-1-yl]-6-propylpyrimidin-2-ylamino}benzonitrile;
(S)-3-{4-[3-(isopropylamino)pyrrolidin-1-yl]-6-propylpyrimidin-2-ylamino}benzonitrile;
(S)-3-{4-[3-(1-benzoylpiperidin-4-ylamino)pyrrolidin-1-yl]-6-propylpyrimidin-2-ylamino}benzonitrile;
(S)-3-{4-[3-(1-acetylpiperidin-4-ylamino)pyrrolidin-1-yl]-6-propylpyrimidin-2-ylamino}benzonitrile;

(S)-3-{4-[3-(cyclooctylamino)pyrrolidin-1-yl]-6-propylpyrimidin-2-ylamino}benzonitrile;
(S)-3-{4-[3-(cyclobutylamino)pyrrolidin-1-yl]-6-propylpyrimidin-2-ylamino}benzonitrile;
(S)-3-{4-[3-(cyclopentylamino)pyrrolidin-1-yl]-6-propylpyrimidin-2-ylamino}benzonitrile;
(S)-tert-butyl 3-{1-[2-(3-cyanophenylamino)-6-propylpyrimidin-4-yl]pyrrolidin-3-ylamino}azetidine-1-carboxylate;
(S)-3-(4-{3-[2-(benzyloxy)ethylamino]pyrrolidin-1-yl}-6-propylpyrimidin-2-ylamino)benzonitrile;
(S)-N-{1-[2-(3-cyanophenylamino)-6-propylpyrimidin-4-yl]pyrrolidin-3-yl}propionamide;
(S)-N-{1-[2-(3-cyanophenylamino)-6-propylpyrimidin-4-yl]pyrrolidin-3-yl}pivalamide;
(S)-N-{1-[2-(3-cyanophenylamino)-6-propylpyrimidin-4-yl]pyrrolidin-3-yl}-2,2-dimethylbutanamide;
(S,E)-N-{1-[2-(3-cyanophenylamino)-6-propylpyrimidin-4-yl]pyrrolidin-3-yl}-2-methylbut-2-enamide;
(S)-N-{1-[2-(3-cyanophenylamino)-6-propylpyrimidin-4-yl]pyrrolidin-3-yl}hexanamide;
(S)-N-{1-[2-(3-cyanophenylamino)-6-propylpyrimidin-4-yl]pyrrolidin-3-yl}-3-phenylpropanamide;
(S)-N-{1-[2-(3-cyanophenylamino)-6-propylpyrimidin-4-yl]pyrrolidin-3-yl}-2-(1H-indol-3-yl)acetamide;
(S)-N-{1-[2-(3-cyanophenylamino)-6-propylpyrimidin-4-yl]pyrrolidin-3-yl}-2-hydroxy-2-methylpropanamide;
(S)-N-{1-[2-(3-cyanophenylamino)-6-propylpyrimidin-4-yl]pyrrolidin-3-yl}-3-(4-methoxyphenyl)propanamide;
(S)-N-{1-[2-(3-cyanophenylamino)-6-propylpyrimidin-4-yl]pyrrolidin-3-yl}-3-(4-hydroxyphenyl)propanamide;
(S)-N-{1-[2-(3-cyanophenylamino)-6-propylpyrimidin-4-yl]pyrrolidin-3-yl}-4-oxopentanamide;
(S)-N-{1-[2-(3-cyanophenylamino)-6-propylpyrimidin-4-yl]pyrrolidin-3-yl}-2-hydroxyacetamide;
(S)-2-benzyloxy-N-{1-[2-(3-cyanophenylamino)-6-propylpyrimidin-4-yl]pyrrolidin-3-yl}acetamide;
(S)-N-{1-[2-(3-cyanophenylamino)-6-propylpyrimidin-4-yl]pyrrolidin-3-yl}-2-phenoxyacetamide;
(S)-N-{1-[2-(3-cyanophenylamino)-6-propylpyrimidin-4-yl]pyrrolidin-3-yl}-2-(dimethylamino)acetamide;
(S)-N-{1-[2-(3-cyanophenylamino)-6-propylpyrimidin-4-yl]pyrrolidin-3-yl}-3-(dimethylamino)propanamide;
(S)-N-{1-[2-(3-cyanophenylamino)-6-propylpyrimidin-4-yl]pyrrolidin-3-yl}-4-dimethylaminobutanamide;
N-(S)-{1-[2-(3-cyanophenylamino)-6-propylpyrimidin-4-yl]pyrrolidin-3-yl}-2-ethoxyacetamide;
N-(S)-{1-[2-(3-cyanophenylamino)-6-propylpyrimidin-4-yl]pyrrolidin-3-yl}-2-(2-methoxyethoxy)acetamide;
(S)-benzyl 2-{1-[2-(3-cyanophenylamino)-6-propylpyrimidin-4-yl]pyrrolidin-3-ylamino}-2-oxoethylcarbamate;
(S)-tert-butyl 3-{1-[2-(3-cyanophenylamino)-6-propylpyrimidin-4-yl]pyrrolidin-3-ylamino}-3-oxobutylcarbamate;
(S)-tert-butyl 4-{1-[2-(3-cyanophenylamino)-6-propylpyrimidin-4-yl]pyrrolidin-3-ylcarbamoyl}piperidine-1-carboxylate;
(R)-2-methyl-5-[4-(2-methylpyrrolidin-1-yl)-6-propylpyrimidin-2-ylamino]benzonitrile;
(R)-2-amino-5-[4-(2-methylpyrrolidin-1-yl)-6-propylpyrimidin-2-ylamino]benzonitrile;
(S)-2-methyl-5-{4-[3-(methylamino)pyrrolidin-1-yl]-6-propylpyrimidin-2-ylamino}benzonitrile;
(S)-5-{4-[3-(ethylamino)pyrrolidin-1-yl]-6-propylpyrimidin-2-ylamino}-2-methylbenzonitrile;
5-{4-[3-(ethylamino)pyrrolidin-1-yl]-6-propylpyrimidin-2-ylamino}-2-methylbenzonitrile;
(S)-N$^1$-{4-[3-(methylamino)pyrrolidin-1-yl]-6-propylpyrimidin-2-yl}-3-nitrobenzene-1,4-diamine;
(S)-N$^1$-{4-[3-(ethylamino)pyrrolidin-1-yl]-6-propylpyrimidin-2-yl}-3-nitrobenzene-1,4-diamine;
(R)-3-{4-[3-(aminomethyl)pyrrolidin-1-yl]-6-propylpyrimidin-2-ylamino}benzonitrile;
(S)-2-fluoro-5-{4-[3-(methylamino)pyrrolidin-1-yl]-6-propylpyrimidin-2-ylamino}benzonitrile;
(S)-2-fluoro-5-{4-[3-(ethylamino)pyrrolidin-1-yl]-6-propylpyrimidin-2-ylamino}benzonitrile;
5-[4-(3-aminopyrrolidin-1-yl)-6-propylpyrimidin-2-ylamino]-2-fluorobenzonitrile;
N-(4-fluorophenyl)-4-methyl-6-(pyrrolidin-1-yl)pyrimidin-2-amine;
(3R,5S)-1-[2-(4-fluorophenyl)-6-propylpyrimidin-4-yl]-5-(hydroxymethyl)pyrrolidin-3-ol;
(S)-{1-[2-(1H-indol-6-ylamino)-6-propylpyrimidin-4-yl]pyrrolidin-2-yl}methanol;
(R)-{1-[2-(1H-indol-6-ylamino)-6-propylpyrimidin-4-yl]pyrrolidin-2-yl}methanol;
{1-[2-(1H-indol-6-ylamino)-6-propylpyrimidin-4-yl]pyrrolidin-2-yl}methanol;
(R)-N-{4-[2-(methoxymethyl)pyrrolidin-1-yl]-6-propylpyrimidin-2-yl}-1H-indol-6-amine;
N-[4-(2-methylpyrrolidin-1-yl)-6-propylpyrimidin-2-yl]-1H-indol-6-amine;
(S)-methyl 1-[2-(1H-indol-6-ylamino)-6-propylpyrimidin-4-yl]pyrrolidine-2-carboxylate;
N-{1-[2-(1H-indol-6-ylamino)-6-propylpyrimidin-4-yl]pyrrolidin-3-yl}acetamide;
(S)-3-{4-[2-(hydroxymethyl)pyrrolidin-1-yl]-6-propylpyrimidin-2-ylamino}benzonitrile;
(S)-(1-{2-[3-(methylthio)phenylamino]-6-propylpyrimidin-4-yl}pyrrolidin-2-yl)methanol;
(S)-{1-[2-(4-chloro-3-nitrophenylamino)-6-propylpyrimidin-4-yl]pyrrolidin-2-yl}methanol;
(S)-{1-[2-(1H-indol-5-ylamino)-6-propylpyrimidin-4-yl]pyrrolidin-2-yl}methanol;
(S)-{1-[2-(1H-benzo[d]imidazol-5-ylamino)-6-propylpyrimidin-4-yl]pyrrolidin-2-yl}methanol;
(S)-(1-{6-propyl-2-[2-(trifluoromethyl)-1H-benzo[d]imidazol-5-ylamino]pyrimidin-4-yl}pyrrolidin-2-yl)methanol;
(S)-{1-[2-(4-methoxyphenylamino)-6-propylpyrimidin-4-yl]pyrrolidin-2-yl}methanol;
(S)-{1-[2-(3-chlorophenylamino)-6-propylpyrimidin-4-yl]pyrrolidin-2-yl}methanol;
(S)-{1-[2-(3-methoxyphenylamino)-6-propylpyrimidin-4-yl]pyrrolidin-2-yl}methanol;
(S)-(1-{6-propyl-2-[3-(trifluoromethyl)phenylamino]pyrimidin-4-yl}pyrrolidin-2-yl)methanol;
(S)-{1-[2-(5-chloro-2-methylphenylamino)-6-propylpyrimidin-4-yl]pyrrolidin-2-yl}methanol;
(S)-{1-[2-(5-methoxy-2-methylphenylamino)-6-propylpyrimidin-4-yl]pyrrolidin-2-yl}methanol;
(S)-{1-[2-(3-chloro-4-methylphenylamino)-6-propylpyrimidin-4-yl]pyrrolidin-2-yl}methanol;
(S)-{1-[2-(3-nitrophenylamino)-6-propylpyrimidin-4-yl]pyrrolidin-2-yl}methanol;
(S)-{1-[2-(4-fluoro-3-nitrophenylamino)-6-propylpyrimidin-4-yl]pyrrolidin-2-yl}methanol;
(S)-{1-[6-propyl-2-(quinolin-6-ylamino)pyrimidin-4-yl]pyrrolidin-2-yl}methanol;

(S)-{1-[2-(4-methyl-3-nitrophenylamino)-6-propylpyrimidin-4-yl]pyrrolidin-2-yl}methanol;
(S)-(1-{2-[4-amino-3-(trifluoromethyl)phenylamino]-6-propylpyrimidin-4-yl}pyrrolidin-2-yl)methanol;
(S)-{1-[2-(4-amino-3-nitrophenylamino)-6-propylpyrimidin-4-yl]pyrrolidin-2-yl}methanol;
(S)-5-{4-[2-(hydroxymethyl)pyrrolidin-1-yl]-6-propylpyrimidin-2-ylamino}-2-methylbenzonitrile;
(S)-2-fluoro-5-{4-[2-(hydroxymethyl)pyrrolidin-1-yl]-6-propylpyrimidin-2-ylamino}benzonitrile;
(S)-2-amino-5-{4-[2-(hydroxymethyl)pyrrolidin-1-yl]-6-propylpyrimidin-2-ylamino}benzonitrile;
(S)-{1-[6-propyl-2-(quinolin-3-ylamino)pyrimidin-4-yl]pyrrolidin-2-yl}methanol;
(S)-{1-[2-(indolin-6-ylamino)-6-propylpyrimidin-4-yl]pyrrolidin-2-yl}methanol;
(S)-3-{4-[3-(aminoethylamino)pyrrolidin-1-yl]-6-propylpyrimidin-2-ylamino}benzonitrile;
(S)-3-{4-[3-(piperidin-4-ylamino)pyrrolidin-1-yl]-6-propylpyrimidin-2-ylamino}benzonitrile;
(S)-3-{4-[3-(1-butylpipendin-4-ylamino)pyrrolidin-1-yl]-6-propylpyrimidin-2-ylamino}benzonitrile;
(S)-N-{1-[6-butyl-2-(3-cyanophenylamino)pyrimidin-4-yl]pyrrolidin-3-yl}acetamide;
(S)-3-{4-butyl-6-[2-(hydroxymethyl)pyrrolidin-1-yl]pyrimidin-2-ylamino}benzonitrile;
(R)-3-[4-butyl-6-(2-methylpyrrolidin-1-yl)pyrimidin-2-ylamino]benzonitrile;
(S)-3-{4-butyl-6-[3-(methylamino)pyrrolidin-1-yl]pyrimidin-2-ylamino}benzonitrile;
(S)-tert-butyl 1-[6-butyl-2-(3-cyanophenylamino)pyrimidin-4-yl]pyrrolidin-3-ylcarbamate;
(S)-N-{1-[6-butyl-2-(3-cyano-4-methylphenylamino)pyrimidin-4-yl]pyrrolidin-3-yl}acetamide;
(S)-5-{4-butyl-6-[2-(hydroxymethyl)pyrrolidin-1-yl]pyrimidin-2-ylamino}-2-methylbenzonitrile;
(R)-5-[4-butyl-6-(2-methylpyrrolidin-1-yl)pyrimidin-2-ylamino]-2-methylbenzonitrile;
(S)-5-{4-butyl-6-[3-(methylamino)pyrrolidin-1-yl]pyrimidin-2-ylamino}-2-methylbenzonitrile;
(S)-tert-butyl 1-[6-butyl-2-(3-cyano-4-methylphenylamino)pyrimidin-4-yl]pyrrolidin-3-ylcarbamate;
(S)-3-[4-(3-aminopyrrolidin-1-yl)-6-butylpyrimidin-2-ylamino]benzonitrile;
(S)-5-[4-(3-aminopyrrolidin-1-yl)-6-butylpyrimidin-2-ylamino]-2-methylbenzonitrile;
(S)-3-{4-butyl-6-[3-(isopropylamino)pyrrolidin-1-yl]pyrimidin-2-ylamino}benzonitrile;
(S)-3-{4-butyl-6-[3-(diethylamino)pyrrolidin-1-yl]pyrimidin-2-ylamino}benzonitrile;
(S)-3-{4-butyl-6-[3-(cyclopropylmethylamino)pyrrolidin-1-yl]pyrimidin-2-ylamino}benzonitrile;
(S)-5-{4-butyl-6-[3-(isopropylamino)pyrrolidin-1-yl]pyrimidin-2-ylamino}-2-methylbenzonitrile;
(S)-5-{4-butyl-6-[3-(diethylamino)pyrrolidin-1-yl]pyrimidin-2-ylamino}-2-methylbenzonitrile;
(S)-5-{4-butyl-6-[3-(cyclopropylmethylamino)pyrrolidin-1-yl]pyrimidin-2-ylamino}-2-methylbenzonitrile;
(S)-N-{1-[2-(4-chloro-3-nitrophenylamino)-6-propylpyrimidin-4-yl]pyrrolidin-3-yl}acetamide;
(S)-N-(1-{2-[3-(methylthio)phenylamino]-6-propylpyrimidin-4-yl}pyrrolidin-3-yl)acetamide;
(S)-N-{1-[2-(1H-indol-6-ylamino)-6-propylpyrimidin-4-yl]pyrrolidin-3-yl}acetamide;
(S)-N-(1-{6-propyl-2-[3-(trifluoromethyl)phenylamino]pyrimidin-4-yl}pyrrolidin-3-yl)acetamide;
(S)-N-{1-[2-(4-methyl-2-oxo-2H-chromen-7-ylamino)-6-propylpyrimidin-4-yl]pyrrolidin-3-yl}acetamide;
(S)-N-{1-[2-(3-chloro-4-methylphenylamino)-6-propylpyrimidin-4-yl]pyrrolidin-3-yl}acetamide;
(S)-N-{1-[2-(3-nitrophenylamino)-6-propylpyrimidin-4-yl]pyrrolidin-3-yl}acetamide;
(S)-N-{1-[2-(4-fluoro-3-nitrophenylamino)-6-propylpyrimidin-4-yl]pyrrolidin-3-yl}acetamide;
(S)-N-{1-[2-(4-methyl-3-nitrophenylamino)-6-propylpyrimidin-4-yl]pyrrolidin-3-yl}acetamide;
(S)-benzyl 5-[4-(3-acetamidopyrrolidin-1-yl)-6-propylpyrimidin-2-ylamino]-2-methoxyphenylcarbamate;
(S)-N-{1-[2-(3-cyano-4-fluorophenylamino)-6-propylpyrimidin-4-yl]pyrrolidin-3-yl}acetamide;
(S)-N-{1-[2-(3-cyano-4-methylphenylamino)-6-propylpyrimidin-4-yl]pyrrolidin-3-yl}acetamide;
(S)-N-(1-{2-[4-fluoro-3-(trifluoromethyl)phenylamino]-6-propylpyrimidin-4-yl}pyrrolidin-3-yl)acetamide;
(S)-N-{1-[2-(4-amino-3-nitrophenylamino)-6-propylpyrimidin-4-yl]pyrrolidin-3-yl}acetamide;
(S)-N-{1-[2-(5-chloro-2-methylphenylamino)-6-propylpyrimidin-4-yl]pyrrolidin-3-yl}acetamide;
(S)-3-[4-(3-acetamidopyrrolidin-1-yl)-6-propylpyrimidin-2-ylamino]benzamide;
(S)-3-{[4-(3-acetamidopyrrolidin-1-yl)-6-propylpyrimidin-2-yl]amino}-N-methylbenzamide;
(S)-N-[1-(2-{[3-(aminomethyl)phenyl]amino}-6-propylpyrimidin-4-yl)pyrrolidin-3-yl]acetamide;
(S)-3-{[4-(3-acetamidopyrrolidin-1-yl)-6-propylpyrimidin-2-yl]amino}-4-chlorobenzamide;
(S)-N-{1-[2-(4-amino-3-cyanophenylamino)-6-propylpyrimidin-4-yl]pyrrolidin-3-yl}acetamide;
(S)-N-(1-{2-[4-amino-3-(trifluoromethyl)phenylamino]-6-propylpyrimidin-4-yl}pyrrolidin-3-yl)acetamide;
(S)-N-{1-[2-(3-amino-5-cyanophenylamino)-6-propylpyrimidin-4-yl]pyrrolidin-3-yl}acetamide;
(S)-N-{1-[2-(3-amino-4-fluorophenylamino)-6-propylpyrimidin-4-yl]pyrrolidin-3-yl}acetamide;
(S)-N-(1-{2-[3-amino-5-(trifluoromethyl)phenylamino]-6-propylpyrimidin-4-yl}pyrrolidin-3-yl)acetamide;
(S)-N-(1-{2-[(4-aminophenyl)amino]-6-propylpyrimidin-4-yl}pyrrolidin-3-yl)acetamide;
(S)-N-(1-{2-[(4-chloro-3-hydroxyphenyl)amino]-6-propylpyrimidin-4-yl}pyrrolidin-3-yl)acetamide;
(S)-4-{[4-(3-acetamidopyrrolidin-1-yl)-6-propylpyrimidin-2-yl]amino}-2-hydroxybenzoic acid;
(S)-5-{[4-(3-acetamidopyrrolidin-1-yl)-6-propylpyrimidin-2-yl]amino}-2-hydroxybenzoic acid;
(S)-N-(1-{2-[(3-hydroxy-4-methylphenyl)amino]-6-propylpyrimidin-4-yl}pyrrolidin-3-yl)acetamide;
(S)-N-(1-{2-[(3-chloro-4-hydroxyphenyl)amino]-6-propylpyrimidin-4-yl}pyrrolidin-3-yl)acetamide;
(S)-N-(1-{2-[(4-hydroxy-3-methylphenyl)amino]-6-propylpyrimidin-4-yl}pyrrolidin-3-yl)acetamide;
(S)-N-(1-{2-[(3-fluoro-4-hydroxyphenyl)amino]-6-propylpyrimidin-4-yl}pyrrolidin-3-yl)acetamide;
(S)-N-(1-{2-[(3-hydroxy-4-methoxyphenyl)amino]-6-propylpyrimidin-4-yl}pyrrolidin-3-yl)acetamide;
(S)-N-(1-{2-[(3-methoxy-4-methylphenyl)amino]-6-propylpyrimidin-4-yl}pyrrolidin-3-yl)acetamide;
(S)-N-[1-(2-{[4-methyl-3-(trifluoromethyl)phenyl]amino}-6-propylpyrimidin-4-yl)pyrrolidin-3-yl]acetamide;
(S)-N-(1-{2-[(3,4-dimethylphenyl)amino]-6-propylpyrimidin-4-yl}pyrrolidin-3-yl)acetamide;
(S)-N-(1-{2-[(3-fluoro-4-methylphenyl)amino]-6-propylpyrimidin-4-yl}pyrrolidin-3-yl)acetamide;

(S)-N-{1-[2-(3-amino-4-methoxyphenylamino)-6-propylpyrimidin-4-yl]pyrrolidin-3-yl}acetamide;
(S)-N-{1-[2-(3-amino-4-chlorophenylamino)-6-propylpyrimidin-4-yl]pyrrolidin-3-yl}acetamide;
(S)-N-{1-[2-(3-amino-4-methylphenylamino)-6-propylpyrimidin-4-yl]pyrrolidin-3-yl}acetamide;
N-{1-[2-(4-amino-3-nitrophenylamino)-6-propylpyrimidin-4-yl]pyrrolidin-3-yl}acetamide
N-{1-[2-(3-cyanophenylamino)-6-propylpyrimidin-4-yl]pyrrolidin-3-yl}acetamide;
N-{1-[2-(3-nitrophenylamino)-6-propylpyrimidin-4-yl]pyrrolidin-3-yl}acetamide;
N-{1-[2-(4-fluoro-3-nitrophenylamino)-6-propylpyrimidin-4-yl]pyrrolidin-3-yl}acetamide;
N-{1-[2-(4-chloro-3-nitrophenylamino)-6-propylpyrimidin-4-yl]pyrrolidin-3-yl}acetamide;
N-{1-[2-(3-methoxyphenylamino)-6-propylpyrimidin-4-yl]pyrrolidin-3-yl}acetamide;
N-{1-[2-(5-methoxy-2-methylphenylamino)-6-propylpyrimidin-4-yl]pyrrolidin-3-yl}acetamide;
N-{1-[2-(4-methoxyphenylamino)-6-propylpyrimidin-4-yl]pyrrolidin-3-yl}acetamide;
N-(1-{6-propyl-2-[3-(trifluoromethyl)phenylamino]pyrimidin-4-yl}pyrrolidin-3-yl)acetamide;
N-{1-[2-(3-chlorophenylamino)-6-propylpyrimidin-4-yl]pyrrolidin-3-yl}acetamide;
N-{1-[2-(5-chloro-2-methylphenylamino)-6-propylpyrimidin-4-yl]pyrrolidin-3-yl}acetamide;
N-{1-[2-(3-chloro-4-methylphenylamino)-6-propylpyrimidin-4-yl]pyrrolidin-3-yl}acetamide;
N-(1-{2-[3-(methylthio)phenylamino]-6-propylpyrimidin-4-yl}pyrrolidin-3-yl)acetamide;
N-{1-[2-(1H-indol-5-ylamino)-6-propylpyrimidin-4-yl]pyrrolidin-3-yl}acetamide;
N-(1-{6-propyl-2-[2-(trifluoromethyl)-1H-benzo[d]imidazol-5-ylamino]pyrimidin-4-yl}pyrrolidin-3-yl)acetamide;
N-{1-[6-propyl-2-(quinolin-6-ylamino)pyrimidin-4-yl]pyrrolidin-3-yl}acetamide;
N-{1-[2-(4-methyl-2-oxo-2H-chromen-7-ylamino)-6-propylpyrimidin-4-yl]pyrrolidin-3-yl}acetamide;
N-{1-[6-propyl-2-(quinolin-3-ylamino)pyrimidin-4-yl]pyrrolidin-3-yl}acetamide;
N-{1-[2-(4-amino-3-cyanophenylamino)-6-propylpyrimidin-4-yl]pyrrolidin-3-yl}acetamide;
N-{1-[2-(3-amino-4-fluorophenylamino)-6-propylpyrimidin-4-yl]pyrrolidin-3-yl}acetamide;
(R)-N-(4-chloro-3-nitrophenyl)-4-(2-methylpyrrolidin-1-yl)-6-propylpyrimidin-2-amine;
(R)-4-(2-methylpyrrolidin-1-yl)-N-[3-(methylthio)phenyl]-6-propylpyrimidin-2-ylamine;
(R)-N-[4-(2-methylpyrrolidin-1-yl)-6-propylpyrimidin-2-yl]-1H-indol-6-amine;
(R)-4-(2-methylpyrrolidin-1-yl)-6-propyl-N-[3-(trifluoromethyl)phenyl]pyrimidin-2-amine;
(R)-4-methyl-7-[4-(2-methylpyrrolidin-1-yl)-6-propylpyrimidin-2-ylamino]-2H-chromen-2-one;
(R)-N-(3-chloro-4-methylphenyl)-4-(2-methylpyrrolidin-1-yl)-6-propylpyrimidin-2-amine;
(R)-4-(2-methylpyrrolidin-1-yl)-N-(3-nitrophenyl)-6-propylpyrimidin-2-ylamine;
(R)-N-(4-fluoro-3-nitrophenyl)-4-(2-methylpyrrolidin-1-yl)-6-propylpyrimidin-2-amine;
(R)-N-(4-methyl-3-nitrophenyl)-4-(2-methylpyrrolidin-1-yl)-6-propylpyrimidin-2-amine;
(R)-N-[4-fluoro-3-(trifluoromethyl)phenyl]-4-(2-methylpyrrolidin-1-yl)-6-propylpyrimidin-2-ylamine;
(R)-$N^1$-[4-(2-methylpyrrolidin-1-yl)-6-propylpyrimidin-2-yl]-3-(trifluoromethyl)benzene-1,4-diamine;
(R)-benzyl 2-methoxy-5-[4-(2-methylpyrrolidin-1-yl)-6-propylpyrimidin-2-ylamino]phenylcarbamate;
(R)-2-fluoro-5-[4-(2-methylpyrrolidin-1-yl)-6-propylpyrimidin-2-ylamino]benzonitrile;
(R)-$N^1$-[4-(2-methylpyrrolidin-1-yl)-6-propylpyrimidin-2-yl]-3-nitrobenzene-1,4-diamine;
(R)-1-{6-[4-(2-methylpyrrolidin-1-yl)-6-propylpyrimidin-2-ylamino]indolin-1-yl}ethanone;
(R)-N-(5-chloro-2-methylphenyl)-4-(2-methylpyrrolidin-1-yl)-6-propylpyrimidin-2-amine;
(R)-4-methoxy-$N^1$-[4-(2-methylpyrrolidin-1-yl)-6-propylpyrimidin-2-yl]benzene-1,3-diamine;
(R)-4-chloro-$N^1$-[4-(2-methylpyrrolidin-1-yl)-6-propylpyrimidin-2-yl]benzene-1,3-diamine;
(R)-4-fluoro-$N^1$-[4-(2-methylpyrrolidin-1-yl)-6-propylpyrimidin-2-yl]benzene-1,3-diamine;
(R)-4-methyl-$N^1$-[4-(2-methylpyrrolidin-1-yl)-6-propylpyrimidin-2-yl]benzene-1,3-diamine;
(S)-3-{4-[3-(2-hydroxyethylamino)pyrrolidin-1-yl]-6-propylpyrimidin-2-ylamino}benzonitrile;
(S)-N-{1-[2-(4-amino-3-nitrophenylamino)-6-butylpyrimidin-4-yl]pyrrolidin-3-yl}acetamide;
(S)-$N^1$-{4-butyl-6-[3-(methylamino)pyrrolidin-1-yl]pyrimidin-2-yl}-3-nitrobenzene-1,4-diamine;
(S)-$N^1$-[4-(3-aminopyrrolidin-1-yl)-6-propylpyrimidin-2-yl]-5-(trifluoromethyl)benzene-1,3-diamine;
(S)-$N^1$-[4-(3-aminopyrrolidin-1-yl)-6-propylpyrimidin-2-yl]-3-methylbenzene-1,4-diamine;
(S)-4-(3-aminopyrrolidin-1-yl)-N-(4-chloro-3-nitrophenyl)-6-propylpyrimidin-2-amine;
(S)-4-(3-aminopyrrolidin-1-yl)-N-[3-(methylthio)phenyl]-6-propylpyrimidin-2-amine;
(S)-N-[4-(3-aminopyrrolidin-1-yl)-6-propylpyrimidin-2-yl]-1H-indol-6-amine;
(S)-4-(3-aminopyrrolidin-1-yl)-6-propyl-N-[3-(trifluoromethyl)phenyl]pyrimidin-2-amine;
(S)-4-(3-aminopyrrolidin-1-yl)-N-(5-chloro-2-methylphenyl)-6-propylpyrimidin-2-amine;
(S)-4-(3-aminopyrrolidin-1-yl)-N-(3-chloro-4-methylphenyl)-6-propylpyrimidin-2-amine;
(S)-4-(3-aminopyrrolidin-1-yl)-N-(3-nitrophenyl)-6-propylpyrimidin-2-amine;
(S)-4-(3-aminopyrrolidin-1-yl)-N-(4-methyl-3-nitrophenyl)-6-propylpyrimidin-2-amine;
(S)-$N^1$-[4-(3-aminopyrrolidin-1-yl)-6-propylpyrimidin-2-yl]-3-(trifluoromethyl)benzene-1,4-diamine;
(S)-5-[4-(3-aminopyrrolidin-1-yl)-6-propylpyrimidin-2-ylamino]-2-fluorobenzonitrile;
(S)-5-[4-(3-aminopyrrolidin-1-yl)-6-propylpyrimidin-2-ylamino]-2-methylbenzonitrile;
(S)-2-amino-5-[4-(3-aminopyrrolidin-1-yl)-6-propylpyrimidin-2-ylamino]benzonitrile;
(S)-benzyl 5-[4-(3-aminopyrrolidin-1-yl)-6-propylpyrimidin-2-ylamino]-2-methoxyphenylcarbamate;
(S)-4-(3-aminopyrrolidin-1-yl)-N-[4-fluoro-3-(trifluoromethyl)phenyl]-6-propylpyrimidin-2-amine;
(S)-4-(3-aminopyrrolidin-1-yl)-N-(4-fluoro-3-nitrophenyl)-6-propylpyrimidin-2-amine;
(S)-$N^1$-[4-(3-aminopyrrolidin-1-yl)-6-propylpyrimidin-2-yl]-3-nitrobenzene-1,4-diamine;
(S)-4-(3-aminopyrrolidin-1-yl)-N-[3,5-bis(trifluoromethyl)phenyl]-6-propylpyrimidin-2-amine;
(S)-4-(3-aminopyrrolidin-1-yl)-N-(3,5-dimethoxyphenyl)-6-propylpyrimidin-2-amine;

(S)-3-amino-5-{[4-(3-aminopyrrolidin-1-yl)-6-propylpyrimidin-2-yl]amino}benzonitrile;
(S)-3-[4-(3-aminopyrrolidin-1-yl)-6-propylpyrimidin-2-ylamino]benzenesulfonamide;
(S)-N¹-{4-[2-(methoxymethyl)pyrrolidin-1-yl]-6-propylpyrimidin-2-yl}benzene-1,3-diamine;
(S)-4-fluoro-N¹-{4-[2-(methoxymethyl)pyrrolidin-1-yl]-6-propylpyrimidin-2-yl}benzene-1,3-diamine;
(S)-N¹-{4-[2-(methoxymethyl)pyrrolidin-1-yl]-6-propylpyrimidin-2-yl}-4-methylbenzene-1,3-diamine;
(S)-4-methoxy-N¹-{4-[2-(methoxymethyl)pyrrolidin-1-yl]-6-propylpyrimidin-2-yl}benzene-1,3-diamine;
(S)-N-{4-[2-(methoxymethyl)pyrrolidin-1-0]-6-propylpyrimidin-2-yl}indolin-6-amine;
(S)-N¹-[4-(3-aminopyrrolidin-1-yl)-6-propylpyrimidin-2-yl]-4-methylbenzene-1,3-diamine;
(S)-N¹-[4-(3-aminopyrrolidin-1-yl)-6-propylpyrimidin-2-yl]-4-fluorobenzene-1,3-diamine;
(S)-N-(4-chloro-3-nitrophenyl)-4-[3-(cyclopropylmethylamino)pyrrolidin-1-yl]-6-propylpyrimidin-2-amine;
(S)-4-[3-(cyclopropylmethylamino)pyrrolidin-1-yl]-N-(4-fluoro-3-nitrophenyl)-6-propylpyrimidin-2-amine;
(S)-4-[3-(cyclopropylmethylamino)pyrrolidin-1-yl]-N-(4-methyl-3-nitrophenyl)-6-propylpyrimidin-2-amine;
(S)-4-[3-(cyclopropylmethylamino)pyrrolidin-1-yl]-N-(3-nitrophenyl)-6-propylpyrimidin-2-amine;
(S)-5-{4-[3-(cyclopropylmethylamino)pyrrolidin-1-yl]-6-propylpyrimidin-2-ylamino}-2-fluorobenzonitrile;
(S)-5-{4-[3-(cyclopropylmethylamino)pyrrolidin-1-yl]-6-propylpyrimidin-2-ylamino}-2-methylbenzonitrile;
(S)-4-[3-(cyclopropylmethylamino)pyrrolidin-1-yl]-N-[3-(methylthio)phenyl]-6-propylpyrimidin-2-amine;
(S)-4-[3-(cyclopropylmethylamino)pyrrolidin-1-yl]-6-propyl-N-[3-(trifluoromethyl)phenyl]pyrimidin-2-amine;
(S)-N-(5-chloro-2-methylphenyl)-4-[3-(cyclopropylmethylamino)pyrrolidin-1-yl]-6-propylpyrimidin-2-amine;
(S)-N-(3-chloro-4-methylphenyl)-4-[3-(cyclopropylmethylamino)pyrrolidin-1-yl]-6-propylpyrimidin-2-amine;
(S)-4-[3-(cyclopropylmethylamino)pyrrolidin-1-yl]-N-[4-fluoro-3-(trifluoromethyl)phenyl]-6-propylpyrimidin-2-amine;
(S)-N¹-{4-[3-(cyclopropylmethylamino)pyrrolidin-1-yl]-6-propylpyrimidin-2-yl}-4-methylbenzene-1,3-diamine;
(S)-N¹-{4-[3-(cyclopropylmethylamino)pyrrolidin-1-yl]-6-propylpyrimidin-2-yl}benzene-1,3-diamine;
3-{4-[3-(cyclopropylmethylamino)pyrrolidin-1-yl]-6-propylpyrimidin-2-ylamino}benzonitrile;
(S)-{1-[6-ethyl-2-(4-fluorophenylamino)pyrimidin-4-yl]pyrrolidin-2-yl}methanol;
(S)-N-{1-[6-ethyl-2-(4-fluorophenylamino)pyrimidin-4-yl]pyrrolidin-3-yl}acetamide;
(S)-4-ethyl-N-(4-fluorophenyl)-6-(2-methoxymethylpyrrolidin-1-yl)pyrimidin-2-amine;
4-ethyl-N-(4-fluorophenyl)-6-(2-methylpyrrolidin-1-yl)pyrimidin-2-amine;
(S)-4-ethyl-6-[3-(ethylamino)pyrrolidin-1-yl]-N-(4-fluorophenyl)pyrimidin-2-amine;
(S)-3-[4-(3-phenoxypyrrolidin-1-yl)-6-propylpyrimidin-2-ylamino]benzonitrile;
(S)-2-amino-N-{1-[2-(3-cyanophenylamino)-6-propylpyrimidin-4-yl]pyrrolidin-3-yl}acetamide;
(S)-{1-[2-(3-amino-4-methylphenylamino)-6-propylpyrimidin-4-yl]pyrrolidin-2-yl}methanol;
(S)-{1-[2-(3-amino-4-fluorophenylamino)-6-propylpyrimidin-4-yl]pyrrolidin-2-yl}methanol;
(S)-{1-[2-(3-amino-4-chlorophenylamino)-6-propylpyrimidin-4-yl]pyrrolidin-2-yl}methanol;
(S)-3-[4-(2-formylpyrrolidin-1-yl)-6-propylpyrimidin-2-ylamino]benzonitrile;
(S)-3-(4-{2-[(methylamino)methyl]pyrrolidin-1-yl}-6-propylpyrimidin-2-ylamino)benzonitrile;
(S)-3-(4-{2-[(cyclobutylamino)methyl]pyrrolidin-1-yl}-6-propylpyrimidin-2-ylamino)benzonitrile;
(S)-3-(4-{2-[(4-fluorobenzylamino)methyl]pyrrolidin-1-yl}-6-propylpyrimidin-2-ylamino)benzonitrile;
(S)-3-(4-propyl-6-{2-[(propylamino)methyl]pyrrolidin-1-yl}pyrimidin-2-ylamino)benzonitrile;
(S)-3-(4-{2-[(2-hydroxyethylamino)methyl]pyrrolidin-1-yl}-6-propylpyrimidin-2-ylamino)benzonitrile;
(S)-2-methyl-5-{4-propyl-6-[3-(propylamino)pyrrolidin-1-yl]pyrimidin-2-ylamino}benzonitrile;
(S)-2-methyl-5-(4-{3-[3-(methylthio)propylamino]pyrrolidin-1-yl}-6-propylpyrimidin-2-ylamino)benzonitrile;
(S)-5-(4-{3-[(1H-pyrrol-2-yl)methylamino]pyrrolidin-1-yl}-6-propylpyrimidin-2-ylamino)-2-methylbenzonitrile;
(S)-5-{4-[3-(4-hydroxybenzylamino)pyrrolidin-1-yl]-6-propylpyrimidin-2-ylamino}-2-methylbenzonitrile;
(S)-5-{4-[3-(isopropylamino)pyrrolidin-1-yl]-6-propylpyrimidin-2-ylamino}-2-methylbenzonitrile;
(S)-5-{4-[3-(cyclobutylamino)pyrrolidin-1-yl]-6-propylpyrimidin-2-ylamino}-2-methylbenzonitrile;
(S)-5-{4-[3-(cyclopentylamino)pyrrolidin-1-yl]-6-propylpyrimidin-2-ylamino}-2-methylbenzonitrile;
(S)-5-{4-[3-(cyclohexylamino)pyrrolidin-1-yl]-6-propylpyrimidin-2-ylamino}-2-methylbenzonitrile;
(S)-2-methyl-5-{4-[3-(pentylamino)pyrrolidin-1-yl]-6-propylpyrimidin-2-ylamino}benzonitrile;
(S)-2-methyl-5-{4-[3-(neopentylamino)pyrrolidin-1-yl]-6-propylpyrimidin-2-ylamino}benzonitrile;
(S)-5-(4-{3-[(4,5-dimethylfuran-2-yl)methylamino]pyrrolidin-1-yl}-6-propylpyrimidin-2-ylamino)-2-methylbenzonitrile;
(S)-N-{1-[2-(3-cyano-4-methylphenylamino)-6-propylpyrimidin-4-yl]pyrrolidin-3-yl}propionamide;
(S)-N-{1-[2-(3-cyano-4-methylphenylamino)-6-propylpyrimidin-4-yl]pyrrolidin-3-yl}-2-phenylacetamide;
(S)-N-{1-[2-(3-cyano-4-methylphenylamino)-6-propylpyrimidin-4-yl]pyrrolidin-3-yl}-2-(piperidin-1-yl)acetamide;
(S)-N-{1-[2-(3-cyano-4-methylphenylamino)-6-propylpyrimidin-4-yl]pyrrolidin-3-yl}-2-(pyridin-3-yl)acetamide;
(S)-N-{1-[2-(3-cyano-4-methylphenylamino)-6-propylpyrimidin-4-yl]pyrrolidin-3-yl}-2-(pyridin-4-yl)acetamide;
(S)-N-{1-[2-(3-cyano-4-methylphenylamino)-6-propylpyrimidin-4-yl]pyrrolidin-3-yl}-2-(thiophen-2-yl)acetamide;
(S)-N-{1-[2-(3-cyano-4-methylphenylamino)-6-propylpyrimidin-4-yl]pyrrolidin-3-yl}methanesulfonamide;
(S)-1-(1-{2-[(3-cyano-4-methylphenyl)amino]-6-propylpyrimidin-4-yl}pyrrolidin-3-yl)-3-ethylurea;
(R)-3-(4-{3-[(diethylamino)methyl]pyrrolidin-1-yl}-6-propylpyrimidin-2-ylamino)benzonitrile;
(S)-N-{1-[6-butyl-2-(4-methyl-3-nitrophenylamino)pyrimidin-4-yl]pyrrolidin-3-yl}acetamide;
(S)-N-{1-[6-butyl-2-(4-fluoro-3-nitrophenylamino)pyrimidin-4-yl]pyrrolidin-3-yl}acetamide;

(S)-N-{1-[6-butyl-2-(4-chloro-3-nitrophenylamino)pyrimidin-4-yl]pyrrolidin-3-yl}acetamide;
(S)-N-{1-[2-(3-amino-5-cyanophenylamino)-6-butylpyrimidin-4-yl]pyrrolidin-3-yl}acetamide;
(S)-N-(1-{2-[3-amino-5-(trifluoromethyl)phenylamino]-6-butylpyrimidin-4-yl}pyrrolidin-3-yl)acetamide;
(S)-N-(1-{2-[4-amino-3-(trifluoromethyl)phenylamino]-6-butylpyrimidin-4-yl}pyrrolidin-3-yl)acetamide;
(S)-N-(1-{6-butyl-2-[4-fluoro-3-(trifluoromethyl)phenylamino]pyrimidin-4-yl}pyrrolidin-3-yl)acetamide;
(S)-N-{1-[6-butyl-2-(3-cyano-4-fluorophenylamino)pyrimidin-4-yl]pyrrolidin-3-yl}acetamide;
(S)-N-{1-[2-(3-amino-4-fluorophenylamino)-6-butylpyrimidin-4-yl]pyrrolidin-3-yl}acetamide;
(S)-N-{1-[2-(3-amino-4-chlorophenylamino)-6-butylpyrimidin-4-yl]pyrrolidin-3-yl}acetamide;
(S)-N-{1-[2-(4-amino-3-cyanophenylamino)-6-butylpyrimidin-4-yl]pyrrolidin-3-yl}acetamide;
(S)-2-amino-5-{4-butyl-6-[3-(methylamino)pyrrolidin-1-yl]pyrimidin-2-ylamino}benzonitrile;
(S)-4-butyl-N-(4-methyl-3-nitrophenyl)-6-[3-(methylamino)pyrrolidin-1-yl]pyrimidin-2-amine;
(S)-4-butyl-N-(4-fluoro-3-nitrophenyl)-6-[3-(methylamino)pyrrolidin-1-yl]pyrimidin-2-amine;
(S)-4-butyl-N-(4-chloro-3-nitrophenyl)-6-[3-(methylamino)pyrrolidin-1-yl]pyrimidin-2-amine;
(S)-3-amino-5-{4-butyl-6-[3-(methylamino)pyrrolidin-1-yl]pyrimidin-2-ylamino}benzonitrile;
(S)-$N^1$-{4-butyl-6-[3-(methylamino)pyrrolidin-1-yl]pyrimidin-2-yl}-5-(trifluoromethyl)benzene-1,3-diamine;
(S)-$N^1$-{4-butyl-6-[3-(methylamino)pyrrolidin-1-yl]pyrimidin-2-yl}-3-(trifluoromethyl)benzene-1,4-diamine;
(S)-4-butyl-N-[4-fluoro-3-(trifluoromethyl)phenyl]-6-[3-(methylamino)pyrrolidin-1-yl]pyrimidin-2-amine;
(S)-5-{4-butyl-6-[3-(methylamino)pyrrolidin-1-yl]pyrimidin-2-ylamino}-2-fluorobenzonitrile;
(S)-$N^1$-{4-butyl-6-[3-(methylamino)pyrrolidin-1-yl]pyrimidin-2-yl}-4-fluorobenzene-1,3-diamine;
(S)-$N^1$-{4-butyl-6-[3-(methylamino)pyrrolidin-1-yl]pyrimidin-2-yl}-4-chlorobenzene-1,3-diamine;
(S)-2-amino-5-{4-butyl-6-[3-(ethylamino)pyrrolidin-1-yl]pyrimidin-2-ylamino}benzonitrile;
(S)-3-{4-butyl-6-[3-(ethylamino)pyrrolidin-1-yl]pyrimidin-2-ylamino}benzonitrile;
(S)-5-{4-butyl-6-[3-(ethylamino)pyrrolidin-1-yl]pyrimidin-2-ylamino}-2-methylbenzonitrile;
(S)-$N^1$-{4-butyl-6-[3-(ethylamino)pyrrolidin-1-yl]pyrimidin-2-yl}-3-nitrobenzene-1,4-diamine;
(S)-4-butyl-6-[3-(ethylamino)pyrrolidin-1-yl]-N-(4-methyl-3-nitrophenyl)pyrimidin-2-amine;
(S)-4-butyl-6-[3-(ethylamino)pyrrolidin-1-yl]-N-(4-fluoro-3-nitrophenyl)pyrimidin-2-amine;
(S)-4-butyl-N-(4-chloro-3-nitrophenyl)-6-[3-(ethylamino)pyrrolidin-1-yl]pyrimidin-2-amine;
(S)-3-amino-5-{4-butyl-6-[3-(ethylamino)pyrrolidin-1-yl]pyrimidin-2-ylamino}benzonitrile;
(S)-$N^1$-{4-butyl-6-[3-(ethylamino)pyrrolidin-1-yl]pyrimidin-2-yl}-5-(trifluoromethyl)benzene-1,3-diamine;
(S)-$N^1$-{4-butyl-6-[3-(ethylamino)pyrrolidin-1-yl]pyrimidin-2-yl}-3-(trifluoromethyl)benzene-1,4-diamine;
(S)-4-butyl-6-[3-(ethylamino)pyrrolidin-1-yl]-N-[4-fluoro-3-(trifluoromethyl)phenyl]pyrimidin-2-amine;
(S)-5-{4-butyl-6-[3-(ethylamino)pyrrolidin-1-yl]pyrimidin-2-ylamino}-2-fluorobenzonitrile;
(S)-$N^1$-{4-butyl-6-[3-(ethylamino)pyrrolidin-1-yl]pyrimidin-2-yl}-4-fluorobenzene-1,3-diamine;
(S)-$N^1$-{4-butyl-6-[3-(ethylamino)pyrrolidin-1-yl]pyrimidin-2-yl}-4-chlorobenzene-1,3-diamine;
(S)-N-{1-[2-(3-cyano-4-methylphenylamino)-6-propylpyrimidin-4-yl]pyrrolidin-3-yl}-2-hydroxyacetamide;
(S)-N-{1-[2-(3-cyano-4-fluorophenylamino)-6-propylpyrimidin-4-yl]pyrrolidin-3-yl}-2-hydroxyacetamide;
(S)-N-{1-[2-(3-amino-5-cyanophenylamino)-6-propylpyrimidin-4-yl]pyrrolidin-3-yl}-2-hydroxyacetamide;
(S)-N-(1-{2-[3-amino-5-(trifluoromethyl)phenylamino]-6-propylpyrimidin-4-yl}pyrrolidin-3-yl)-2-hydroxyacetamide;
(S)-N-(1-{2-[4-amino-3-(trifluoromethyl)phenylamino]-6-propylpyrimidin-4-yl}pyrrolidin-3-yl)-2-hydroxyacetamide;
(S)-N-(1-{2-[4-fluoro-3-(trifluoromethyl)phenylamino]-6-propylpyrimidin-4-yl}pyrrolidin-3-yl)-2-hydroxyacetamide;
(S)-N-{1-[2-(3-amino-4-fluorophenylamino)-6-propylpyrimidin-4-yl]pyrrolidin-3-yl}-2-hydroxyacetamide;
(S)-N-{1-[2-(3-amino-4-chlorophenylamino)-6-propylpyrimidin-4-yl]pyrrolidin-3-yl}-2-hydroxyacetamide;
(S)-N-{1-[2-(3-chloro-4-methylphenylamino)-6-propylpyrimidin-4-yl]pyrrolidin-3-yl}-2-hydroxyacetamide;
(S)-2-hydroxy-N-(1-{2-[4-methyl-3-(trifluoromethyl)phenylamino]-6-propylpyrimidin-4-yl}pyrrolidin-3-yl)acetamide;
(S)-4-fluoro-$N^1$-{4-[3-(methylamino)pyrrolidin-1-yl]-6-propylpyrimidin-2-yl}benzene-1,3-diamine;
(S)-3-amino-5-({4-[3-(methylamino)pyrrolidin-1-yl]-6-propylpyrimidin-2-yl}amino)benzonitrile;
(S)-2-amino-5-({4-[3-(methylamino)pyrrolidin-1-yl]-6-propylpyrimidin-2-yl}amino)benzonitrile;
(S)-$N^1$-{4-[3-(methylamino)pyrrolidin-1-yl]-6-propylpyrimidin-2-yl}-5-(trifluoromethyl)benzene-1,3-diamine;
(S)-$N^1$-{4-[3-(ethylamino)pyrrolidin-1-yl]-6-propylpyrimidin-2-yl}-3-(trifluoromethyl)benzene-1,4-diamine;
(S)-2-amino-5-({4-[3-(ethylamino)pyrrolidin-1-yl]-6-propylpyrimidin-2-yl}amino)benzonitrile;
(S)-N-[4-fluoro-3-(trifluoromethyl)phenyl]-4-[3-(methylamino)pyrrolidin-1-yl]-6-propylpyrimidin-2-amine;
(S)-4-[3-(ethylamino)pyrrolidin-1-yl]-N-[4-fluoro-3-(trifluoromethyl)phenyl]-6-propylpyrimidin-2-amine; and
(S)-N-(1-{2-[(3,4-diaminophenyl)amino]-6-propylpyrimidin-4-yl}pyrrolidin-3-yl)acetamide.

* * * * *

UNITED STATES PATENT AND TRADEMARK OFFICE
CERTIFICATE OF CORRECTION

PATENT NO. : 9,890,138 B2
APPLICATION NO. : 14/001489
DATED : February 13, 2018
INVENTOR(S) : Hyun-Joo Lee et al.

It is certified that error appears in the above-identified patent and that said Letters Patent is hereby corrected as shown below:

On the Title Page

Please delete "(*) Notice: Subject to any disclaimer, the term of this patent is extended or adjusted under 35 U.S.C. 154(b) by 664 days. This patent is subject to a terminal disclaimer." and replace with -- (*) Notice: Subject to any disclaimer, the term of this patent is extended or adjusted under 35 U.S.C. 154(b) by 664 days. --

Please delete "(45) Date of Patent: *Feb. 13, 2018" and replace with -- (45) Date of Patent: Feb. 13, 2018 --

Signed and Sealed this
Ninth Day of October, 2018

Andrei Iancu
*Director of the United States Patent and Trademark Office*